United States Patent
Foitzik et al.

(10) Patent No.: US 9,266,864 B2
(45) Date of Patent: *Feb. 23, 2016

(54) VEGFR3 INHIBITORS

(71) Applicant: CANCER THERAPEUTICS CRC PTY LIMITED, Bundoora, Victoria (AU)

(72) Inventors: Richard Charles Foitzik, Parkville (AU); Neil Choi, Parkville (AU); Benjamin Joseph Morrow, Parkville (AU); Catherine Fae Hemley, Parkville (AU); Gillian Elizabeth Lunniss, Parkville (AU); Michelle Ang Camerino, Parkville (AU); Danny Ganame, Bundoora (AU); Paul Anthony Stupple, Bundoora (AU); Romina Lessene, Bundoora (AU); Wilhelmus Johannes Antonius Kersten, Bundoora (AU); Andrew John Harvey, Thebarton (AU); Ian Peter Holmes, Parkville (AU)

(73) Assignee: CANCER THERAPEUTICS CRC PTY LIMITED, Bundoora, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/968,932

(22) Filed: Aug. 16, 2013

(65) Prior Publication Data

US 2014/0080798 A1 Mar. 20, 2014

Related U.S. Application Data

(60) Provisional application No. 61/684,254, filed on Aug. 17, 2012.

(51) Int. Cl.

| | |
|---|---|
| *C07D 401/14* | (2006.01) |
| *A61K 31/505* | (2006.01) |
| *C07D 405/12* | (2006.01) |
| *A61K 31/506* | (2006.01) |
| *C07D 295/155* | (2006.01) |
| *C07D 239/42* | (2006.01) |
| *C07D 401/12* | (2006.01) |
| *C07D 295/192* | (2006.01) |
| *C07D 403/12* | (2006.01) |
| *C07D 403/14* | (2006.01) |
| *A61K 45/06* | (2006.01) |

(52) U.S. Cl.
CPC ............ *C07D 405/12* (2013.01); *A61K 31/505* (2013.01); *A61K 31/506* (2013.01); *A61K 45/06* (2013.01); *C07D 239/42* (2013.01); *C07D 295/155* (2013.01); *C07D 295/192* (2013.01); *C07D 401/12* (2013.01); *C07D 401/14* (2013.01); *C07D 403/12* (2013.01); *C07D 403/14* (2013.01)

(58) Field of Classification Search
CPC .. C07D 239/42; C07D 401/12; C07D 401/14; C07D 403/12; C07D 403/14; A61K 31/505; A61K 31/506
USPC .............. 544/295, 330, 331; 514/252.14, 275
See application file for complete search history.

(56) References Cited

FOREIGN PATENT DOCUMENTS

| | | |
|---|---|---|
| CA | 2 463 989 A1 | 4/2003 |
| CA | 2 808 540 A1 | 2/2012 |
| CN | 103113355 A | 5/2013 |
| WO | WO 03/032997 A1 | 4/2003 |
| WO | WO 2010/053438 A1 | 5/2010 |
| WO | WO 2010/111406 A2 | 9/2010 |
| WO | WO 2012/022408 A1 | 2/2012 |
| WO | WO 2012/110773 A1 | 8/2012 |
| WO | WO 2012/110774 A1 | 8/2012 |
| WO | WO 2012/115479 A2 | 8/2012 |
| WO | WO 2014/012942 A1 | 1/2014 |
| WO | WO 2014/026243 A1 | 2/2014 |
| WO | WO 2014/027199 | * 2/2014 |

OTHER PUBLICATIONS

Pearce et al., Failure modes in anticancer drug discovery and development, Cancer Drug Design and Discovery Edited by Stephen Neidle, Chapter 18, pp. 424-435 (2008).*

Johnson et al., Relationships between drug activity in NCI preclinical in vitro and in vivo models and early clinical trials, British Journal of Cancer (2001) 64(10): 1424-1431.*

Simone, Oncology: Introduction, Cecil Textbook of Medicine, 20th Edition, vol. 1, pp. 1004-1010, 1996.*

(Continued)

Primary Examiner — Deepak Rao
(74) Attorney, Agent, or Firm — Nixon & Vanderhye P.C.

(57) ABSTRACT

This invention relates to compounds of the formula (I):

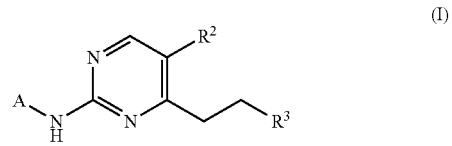

(I)

The invention also relates to processes for the preparation of the compound of the formula (I), pharmaceutical agents or compositions containing the compound or a method of using the compound for the treatment of proliferative diseases, such as cancer, as well as the treatment of diseases ameliorated by the control and/or inhibition of lymphangiogenesis.

41 Claims, No Drawings

(56) References Cited

OTHER PUBLICATIONS

Gura, Systems for identifying New Drugs Are Often Faulty, Cancer Models, Science, vol. 278, No. 5340, pp. 1041-1042, Nov. 1997.*
Alitalo et al., Interaction of tumor cells and lymphatic vessels in cancer progression, Oncogene (2012), 31(42), 4499-4508.*
Bundgaard, Design of Prodrugs, p. 1, 1985.*
Wolff, Some consideration for prodrug design, Burger's Medicinal Chemistry and Drug Discovery, 5th Edition, vol. I Principles and Practice, pp. 975-977, 1995.*
Banker et al., Prodrugs, Modern Pharmaceutics, Third Edition and Expanded, pp. 451 and 596 (1996).*
Silverman, Prodrugs and Drug Delivery Systems, The Organic Chemistry of Drug Design and Drug Action, pp. 352-399, 1992.*
Coats et al, "Correlation analysis of pyrimidine folic acid antagonists as antibacterial agents .I.", European Journal of Medicinal Chemistry, (1979), 14(3), 261-270.
Murray et al, "Dimetalated Heterocycles as Synthetic Intermediates V. Dianions Derived from Certain 2-Hydroxy-4-methylpyrimidines, 2-Amino-4-methylpyrimidines, and Related Compounds", Journal of Organic Chemistry, 1974, vol. 39, No. 5, 595-600.
Kreutzberger et al, "Cyclisierungsreaktionen an 4-Nitrophenylguanidin", Chemiker-Zeitung, 1981, 105(7-7), 229-232.
ASX Announcement, May 16, 2013, Bionomics press release about CTx-0357927, "CTx and Bionomics' Program Reaches Key Milestone".
Written Opinion mailed Nov. 20, 2013, issued in connection with PCT/AU2013/000912.
International Search Report mailed Nov. 20, 2013, issued in connection with PCT/AU2013/000912.
Hescot et al, "Pancreatic Atrophy—A New Late Toxic Effect of Sorafenib", The New England Journal of Medicine 369:15, pp. 475-476, Oct. 10, 2013.
Alam et al, "SAR131675, a Potent and Selective VEGFR-3-TK Inhibitor with Antilymphangiogenic, Antitumoral, and Antimetastatic Activities", Mol Cancer Ther; 11(8); 1637-49, 2012.
Loges et al, "Mechanisms of Resistance to Anti-Angiogenic Therapy and Development of Third-Generation Anti-Angiogenic Drug Candidates", Genes & Cancer 1(1) 12-25, 2010.
Duong et al, "Tumor Lymphangiogenesis as a Potential Therapeutic Target", Journal of Oncology, Article ID 204946, 23 pages, vol. 2012.
Meanwell, N. A. "Improving Drug Candidates by Design: A Focus on Physicochemical Properties As a Means of Improving Compound Disposition and Safety", Chemical Research in Toxicology 2011 24 (9), 1420-1456.
Kerns, E. H. & Di, L. (2008). "Drug-like Properties: Concepts, Structure Design and Methods" Lavergne, TN: Academic Press, pp. 45 and 152.
U.S. Patent Office, Office Action mailed Jul. 8, 2015 in U.S. Appl. No. 14/422,084, filed Feb. 17, 2015, Foitzik et al.
Jordan, V. C. "Tamoxifen: A Most Unlikely Pioneering Medicine", Nature Reviews: Drug Discovery, 2, 2003, 205.
Vippagunta, et al. "Crystalline Solids", Advanced Drug Delivery Reviews, 48, 2001, 18.
Hackam, et al. "Translation of Research Evidence From Animals to Humans", JAMA, 296(14), 2006, 1731-1732.
Supplemental European Search Report dated May 29, 2015, issued in connection with European Patent Application No. 13829826.0.

* cited by examiner

VEGFR3 INHIBITORS

This application claims the benefit from U.S. Provisional Application No. 61/684,254, filed 17 Aug. 2012, the entire contents of which is hereby incorporated by reference.

This invention relates to 2,4,5-substituted pyrimidines that inhibit vascular endothelial growth factor receptor 3 (VEGFR3), also known as Fms related tyrosine kinase 4 (FLT4), processes for their preparation or pharmaceutical agents or compositions containing such compounds. This invention also relates to a method of using such compounds for the treatment of proliferative diseases, such as cancer, as well as the treatment of diseases ameliorated by the control and/or inhibition of lymphangiogenesis.

BACKGROUND

Cancer remains a major cause of death in the 21st century. Consequently, considerable drug research and development effort is currently placed on the discovery of therapeutics that may provide life extending or curative options to cancer sufferers.

While there are many different varieties of cancer, each exhibiting a different array of genetic and growth properties, a common denominator among many solid cancer types is the ability to metastasize. Until the occurrence of metastasis, tumors are confined to one area of the body and may be controlled through surgical intervention and/or radiotherapy. However, metastasis causes cancer cells to spread to disparate parts of the body and while surgical intervention may remove the primary tumor lesion, removal of all metastatic lesions is very difficult to manage.

Tumor metastasis is a multistage process, involving the breakdown of extracellular matrix, invasion of local tissue parenchyma, intravasation into regional blood vessels and lymphatics, survival in the circulation and finally extravasation, survival and growth in secondary tissue sites (*Front. Biosci.* (*Elite Ed*). 2012; 4: 1888-1897).

Metastasis may occur through blood vessels or lymphatic vessels. Lymphatic vessels differ from blood vessels in several ways. Large collecting lymphatic vessels contain vascular smooth muscle cells in their wall, as well as valves, which prevent the backflow of lymph. However, lymphatic capillaries, unlike typical blood capillaries, lack pericytes and continuous basal lamina and contain large inter-endothelial valve-like openings (*J. Theor. Med.* 2003; 5: 59-66). Due to their greater permeability, lymphatic capillaries are more effective than blood capillaries in allowing tumor cells to pass. Experimental evidence demonstrates that lymphangiogenesis (the formation of new lymphatic vessels) within a growing tumor lesion promotes metastasis through lymphatic vessels. The control of lymphangiogenesis presents an attractive therapeutic strategy for preventing lymph node metastasis (*J. Clin. Onc.* 2007; 25: 4298-4307).

The lymphatic system is comprised of capillaries and larger collecting vessels continuously lined by endothelial cells which return extravasated fluid and macromolecules from the interstitial space back to the blood circulation. Metastasis to regional lymph nodes via lymphatic vessels is a tumor progression process that is common to many cancer types. The extent of lymph node involvement is a major determinant for the staging of many types of cancer and is an important prognostic factor that is used as the basis for surgical and radiation treatment intervention of the affected lymph nodes.

Molecular signalling through binding of the growth factors VEGFC or VEGFD to their membrane receptor VEGFR3 has been shown to play a central role in the process of lymphangiogenesis (*Brit. J. Cancer* 2006; 94: 1355-1360). Stimulation of the VEGFR3 receptor occurs through the phosphorylation of its intracellular region and triggers a downstream signalling cascade that drives lymphatic endothelial cell proliferation, migration and differentiation leading to formation of lymphatic vessels (*Exp. Cell Res.* 2006; 312: 575-583). Increased expression of VEGFC or VEGFD has been shown to promote tumor associated lymphangiogenesis enabling lymphatic-mediated metastasis to regional lymph nodes. These observations have been reported for several different tumor types, including colorectal (*Oncol. Rep.* 2009; 22: 1093-1100) lung (*Ann. Oncol.* 2010; 21: 223-231), gastric (*Surgery* 2009; 146: 896-905), kidney (*Oncol. Rep.* 2008; 20: 721-725) prostate (*Clin. Cancer Res.* 2004; 10: 5137-5144) and ovarian (*Cancer* 2004; 101: 1364-1374). Blockade of VEGFC, VEGFD/VEGFR3 mediated signalling has been shown to inhibit lymphangiogenesis and suppress lymph node metastasis in several tumor experimental models in rodents (*Ann. N.Y. Acad. Sci.* 2008; 113: 225-234; *Int. J. Cancer* 2009; 125: 2747-2756).

VEGFR3 is a transmembrane tyrosine kinase receptor that is broadly expressed in endothelial cells during embryogenesis (*Biochem. J.* 2011; 437: 169-183). In the latter stages of development VEGFR3 expression becomes restricted to developing lymphatic vessels. In adults, VEGFR3 expression is primarily restricted to lymphatic endothelium and a subset of CD34+ hematopoietic cells. In addition, fenestrated capillaries and veins in certain endocrine organs, as well as monocytes, macrophages and some dendritic cells (DCs), continue to express VEGFR3 in adults. Disruption of the VEGFR3 gene in mouse embryos results in the failure of vascular network formation and death after embryonic day 9.5 (*Biochem. J.* 2011; 437: 169-183). This observation demonstrates that VEGFR3 plays an essential role in the development of embryonic vasculature. In cancer, VEGFR3 is overexpressed in lymphatic sinuses in metastatic lymph nodes and in lymphangiomas. Furthermore, in many instances cancer cells themselves express VEGFR3. VEGFR3 expressing cancer cells have been shown to be dependent on VEGFR3/VEGFC signalling for their proliferation (*Eur. J. Canc.* 2011; 47: 2353-2363).

Based on the foregoing, it is apparent that inhibition of VEGFR3 signalling has strong potential as therapeutic strategy for mammalian subjects that have been diagnosed with a disease characterised by proliferation of endothelial cells that express this receptor. In the case of cancer, targeting VEGFR3 is likely to result in therapeutic benefit through suppression of lymphatic metastasis and suppression of growth in cancer cells that express VEGFR3.

Interestingly, and perhaps importantly from the view point of target selection within the VEGFR3 axis, in mice in which both the VEGFC and the VEGFD genes have been homozygously deleted, the blood vasculature develops normally, unlike the embryonic cardiovascular phenotype of VEGFR3 homozygous knockout mice: i.e. deletion of these two ligands is not the same as deletion of the receptor (*Mol. Cell. Biol.* 2008; 28: 4843-4850). These data raise the possibility that another ligand for VEGFR3 exists or that VEGFR3 may be able to act by an as-yet-unknown manner independent of its ligands VEGFC and VEGFD. The foregoing suggest that targeting VEGFR3 is more advantageous to blocking VEGFC/D-VEGFR3 signalling compared to targeting either VEGFC or VEGFD alone.

Whilst there are a number of studies reported involving tyrosine kinase inhibitors with various levels of VEGFR3 activity and selectivity (*Nat. Rev. Drug Discov.* 2006; 5: 835-

844; *Mol. Cancer. Ther.* 2007; 6: 2012-2021; *Cancer Res.* 2009; 69: 8009-8016; *Mol. Cancer. Ther.* 2012; 11: 1637-1649) these studies have some limitations, resulting in part at least from inhibition at other tyrosine kinases.

Nonetheless, collectively these studies strengthen the conclusion that inhibition of VEGFR3 suppresses or reduces lymphangiogenesis and/or lymphogenic metastasis.

Accordingly, compounds that selectively inhibit VEGFR3 would be useful for the treatment of proliferative diseases, such as cancer.

As described above, VEGFR3 plays an important role in the control of lymphangiogenesis. Accordingly, inhibitors of VEGFR3 may have utility in the treatment of diseases other than cancer where control/inhibition of lymphangiogenesis has a therapeutic benefit. The lymphatic system plays a major role in chronic inflammatory diseases and in transplant rejection. Inhibition of lymphangiogenesis through suppression of VEGFR3 function may provide a viable therapeutic strategy in these conditions.

For example, preclinical studies have demonstrated that the expression of VEGFR3 in the cornea and ocular surface is modified during corneal neovascularisation and that VEGFR3 mediates corneal dendritic cell migration to lymph nodes and induction of immunity to corneal transplant. High-risk corneal transplantation, where grafting is performed on inflamed and highly vascularized host beds, has a very poor success rate, with rejection rates as high as 90% (*J. Leukoc Biol.* 2003; 74: 172-178). In preclinical models, treatment with a VEGFR3 antibody leads to significant suppression of corneal graft rejection (*Nat. Med.* 2004; 10: 813-815).

Choroidal neovascularization (CNV), the creation of new blood vessels in the choroid layer of the eye, leads to chronic inflammation which is implicated in the pathogenesis of age related macular degeneration (AMD) and is driven by factors which include uncontrolled expression of the vascular endothelial growth factor (VEGF) family members VEGFA and VEGFC (*J. Cell. Physiol.* 2012; 227(1): 116-26). Treatments for AMD have been developed that target VEGFA, for example the anti-VEGFA antibodies ranibizumab and bevacizumab and the anti-VEGF aptamer pegaptanib, but to date no treatments have been clinically evaluated that mediate effects through modulation of VEGFC and its cognate receptor VEGFR3.

Accordingly, compounds that inhibit VEGFR3 may be useful for the prevention and/or treatment of eye diseases, for example corneal graft rejection and age related macular degeneration.

Furthermore, there is increasing evidence that lymphatic vessels have an active role in chronic inflammation of the skin. Lymphatic endothelial cell proliferation and lymphatic hyperplasia have been described in chronic skin inflammation in mice and have been reported for skin lesions in psoriasis patients (*Blood* 2004; 104: 1048-1057).

Accordingly, compounds that inhibit VEGFR3 may be useful for the prevention and/or treatment of skin inflammations, such as skin lesions in patients with psoriasis.

Lymphangiogenesis has also been found to be associated with kidney transplant rejection. VEGFC producing macrophages induce formation of new lymphatics which induce and support the maintenance of an alloreactive immune response in renal transplants (*Nat. Med.* 2006; 12: 230-234).

Accordingly, compounds that inhibit VEGFR3 may be useful for the prevention and/or treatment of rejection in renal transplantation.

Co-pending application PCT/GB2012/000175 discloses compounds which inhibit FAK and VEGFR3.

SUMMARY

The present inventors have discovered a particular class of compounds which are effective as VEGFR3 inhibitors. These compounds may exhibit selectivity for VEGFR3 over kinases such as FAK and/or VEGFR2.

In a first aspect, the present invention provides compounds of the following formula (I) or isomers, salts, solvates or prodrugs thereof:

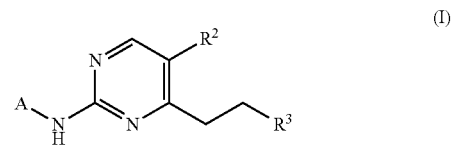

wherein:

A is an optionally substituted 5-10 membered heteroaryl group linked to the NH group through an aromatic ring carbon atom, in which the heteroaryl ring system contains 1 to 4 heteroatoms selected from N, O and S; and A may bear a single substituent $R^{1A}$ which is not alpha to the NH group, and may optionally further bear one, two or three substituents $R^{1C}$, where $R^{1A}$ is selected from:

(i) $CH(R^{C1})NHZ^1$, where $R^{C1}$ is selected from H, $C_{1-2}$ alkyl and $Z^1$ is selected from H, $C_{1-3}$ alkyl optionally substituted by OH, $C(=O)OC_{1-3}$ alkyl and $C(=O)Me$;

(ii) $XNHZ^2$, where X is selected from $CMe_2$, cyclopropylidene, cyclobutylidene, cyclopentylidene and oxetanylidene and $Z^2$ is selected from H, $C_{1-3}$ alkyl optionally substituted by OH, $C(=O)OC_{1-3}$ alkyl and $C(=O)Me$;

(iii) a group selected from $R^{1A1}$ to $R^{1A11}$:

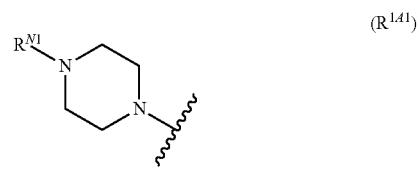

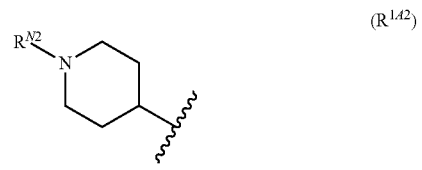

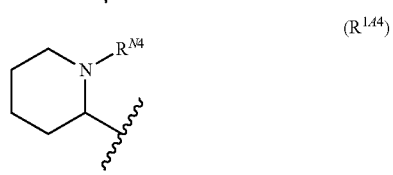

-continued

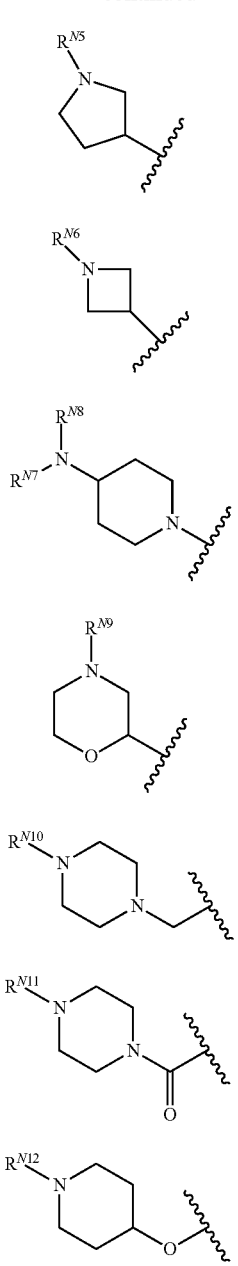

wherein:
$R^{N1}$ is selected from H, $C_{1-4}$ alkyl, $C_{3-4}$ cycloalkyl and C(=O)Me;
$R^{N2}$ is selected from H, $C_{1-4}$ alkyl, $C_{3-4}$ cycloalkyl and C(=O)Me;
$R^{N3}$ is selected from H, $C_{1-4}$ alkyl, $C_{3-4}$ cycloalkyl and C(=O)Me;
$R^{N4}$ is selected from H and $CH_3$;
$R^{N5}$ is selected from H, $C_{1-4}$ alkyl, $C_{3-4}$ cycloalkyl and C(=O)Me;
$R^{N6}$ is selected from H, $C_{1-4}$ alkyl, $C_{3-4}$ cycloalkyl and C(=O)Me;
$R^{N7}$ and $R^{N8}$ are independently selected from H and $CH_3$;
$R^{N9}$ is selected from H, $C_{1-4}$ alkyl, $C_{3-4}$ cycloalkyl and C(=O)Me;
$R^{N10}$ is selected from H, $C_{1-4}$ alkyl, $C_{3-4}$ cycloalkyl and C(=O)Me;
$R^{N11}$ is selected from H, $C_{1-4}$ alkyl, $C_{3-4}$ cycloalkyl and C(=O)Me; and
$R^{N12}$ is selected from H, $C_{1-4}$ alkyl, $C_{3-4}$ cycloalkyl and C(=O)Me;
and where each $R^{1C}$ is independently selected from:
(i) $C_{1-3}$ alkyl;
(ii) $CF_3$;
(iii) F;
(iv) Cl;
(v) O—($C_{1-3}$ alkyl);
(vi) CN; and
(vii) =O;
$R^2$ is selected from H, halo, $C_{1-4}$ alkyl, $CF_3$, $CF_2H$, CN and methoxy;
$R^3$ is selected from substituted phenyl and a substituted 6 membered heteroaryl group, where the heteroaryl ring system contains 1 or 2 N heteroatoms, where
$R^3$ bears a substituent $R^4$ either alpha or beta to the —$C_2H_4$— group, and may additionally bear further substituents selected from F, methyl and $CF_3$; and
$R^4$ is —$CH_2$—C(O)N($R^{N13}$)$Z^3$, where $R^{N13}$ is selected from H and $CH_3$; and $Z^3$ is selected from H, $CH_3$ and $OCH_3$.

In some embodiments, the compounds of the first aspect of the present invention are of formula (I) as defined above with the proviso that the compound is not:

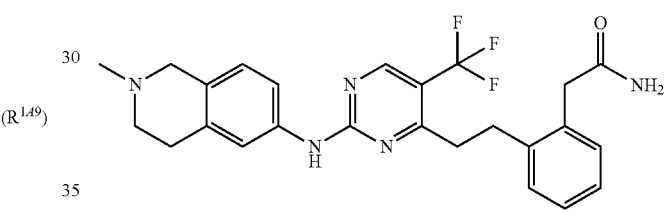

C21

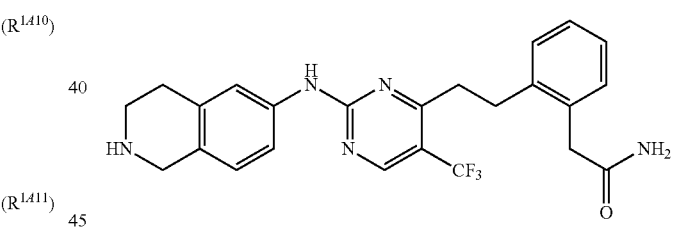

C32

In a second aspect, the present invention provides compounds of the following formula (II) or isomers, salts, solvates or prodrugs thereof:

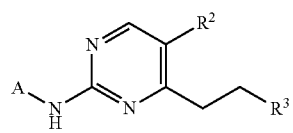

(II)

wherein:
A is optionally substituted phenyl;
when A is optionally substituted phenyl, A may bear a substituent $R^{1A}$ which is not alpha to the NH group and may optionally further bear one or two substituents $R^{1B}$ which are not alpha to the NH group, where $R^{1A}$ is selected from:
(i) CH($R^{C1}$)NH$Z^1$, where $R^{C1}$ is selected from H, $C_{1-2}$ alkyl and $Z^1$ is selected from H, $C_{1-3}$ alkyl optionally substituted by OH, C(=O)O$C_{1-3}$ alkyl and C(=O)Me;

(ii) XNHZ², where X is selected from CMe₂, cyclopropylidene, cyclobutylidene, cyclopentylidene and oxetanylidine and Z² is selected from H, C₁₋₃ alkyl optionally substituted by OH, C(=O)OC₁₋₃ alkyl and C(=O)Me;

(iii) a group selected from $R^{1A1}$ to $R^{1A11}$:

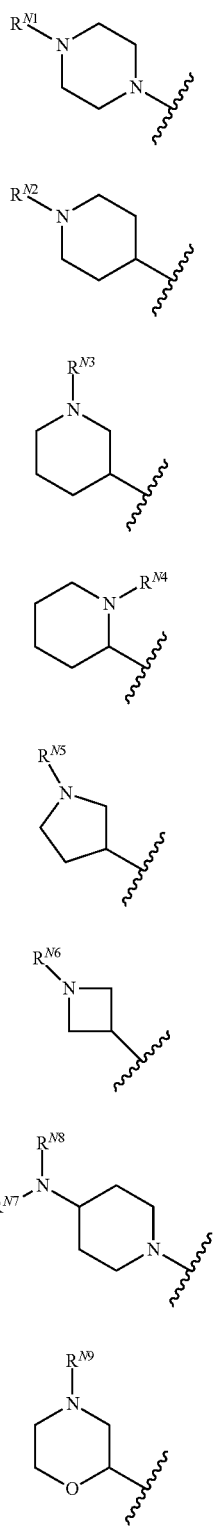

($R^{1A1}$)
($R^{1A2}$)
($R^{1A3}$)
($R^{1A4}$)
($R^{1A5}$)
($R^{1A6}$)
($R^{1A7}$)
($R^{1A8}$)

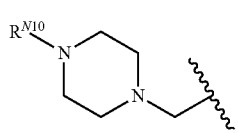

($R^{1A9}$)

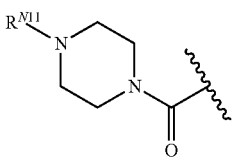

($R^{1A10}$)

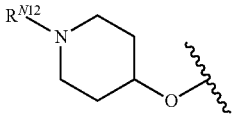

($R^{1A11}$)

wherein:

$R^{N1}$ is selected from H, C₁₋₄ alkyl, C₃₋₄ cycloalkyl and C(=O)Me;

$R^{N2}$ is selected from H, C₁₋₄ alkyl, C₃₋₄ cycloalkyl and C(=O)Me;

$R^{N3}$ is selected from H, C₁₋₄ alkyl, C₃₋₄ cycloalkyl and C(=O)Me;

$R^{N4}$ is selected from H and CH₃;

$R^{N5}$ is selected from H, C₁₋₄ alkyl, C₃₋₄ cycloalkyl and C(=O)Me;

$R^{N6}$ is selected from H, C₁₋₄ alkyl, C₃₋₄ cycloalkyl and C(=O)Me;

$R^{N7}$ and $R^{N8}$ are independently selected from H and CH₃;

$R^{N9}$ is selected from H, C₁₋₄ alkyl, C₃₋₄ cycloalkyl and C(=O)Me;

$R^{N10}$ is selected from H, C₁₋₄ alkyl, C₃₋₄ cycloalkyl and C(=O)Me;

$R^{N11}$ is selected from H, C₁₋₄ alkyl, C₃₋₄ cycloalkyl and C(=O)Me; and $R^{N12}$ is selected from H, C₁₋₄ alkyl, C₃₋₄ cycloalkyl and C(=O)Me;

and where each $R^{1B}$ is independently selected from:

(i) C₁₋₃ alkyl;
(ii) CF₃;
(iii) F;
(iv) Cl;
(v) O—(C₁₋₃ alkyl); and
(vi) CN;

R² is selected from H, halo, C₁₋₄ alkyl, CF₃, CF₂H, CN and methoxy;

R³ is selected from substituted phenyl and a substituted 6 membered heteroaryl group, where the heteroaryl ring system contains 1 or 2 N heteroatoms, where R³ bears a substituent R⁴ either alpha or beta to the —C₂H₄— group, and may additionally bear further substituents selected from F, methyl and CF₃; and R⁴ is —CH₂—C(O)N($R^{N13}$)Z³, where $R^{N13}$ is selected from H and CH₃; and Z³ is selected from H, CH₃ and OCH₃.

In some embodiments, the compounds of the second aspect of the present invention are of formula (II) or isomers, salts, solvates or prodrugs thereof as defined above with the proviso that the compound is not any of the following compounds:

-continued

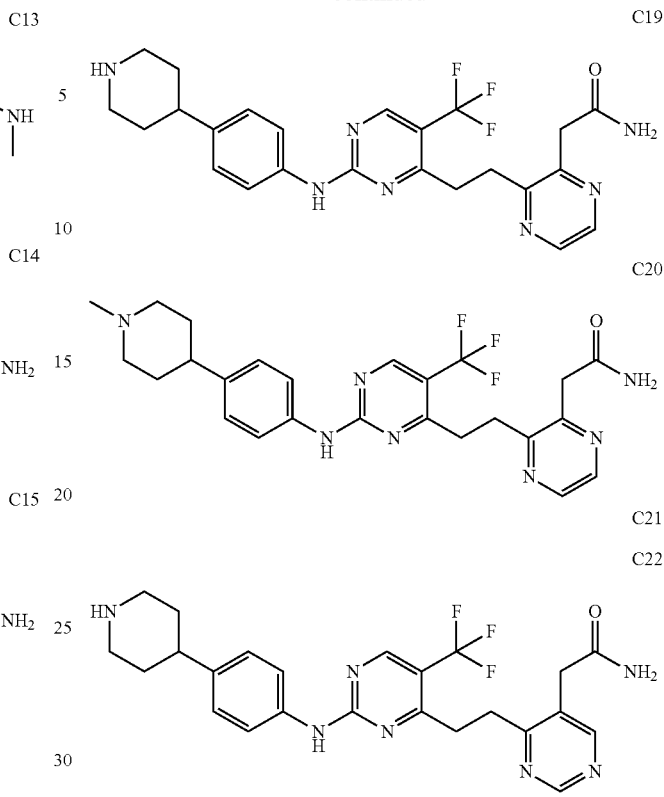
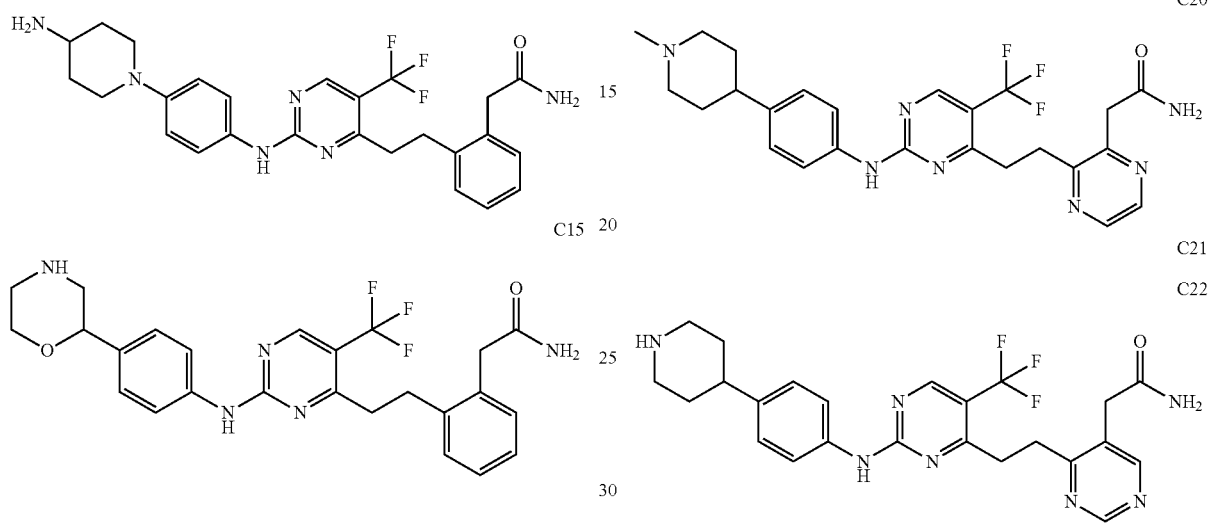
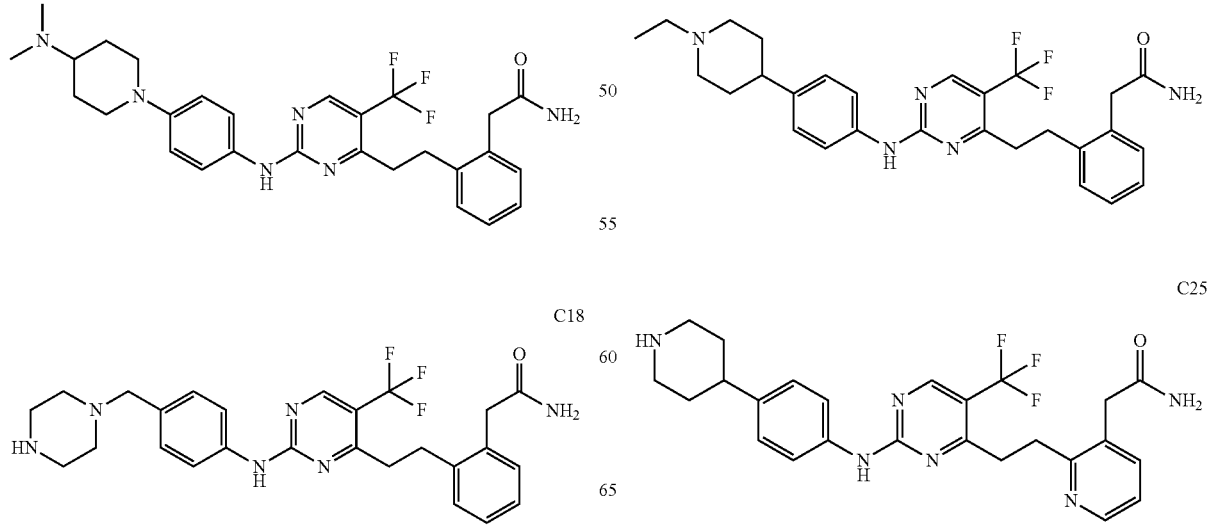

-continued
C26
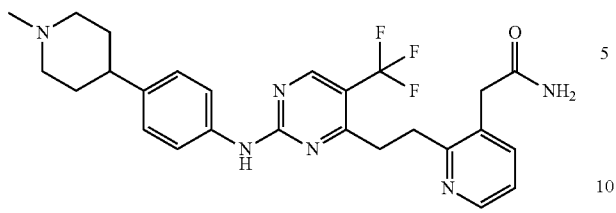
C27
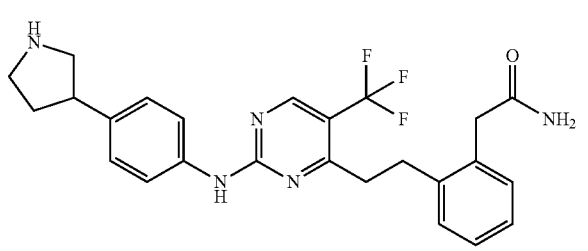
C28
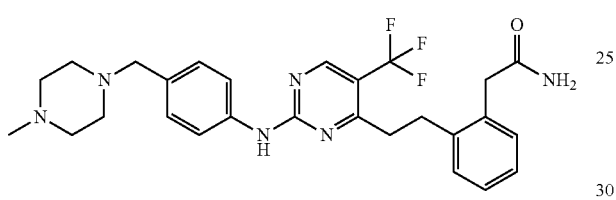
C29
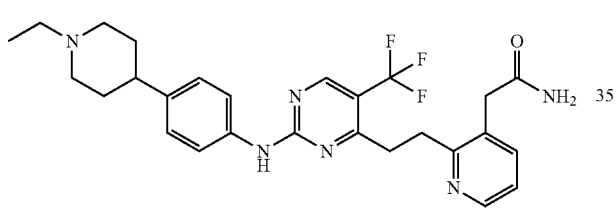
C30
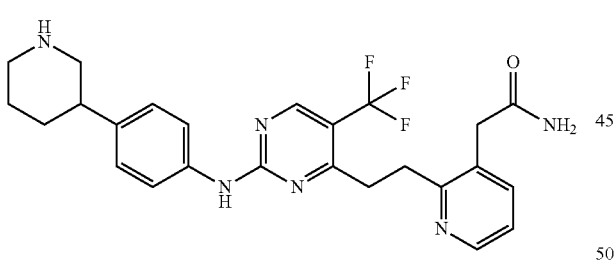
C31
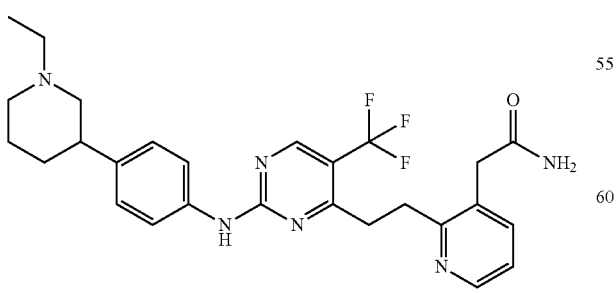
when $R^3$ is selected from:
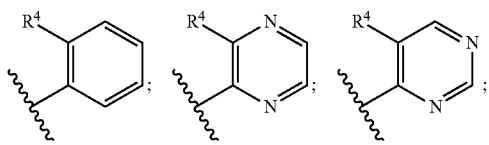
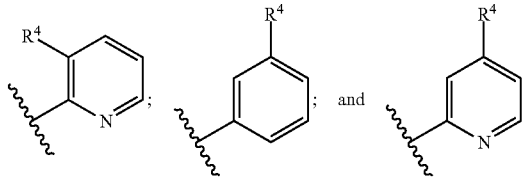
A is either:
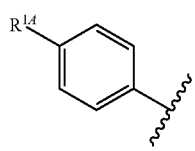
where $R^{1A}$ is selected from
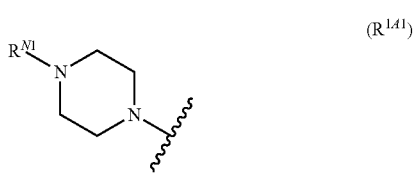 (R$^{1A1}$)
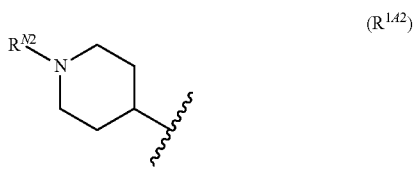 (R$^{1A2}$)
 (R$^{1A3}$)
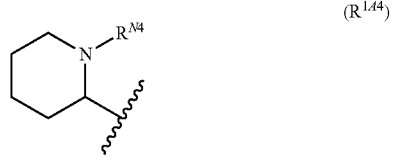 (R$^{1A4}$)
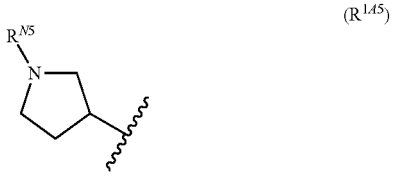 (R$^{1A5}$)
In some embodiments, the compounds of the second aspect are of formula (II) as defined above with the proviso that:

-continued

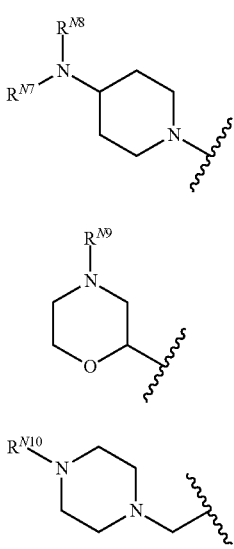

(R^{147})

(R^{148})

(R^{149})

and R^{N1} is selected from H, $C_{1-3}$ alkyl, and C(=O)Me;
R^{N2} is selected from H, $C_{1-3}$ alkyl, and C(=O)Me;
R^{N3} is selected from H, $C_{1-3}$ alkyl, and C(=O)Me;
R^{N4} is selected from H and $CH_3$;
R^{N5} is selected from H, $C_{1-3}$ alkyl, and C(=O)Me;
R^{N7} and R^{N8} are independently selected from H and $CH_3$;
R^{N9} is selected from H, $C_{1-3}$ alkyl, and C(=O)Me;
R^{N10} is selected from H, $C_{1-3}$ alkyl, and C(=O)Me;
or

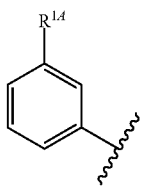

where R^{14} is

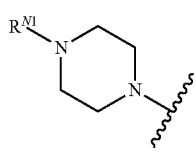

(R^{141})

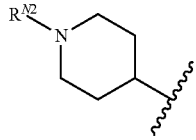

(R^{142})

and R^{N1} is selected from H, $C_{1-3}$ alkyl, and C(=O)Me;
R^{N2} is selected from H, $C_{1-3}$ alkyl, and C(=O)Me;
then $R^2$ is not selected from $CF_3$, halo, $CF_2H$ and CN.

A third aspect of the invention provides a process for the preparation of a compound of formula (I) or formula (II) or isomers, salts, solvates or prodrugs thereof of either the first aspect or the second aspect, comprising reacting a compound of formula F1

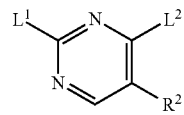

F1 with a compound of formula A-$NH_2$ to displace the group $L^1$ and with a compound of formula HC=$R^3$ to displace the group $L^2$; or with a compound of formula HC=$R^3$ to displace the group $L^2$ and with a compound of formula A-$NH_2$ to displace the group $L^1$, wherein A, $R^2$ and $R^3$ are as defined in formula (I) or (II) above and $L^1$ and $L^2$ are leaving groups.

A fourth aspect of the invention provides a pharmaceutical agent comprising a compound of the formula (I) or formula (II) or isomers, salts, solvates or prodrugs thereof of either the first aspect or the second aspect.

There is also provided use of a compound of formula (I) or formula (II) or isomers, salts, solvates, protected forms or prodrugs thereof of either the first aspect or the second aspect as a pharmaceutical agent.

There is further provided a compound of formula (I) or formula (II) or isomers, salts, solvates or prodrugs thereof of either the first aspect or the second aspect for use as a pharmaceutical agent.

The pharmaceutical agent may be an anticancer agent, a lyphangiogenesis inhibitor, an antimetatstasis agent or a VEGFR3 inhibitor.

A fifth aspect of the present invention provides a composition comprising a compound of formula (I) or formula (II) or an isomer, salt, solvate or prodrug thereof of either the first aspect or the second aspect and a pharmaceutically acceptable carrier or diluent.

A sixth aspect of the invention provides a compound of formula (I) or formula (II) or an isomer, salt, solvate or prodrug thereof of either the first aspect or the second aspect, agent of the fourth aspect or composition of the fifth aspect for use in a method of therapy.

A seventh aspect of the invention provides for the use of a compound of formula (I) or formula (II) or an isomer, salt, solvate or prodrug thereof, of either the first aspect or the second aspect, agent of the fourth aspect or composition of the fifth aspect in the preparation of a medicament for treating a disease or condition ameliorated by the inhibition of VEGFR3. The seventh aspect of the invention also provides a compound of formula (I) or (II) of either the first aspect or the second aspect, agent of the fourth aspect or composition of the fifth aspect for use in the method of treatment of a disease or condition ameliorated by the inhibition of VEGFR3.

An eighth aspect of the invention provides for the use of a compound of formula (I) or formula (II) or an isomer, salt, solvate or prodrug thereof of either the first aspect or the second aspect, agent of the fourth aspect or composition of the fifth aspect in the preparation of a medicament for treating cancer. The eighth aspect of the invention also provides a compound of formula (I) or formula (II) or an isomer, salt, solvate or prodrug thereof of either the first aspect or the second aspect, agent of the fourth aspect or composition of the fifth aspect for use in the method of treatment of cancer.

A further aspect of the invention provides a compound of formula (I) or formula (II) or an isomer, salt, solvate or prodrug thereof of either the first aspect or the second aspect, agent of the fourth aspect or composition of the fifth aspect for use in a method of treatment of the human or animal body, preferably in the form of a pharmaceutical composition.

Another aspect of the invention provides a method of inhibiting VEGFR3 in vitro or in vivo, comprising contacting a cell or cell lysates with an effective amount of a compound of formula (I) or formula (II) or an isomer, salt, solvate or prodrug thereof of either the first aspect or the second aspect, agent of the fourth aspect or composition of the fifth aspect.

A still further aspect of the invention provides an anticancer treatment comprising a compound of formula (I) or formula (II) or an isomer, salt, solvate or prodrug thereof of either the first aspect or the second aspect, agent of the fourth aspect or composition of the fifth aspect and an anti-tumour agent.

Each of the groups A, and $R^1$ to $R^4$ from the first and second aspects of the invention will be discussed in more detail below.

A

A is selected from optionally substituted phenyl (in the second aspect of the invention) and an optionally substituted 5-10 membered heteroaryl group linked to the NH group through an aromatic ring carbon atom (in the first aspect of the invention), in which the heteroaryl ring system contains 1 to 4 heteroatoms selected from N, O and S.

If A is unsubstituted phenyl, it has the structure:

(A¹)

If A is substituted phenyl, the $R^{1A}$ group can either be meta or para, and so A can have the structures:

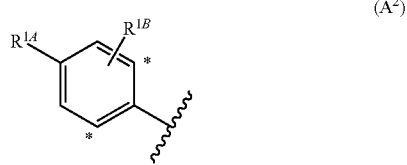

(A²)

(A³)

(A⁴)

where the $R^{1B}$ group cannot be alpha to the connection point to the rest of the compound (i.e., it cannot be in the asterixed positions).

When A is a 5-10 membered heteroaryl group linked to the NH group through an aromatic ring carbon atom, in which the heteroaryl ring system contains 1 to 4 heteroatoms selected from N, O and S, it is a monovalent moiety obtained by removing a hydrogen atom from an aromatic ring atom of an heteroaromatic compound (i.e. a compound having at least one heteroaromatic ring), which moiety has from 5 to 10 ring atoms. Preferably, each ring has from 5 to 7 ring atoms.

Examples of monocyclic heteroaryl groups include, but are not limited to, those derived from:

$N_1$: pyrrole (azole) (5-membered), pyridine (azine) (6-membered);

$O_1$: furan (oxole) (5-membered);

$S_1$: thiophene (thiole) (5-membered);

$N_1O_1$: oxazole (5-membered), isoxazole (5-membered), isoxazine (6-membered);

$N_2O_1$: oxadiazole (furazan) (5-membered);

$N_3O_1$: oxatriazole (5-membered);

$N_1S_1$: thiazole (5-membered), isothiazole (5-membered);

$N_2$: imidazole (1,3-diazole) (5-membered), pyrazole (1,2-diazole) (5-membered), pyridazine (1,2-diazine) (6-membered), pyrimidine (1,3-diazine) (6-membered) (e.g., cytosine, thymine, uracil), pyrazine (1,4-diazine) (6-membered);

$N_3$: triazole (5-membered), triazine (6-membered); and, $N_4$: tetrazole (5-membered).

Examples of heteroaryl groups which comprise fused rings, include, but are not limited to, those derived from:

9-membered (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

10-membered (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$).

Thus, when A is a 5 to 10 membered heteroaryl group, it may be selected from any of the groups listed above.

In some embodiments, A is a 5 or 6 membered heteroaryl group linked to the NH group through an aromatic ring carbon atom, in which the heteroaryl ring system contains 1 or 2 heteroatoms selected from N, O and S. Preferably the heteroatoms are N atoms.

If A is 6-membered heteroaryl, the $R^{1A}$ group can either be meta or para to the NH group. If A is 5-membered heteroaryl or a 7 to 10 membered heteroaryl, the $R^{1A}$ group is not alpha to the —NH— group. Thus, when A is 5-membered heteroaryl, the $R^{1A}$ group is beta to the —NH— group $R^{1A}$ $R^{1A}$ may have one of the following structures:

$CH_2NHZ^1$;

$CH(CH_3)NHZ^1$;

$CH(C_2H_5)NHZ^1$;

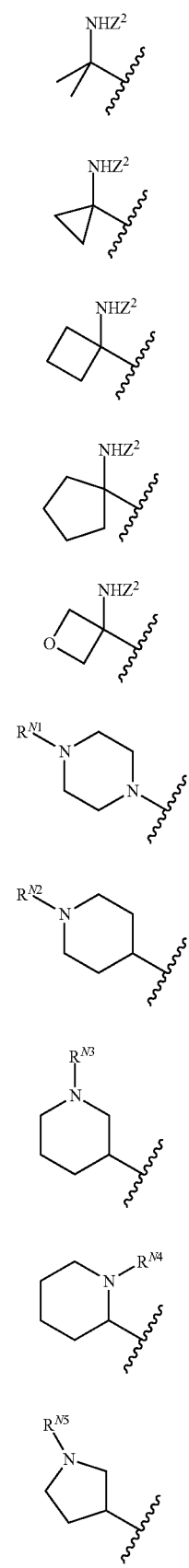

wherein:
R$^{N1}$ is selected from H, C$_{1-4}$ alkyl, C$_{3-4}$ cycloalkyl and C(=O)Me;
R$^{N2}$ is selected from H, C$_{1-4}$ alkyl, C$_{3-4}$ cycloalkyl and C(=O)Me;
R$^{N3}$ is selected from H, C$_{1-4}$ alkyl, C$_{3-4}$ cycloalkyl and C(=O)Me;
R$^{N4}$ is selected from H and CH$_3$;
R$^{N5}$ is selected from H, C$_{1-4}$ alkyl, C$_{3-4}$ cycloalkyl and C(=O)Me;
R$^{N6}$ is selected from H, C$_{1-4}$ alkyl, C$_{3-4}$ cycloalkyl and C(=O)Me;
R$^{N7}$ and R$^{N8}$ are independently selected from H and CH$_3$;
R$^{N9}$ is selected from H, C$_{1-4}$ alkyl, C$_{3-4}$ cycloalkyl and C(=O)Me;
R$^{N10}$ is selected from H, C$_{1-4}$ alkyl, C$_{3-4}$ cycloalkyl and C(=O)Me;
R$^{N11}$ is selected from H, C$_{1-4}$ alkyl, C$_{3-4}$ cycloalkyl and C(=O)Me; and
R$^{N12}$ is selected from H, C$_{1-4}$ alkyl, C$_{3-4}$ cycloalkyl and C(=O)Me.

Each of R$^{N1}$, R$^{N2}$, R$^{N3}$, R$^{N5}$, R$^{N6}$, R$^{N9}$, R$^{N10}$, R$^{N11}$ and R$^{N12}$ is independently selected from H, C$_{1-4}$ alkyl (i.e. methyl, ethyl, prop-1-yl, prop-2-yl, n-butyl, iso-butyl, sec-butyl, tert-butyl), C$_{3-4}$ cycloalkyl (i.e. cyclopropyl, methylcyclopropyl, cyclobutyl) and C(=O)Me. Each of R$^{N4}$, R$^{N7}$ and R$^{N8}$ is independently selected from either H or methyl.

Each of Z$^1$ and Z$^2$ is independently selected from H, C$_{1-3}$ alkyl (i.e. methyl, ethyl, prop-1-yl and prop-2-yl), optionally substituted by OH, C(=O)OC$_{1-3}$ alkyl (i.e. C(=O)O-methyl, C(=O)O-ethyl, C(=O)O-prop-1-yl and C(=O)O-prop-2-yl) and C(=O)Me.

R$^{1B}$

Each R$^{1B}$ group may be C$_{1-3}$ alkyl (i.e. methyl, ethyl, prop-1-yl and prop-2-yl), CF$_3$, F, Cl, O—C$_{1-3}$ alkyl (i.e. methoxy, ethoxy, prop-1-oxy and prop-2-oxy) or CN. These groups may be any available ring position on A, except that which is alpha to the NH group. There may be up to 2 R$^{1B}$ groups (i.e. 1 or 2).

R$^{1C}$

Each R$^{1C}$ group may be C$_{1-3}$ alkyl (i.e. methyl, ethyl, prop-1-yl and prop-2-yl), CF$_3$, F, Cl, O—C$_{1-3}$ alkyl (i.e. methoxy, ethoxy, prop-1-oxy and prop-2-oxy), CN or =O. These groups may be substituted at any available ring position on A. There may be up to 3 R$^{1C}$ groups (i.e. 1, 2 or 3) depending on the nature of A, and in particular on the number of ring atoms and ring heteroatoms, as well as whether R$^{1A}$ is present.

R$^2$

R$^2$ is selected from H, halo (i.e. F, Cl, Br, I), C$_{1-4}$ alkyl (i.e. methyl, ethyl, prop-1-yl and prop-2-yl, n-butyl, iso-butyl, sec-butyl, tert-butyl), CF$_3$, CF$_2$H, CN and methoxy.

In some embodiments, the halo group is either F or Cl.

R$^3$

R$^3$ is selected from substituted phenyl and a substituted 6 membered heteroaryl group, where the heteroaryl ring system contains 1 or 2 N heteroatoms.

When R$^3$ is substituted phenyl, it has the structure:

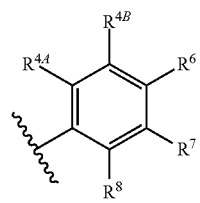
(R$^{3a}$)

where R$^6$, R$^7$ and R$^8$ are independently selected from H, F, methyl and CF$_3$. One of R$^{4A}$ and R$^{4B}$ is R$^4$, and the other is selected from H, F, methyl and CF$_3$.

When R$^3$ is a substituted 6 membered heteroaryl group, where the heteroaryl ring system contains 1 or 2 N heteroatoms, it may be selected from the any of the groups: pyridyl; pyridazinyl (1,2-diazinyl); pyrimidinyl (1,3-diazinyl); and pyrazinyl (1,4-diazinyl).

When R$^3$ is a substituted 6 membered heteroaryl group, it may have one of the following structures:

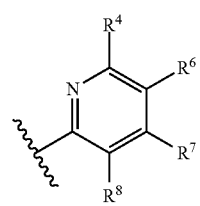
(R$^{3b}$)

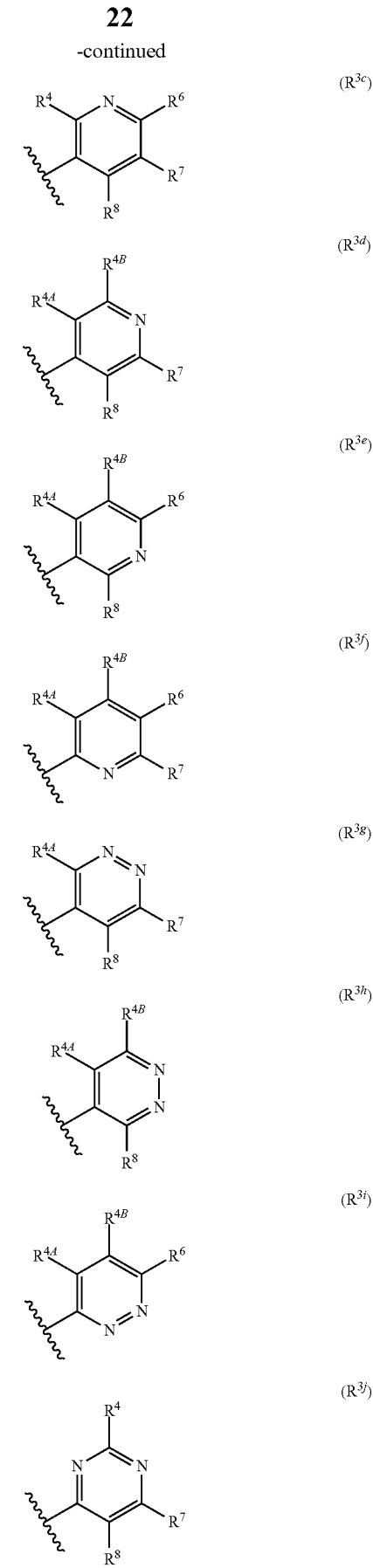

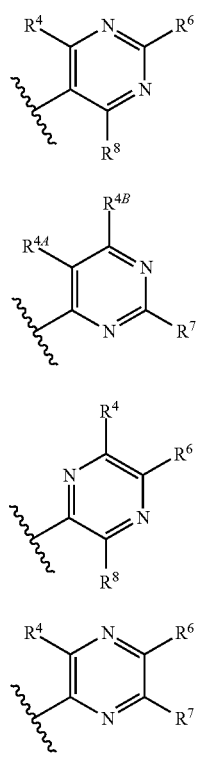

(R3k)

(R3l)

(R3m)

(R3n)

where $R^6$, $R^7$ and $R^8$ (if present) are independently selected from H, F, methyl and $CF_3$. One of $R^{4A}$ and $R^{4B}$ (if present) is $R^4$, and the other is selected from H, F, methyl and $CF_3$.

When $R^4$ is alpha to the —$C_2H_4$— group, it may also be described as being ortho. When $R^4$ is beta to the —$C_2H_4$— group, it may also be described as being meta.

The further optional substituents on $R^3$ are independently selected from F, methyl and $CF_3$. These further groups may be at any available ring position on $R^3$, except that occupied by $R^4$. There may be up to 4 further optional substituents groups (i.e. 1, 2, 3 or 4) depending on the nature of $R^3$, and in particular on the number of ring heteroatoms.

$R^4$ $R^4$ is —$CH_2$—$C(O)N(R^{N13})Z^3$.

$R^{N13}$ is selected from H and $CH_3$, and $Z^3$ is selected from H, $CH_3$ or $OCH_3$. Thus, $R^4$ is selected from:

—$CH_2$—$C(O)NH_2$;  (i)

—$CH_2$—$C(O)NHMe$;  (ii)

—$CH_2$—$C(O)NMe_2$;  (iii)

—$CH_2$—$C(O)N(OMe)H$; and  (iv)

—$CH_2$—$C(O)N(OMe)Me$.  (v)

Proviso

In some embodiments of the second aspect, compounds of WO2012/110773 are disclaimed from the present application (C1-C32 below):

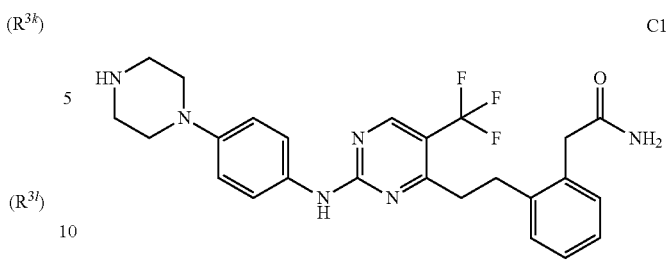

C1

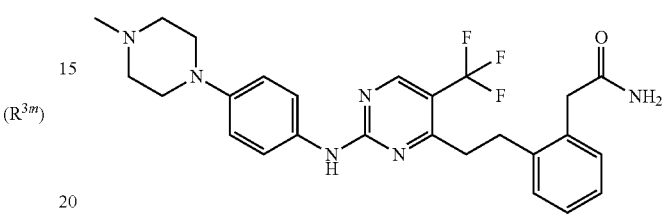

C2

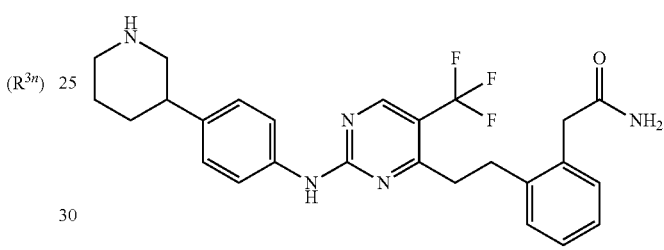

C3

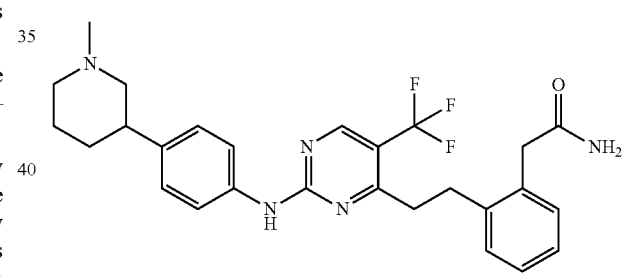

C4

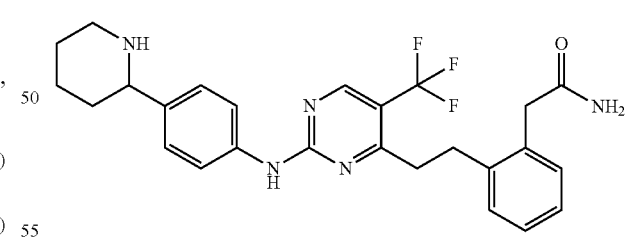

C5

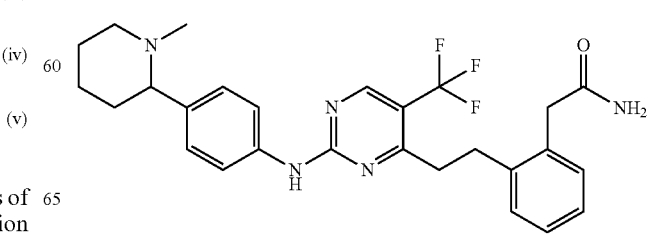

C6

-continued
C7
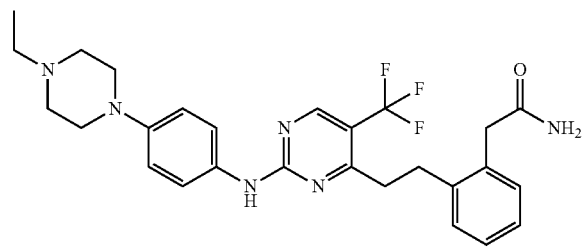
C8
C9
C10
C11
C12
-continued
C13
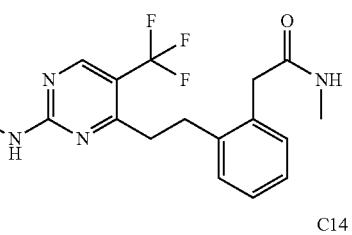
C14
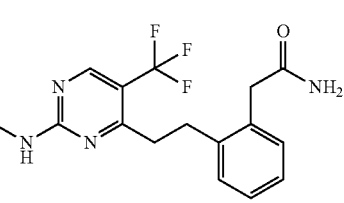
C15
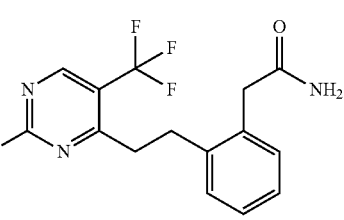
C16
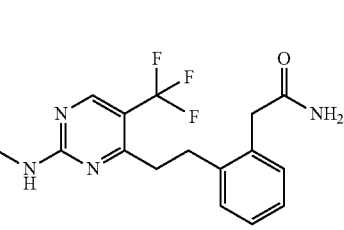
C17
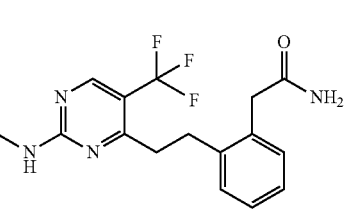
C18
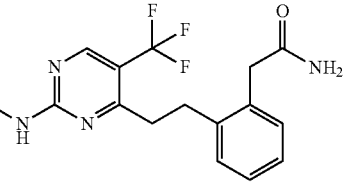

-continued
C19
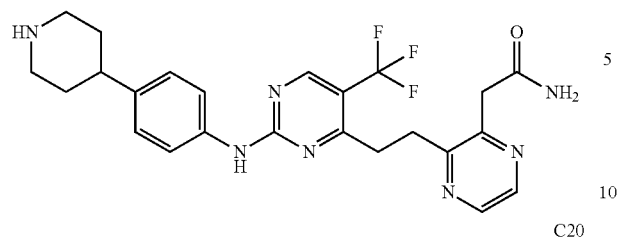
C20
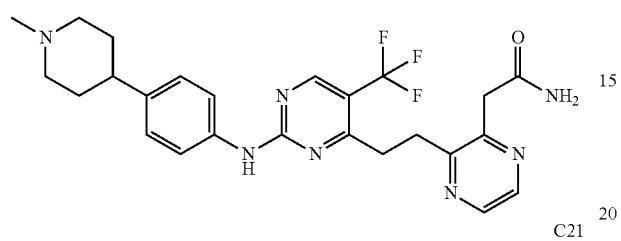
C21
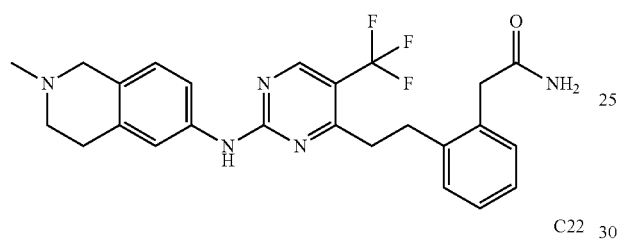
C22
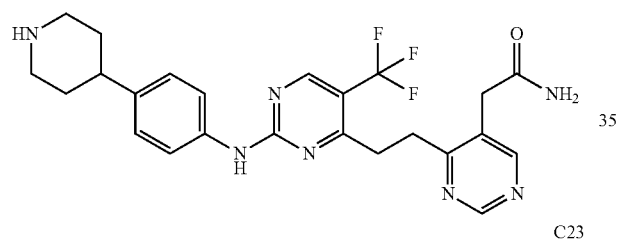
C23
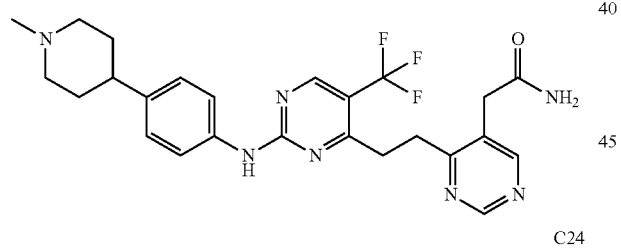
C24
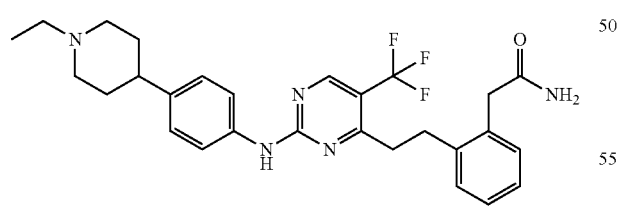
C25
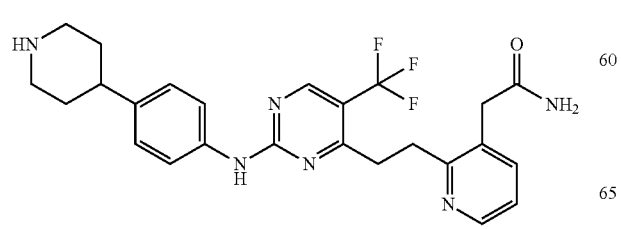
-continued
C26
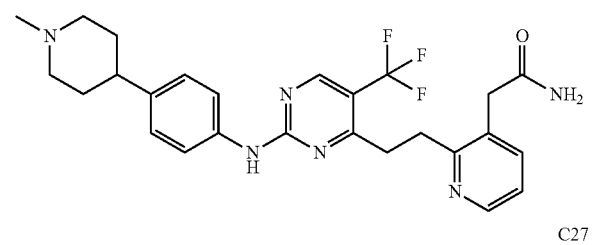
C27
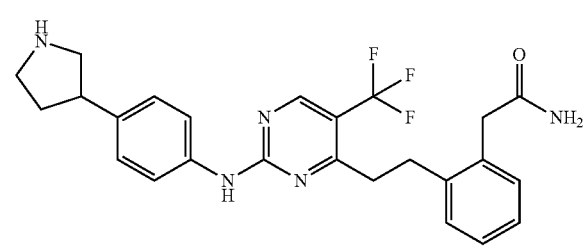
C28
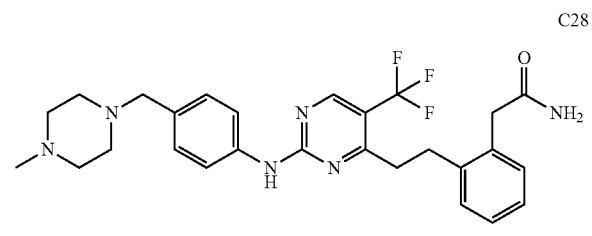
C29
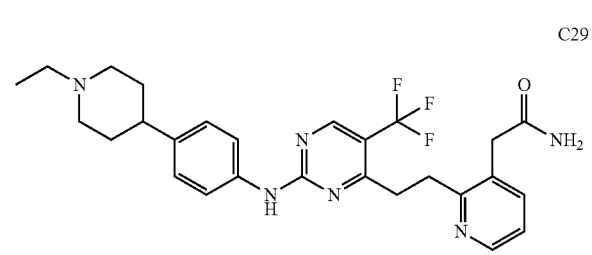
C30
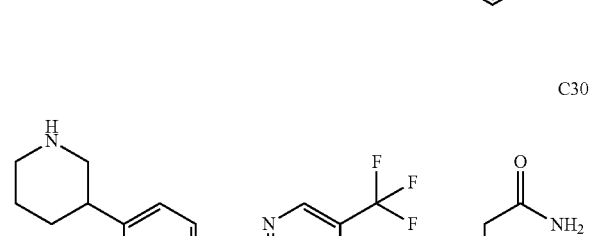
C31
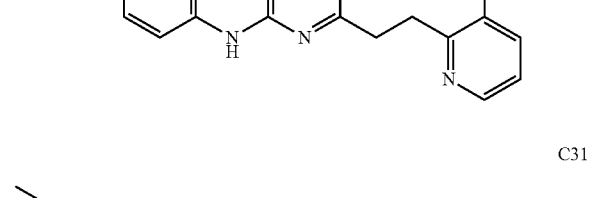

-continued

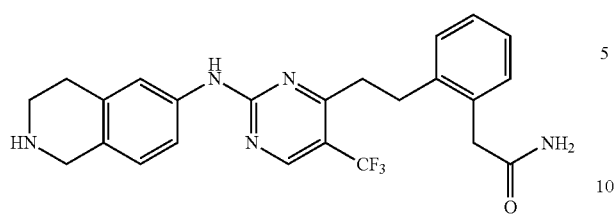
C32

In other embodiments of the second aspect, the compounds of the present invention do not include those disclosed in WO2012/110773, which is incorporated herein by reference. In particular, when $R^3$ is selected from:

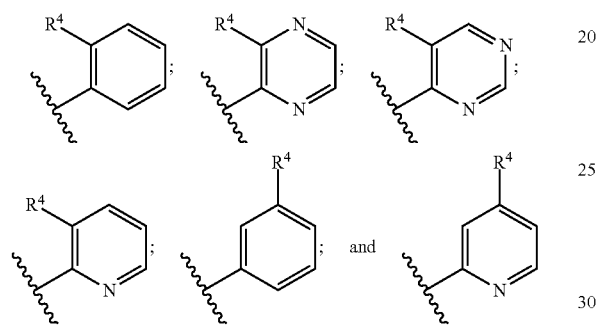

and

A is either:

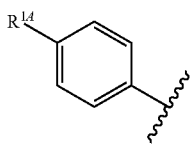

where $R^{1A}$ is selected from

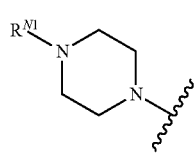
($R^{141}$)

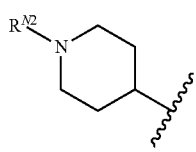
($R^{142}$)

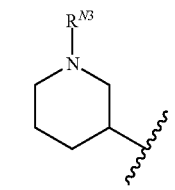
($R^{143}$)

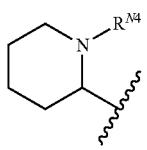
($R^{144}$)

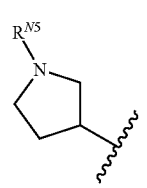
($R^{145}$)

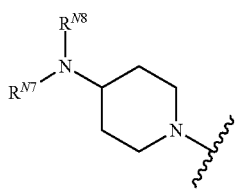
($R^{147}$)

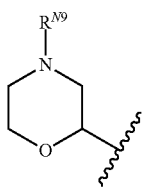
($R^{148}$)

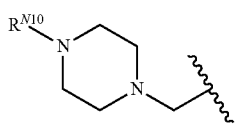
($R^{149}$)

and $R^{N1}$ is selected from H, $C_{1-3}$ alkyl, and C(=O)Me;
$R^{N2}$ is selected from H, $C_{1-3}$ alkyl, and C(=O)Me;
$R^{N3}$ is selected from H, $C_{1-3}$ alkyl, and C(=O)Me;
$R^{N4}$ is selected from H and $CH_3$;
$R^{N5}$ is selected from H, $C_{1-3}$ alkyl, and C(=O)Me;
$R^{N7}$ and $R^{N8}$ are independently selected from H and $CH_3$;
$R^{N9}$ is selected from H, $C_{1-3}$ alkyl, and C(=O)Me;
$R^{N10}$ is selected from H, $C_{1-3}$ alkyl, and C(=O)Me;
or

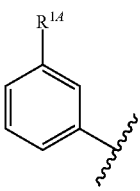

where $R^{1A}$ is

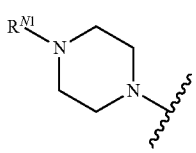
($R^{141}$)

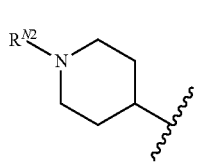

and $R^{N1}$ is selected from H, $C_{1-3}$ alkyl, and C(=O)Me; $R^{N2}$ is selected from H, $C_{1-3}$ alkyl, and C(=O)Me; then $R^2$ is not selected from $CF_3$, halo, $CF_2H$ and CN.

Includes Other Forms

Included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (—N⁺HR¹R²), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms of a hydroxyl group.

Alpha/Beta

The terms alpha and beta are used herein to indicate the relative position of substituent groups on rings. For the avoidance of doubt, their meaning is illustrated with the structure below:

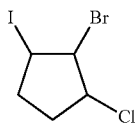

wherein the bromo group is alpha to the chloro group, and the iodo group is beta to the chloro group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

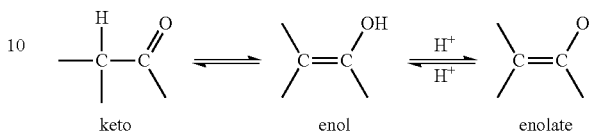

Note that specifically included in the term "isomer" are compounds with one or more isotopic substitutions. For example, H may be in any isotopic form, including ¹H, ²H (D), and ³H (T); C may be in any isotopic form, including ¹²C, ¹³C and ¹⁴C; O may be in any isotopic form, including ¹⁶O and ¹⁸O; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al. J. Pharm. Sci., 66, 1-19 (1977).

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al³⁺. Examples of suitable organic cations include, but are not limited to, ammonium ion (i.e., NH₄⁺) and substituted ammonium ions (e.g., NH₃R⁺, NH₂R₂⁺, NHR₃⁺, NR₄⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as an ester for example, as: an C$_{1-7}$ alkyl ester (e.g. a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties. For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is C1-7 alkyl (e.g. -Me, -Et); C$_{1-7}$ aminoalkyl (e.g. aminoethyl; 2-(N,N-diethylamino)ethyl; 2-(4-morpholino)ethyl); and acyloxy-C$_{1-7}$ alkyl (e.g. acyloxymethyl; acyloxyethyl; e.g. pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl) carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Selectivity

The selectivity of the compounds for inhibiting VEGFR3 over other kinases, such as FAK and/or VEGFR2 can be demonstrated by cellular assay results (see, for example, the VEGFR3 and VEGFR2 assays described below).

FURTHER EMBODIMENTS

The following embodiments and preferences relate to both first and second aspects of the invention and may be combined with one another as appropriate.

A

In the second aspect, A is optionally substituted phenyl and can have the structures:

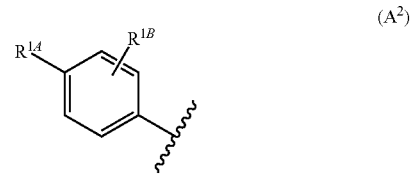

(A$^2$)

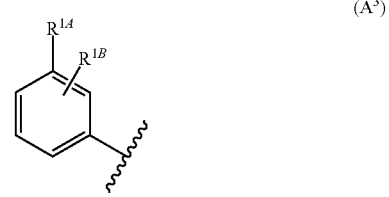

(A$^3$)

(A$^4$)

where the R$^{1B}$ group cannot be alpha the connection point to the rest of the compound.

In these embodiments (i.e. when A is phenyl), it may be preferred that either there are no R$^{1B}$ substituents, or a single $R^{1B}$ substituent. If there is a single $R^{1B}$ substituent it is may be meta or para, so further preferred A groups include:

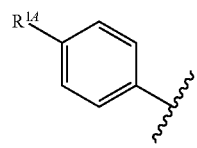
(A$^{2A}$)

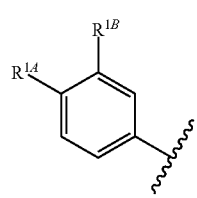
(A$^{2B}$)

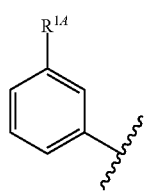
(A$^{3A}$)

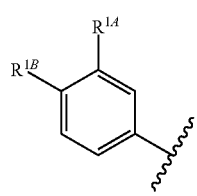
(A$^{3B}$)

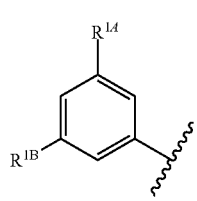
(A$^{3C}$)

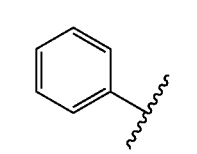
(A$^{4A}$)

In some embodiments of the first aspect, A is an optionally substituted 6 membered heteroaryl group. 6 membered heteroaryl groups include, but are not limited to: pyridyl, isoxazinyl, pyridazinyl, pyrimidinyl, pyrazinyl and triazinyl.

In these embodiments, it may be preferred that A is pyridyl, which can have the structures:

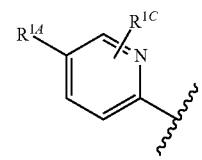
(A$^{5}$)

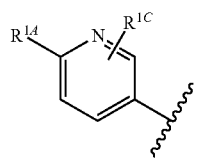
(A$^{6}$)

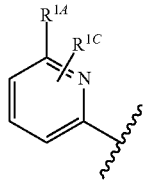
(A$^{7}$)

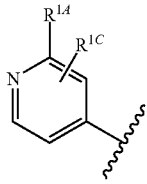
(A$^{8}$)

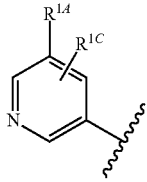
(A$^{9}$)

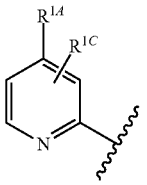
(A$^{10}$)

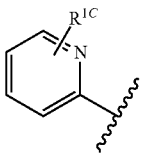
(A$^{11}$)

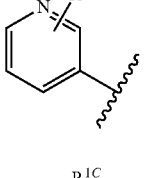
(A$^{12}$)

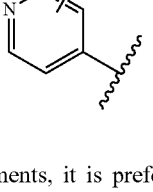
(A$^{13}$)

In these embodiments, it is preferred that when $R^{1A}$ is present $R^{1C}$ is not an oxo (=O) group. Of these structures, A$^{6}$ may be further preferred.

In these embodiments (i.e. when A is 6 membered heteroaryl group), it may be preferred that there are no $R^{1C}$ substituents. Thus, when A is pyridyl and there are no $R^{1C}$ groups, it may have the structures:

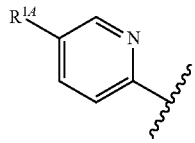
($A^{5A}$)

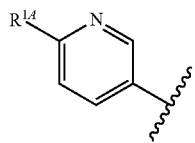
($A^{6A}$)

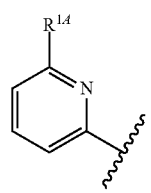
($A^{7A}$)

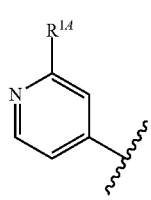
($A^{8A}$)

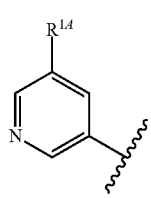
($A^{9A}$)

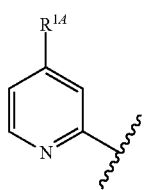
($A^{10A}$)

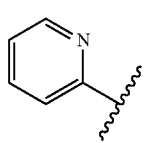
($A^{11A}$)

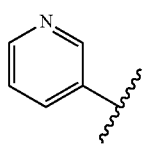
($A^{12A}$)

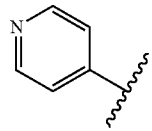
($A^{13A}$)

Of these structures $A^{6A}$ may be further preferred.

In some embodiments of the first aspect, A is an optionally substituted 5 membered heteroaryl group. 5 membered heteroaryl groups include, but are not limited to: pyrrolyl; furanyl; thiophenyl; oxazolyl; isoxazolyl; oxadiazolyl; oxatriazolyl; thiazolyl; isothiazolyl; imidazolyl; pyrazolyl; triazolyl and tetrazolyl.

In these embodiments, it may be preferred that A is pyrazolyl, which can have the structures:

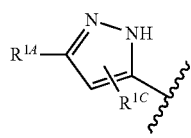
($A^{14}$)

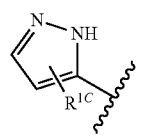
($A^{15}$)

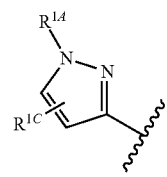
($A^{16}$)

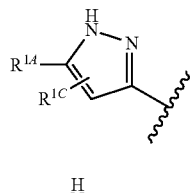
($A^{17}$)

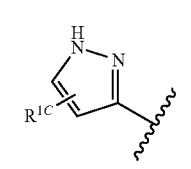
($A^{18}$)

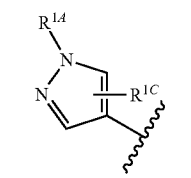
($A^{19}$)

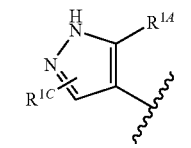
($A^{20}$)

(A²¹) 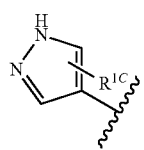

In these embodiments, it is preferred that $R^{1C}$ is not an oxo (=O) group. Of these structures $A^{16}$ and $A^{18}$ may be further preferred.

In these embodiments (i.e. when A is a 5 membered heteroaryl group), it may be preferred that there are no $R^{1C}$ substituents. Thus, when A is pyrazolyl and there are no $R^{1C}$ groups, it may have the structures:

(A¹⁴ᴬ) 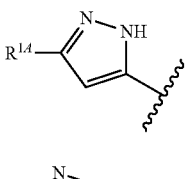

(A¹⁵ᴬ) 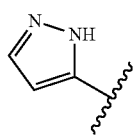

(A¹⁶ᴬ) 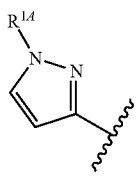

(A¹⁷ᴬ) 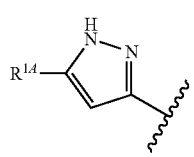

(A¹⁸ᴬ) 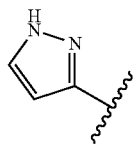

(A¹⁹ᴬ) 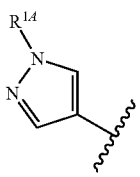

(A²⁰ᴬ) 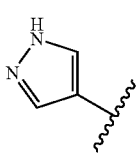

Of these structures $A^{19A}$ may be further preferred.
Thus particularly preferred structures for A include:

(A²⁴) 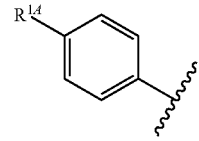

(A²ᴮ) 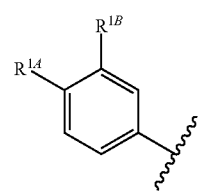

(A⁶ᴬ) 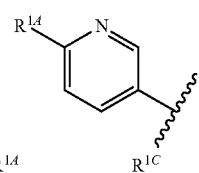

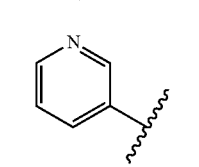

(A¹²ᴬ) 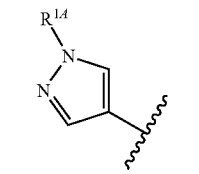

(A¹⁹ᴬ) 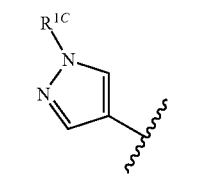

(A¹⁹ᴮ) 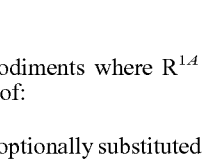

$R^{1A}$

In some embodiments where $R^{1A}$ is $CH(R^{C1})NHZ^1$, $Z^1$ may be any one of:
(i) H;
(ii) $C_{1-3}$ alkyl optionally substituted by OH, preferably Me, or $CH_2CH_2OH$;
(iii) $C(=O)OC_{1-3}$ alkyl, preferably $C(=O)OMe$; and
(iv) $C(=O)Me$.

In some of these embodiments, $Z^1$ may be selected from H, $CH_2CH_2OH$ and $C(=O)Me$. Thus, in these embodiments, $R^{1A}$ is selected from: $CH_2NH_2$; $CH(CH_3)NH_2$; $CH(C_2H_5)NH_2$; $CH_2NHCH_2CH_2OH$; $CH(CH_3)NHCH_2CH_2OH$; and $CH(C_2H_5)NHCH_2CH_2OH$. In some embodiments where $R^{1A}$ is $CH(R^{C1})NHZ^1$, $R^{C1}$ may be selected from H and methyl.

Thus, in these embodiments, $R^{1A}$ is selected from: $CH_2NHZ^1$; and $CH(CH_3)NHZ^1$.

In some embodiments where $R^{1A}$ is $CH(R^{C1})NHZ^1$, $Z^1$ may be selected from H and $CH_2CH_2OH$ and $R^{C1}$ may be selected from H and methyl. Thus, in these embodiments, $R^{1A}$ is selected from: $CH_2NH_2$; $CH_2NHCH_2CH_2OH$; $CH(CH_3)NH_2$; and $CH(CH_3)NHCH_2CH_2OH$.

In some embodiments where $R^{1A}$ is $XNHZ^2$, $Z^2$ may be any one of:

(i) H;

(ii) $C_{1-3}$ alkyl optionally substituted by OH, preferably Me, or $CH_2CH_2OH$;

(iii) C(=O)O$C_{1-3}$ alkyl, preferably C(=O)OMe; and (iv) C(=O)Me.

In some embodiments where $R^{1A}$ is $XNHZ^2$, $Z^2$ may be H. Thus, in these embodiments, $R^{1A}$ has the structures:

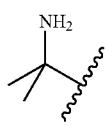
($R^{LX1A}$)

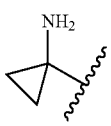
($R^{LX2A}$)

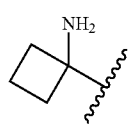
($R^{LX3A}$)

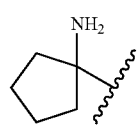
($R^{LX4A}$)

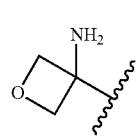
($R^{LX5A}$)

In some embodiments where $R^{1A}$ is $XNHZ^2$, $Z^2$ may be C(=O)OMe. Thus, in these embodiments, $R^{1A}$ has the structures:

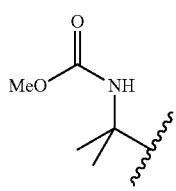
($R^{LX1B}$)

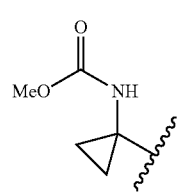
($R^{LX2B}$)

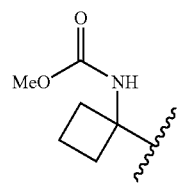
($R^{LX3B}$)

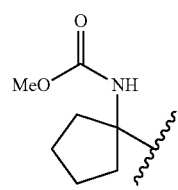
($R^{LX4B}$)

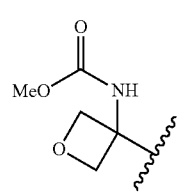
($R^{LX5B}$)

In some embodiments where $R^{1A}$ is $XNHZ^2$, X may be selected from $CMe_2$, and cyclobutylidene. Thus, in these embodiments, $R^{1A}$ has the structures:

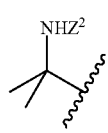
($R^{LX1}$)

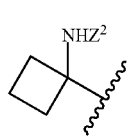
($R^{LX3}$)

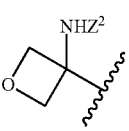
($R^{LX5A}$)

In some embodiments where $R^{1A}$ is $XNHZ^2$, $Z^2$ may be selected from H and C(=O)OMe, and X may be selected from $CMe_2$, and cyclobutylidene. Thus, in these embodiments, $R^{1A}$ has the structures:

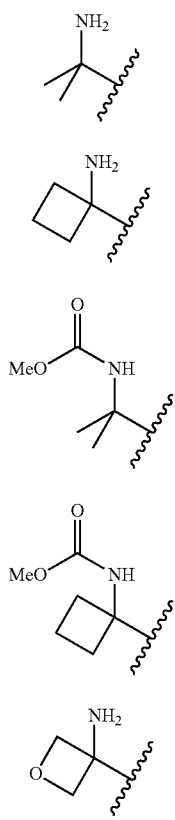

(R<sup>LX1A</sup>)
(R<sup>LX3A</sup>)
(R<sup>LX1B</sup>)
(R<sup>LX3B</sup>)
(R<sup>LX5A</sup>)

In some embodiments, $R^{1A}$ is:

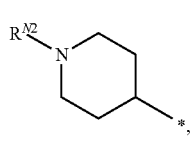

(R<sup>LA1</sup>)

wherein $R^{N1}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N1}$ is C(=O)Me. In others of these embodiments, it may be preferred that $R^{N1}$ is H, methyl or ethyl.

In some embodiments, $R^{1A}$ is:

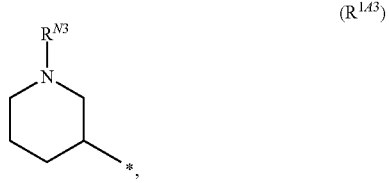

(R<sup>LA2</sup>)

wherein $R^{N2}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N2}$ is C(=O)Me. In others of these embodiments, it may be preferred that $R^{N2}$ is H, methyl or ethyl, more preferably H or methyl.

In some embodiments, $R^{1A}$ is:

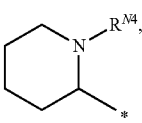

(R<sup>LA3</sup>)

wherein $R^{N3}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N3}$ is C(=O)Me. In others of these embodiments, it may be preferred that $R^{N3}$ is H, methyl or ethyl, more preferably H or methyl.

In some embodiments, $R^{1A}$ is:

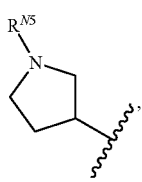

(R<sup>LA4</sup>)

wherein $R^{N4}$ is selected from H or methyl. In some of these embodiments, it may be preferred that $R^{N4}$ is H.

In some embodiments, $R^{1A}$ is:

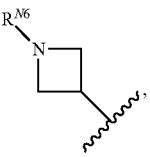

(R<sup>LA5</sup>)

wherein $R^{N5}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N5}$ is C(=O)Me. In others of these embodiments, it may be preferred that $R^{N5}$ is H, methyl or ethyl, more preferably H or methyl.

In some embodiments, $R^{1A}$ is:

(R<sup>LA6</sup>)

wherein $R^{N6}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N6}$ is C(=O)Me. In others of these embodiments, it may be preferred that $R^{N6}$ is H, methyl or ethyl, more preferably H or methyl.

In some embodiments, $R^{1A}$ is:

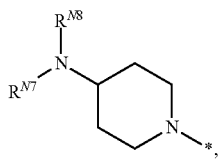

(R$^{1A7}$)

wherein $R^{N7}$ and $R^{N8}$ are both H or both methyl. In some of these embodiments, it may be preferred that $R^{N7}$ and $R^{N8}$ are both H.

In some embodiments, $R^{1A}$ is:

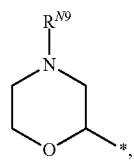

(R$^{1A8}$)

wherein $R^{N9}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N9}$ is C(=O)Me. In others of these embodiments, it may be preferred that $R^{N9}$ is H, methyl or ethyl, more preferably H or methyl.

In some embodiments, $R^{1A}$ is:

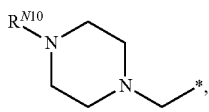

(R$^{1A9}$)

wherein $R^{N10}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N10}$ is C(=O)Me. In others of these embodiments, it may be preferred that $R^{N10}$ is H, methyl or ethyl, more preferably H or methyl.

In some embodiments, $R^{1A}$ is:

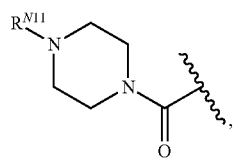

(R$^{1A10}$)

wherein $R^{N11}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N11}$ is C(=O)Me. In others of these embodiments, it may be preferred that $R^{N11}$ is H, methyl or ethyl, more preferably H or methyl.

In some embodiments, $R^{1A}$ is:

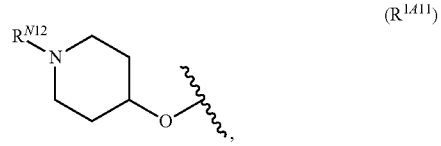

(R$^{1A11}$)

wherein $R^{N12}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N12}$ is C(=O)Me. In others of these embodiments, it may be preferred that $R^{N12}$ is H, methyl or ethyl, more preferably H or methyl.

Particularly preferred $R^{1A}$ groups include:

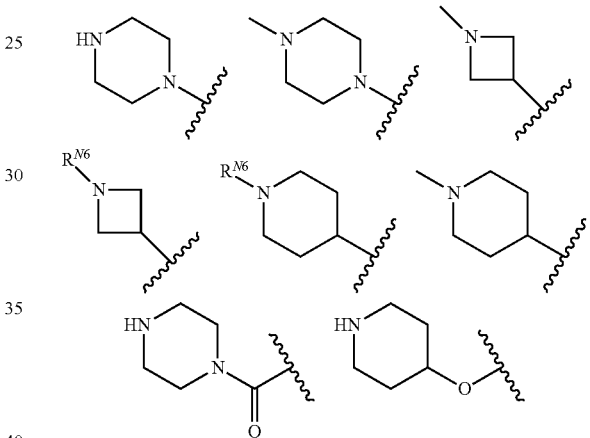

$R^{1B}$ (Second Aspect)

In some embodiments, no $R^{1B}$ substituents are present.

In some embodiments, $R^{1B}$ is preferably $C_{1-3}$ alkyl and more preferably methyl.

In some embodiments, a single $R^{1B}$ substituent is present. It may be $C_{1-3}$ alkyl; $CF_3$; F; Cl; O—($C_{1-3}$ alkyl); and CN. In some of these embodiments, it is preferably F or $C_{1-3}$ alkyl, and more preferably F or methyl.

$R^{1C}$ (First Aspect)

In some embodiments, no $R^{1C}$ substituents are present.

In some embodiments, $R^{1C}$ is preferably $C_{1-3}$ alkyl and more preferably methyl.

In some embodiments, a single $R^{1C}$ substituent is present. It may be $C_{1-3}$ alkyl; $CF_3$; F; Cl; O—($C_{1-3}$ alkyl); CN; and =O. In some of these embodiments, it is preferably $C_{1-3}$ alkyl, and more preferably methyl.

$R^2$

In some embodiments, $R^2$ is H.

In some embodiments, $R^2$ is halo (i.e. F, Cl, Br, I). In some of these embodiments, the halo group is either F or Cl.

In some embodiments, $R^2$ is $C_{1-4}$ alkyl (i.e. methyl, ethyl, prop-1-yl and prop-2-yl, n-butyl, iso-butyl, sec-butyl, tert-butyl). In some of these embodiments, the $C_{1-4}$ alkyl group is methyl or ethyl, and methyl may be preferred.

In some embodiments, $R^2$ is selected from $CF_3$ and $CF_2H$. In some of these embodiments, $R^2$ is $CF_3$.

In some embodiments, $R^2$ is CN.
In some embodiments, $R^2$ is methoxy.
$R^3$

In some embodiments, $R^3$ is substituted phenyl, and therefore it has the structure:

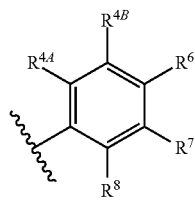
(R3a)

where $R^6$, $R^7$ and $R^8$ are independently selected from H, F, methyl and $CF_3$. One of $R^{4A}$ and $R^{4B}$ is $R^4$, and the other is selected from H, F, methyl and $CF_3$. In some of these embodiments, the group of $R^{4A}$ and $R^{4B}$ that is not $R^4$, and $R^6$, $R^7$ and $R^8$ are all H. In others of these embodiments, one of the group of $R^{4A}$ and $R^{4B}$ that is not $R^4$, $R^6$, $R^7$ and $R^8$ is not H, and therefore is F, methyl or $CF_3$. The group that is not H may preferably be $R^6$ or $R^7$.

In some embodiments, $R^3$ is substituted phenyl, $R^{4B}$, $R^6$, $R^7$ and $R^8$ are all H, and $R^{4A}$ is $R^4$.

In some embodiments, $R^3$ is a substituted 6 membered heteroaryl group, where the heteroaryl ring system contains 1 or 2 N heteroatoms. In these embodiments, it may be preferred that $R^3$ is pyridyl, which can have the structures:

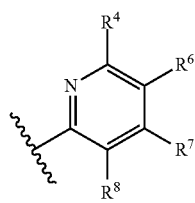
(R3b)

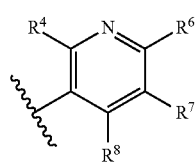
(R3c)

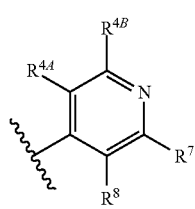
(R3d)

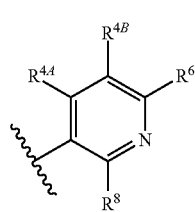
(R3e)

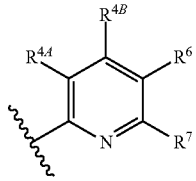
(R3f)

where $R^6$, $R^7$ and $R^8$ (if present) are independently selected from H, F, methyl and $CF_3$. One of $R^{4A}$ and $R^{4B}$ (if present) is $R^4$, and the other is selected from H, F, methyl and $CF_3$. Of these structures, $R^{3d}$ and $R^{3e}$ may be preferred. In some of these embodiments, the group of $R^{4A}$ and $R^{4B}$ that is not $R^4$, and $R^6$, $R^7$ and $R^8$ (if present) are all H. In others of these embodiments, one of the group of $R^{4A}$ and $R^{4B}$ that is not $R^4$, $R^6$, $R^7$ and $R^8$ (if present) is not H, and therefore is F, methyl or $CF_3$. In some embodiments, it may be preferred that a F substituent is not alpha to a ring nitrogen atom.

$R^4$

In some embodiments $R^4$ is alpha to the $-C_2H_4-$ group.
In some embodiments $R^4$ is beta to the $-C_2H_4-$ group.
In some embodiments, $R^{N13}$ is H.
In other embodiments, $R^{N13}$ is Me.
In some embodiments, $Z^3$ is H.
In other embodiments, $Z^3$ is Me.
In other embodiments, $Z^3$ is OMe.

In some embodiments of the present invention the compounds of formula (I) are of formula (Ia) or isomers, salts, solvates, protected forms or prodrugs thereof wherein:

A is an optionally substituted 5 or 6 membered heteroaryl group linked to the NH group through an aromatic ring carbon atom, in which the heteroaryl ring system contains 1 or 2 N atoms, and;

A may bear a substituent $R^{1A}$ which is not alpha to the NH group and may optionally further bear a substituent $R^{1C}$ which are not alpha to the NH group, where $R^{1A}$ is selected from:

(i) $CH(R^{C1})NHZ^1$, where $R^{C1}$ is selected from $C_{1-2}$ alkyl and $Z^1$ is selected from H and $C_{1-3}$ alkyl optionally substituted by OH;

(ii) $XNHZ^2$, where X is cyclobutylidene, and $Z^2$ is $C(=O)OC_{1-3}$ alkyl;

(iii) a group selected from:

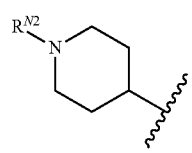
(R1A2)

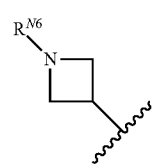
(R1A6)

wherein:
$R^{N2}$ is selected from H and $C_{1-4}$ alkyl;
$R^{N6}$ is H;
and where $R^{1C}$ is $C_{1-3}$ alkyl;
$R^2$ is selected from $C_{1-4}$ alkyl and $CF_3$;

$R^3$ is substituted phenyl, where $R^3$ bears a substituent $R^4$ alpha to the $-C_2H_4-$ group, and may additionally bear a further substituent F; and $R^4$ is $-CH_2-C(O)N(R^{N13})Z^3$, where $R^{N13}$ is H; and $Z^3$ is H.

In some embodiments of the present invention the compounds of formula (I) are of formula (Ib) or isomers, salts, solvates, protected forms or prodrugs thereof wherein:

A is an optionally substituted 5 or 6 membered heteroaryl group linked to the NH group through an aromatic ring carbon atom, in which the heteroaryl ring system contains 1 or 2 N atoms, and;

A may bear a substituent $R^{1A}$ which is not alpha to the NH group and may optionally further bear a substituent $R^{1C}$ which are not alpha to the NH group, where $R^{1A}$ is $R^{1A2}$:

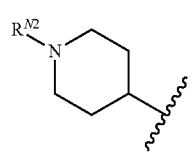
(R$^{1A2}$)

wherein:
$R^{N2}$ is selected from H and $C_{1-4}$ alkyl;
and where $R^{1C}$ is $C_{1-3}$ alkyl;
$R^2$ is selected from $C_{1-4}$ alkyl;
$R^3$ is substituted phenyl, where $R^3$ bears a substituent $R^4$ alpha to the $-C_2H_4-$ group; and
$R^4$ is $-CH_2-C(O)N(R^{N13})Z^3$, where $R^{N13}$ is H; and $Z^3$ is H.

In some embodiments of the present invention the compounds of formula (I) are of formula (Ic) or isomers, salts, solvates, protected forms or prodrugs thereof wherein:

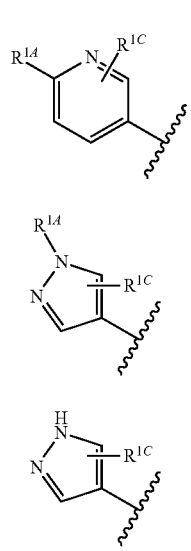

wherein $R^{1A}$ is selected from:
(i) $CH(R^{C1})NHZ^1$, where $R^{C1}$ is selected from H and methyl and $Z^1$ is selected from H and $CH_2CH_2OH$;
(ii) $XNHZ^2$, where X is selected from cyclobutylidene and oxetanylidine and $Z^2$ is selected from H and $C(=O)OMe$;
(iii) a group selected from $R^{1A1}$, $R^{1A2}$, $R^{1A6}$ and $R^{1A11}$:

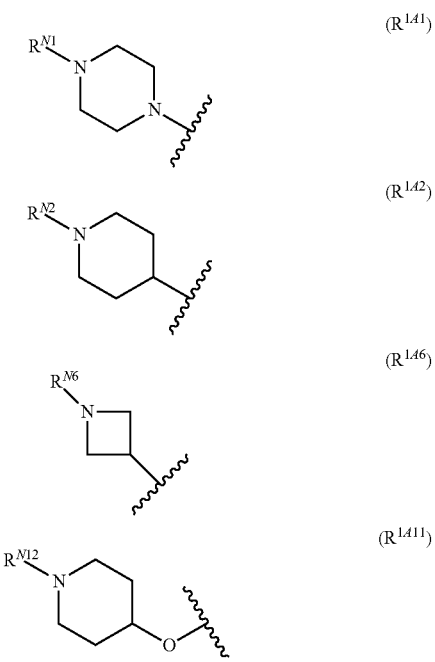

wherein:
$R^{N1}$ is selected from H and Me;
$R^{N2}$ is selected from H and Me;
$R^{N6}$ is selected from H and Me; and
$R^{N12}$ is selected from H and Me;

and where there may be a single $R^{1C}$ group which is methyl;
$R^2$ is selected from H, methyl and $CF_3$;
$R^3$ is:

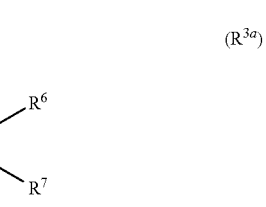
(R$^{3a}$)

where $R^5$, $R^6$ and $R^7$ are independently selected from H, F, methyl and $CF_3$, and only one of them is not H; and
$R^4$ is $-CH_2-C(O)NH_2$.

In some embodiments of the present invention the compounds of formula (II) are of formula (IIa) or isomers, salts, solvates, protected forms or prodrugs thereof wherein:

A is substituted phenyl;
A may bear a substituent $R^{1A}$ which is not alpha to the NH group and may optionally further bear a substituent $R^{1B}$ which is not alpha to the NH group, where $R^{1A}$ is selected from:
(i) $CH(R^{C1})NHZ^1$, where $R^{C1}$ is selected from H and $C_{1-2}$ alkyl and $Z^1$ is selected from H, $C_{1-3}$ alkyl optionally substituted by OH and $C(=O)Me$;
(ii) $XNHZ^2$, where X is selected from cyclobutylidene and oxetanylidine and $Z^2$ is selected from H and $C(=O)OC_{1-3}$ alkyl;

(iii) a group selected from:

(R^{IA1})

(R^{IA2})

(R^{IA6})

(R^{IA10})

(R^{IA11})

wherein:
R^{N1} is H;
R^{N2} is selected from H and $C_{1-4}$ alkyl;
R^{N6} is H;
R^{N11} is H; and
R^{N12} is H;
and where each R^{1B} is independently selected from:
(i) $C_{1-3}$ alkyl;
(iii) F;
R^2 is selected from H, halo, $C_{1-4}$ alkyl, $CF_3$ and methoxy;
R^3 is substituted phenyl, where R^3 bears a substituent R^4 alpha to the —$C_2H_4$— group, and may additionally bear a further substituent selected from F, methyl and $CF_3$; and
R^4 is —$CH_2$—C(O)N(R^{N13})Z^3, where R^{N13} is H; and Z^3 is H.

In some embodiments of the present invention the compounds of formula (II) are of formula (IIb) or isomers, salts, solvates, protected forms or prodrugs thereof wherein:
A is substituted phenyl;
A may bear a substituent R^{1A} which is not alpha to the NH group and may optionally further bear a substituent R^{1B} which is not alpha to the NH group, where R^{1A} is selected from:
(i) CH(R^{C1})NHZ^1, where R^{C1} is selected from H and $C_{1-2}$ alkyl and Z^1 is selected from H and $C_{1-3}$ alkyl optionally substituted by OH;
(ii) XNHZ^2, where X is oxetanylidine and Z^2 is H;

(iii) a group selected from:

(R^{IA1})

(R^{IA2})

(R^{IA6})

(R^{IA10})

(R^{IA11})

wherein:
R^{N1} is H;
R^{N2} is selected from H and $C_{1-4}$ alkyl;
R^{N6} is H;
R^{N11} is H; and
R^{N12} is H;
and where each R^{1B} is $C_{1-3}$alkyl;
R^2 is selected from halo, $C_{1-4}$ alkyl, $CF_3$ and methoxy;
R^3 is substituted phenyl, where R^3 bears a substituent R^4 alpha to the —$C_2H_4$— group, and may additionally bear a further substituent selected from methyl and $CF_3$; and
R^4 is —$CH_2$—C(O)N(R^{N13})Z^3, where R^{N13} is H; and Z^3 is H.

In some embodiments of the present invention the compounds of formula (II) are of formula (IIc) or isomers, salts, solvates, protected forms or prodrugs thereof wherein:
A is:

(A^2)

wherein R^{1A} is selected from:
(i) CH(R^{C1})NHZ^1, where R^{C1} is selected from H and methyl and Z^1 is selected from H and $CH_2CH_2OH$;

(ii) XNHZ², where X is selected from cyclobutylidene and oxetanylidene and Z² is selected from H and C(=O)OMe;
(iii) a group selected from $R^{141}$, $R^{142}$, $R^{146}$ and $R^{1411}$:

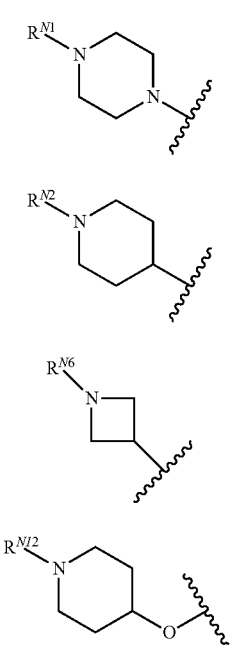

wherein:
$R^{N1}$ is selected from H and Me;
$R^{N2}$ is selected from H and Me;
$R^{N6}$ is selected from H and Me; and
$R^{N12}$ is selected from H and Me;
and where there may be a single $R^{1B}$ group which is selected from F and methyl;
$R^2$ is selected from H, methyl and $CF_3$;
$R^3$ is:

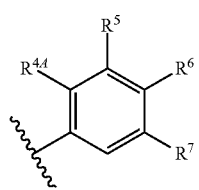

where $R^5$, $R^6$ and $R^7$ are independently selected from H, F, methyl and $CF_3$, and only one of them is not H; and
$R^4$ is —$CH_2$—C(O)$NH_2$.

The preferences expressed in relation to compounds of formulae I and II also apply to compounds of formulae Ia, Ib, Ic, IIa, IIb and IIc, where appropriate.

Embodiments of the inventions are compounds of the examples, including compounds 1 to 41. Embodiments of particular interest include compounds 5, 6, 14, 16, 24, 28, 30 and 31.

General Synthesis Methods

The compounds of the invention can be prepared by employing the following general methods and using procedures described in detail in the experimental section. The reaction conditions referred to are illustrative and non-limiting.

The process for the preparation of a compound of formula (I) or formula (II) or isomers, salts, solvates or prodrug thereof comprises reacting a compound of formula F1

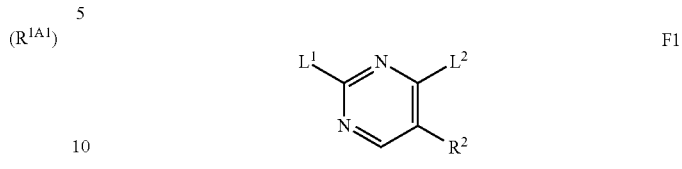

with a compound of formula A-$NH_2$ to displace the group $L^1$ and with a compound of formula HC≡$R^3$ to displace the group $L^2$, or
with a compound of formula HC≡$R^3$ to displace the group $L^2$ and with a compound of formula A-$NH_2$ to displace the group $L^1$,
wherein A, $R^2$ and $R^3$ are as defined in formula (I) or (II) above and $L^1$ and $L^2$ are leaving groups.

It will be appreciated that the compound of formula A-$NH_2$ and the compound of formula HC≡$R^3$ can be reacted with the compound of formula F1 separately or sequentially in any order or simultaneously.

The leaving groups $L^1$ and $L^2$ may be any suitable leaving groups, such as a halogen atom (F, Cl, Br, I), —SR or —$SO_2$R where R is a $C_{1-4}$ straight chain or branched alkyl group. In some embodiments, $L^1$ and $L^2$ may be the same or different and may be selected from the group consisting of Cl, Br, I, SMe, $SO_2$Me.

Compounds of formulae I and II, as described above, can be prepared by synthetic strategies outlined below, wherein the definitions above apply:

Scheme A

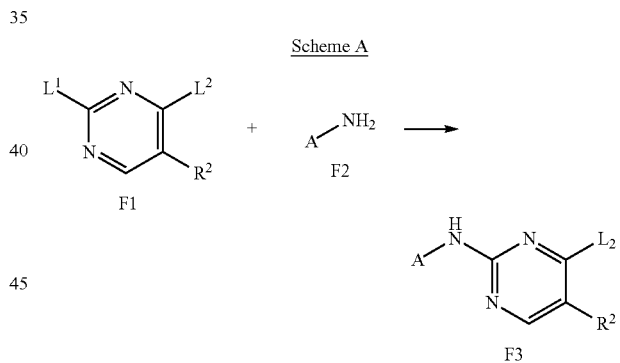

Compounds of formula F1 may be reacted with substituted commercial or synthetic amino substituted compounds of formula F2 (as prepared in scheme C to N) to form intermediates of formula F3 where $L^1$ and $L^2$ may be the same or different and include Cl, Br, I, SMe, $SO_2$Me.

Compounds of the formula F1 may be prepared where $L^1$ and $L^2$ are different to allow regioselective substitution or when $L^1$=$L^2$ suitable reaction conditions can be employed (choice of solvent, reaction temperature, addition of a Lewis acid, for example $ZnCl_2$ in $Et_2O$) to allow $L^1$ to be selectively displaced over $L^2$. Where regiochemical mixtures and di-substitution are obtained the regioisomers may be separated by chromatography.

Compounds of the formula F1 where $L^1$=$L^2$ are either commercially available, for example 2,4-dichloro-5-(trifluoromethyl)pyrimidine, 2,4-dichloro-5-fluoropyrimidine, 2,4,5-trichloropyrimidine, 2,4-dichloro-5-bromopyrimidine, 2,4-dichloro-5-iodopyrimidine, 2,4-dichloro-5-methylpyrimidine, 2,4-dichloro-5-cyanopyrimidine or may be prepared readily from commercial starting materials. Where $R^2=CF_3$ and differentiation of $L^1$ and $L^2$ is desirable, the method outlined in scheme B may be employed.

Scheme B

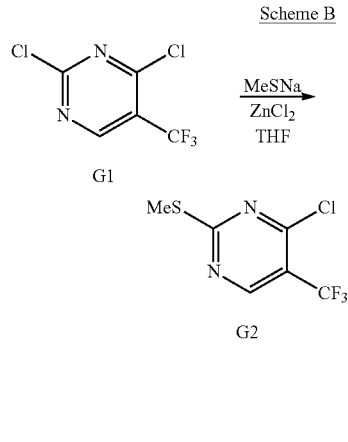

Commercially available 2,4-dichloro-5-(trifluoromethyl) pyrimidine (G1) can be selectively reacted with sodium thiomethoxide in the presence of zinc(II) chloride to give 2-thiomethyl-4-chloro-5-(trifluoromethyl)pyrimidine (G2). 2-Thiomethyl-4-chloro-5-(trifluoromethyl)pyrimidine (G2) can be further reacted, for example by conversion to 2-thiomethyl-4-iodo-5-(trifluoromethyl)pyrimidine (G3) under Finkelstein conditions and/or by oxidation with m-CPBA to give the corresponding sulfone if further differentiation of the 2 and 4-position is required or if additional activation is desirable.

Examples of commercially available amino compounds of the formula F2 include, but are not limited to those depicted in table 1.

TABLE 1

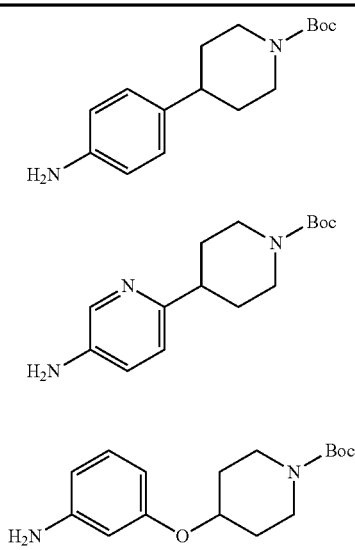

TABLE 1-continued

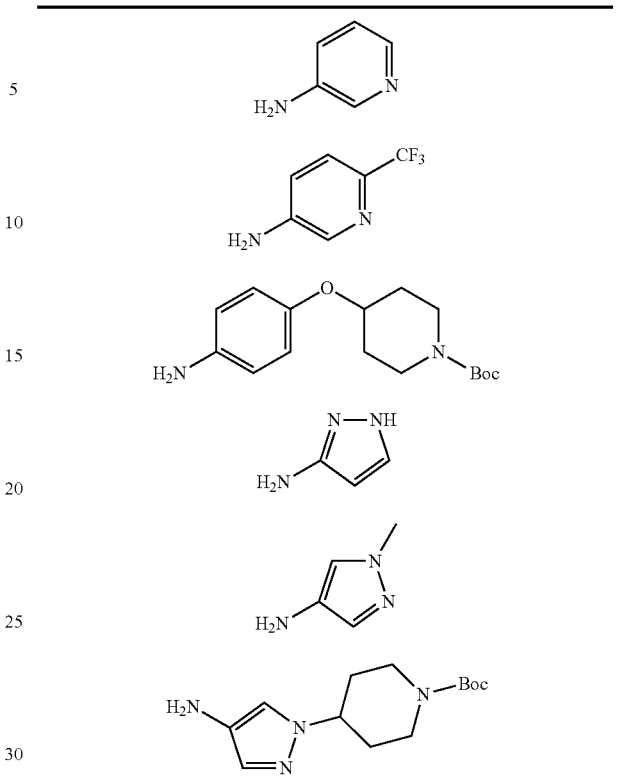

It will be appreciated that compounds of the formula F2, both commercial and synthetic, can be further modified either prior or post coupling to pyrimidines of the formula F1 via an extensive range of chemistries including, but not limited to hydrolysis, alkylation, acylation, electrophilic halogenation and Mitsunobu coupling.

In addition to commercially available amino compounds of the formula F2, numerous analogous nitro containing compounds are also commercially available including, but not limited to those depicted in table 2.

TABLE 2

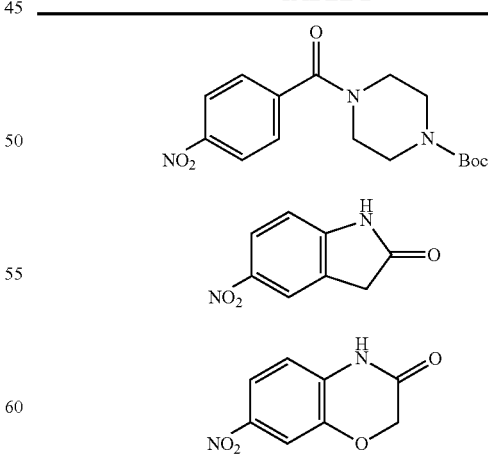

It will be appreciated that such compounds can be reduced under suitable conditions, for example in the presence of palladium under an atmosphere of hydrogen, to give amino compounds of the formula F2.

Synthetic amino compounds of the invention may be prepared via a range of procedures. It will be appreciated that heterocyclic analogues may also be prepared by analogous methods to those outlined below via substitution of phenyl containing starting materials with suitable heteroaromatic systems.

Scheme C

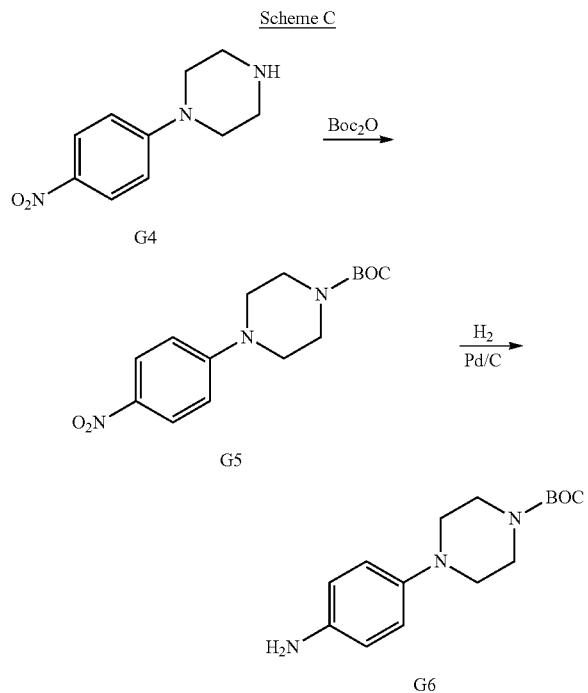

Commercially available 1-(4-nitrophenyl)piperazine (G4), or a salt thereof, can be reacted with Boc anhydride to give tert-butyl 4-(4-nitrophenyl)piperazine-1-carboxylate (G5). Subsequent reduction via hydrogenation in the presence of a catalyst, for example palladium on charcoal, gives the corresponding aniline, tert-butyl 4-(4-aminophenyl)piperazine-1-carboxylate (G6).

Scheme D

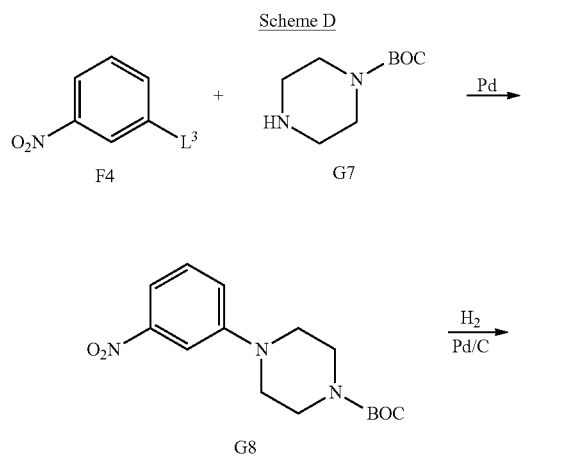

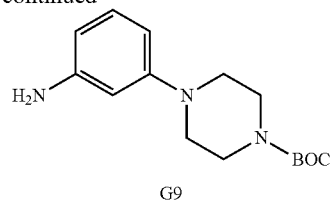

tert-Butyl 4-(3-aminophenyl)piperazine-1-carboxylate (G9) can be prepared by coupling of commercially available tert-butyl piperazine-1-carboxylate (G7) and compounds of the formula F4, where $L^3$=I or Br, in a Buchwald type reaction to give tert-butyl 4-(3-nitrophenyl)piperazine-1-carboxylate (G8). Reduction with hydrogen in the presence of a catalyst, for example palladium on charcoal, gives tert-butyl 4-(3-aminophenyl)piperazine-1-carboxylate (G9).

Scheme E

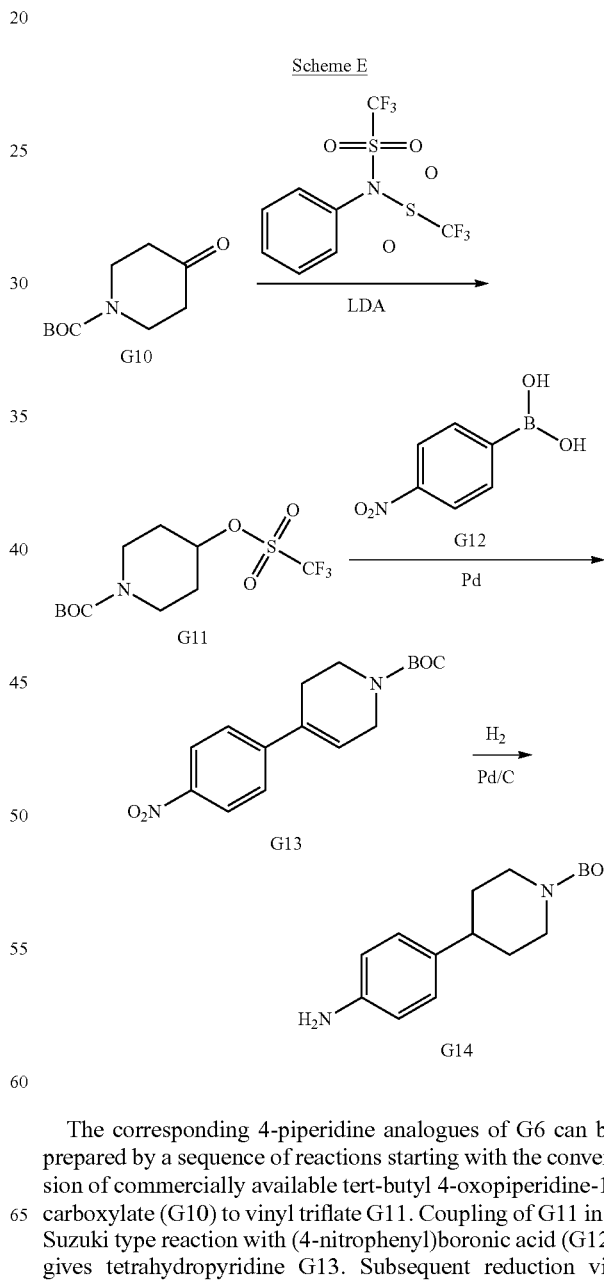

The corresponding 4-piperidine analogues of G6 can be prepared by a sequence of reactions starting with the conversion of commercially available tert-butyl 4-oxopiperidine-1-carboxylate (G10) to vinyl triflate G11. Coupling of G11 in a Suzuki type reaction with (4-nitrophenyl)boronic acid (G12) gives tetrahydropyridine G13. Subsequent reduction via hydrogenation in the presence of a catalyst, for example palladium on charcoal, gives tert-butyl 4-(4-aminophenyl)piperidine-1-carboxylate (G14).

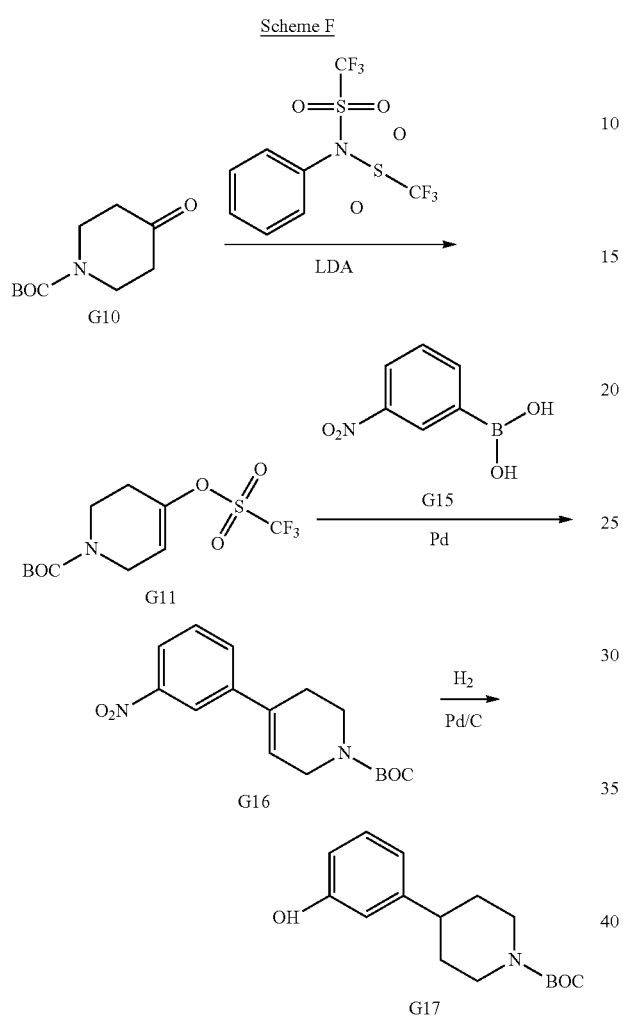

The corresponding 4-(3-aminophenyl)piperidine analogue of G9 can be prepared by a sequence of reactions starting with the conversion of commercially available tert-butyl 4-oxopiperidine-1-carboxylate (G10) to vinyl triflate G11. Coupling of G11 in a Suzuki type reaction with (3-nitrophenyl)boronic acid (G15) gives tetrahydropyridine G16. Subsequent reduction via hydrogenation in the presence of a catalyst, for example palladium on charcoal, gives tert-butyl 4-(3-aminophenyl)piperidine-1-carboxylate (G17).

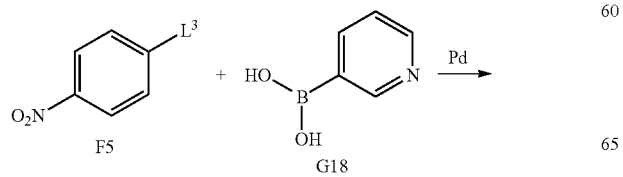

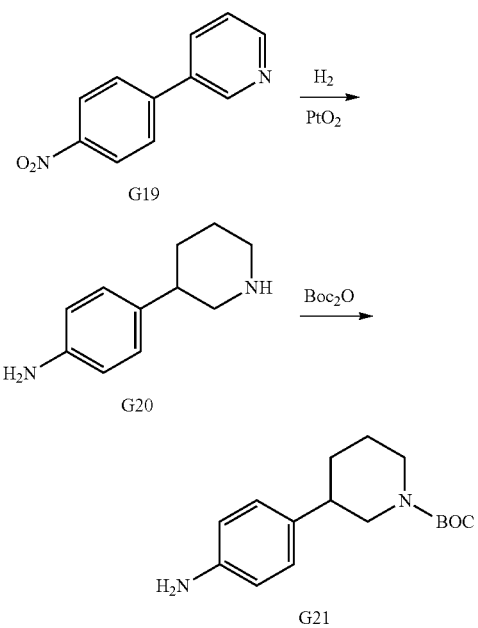

The 3-(4-aminophenyl)piperidine regioisomers of G14 can be prepared by reaction of commercially available compounds of the formula F5, where $L^3$=I or Br, with pyridin-3-ylboronic acid (G18) in a Suzuki type reaction to form 3-(4-nitrophenyl)pyridine (G19). Reduction of G19 with hydrogen in the presence of a catalyst, for example platinum oxide, gives 4-(piperidin-3-yl)aniline (G20) which may be protected using Boc anhydride to give tert-butyl 3-(4-aminophenyl)piperidine-1-carboxylate (G21).

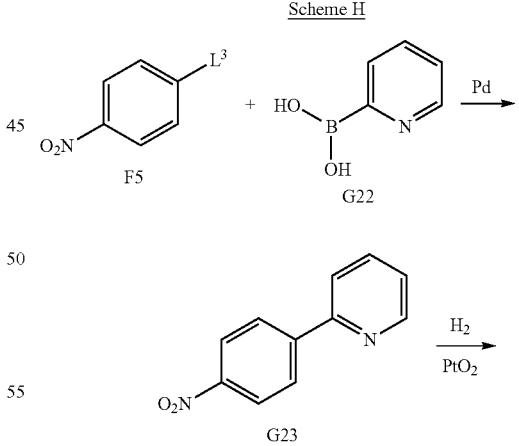

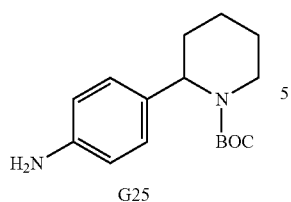

G25

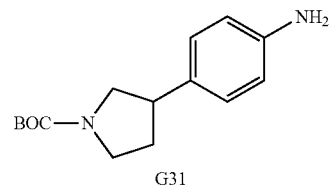

G31

The 2-(4-aminophenyl)piperidine regioisomer of G14 can be prepared by reaction of commercially available compounds of the formula F5, where $L^3$=I or Br, with pyridin-2-ylboronic acid (G22) in a Suzuki type reaction to form 2-(4-nitrophenyl)pyridine (G23). Reduction of G23 with hydrogen in the presence of a catalyst, for example platinum oxide, gives 4-(piperidin-2-yl)aniline (G24) which may be protected using Boc anhydride to give tert-butyl 2-(4-aminophenyl)piperidine-1-carboxylate (G25).

Commercially available tert-butyl 3-oxopyrrolidine-1-carboxylate (G26) can be converted to a mixture of vinyl triflates G27 and G28 in the presence of a triflamide and a suitable base, for example NaHMDS. Coupling of the mixture with (4-nitrophenyl)boronic acid (G12) under Suzuki conditions gives dihydropyrroles G29 and G30. Reduction of this mixture using hydrogen in the presence of a catalyst, for example 10% palladium on charcoal, gives tert-butyl 3-(4-aminophenyl)pyrrolidine-1-carboxylate (G31).

Scheme I

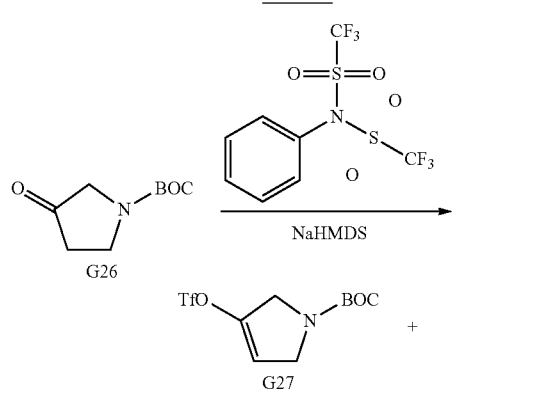

Scheme J

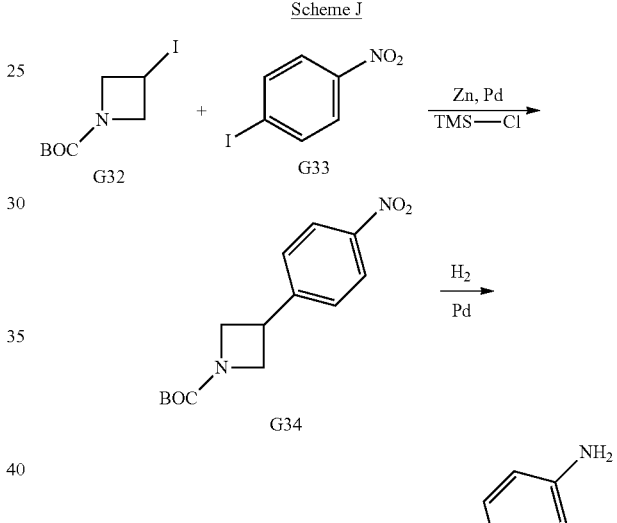

A metal/silyl mediated coupling of commercially available tert-butyl 3-iodoazetidine-1-carboxylate (G32) and 4-iodonitrobenzene (G33) gives tert-butyl 3-(4-nitrophenyl)azetidine-1-carboxylate (G34). Subsequent reduction via hydrogenation in the presence of a catalyst, for example palladium on charcoal, gives the tert-butyl 3-(4-aminophenyl)azetidine-1-carboxylate (G35).

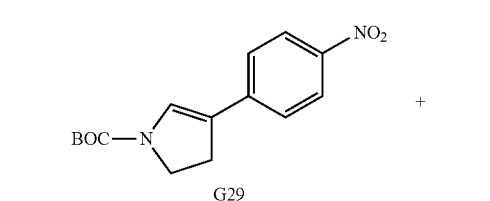

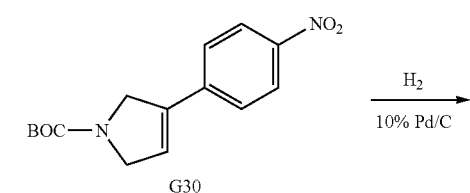

Scheme K

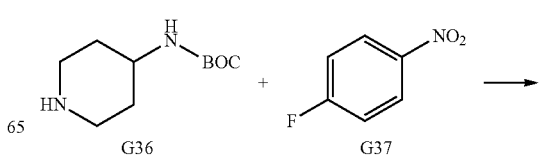

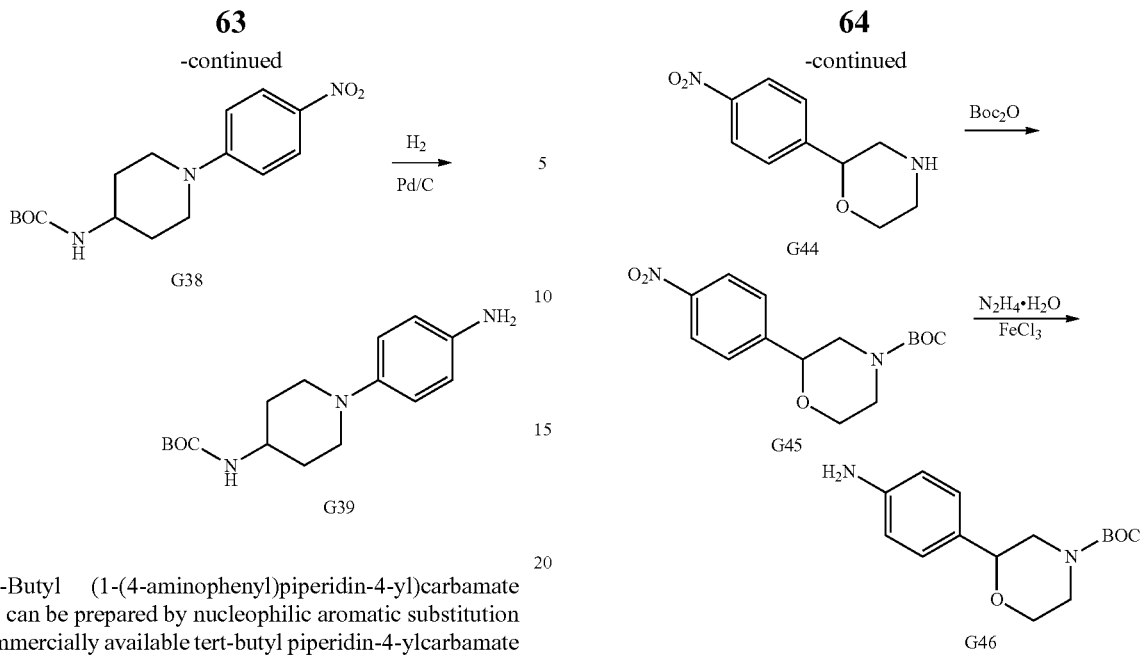

tert-Butyl (1-(4-aminophenyl)piperidin-4-yl)carbamate (G39) can be prepared by nucleophilic aromatic substitution of commercially available tert-butyl piperidin-4-ylcarbamate (G36) and 1-fluoro-4-nitrobenzene (G37) under thermal conditions to give tert-butyl (1-(4-nitrophenyl)piperidin-4-yl)carbamate (G38). Reduction of G38 with hydrogen in the presence of a catalyst, for example 10% palladium on charcoal, gives tert-butyl (1-(4-aminophenyl)piperidin-4-yl)carbamate (G39).

Scheme L

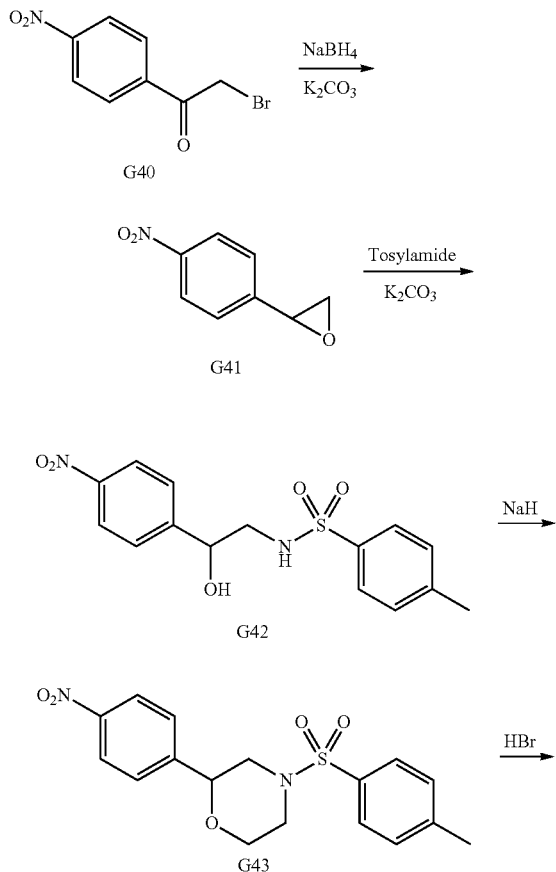

Commercially available 2-bromo-1-(4-nitrophenyl)ethanone (G40) can be reduced and cyclised to give epoxide G41. Opening of the epoxide with tosylamide followed by cyclisation with (2-bromoethyl)diphenylsulfonium trifluoromethanesulfonate gives morpholine G43. Cleavage of the sulphonamide and subsequent re-protection with Boc anhydride gives carbamate G45. Reduction using hydrazine in the presence of iron(III) chloride gives tert-butyl 2-(4-aminophenyl)morpholine-4-carboxylate (G46).

Scheme M

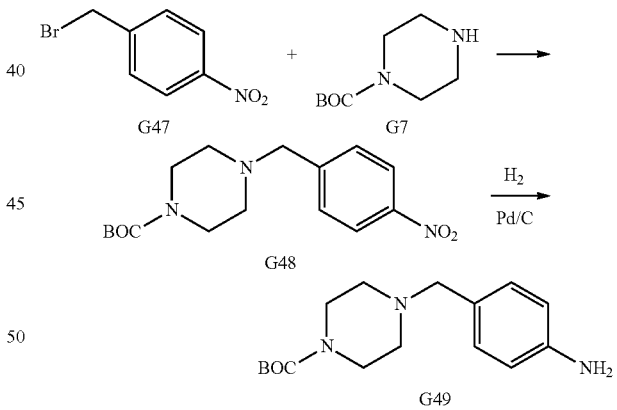

tert-Butyl 4-(4-aminobenzyl)piperazine-1-carboxylate (G49) can be prepared by the nucleophilic displacement of commercially available 1-(bromomethyl)-4-nitrobenzene (G47) with tert-butyl piperazine-1-carboxylate (G7) to give tert-butyl 4-(4-nitrobenzyl)piperazine-1-carboxylate (G48). Subsequent reduction with hydrogen in the presence of a catalyst, for example 10% palladium on charcoal, gives tert-butyl 4-(4-aminobenzyl)piperazine-1-carboxylate (G49).

Compounds of the formula F2 containing benzylamine or substituted benzylamines may either be purchased with suitable protecting groups in place to allow selective reaction at the aniline or synthesised using an Ellman type procedure as out lined in scheme N.

Scheme N

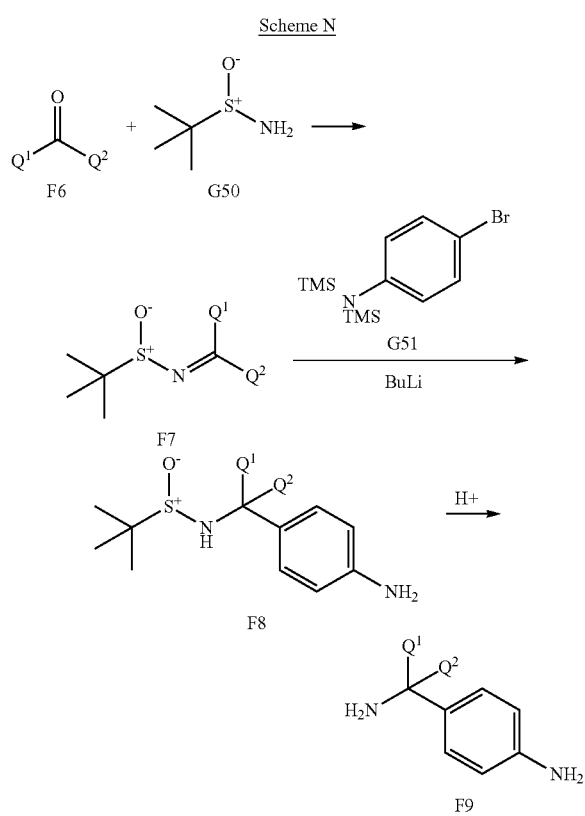

Carbonyl compounds of the formula F6 can be reacted with 2-methylpropane-2-sulfinamide (G50) to give compounds of the formula F7. Compounds of the formula F7 can be reacted with anions prepared from suitably protected amino compounds, for example N-(4-bromophenyl)-1,1,1-trimethyl-N-(trimethylsilyl)silanamine (G51) treated with n-butyllithium, to give compounds of the formula F8. Hydrolysis of compounds of the formula F8 under acidic conditions, for example using aqueous hydrochloric acid, gives compounds of the formula F9. Where necessary, compounds of the formula F9 can be further protected to facilitate regiospecific reactivity. It will be appreciated that $Q^1$ and $Q^2$ may be the same or different and may be fused together to form a ring structure, for example as in cyclobutanone—Substituents $Q^1$ and $Q^2$ form either $R^{C1}$ or part of X in compounds of formula I. It will also be appreciated that anions of suitably protected amino heterocycles may be added to compounds of the formula F7 to give heterocyclic analogues of compounds of the formula F9.

Where compounds are required where $R^3$ is aryl or substituted aryl compounds of the formula F13 may be prepared as outlined in scheme O.

Scheme O

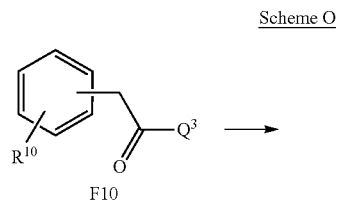

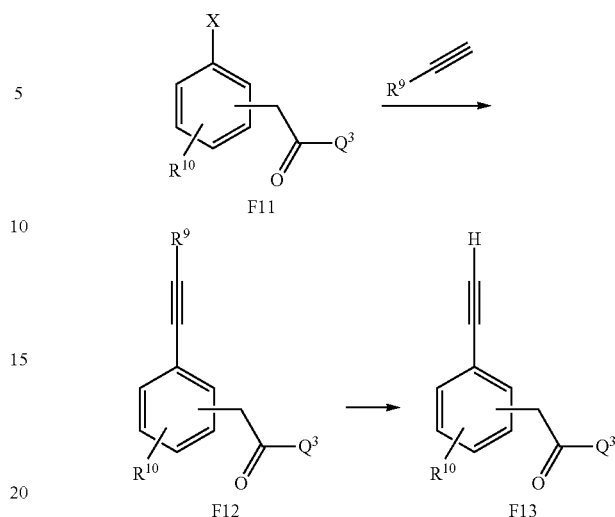

Compounds of the formulae F10 and F11 where $R^{1C}$ are independently H, F, Me or $CF_3$; $Q^3$ may be OH, O-alkyl, $NH_2$ or substituted N and X=Cl, Br or I, are either commercially available or may be prepared synthetically. It will be appreciated that for compounds of the formula F10 and F11 that the nature of $Q^3$ can be readily changed. For example, a carboxylic acid may be converted to a corresponding ester or amide as required and conversely esters and amides can be hydrolysed to give carboxylic acids. Halogenation, for example using N-bromosuccinimide, of compounds of the formula F10 gives compounds of the formula F11, Compounds of the formula F11 may be reacted under Sonagashira type coupling conditions to give acetylenes of the formula F12 where $R^9$=TMS, TES or $C(CH_3)_2OH$. $R^9$ may then be removed to generate compounds of the formula F13. When $R^9$=TMS or TES potassium carbonate or tetra-n-butyl ammonium fluoride may be employed to induce this transformation. When $R^9$=$C(CH_3)_2OH$, sodium hydride in refluxing toluene may be used.

Alternatively, when compounds in which $R^3$=heteroaryl are desired, heteroaryl analogues of F13 may be prepared as outlined in Schemes P, Q and R.

Scheme P

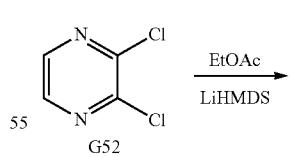

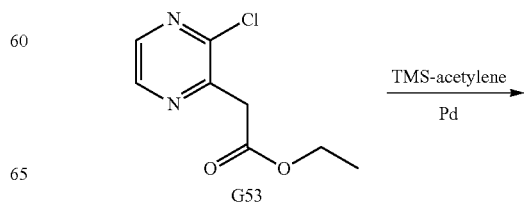

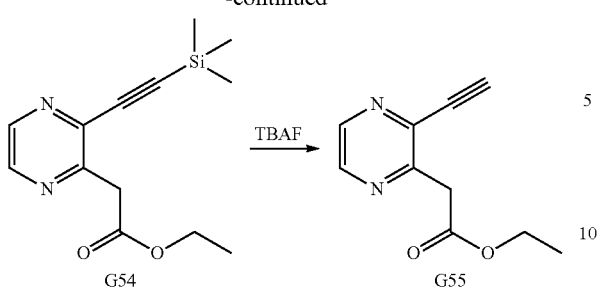

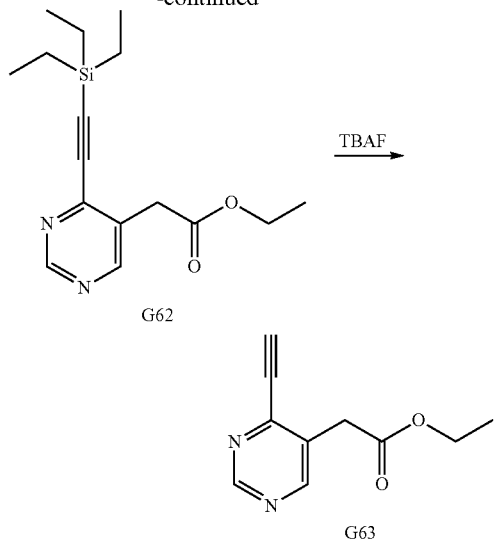

For pyrazine containing analogues, 2,3-di-chloropyrazine (G52) can be reacted with ethyl acetate in the presence of LiHMDS to give ester G53. Coupling of ester G53 with TMS acetylene under Sonagashira conditions gives ethyl 2-(3-((trimethylsilyl)ethynyl)pyrazin-2-yl)acetate (G54). Removal of the trimethylsilyl group using TBAF gives ethyl 2-(3-ethynylpyrazin-2-yl)acetate (G55).

Scheme Q

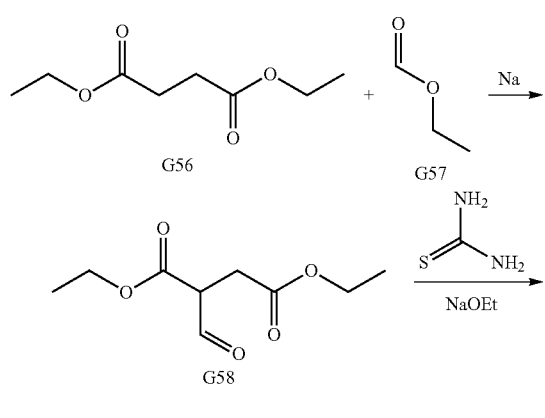

For pyrimidine analogues, diethyl succinate (G56) and ethyl formate (G57) can be condensed to give aldehyde G58 in the presence of sodium metal. Cyclisation using thiourea gives 4-oxo-2-thioxo-1,2,3,4-tetrahydropyrimidine (G59). Desulfurisation using Raney-nickel gives pyrimidone G60, which can be converted to 4-chloro pyrimidine G61 using phosphorous oxychloride. Coupling of compound G61 with TES-acetylene under Sonagashira conditions, followed by removal of the triethylsilyl group using TBAF gives ethyl 2-(4-ethynylpyrimidin-5-yl)acetate (G63). It will be appreciated that the regioisomeric pyrimidine can be accessed by analogous series of reactions from the isomer of G59.

Scheme R

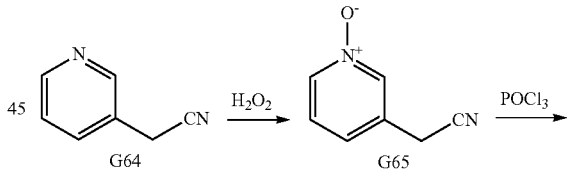

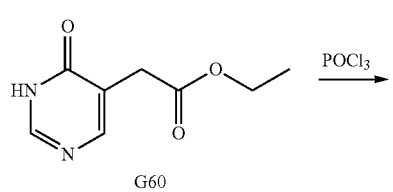

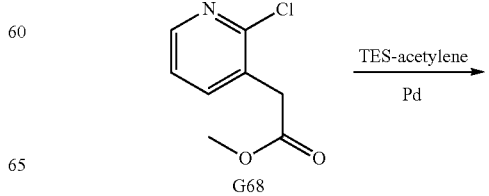

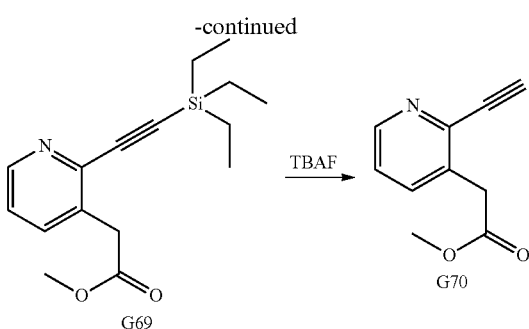

For 3-pyridyl acetates, 2-(pyridin-3-yl)acetonitrile (G64) can be oxidised to N-oxide G65. Chlorination with phosphorous oxychloride gives 2-chloropyridine G66 which can be hydrolysed with sodium hydroxide to acetic acid G67. Ester formation using methanol gives 2-chloropyridine ester G68. Coupling of compounds ester G68 with TES-acetylene under Sonagashira conditions, followed by removal of the triethylsilyl group using TBAF gives methyl 2-(2-ethynylpyridin-3-yl)acetate (G70). It will be appreciated that the other regioisomeric pyridine analogues can be prepared using an analogous sequence starting from other commercially available pyridyl acetates.

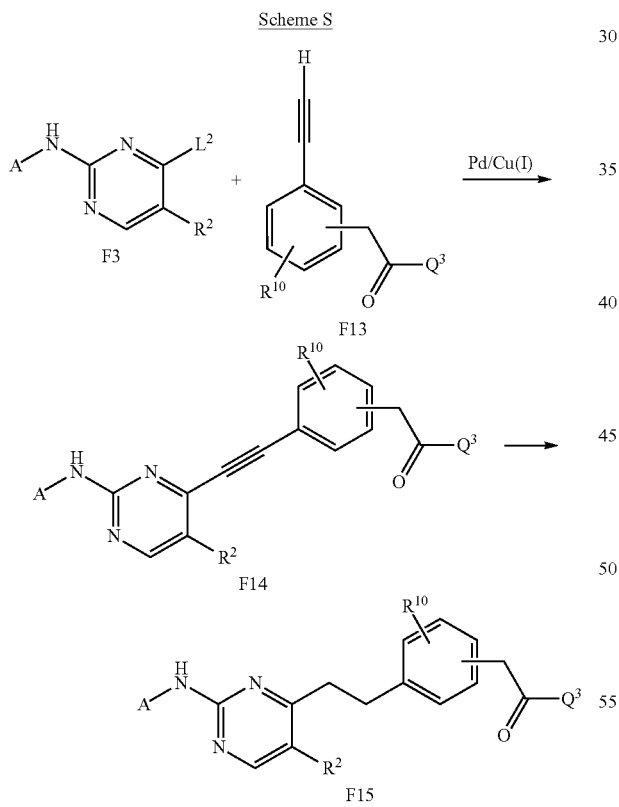

Pyrimidines of the formula F3 may be reacted with terminal acetylenes of the formula F13 to give acetylenes of the formula F14 in a Sonagashira type coupling. The acetylene in compounds of the formula F14 may be reduced to an alkane of the formula F15 using hydrogen gas in the presence of a transition metal catalyst. The exact choice of catalyst and conditions employed is dependent on the nature of $R^2$. For example, where $R^2$=F, $CF_3$, methyl or methoxy, 10% Pd/C may be used, where $R^2$=Cl, platinum oxide is employed. Functional group manipulation may be carried on compounds of the formula F15 if necessary. For example, compounds of the formula F15 where $Q^3$=O-alkyl (i.e. esters) may then be deprotected to give carboxylic acids of the formula F15 where $Q^3$=OH. In esters where $Q^3$=OMe, lithium hydroxide solutions may be employed. Where $Q^3$=Ot-Bu, acidic solutions, for example trifluoroacetic acid in dichloromethane may be used to facilitate hydrolysis. It will be appreciated that under acidic conditions Boc protecting groups in A will also be cleaved.

Compounds of the formula F15 where $Q^3$=OH may then be converted to amides and substituted amides as described in formula (I) using a suitable choice of amine in the presence of a coupling agents for example EDCl.HCl or HATU.

It will be appreciated that heteroaromatic analogues of compounds of the formula F13 (as described in schemes P, Q and R) may be coupled in an analogous manner to that described in scheme S and then further elaborated to amides as described above.

Compounds of the formula F15, in which $Q^3$=an amide or substituted amide may then be further modified by derivitisation of amine functionality present in A. For example, compounds of the formula F15 where A was prepared as described in schemes C to M, in which a tert-butyl carbamate is present, may be hydrolysed in the presence of mild acid, for example trifluoroacetic acid, to give the parent amine. The amine functionality maybe further derivatised by reductive alkylation with formaldehyde in the presence of sodium triacetoxyborohydride to give N-Me analogues; by reductive alkylation with acetaldehyde in the presence of sodium triacetoxyborohydride to give N-Et analogues or the N-acetyl analogues may be prepared by reaction with a suitable acylating agent, for example acetic anhydride.

Alternatively, a complementary approach to that described scheme S can be employed, where $R^2$ is not $CF_3$, whereby pyrimidines of the formula F1 are initially coupled to acetylenes of the formula F13 as detailed in scheme T.

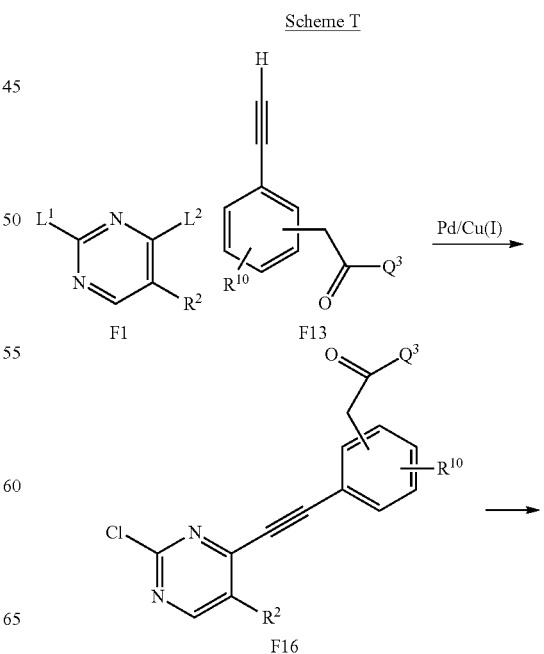

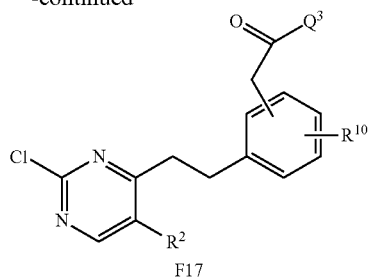

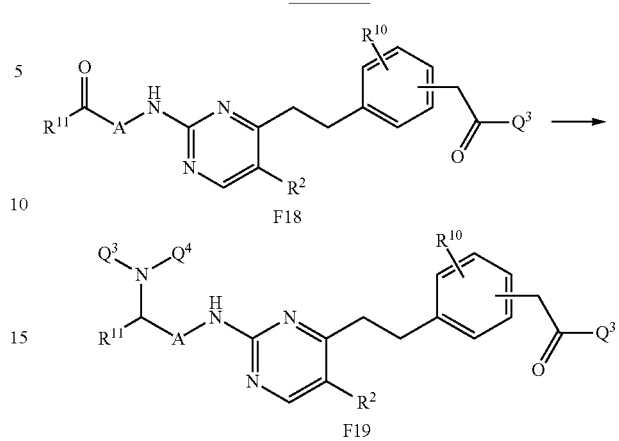

Pyrimidines of the formula F1 may be coupled to acetylenes of the formula F13 to give acetylenes of the formula F16 in a Sonagashira type coupling. Depending on the nature of $R^2$ these couplings may either be regioselective, or where mixtures are obtained, regioisomers may be separated by chromatography. The acetylene in compounds of the formula F16 may be reduced to an alkane of the formula F17 using hydrogen gas in the presence of a transition metal catalyst. The exact choice of catalyst and conditions employed is dependent on the nature of $R^2$. For example, where $R^2$=Me, 10% Pd/C may be used, where $R^2$=Cl, platinum oxide is employed. The desired amide may already be present in compounds of the formula F13, or alternatively an ester may be used and subsequently derivatised as described above.

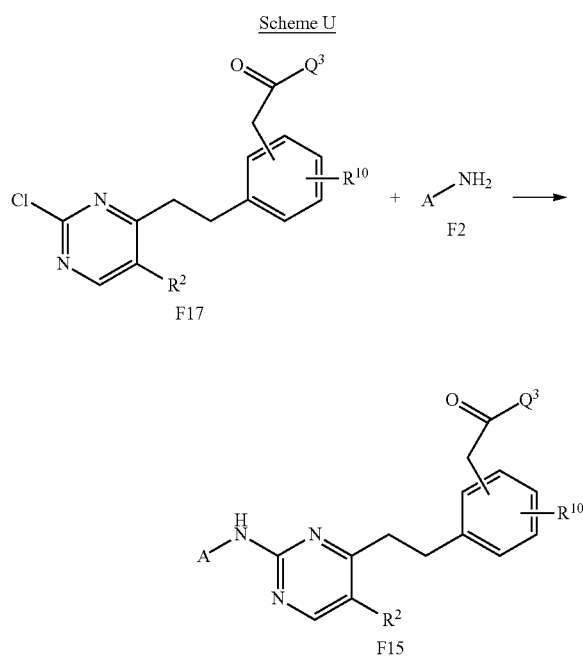

Compounds of the formula F17 may then be reacted with amino compounds of the formula F2, prepared as described above, to give compounds of the formula F15. Such couplings may either be mediated under acidic conditions, for example using trifluoroacetic acid in trifluoroethanol or using palladium catalysis in a Buchwald/Hartwig type coupling.

Compounds of the formula 15 may then be further elaborated as desired as described above.

Ketones of formula F18 where $R^{11}$ is an alkyl group or similar may be substituted with amines to form compounds of formula F19. It will be appreciated that Q4 and Q5 may be the same such as H to form a primary amine or different such as NHMe and may also be fused together to form a ring structure, for example but not limited to azetidine, pyrrolidine, piperazine, morpholine and piperidine.

Use of Compounds of the Invention

The present invention provides active compounds, specifically, active 2,4,5-substituted pyrimidines.

The term "active", as used herein, pertains to compounds which are capable of inhibiting VEGFR3 activity, and specifically includes both compounds with intrinsic activity (drugs) as well as prodrugs of such compounds, which prodrugs may themselves exhibit little or no intrinsic activity.

Assays which may be used in order to assess the VEGFR3 inhibition offered by a particular compound are described in the examples below.

The present invention further provides a method of inhibiting VEGFR3 activity in a cell, comprising contacting said cell with an effective amount of an active compound, preferably in the form of a pharmaceutically acceptable composition. Such a method may be practised in vitro or in vivo.

The present invention further provides active compounds which inhibit VEGFR3 activity, as well as methods of inhibiting VEGFR3 activity, comprising contacting a cell with an effective amount of an active compound, whether in vitro or in vivo.

Active compounds may also be used as part of an in vitro assay, for example, in order to determine whether a candidate host is likely to benefit from treatment with the compound in question.

The invention further provides active compounds for use in a method of treatment of the human or animal body. Such a method may comprise administering to such a subject a therapeutically-effective amount of an active compound, preferably in the form of a pharmaceutical composition.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount" as used herein, pertains to that amount of an active compound, or a material, composition or dosage from comprising an active compound, which is effective for producing some desired therapeutic effect, commensurate with a reasonable benefit/risk ratio.

Cancer

The present invention provides active compounds which are anticancer agents. One of ordinary skill in the art is readily able to determine whether or not a candidate compound treats a cancerous condition for any particular cell type, either alone or in combination.

The invention provides the use of the active compounds for the treatment of cancer in the human or animal body. The invention further provides active compounds for use in a method of treatment of cancer in the human or animal body. Such a use or method may comprise administering to such a subject a therapeutically-effective amount of an active compound, preferably in the form of a pharmaceutical composition.

Examples of cancers include, but are not limited to, bone cancer, brain stem glioma, breast cancer, cancer of the adrenal gland, cancer of the anal region, cancer of the bladder, cancer of the endocrine system, cancer of the oesophagus, cancer of the head or neck, cancer of the kidney or ureter, cancer of the liver, cancer of the parathyroid gland, cancer of the penis, cancer of the small intestine, cancer of the thyroid gland, cancer of the urethra, carcinoma of the cervix, carcinoma of the endometrium, carcinoma of the fallopian tubes, carcinoma of the renal pelvis, carcinoma of the vagina, carcinoma of the vulva, chronic or acute leukemia, colon cancer, melanoma such as cutaneous or intraocular melanoma, haemetological malignancies, Hodgkin's disease, lung cancer, lymphocytic lymphomas, neoplasms of the central nervous system (CNS), ovarian cancer, pancreatic cancer, pituitary adenoma, primary CNS lymphoma, prostate cancer, rectal cancer, renal cell carcinoma, sarcoma of soft tissue, skin cancer, spinal axis tumors, stomach cancer and uterine cancer. In some embodiments, the cancer is melanoma, breast cancer or head and neck cancer.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

Compounds of the present invention may also be useful in inhibiting lymphangiogenesis and/or suppressing lymph node metastasis. Compounds of the present invention may also be useful in preventing the spread of cancer and in the prevention of metastasis.

In one embodiment there is provided the use of a compound of formula (I) or formula (II) or an isomer, salt, solvate, protected form or prodrug thereof to prevent the spread of cancer or prevent metastasis. There is also provided a compound of formula (I) or formula (II) or an isomer, salt, solvate or prodrug thereof for use in a method for preventing the spread of cancer or preventing of metastasis.

In another embodiment there is provided an anti-cancer treatment comprising a compound of formula (I) or formula (II) or an isomer, salt, solvate or prodrug thereof and an anti-tumour agent.

The anti cancer treatment defined herein may be applied as a sole therapy or may involve, in addition to the compound of the invention, conventional surgery or radiotherapy or chemotherapy. Such chemotherapy may include one or more of the following categories of anti-tumour agents: —

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); anti-tumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and docetaxel (Taxotere) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661 and 4-((2,4-dichloro-5-methoxyphenyl)amino)-6-methoxy-7-(3-(4-methylpiperazin-1-yl)propoxy)quinoline-3-carbonitrile (bosutinib, SKI-606; Cancer research (2003), 63(2), 375-81), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (Cl 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic and antilymphangiogenic agents such as those which inhibit the effects of vascular endothelial growth factor, [for example the anti vascular endothelial cell growth factor A (VEGFA) antibody bevacizumab (AvastinT), the anti vascular endothelial cell growth factor A (VEGFA) antibody ranibizumab, the anti-VEGF aptamer pegaptanib, the anti vascular endothelial growth factor receptor 3 (VEGFR3) antibody IMC-3C5, the anti vascular endothelial cell growth factor C (VEGFC) antibody VGX-100, the anti vascular endothelial cell growth factor D (VEGFD) antibody VGX-200, the soluble form of the vascular endothelial growth factor receptor 3 (VEGFR3) VGX-300 and VEGF receptor tyrosine kinase inhibitors such as 4-(4-bromo-2-fluoroanilino)-6-methoxy-7-(1-methylpiperidin-4-yl-methoxy)quinazoline (vandetanib; ZD6474; Example 2 within WO 01/32651), 4-(4-fluoro-2-methylindol-5-yloxy)-6-methoxy-7-(3-pyrrolidin-1-ylpropoxy)quinazoline (cediranib; AZD2171; Example 240 within WO 00/47212), vatalanib (PTK787; WO 98/35985), pazopanib (GW786034), axitinib (AG013736), sorafenib and sunitinib (SU11248; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies A combination of particular interest is with docetaxel. Other possible combinations of interest include with gemcitabine, cisplatin and the camptothecin prodrug irinotecan.

Diseases Ameliorated by the Control and/or Inhibition of Lymphangiogenesis

The present invention provides active compounds which are useful in preventing and/or treating diseases or conditions ameliorated by the control and/or inhibition of lymphangiogenesis.

In one embodiment there is provided the use of a compound of formula (I) or formula (II) or an isomer, salt, solvate, protected form or prodrug thereof to inhibit, suppress or reduce lymphangiogenesis. There is also provided a compound of formula (I) or formula (II) or an isomer, salt, solvate, protected form or prodrug thereof for use in the method of inhibiting, suppressing or reducing lymphangiogenesis.

As discussed above, these diseases or conditions may include:

(a) eye diseases, for example corneal graft rejection and age related macular degeneration;

(b) skin inflammations, such as skin lesions in patients with psoriasis;

(c) rejection in renal transplantation.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intravitreal and intrasternal; by implant of a depot, for example, subcutaneously, intravitreal or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences*, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), methoxy (MeO), ethoxy (EtO), trimethylsilyl (TMS), tert-butyloxycarbonyl (Boc), and acetyl (Ac).

For convenience, many chemical compounds are represented using well known abbreviations, including but not limited to, methanol (MeOH), ethanol (EtOH), ether or diethyl ether ($Et_2O$), ethyl acetate (EtOAc), triethylamine ($Et_3N$), dichloromethane (methylene chloride, DCM), trifluoroacetic acid (TFA), trifluoroethanol (TFE), dimethylformamide (DMF), sodium sulphate ($Na_2SO_4$), tetrahydrofuran (THF), meta-chloroperbenzoic acid (mCPBA), hexamethyldisilazane sodium salt (NaHMDS), O-(7-azabenzotriazol-1-yl)-N,N,N',N'-tetramethyluronium hexafluorophosphate (HATU), dimethylsulfoxide (DMSO), magnesium sulphate ($MgSO_4$), sodium hydrogen carbonate ($NaHCO_3$), tert-butanol (t-BuOH), 1-ethyl-3-(3-dimethylaminopropyl) carbodiimide hydrochloride salt (EDCl.HCl), tetra-n-butylammonium fluoride (TBAF), N,N-diisopropylethylamine (DIPEA), 1-hydroxybenzotriazole (HOBt), trans-dichlorobis (triphenylphosphine)palladium(II) ($PdCl_2(PPh_3)_2$), tris (dibenzylideneacetone) dipalladium(0) ($Pd_2(dba)_3$), tri-t-butyl phosphonium tetrafluoroborate ($t-Bu_3PH.BF_4$), 4,5-bis (diphenylphosphino)-9,9-dimethylxanthene (Xantphos), triphenylphosphine ($PPh_3$) and 1,2-dichloroethane (DCE).

General Experimental Details

Unless otherwise stated the following generalisations apply.

In the examples below, in case the structures contain one or more stereogenic centres and the stereochemistry is depicted in the diagram, the respective stereochemistry is assigned in an arbitrary absolute configuration. These structures depict single enantiomers as well as mixtures of enantiomers in all ratios, and/or mixtures of diastereoisomers in all ratios.

[1]NMR spectra were recorded on either a Bruker Avance DRX300 (300 MHz) or a Bruker Ultrashield plus (400 MHz). The multiplicity of a signal is designated by the following abbreviations: s, singlet; d, doublet; dd, doublet of doublets; t, triplet; tt, triplet of triplets; td, triplet of doublets; q, quartet; br, broad; m, multiplet. All observed coupling constants, J, are reported in Hertz.

LC/MS data was generated using either an Agilent 6100 Series Single Quad LC/MS (LCMS-A) or Waters ZQ 3100 system (LCMS-B).

LCMS Method A (LCMS-A)
Instrument: Agilent 6100 Series Single Quad LC/MS
Agilent 1200 Series HPLC
Pump: 1200 Series G1311A Quaternary pump
Autosampler: 1200 Series G1329A Thermostatted Autosampler
Detector: 1200 Series G1314B Variable Wavelength Detector
LC Conditions:
Reverse Phase HPLC analysis
Column: Luna C8(2) 5µ 50×4.6 mm 100 A
Column temperature: 30° C.
Injection Volume: 5 µL
Solvent A: Water 0.1% Formic Acid
Solvent B: Acetonitrile 0.1% Formic Acid
Gradient: 5-100% B over 10 min
Detection: 254 nm or 214 nm
MS Conditions:
Ion Source Quadrupole
Ion Mode Multimode-ES
Drying gas temp: 300° C.
Vaporizer temperature: 200° C.
Capillary voltage (V): 2000 (positive)
Capillary voltage (V): 4000 (negative)
Scan Range: 100-1000
Step size: 0.1 sec
Acquisition time: 10 min
LCMS Method B (LCMS-B)
Instrument: Waters ZQ 3100-Mass Detector Waters 2545-Pump
Waters SFO System Fluidics Organizer
Waters 2996 Diode Array Detector
Waters 2767 Sample Manager
LC Conditions:
Reverse Phase HPLC analysis
Column: XBridge TM C18 5 μm 4.6×100 mm
Injection Volume 10 μL
Solvent A: Water 0.1% Formic Acid
Solvent B: Acetonitrile 0.1% Formic Acid
Gradient: 10-100% B over 10 min
Flow rate: 1.5 ml/min
Detection: 100-600 nm
MS Conditions:
Ion Source Single-quadrupole
Ion Mode: ES positive
Source Temp: 150° C.
Desolvation Temp: 350° C.
Detection: Ion counting
Capillary (KV): 3.00
Cone (V): 30
Extractor (V): 3
RF Lens (V): 0.1
Scan Range: 100-1000 Amu
Scan Time: 0.5 sec
Acquisition time: 10 min
Gas Flow: 100 L/hr
Desolvation: 650 L/hr
Semi-preparative HPLC separations were achieved using a Waters ZQ 3100 system (HPLC)
Semi-Preparative HPLC (HPLC)
Instrument:
Waters ZQ 3100-Mass Detector
Waters 2545-Pump
Waters SFO System Fluidics Organizer
Waters 2996 Diode Array Detector
Waters 2767 Sample Manager
LC Conditions:
Reverse Phase HPLC analysis
Column: XBridge TM C18 5 μm, 19×50 mm
Injection Volume 500 μL
Solvent A: Water 0.1% Formic Acid
Solvent B: Acetonitrile 0.1% Formic Acid
Gradient: 25-100% B over 10 min
Flow rate: 19 ml/min
Detection: 100-600 nm
MS Conditions:
Ion Source: Single-quadrupole
Ion Mode: ES positive
Source Temp: 150° C.
Desolvation Temp: 350° C.
Detection: Ion counting
Capillary (KV): 3.00
Cone (V): 30
Extractor (V): 3
RF Lens (V): 0.1
Scan Range: 100-1000 Amu
Scan Time: 0.5 sec
Acquisition time: 10 min
Desolvation: 650 L/hr
Cone: 100 L/hr
LCMS Method C (LCMS-C)
Instrument: Finnigan LCG Advantage Max
Finnigan Surveyor LC Pump
Finnigan Surveyor Autosampler
Finnigan Surveyor PDA Detector
LC Conditions:
Reverse Phase HPLC analysis
Column: Gemini 3 μm C18 20×4.0 mm 110 A
Injection Volume: 10 μL
Solvent A: Water 0.1% Formic Acid
Solvent B: Acetonitrile 0.1% Formic Acid
Gradient: 10-100% B over 10 min
Detection: 100-600 nm
MS Conditions
Ion Source: Ion trap
Ion Mode: ES positive
Temp: 300° C.
Detection: Ion counting
Scan Range: 80-1000 Amu
Scan Time: 0.2 sec
Acquisition time: 10 min Analytical thin-layer chromatography was performed on Merck silica gel 60F254 aluminium-backed plates which were visualised using fluorescence quenching under UV light or using an acidic anisaldehyde or a basic potassium permanganate dip. Flash chromatography was performed using either a Teledyne Isco CombiFlash Rf purification system using standard RediSep® cartridges or a Biotage Isolera purification system using either Grace, RediSep® or Biotage silica cartridges. Microwave irradiation was achieved using a CEM Explorer SP Microwave Reactor. All reactions carried out using microwave irradiation were stirred.

Where necessary, anhydrous solvents were prepared using a Braun purification system or purchased from Sigma-Aldrich.

Synthesis of Key Intermediates

Key Intermediate 1: Methyl 2-(2-ethynylphenyl)acetate (K1)

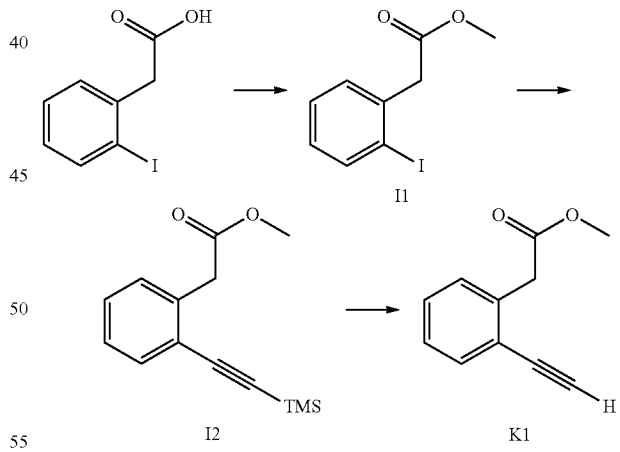

(a) Methyl 2-(2-iodophenyl)acetate (I1)

To a solution of 2-(2-iodophenyl)acetic acid (5.00 g, 19.1 mmol) in MeOH (150 mL) was added concentrated aqueous $H_2SO_4$ (250 μL) and the resulting mixture was stirred at 80° C. under nitrogen for 16 hours. The volatiles were removed by evaporation under reduced pressure and the residue was taken up in EtOAc (100 mL). The resulting solution was washed with 10% aqueous $NaHCO_3$ (100 mL), dried ($MgSO_4$) and the volatiles evaporated under reduced pressure to give the title compound I1 as a clear liquid (5.20 g, 99%); $^1$H NMR (400 MHz, CDCl$_3$) δ 7.85 (dd, J=7.9, 1.0 Hz, 1H), 7.35-7.27 (m, 2H), 6.97 (m, 1H), 3.81 (s, 2H), 3.72 (s, 3H).

(b) Methyl 2-(2-((trimethylsilyl)ethynyl)phenyl)acetate (I2)

A mixture of methyl 2-(2-iodophenyl)acetate (I1) (4.65 g, 16.8 mmol), PdCl$_2$(PPh$_3$)$_2$ (295 mg, 421 µmol), CuI (80.0 mg, 421 µmol) and (trimethylsilyl)acetylene (2.80 mL, 20.2 mmol) in dry degassed THF (20 mL) and Et$_3$N (20 mL) was stirred at room temperature for 16 hours. The volatiles were removed under reduced pressure to give a black residue which was adsorbed onto silica gel and purified using column chromatography (0-5% EtOAc in petroleum benzine 40-60° C.) to give the title compound I2 as a light brown liquid (4.63 g, 99%); $^1$H NMR (400 MHz, CDCl$_3$) δ 7.48 (dd, J=7.5, 0.8 Hz, 1H), 7.32-7.14 (m, 3H), 3.84 (s, 2H), 3.71 (s, 3H), 0.26 (s, 9H). LCMS-B: rt 6.64 min.

(c) Methyl 2-(2-ethynylphenyl)acetate (K1)

TBAF (1.0 M in THF; 28.5 mL, 28.5 mmol) was added to a solution of methyl 2-(2-((trimethylsilyl)ethynyl)phenyl)acetate (I2) (4.63 g, 19.0 mmol) in DCM (200 mL) at 0° C. The solution was stirred at room temperature for 1 hour before washing with 10% aqueous NaHCO$_3$ (100 mL). The organic layer was dried (MgSO$_4$) before removing the volatiles in vacuo to give a dark brown/black residue which was adsorbed onto silica gel and purified by column chromatography (Biotage Isolera, 0-10% EtOAc in petroleum benzine 40-60° C.) to give the title compound K1 as a red liquid (2.76 g, 83%); $^1$H NMR (400 MHz, CDCl$_3$) δ 7.52 (dd, J=7.6, 1.1 Hz, 1H), 7.43-7.16 (m, 3H), 3.88 (d, J=9.6 Hz, 2H), 3.77-3.52 (m, 3H), 3.28 (s, 1H).

Key intermediate 2: Benzyl 4-(4-aminophenyl)piperazine-1-carboxylate (K2)

(a) Benzyl 4-(4-nitrophenyl)piperazine-1-carboxylate (I3)

Benzyl chloroformate (0.515 mL, 3.61 mmol) was added to a mixture of 1-(4-nitrophenyl)piperazine hydrochloride (0.800 g, 3.28 mmol) and Et$_3$N (1.14 mL, 8.21 mmol) in THF (20 mL) at 0° C. The resulting mixture was stirred at 0° C. for 1 hour then at room temperature for 2 hours. DCM (40 mL) was added and the organics were washed with saturated NaHCO$_3$ (40 mL), water (40 mL) then dried over MgSO$_4$. The volatiles removed in vacuo to give the title compound I3 as a yellow solid (1.11 g, 99%); $^1$H NMR (400 MHz, CDCl$_3$) δ 8.04-8.01 (m, 2H), 7.32-7.18 (m, obscured), 7.15 (s, 1H), 6.72-6.69 (m, 2H), 5.06 (s, 2H), 3.62-3.54 (m, 4H), 3.37-3.26 (m, 4H).

(b) Benzyl 4-(4-aminophenyl)piperazine-1-carboxylate (K2)

To a mixture of benzyl 4-(4-nitrophenyl)piperazine-1-carboxylate (I3) (1.11 g, 3.25 mmol) and CoCl$_2$ (0.844 g, 6.50 mmol) in MeOH (30 mL) was added NaBH$_4$ (1.23 g, 32.5 mmol) portion-wise at 0° C. Stirring was continued at 0° C. for 1 hour before aqueous 3 M HCl (10 mL) was added. The mixture was concentrated in vacuo to remove the MeOH and the aqueous layer was extracted twice with diethyl ether. The aqueous layer was basified with 1 M aqueous NaOH and extracted twice with EtOAc. The combined organic extracts were dried (MgSO$_4$), concentrated in vacuo, then adsorbed onto silica gel and purified by silica gel column chromatography (Biotage Isolera, 12 g SiO$_2$ cartridge, 50-60% EtOAc in hexanes) to give the title compound K2 as a purple solid (397 mg, 39%); $^1$H NMR (400 MHz, CDCl$_3$) δ 7.40-7.29 (m, 5H), 6.83-6.78 (m, 2H), 6.68-6.62 (m, 2H), 5.16 (s, 2H), 3.70-3.61 (m, 4H), 3.46 (s, 2H), 3.10-2.86 (m, 4H). LCMS-A: rt 4.650 min; m/z 312.1 [M+H]$^+$.

Key intermediate 3: tert-Butyl 4-(4-aminophenyl)piperazine-1-carboxylate (K3)

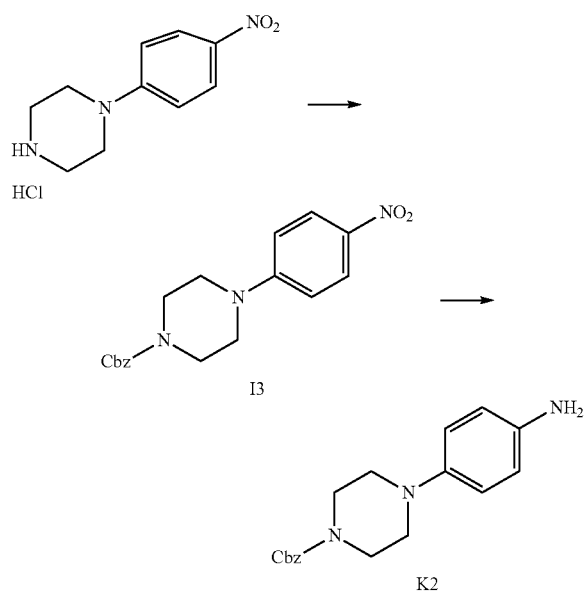

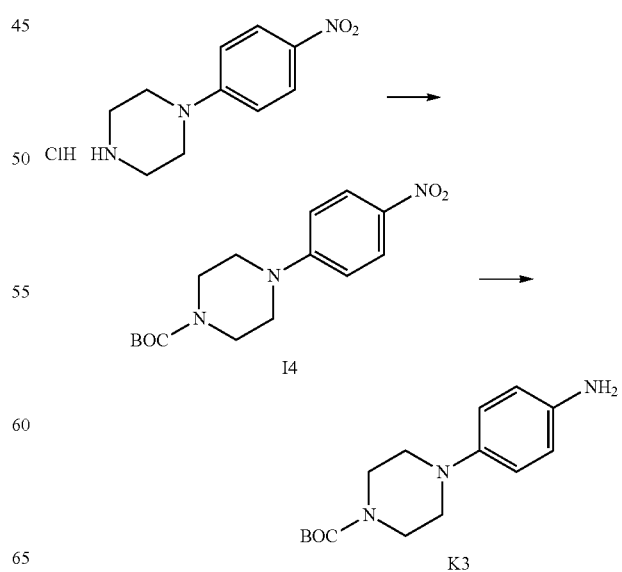

(a) tert-Butyl 4-(4-nitrophenyl)piperazine-1-carboxylate (I4)

To a solution of 1-(4-nitrophenyl)piperazine hydrochloride (5.00 g, 20.5 mmol) in DCM (100 mL) was added Et$_3$N (7.15 mL, 51.3 mmol) and Boc anhydride (4.93 g, 22.6 mmol). The resulting solution was stirred at room temperature for 20 hours before water (100 mL) and DCM (70 mL) were added. The aqueous layer was extracted with DCM (100 mL) then the organics were combined, washed with brine (100 mL), dried (Na$_2$SO$_4$), filtered and concentrated in vacuo to give a yellow-orange residue. The residue was purified by silica gel column chromatography (Biotage Isolera, 120 g SiO$_2$ cartridge, 0-100% EtOAc in petroleum benzine 40-60° C.) to give the title compound I4 as a yellow solid (4.90 g, 78%); $^1$H NMR (400 MHz, d$_6$-DMSO) δ 8.10-8.04 (m, 2H), 7.04-6.97 (m, 2H), 3.48 (m, 8H), 1.42 (s, 9H). LCMS-A: rt 6.13 min; m/z 208.2 [(M-Boc)+2H]$^+$.

(b) tert-Butyl 4-(4-aminophenyl)piperazine-1-carboxylate (K3)

A slurry of 10% Pd/C (0.500 g) in EtOAc (10 mL) was added to a solution of tert-butyl 4-(4-nitrophenyl)piperazine-1-carboxylate (I4) (3.24 g, 10.5 mmol) in EtOAc (90 mL) and the resulting suspension was stirred under a hydrogen atmosphere for 42 hours at room temperature. The catalyst was removed by filtration through Celite, washing with EtOAc (7×10 mL), then the filtrate was evaporated to dryness to give the title compound K3 as a pale pink solid (2.92 g, 99%); $^1$H NMR (400 MHz, d$_6$-DMSO) δ 6.72-6.66 (m, 2H), 6.52-6.45 (m, 2H), 4.60 (s, 2H), 3.44-3.39 (m, 4H), 2.87-2.79 (m, 4H), 1.41 (s, 9H). LCMS-A: rt 4.40 min; m/z 278.2 [M+H]$^+$.

Key intermediate 4: tert-Butyl 4-(5-aminopyridin-2-yl)piperidine-1-carboxylate (K4)

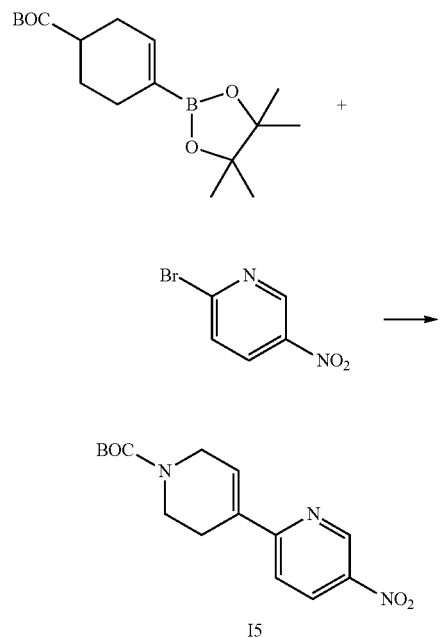

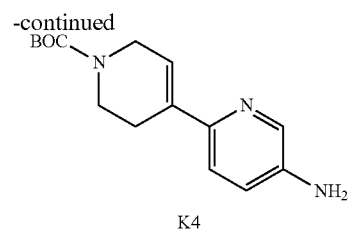

(a) tert-Butyl 5-nitro-5',6'-dihydro-[2,4'-bipyridine]-1'(2'H)-carboxylate (I5)

To a mixture of N-Boc-1,2,3,6-tetrahydropyridine-4-boronic acid pinacol ester (1.52 g, 4.93 mmol), 2-bromo-5-nitropyridine (1.00 g, 4.93 mmol) and PdCl$_2$(PPh$_3$)$_2$ (173 mg, 0.246 mmol) under nitrogen was added dioxane (30 mL) followed by 3 M aqueous Na$_2$CO$_3$ (4.93 mL, 14.8 mmol). The resulting mixture was degassed with a stream of nitrogen for 10 minutes then heated at reflux for 16 hours. On cooling, EtOAc (150 mL) was added and the resulting mixture was washed with water (3×50 mL) and brine (50 mL). The organics were dried (Na$_2$SO$_4$), filtered and concentrated under reduced pressure to give a brown solid that was purified by silica gel column chromatography (Biotage Isolera, 40 g SiO$_2$ cartridge, 0-30% EtOAc in petroleum benzine 40-60° C.) to give the title compound I5 as a yellow solid (1.43 g, 95%); $^1$H NMR (400 MHz, CDCl$_3$) δ 9.37 (dd, J=2.6, 0.5 Hz, 1H), 8.43 (dd, J=8.8, 2.7 Hz, 1H), 7.53 (d, J=8.8 Hz, 1H), 6.95-6.83 (m, 1H), 4.20 (d, J=3.0 Hz, 2H), 3.67 (t, J=5.6 Hz, 2H), 2.70-2.63 (m, 2H), 1.49 (s, 9H). LCMS-A: rt 6.140 min; m/z 304 [M−H]$^−$.

(b) tert-Butyl 4-(5-aminopyridin-2-yl)piperidine-1-carboxylate (K4)

A slurry of 10% Pd/C (500 mg) in DMF (5 mL) was added to a solution of tert-butyl 5-nitro-5',6'-dihydro-[2,4'-bipyridine]-1'(2'H)-carboxylate (I5) (1.40, 4.59 mmol) in DMF (45 mL). The resulting mixture was stirred under a hydrogen atmosphere for 16 hours at room temperature then EtOAc (100 mL) was added and the resulting solution filtered through a Celite pad, washing with EtOAc (150 mL). The filtrate was evaporated to dryness to give a residue that was purified by silica gel chromatography (Biotage Isolera, 40 g SiO$_2$ cartridge, 0-100% EtOAc in petroleum benzine 40-60° C. and then 0-20% MeOH in EtOAc) to give the title compound K4 as a yellow oil (1.18 g, 93%); $^1$H NMR (400 MHz, CDCl$_3$) δ 8.03 (dd, J=2.4, 1.0 Hz, 1H), 7.00-6.87 (m, 2H), 4.22 (br. s, 2H), 3.59 (br. s, 2H), 2.85-2.67 (m, 3H), 1.86 (m, 2H), 1.72-1.59 (m, 2H), 1.46 (s, 9H). LCMS-A: rt 4.416 min; m/z 278 [M+H]$^+$.

Key intermediate 5: tert-Butyl 4-(4-((4-chloro-5-(trifluoromethyl)pyrimidin-2-yl)amino)phenyl)piperidine-1-carboxylate (K5)

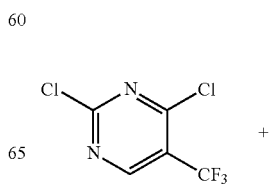

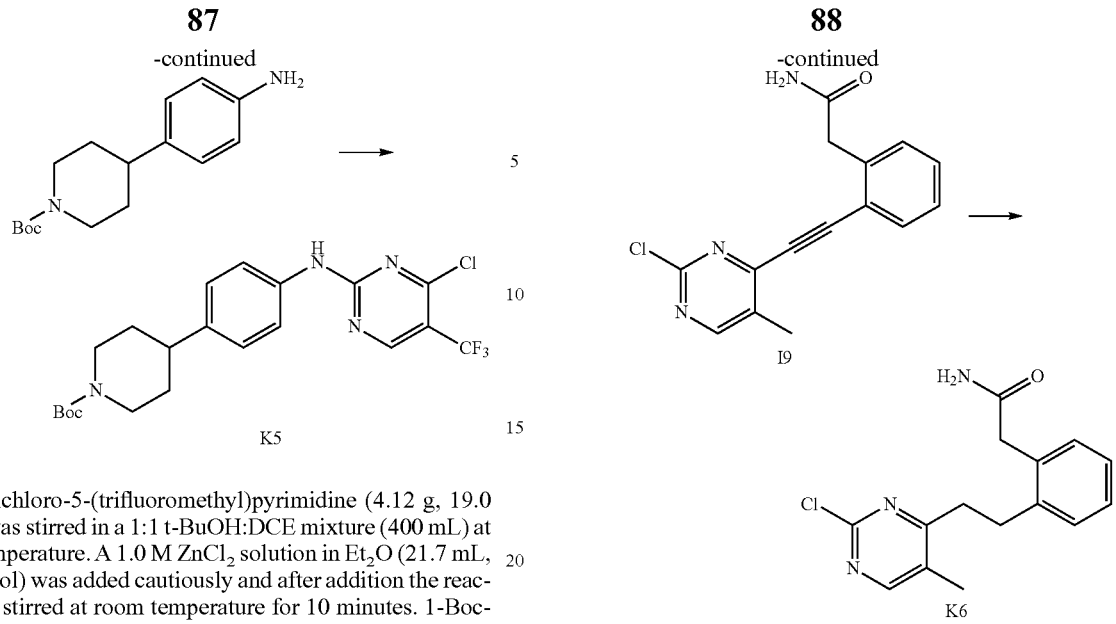

2,4-Dichloro-5-(trifluoromethyl)pyrimidine (4.12 g, 19.0 mmol) was stirred in a 1:1 t-BuOH:DCE mixture (400 mL) at room temperature. A 1.0 M ZnCl$_2$ solution in Et$_2$O (21.7 mL, 21.7 mmol) was added cautiously and after addition the reaction was stirred at room temperature for 10 minutes. 1-Boc-4-(4-aminophenyl)piperidine (5.00 g, 18.1 mmol) was then added followed by Et$_3$N (6.05 mL, 43.4 mmol) and the resulting mixture was stirred at room temperature overnight. The organic solvents were evaporated and the resulting solid was suspended in water (500 mL). The suspension was sonicated for 30 minutes and then filtered. The filter cake was washed with water (2×100 mL) and dried under high vacuum to give the title compound K5 as a tan solid (8.11 g, 98%); $^1$H NMR (400 MHz, d$_6$-DMSO) δ 10.61 (s, 1H), 8.78 (s, 1H), 7.59 (d, J=8.4 Hz, 2H), 7.23 (d, J=8.5 Hz, 2H), 4.07 (d, J=11.1 Hz, 2H), 2.80 (s, 2H), 2.65 (t, J=12.0 Hz, 1H), 1.74 (d, J=12.3 Hz, 2H), 1.42 (s, 11H). LCMS-A: rt 6.834 min; m/z 457 [M+H]$^+$.

Key intermediate 6: 2-(2-(2-(2-Chloro-5-methylpyrimidin-4-yl)ethyl)phenyl)acetamide (K6)

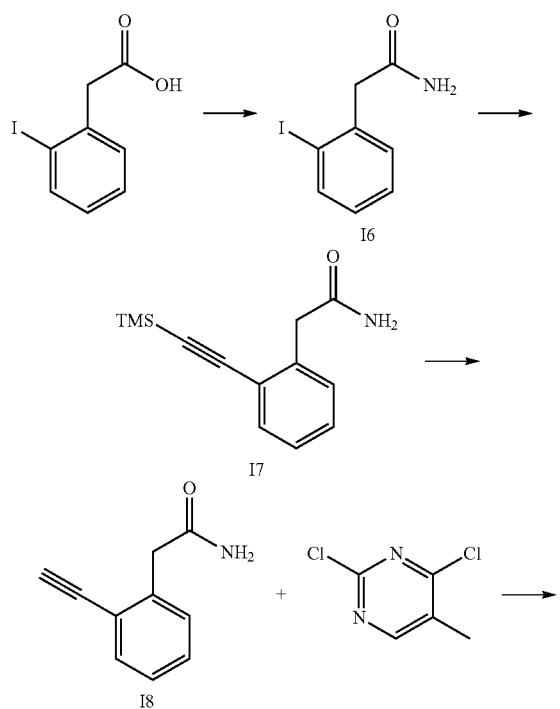

(a) 2-(2-Iodophenyl)acetamide (I6)

A solution of 2-iodophenylacetic acid (20.5 g, 78.2 mmol) in thionyl chloride (70 mL) was stirred at 75° C. for 3 hours. The thionyl chloride was removed in vacuo and the resulting residue was dissolved in DCM (100 mL). Ammonium carbonate (15.03 g, 156.5 mmol) was added and the resulting mixture was stirred at 60° C. for 20 hours. The volatiles were evaporated in vacuo, water (100 mL) was added and the resulting suspension was sonicated for 1 minute, before filtering and washing the filter cake with water then Et$_2$O. After air drying, the title compound I6 was obtained as a light cream coloured solid (12.9 g, 63%); $^1$H NMR (300 MHz, d$_6$-DMSO) δ 7.82 (d, J=8.3 Hz, 1H), 7.41 (brs s, 1H), 7.30-7.37 (m, 2H), 6.95-7.01 (m, 2H), 3.55 (s, 2H). LCMS-B: rt 5.108 min; m/z 262 [M+H]$^+$.

(b) 2-(2-((Trimethylsilyl)ethynyl)phenyl)acetamide (I7)

A mixture of 2-(2-iodophenyl)acetamide (I6) (12.91 g, 49.52 mmol), Et$_3$N (26 mL), ethynyltrimethylsilane (9.08 mL, 64.3 mmol), PdCl$_2$(PPh$_3$)$_2$ (0.347 g, 0.495 mmol) and CuI (0.188 g, 0.989 mmol) in DMF (44 mL) was stirred under a nitrogen atmosphere at 50° C. for 3 hours. The volatiles were removed in vacuo and the resulting residue partitioned between EtOAc (100 mL) and water. The aqueous phase was extracted with EtOAc (3×50 mL), then the combined organic extracts were washed with water (3×70 mL), brine, dried (MgSO$_4$), filtered and evaporated in vacuo to give the title compound I7 as a brown solid (11.4 g, 99%); $^1$H NMR (300 MHz, d$_6$-DMSO) δ 7.40 (d, J=7.5 Hz, 1H), 7.20-7.36 (m, 4H), 6.94 (brs, 1H), 3.58 (s, 2H), 0.24 (s, 9H). LCMS-B: rt 6.884 min; m/z 232 [M+H]$^+$.

(c) 2-(2-Ethynylphenyl)acetamide (I8)

A 1.0 M solution of TBAF in THF (59.1 mL, 59.1 mmol) was slowly added to a cooled (5° C. water/ice bath) solution of 2-(2-((trimethylsilyl)ethynyl)phenyl)acetamide (I7) (11.4 g, 49.3 mmol) in DCM (150 mL) and acetic acid (3.66 mL, 64.1 mmol). The mixture was stirred at 5° C. for 1 hour before 10% aqueous NaHCO₃ solution (150 mL) was added. The resulting mixture was extracted with DCM (3×50 mL) then the combined organics were dried (MgSO₄), filtered and evaporated in vacuo until approximately 15 mL of solvent remained. This solution was diluted with Et₂O (100 mL) and EtOAc (100 mL) resulting in the formation of a precipitate, which was filtered and dried to give 2.81 g of the title compound I8 as a brown solid. The remaining filtrate was adsorbed onto silica gel and purified using column chromatography (CombiFlash Rf, 80 g SiO₂ Cartridge, 0-10% MeOH in DCM). An additional 2.62 g of the title compound I8 was isolated as a brown solid (combined total 5.43 g, 69%); $^1$H NMR (300 MHz, d₆-DMSO) δ 7.44 (d, J=7.5 Hz, 1H), 7.21-7.37 (m, 4H), 6.93 (brs, 1H), 4.32 (s, 1H), 3.59 (s, 2H). LCMS-B: rt 4.734 min; m/z 160 [M+H]⁺.

(d) 2-(2-((2-Chloro-5-methylpyrimidin-4-yl)ethynyl)phenyl)acetamide (I9)

A mixture of 2-(2-ethynylphenyl)acetamide (I8) (5.40 g, 33.9 mmol), 2,4-dichloro-5-methylpyrimidine (6.63 g, 40.7 mmol) and CuI (0.129 g, 0.678 mmol) in 1,4-dioxane (180 mL) and Et₃N (14.2 mL, 101 mmol) was placed under nitrogen. PdCl₂(PPh₃)₂ (0.238 g, 0.339 mmol) was added and the resulting mixture was stirred at 70° C. for 20 minutes, then adsorbed onto silica gel and purified by column chromatography (CombiFlash Rf, 120 g SiO₂ Cartridge, 0-5% MeOH in DCM) to give the title compound I9 as a yellow solid (5.01 g, 51%); $^1$H NMR (300 MHz, d₆-DMSO) δ 8.75 (s, 1H), 7.67 (d, J=7.5 Hz, 1H), 7.35-7.52 (m, 4H), 6.97 (brs, 1H), 3.71 (s, 2H), 2.42 (s, 3H). LCMS-B: rt 5.689 min; m/z 286 [M+H]⁺.

(e) 2-(2-(2-(2-Chloro-5-methylpyrimidin-4-ylethyl)phenyl)acetamide (K6)

A suspension of 2-(2-((2-chloro-5-methylpyrimidin-4-yl)ethynyl)phenyl)acetamide (I9) (5.01 g, 17.5 mmol) in DMF (231 mL) and MeOH (80 mL) containing platinum oxide (0.995 g, 4.38 mmol) was stirred under a hydrogen atmosphere for 40 hours. The resulting mixture was filtered through a pad of Celite and the filtrate concentrated in vacuo. The resulting residue was diluted with ice water (400 mL) to give a precipitate, which was filtered and dried to give the title compound K6 (4.23 g, 83%); $^1$H NMR (300 MHz, d₆-DMSO) δ 8.47 (s, 1H), 7.44 (brs, 1H), 7.21-7.24 (m, 1H), 7.12-7.15 (m, 3H), 6.92 (brs, 1H), 3.47 (s, 2H), 2.99 (s, 4H), 2.15 (s, 3H). LCMS-B: rt 5.528 min; m/z 290 [M+H]⁺.

Key intermediate 7: Methyl 2-(2-((2-chloro-5-methylpyrimidin-4-yl)ethynyl)phenyl)acetate (K7)

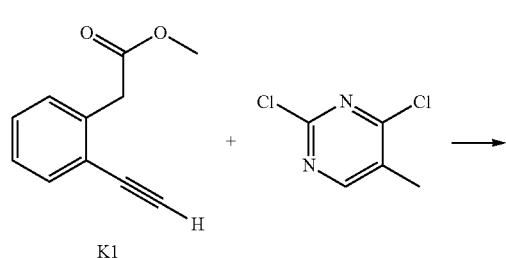

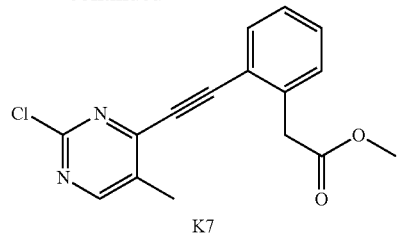

PPh₃ (31 mg, 0.12 mmol), PdCl₂(PPh₃)₂ (84 mg, 0.12 mmol), Et₃N (0.67 mL, 4.8 mmol) and methyl 2-(2-ethynylphenyl)acetate (K1) (0.25 g, 1.4 mmol) were added to a solution of 2,4-dichloro-5-methylpyrimidine (0.20 g, 1.2 mmol) in anhydrous DMF (5.0 mL). The solution was degassed with nitrogen for 10 minutes before the addition of CuI (23 mg, 0.12 mmol). The resulting mixture was heated under microwave irradiation at 120° C. for 15 minutes then diluted with EtOAc (30 mL) and filtered through Celite. The filtrate was evaporated under reduced pressure and the resulting residue adsorbed onto silica gel and purified by column chromatography (Biotage Isolera, 40 g SiO₂ cartridge, 0-35% EtOAc in petroleum benzine 40-60° C.) to give the title compound K7 as a yellow solid (0.28 g, 78%); $^1$H NMR (400 MHz, CDCl₃) δ 8.49 (s, 1H), 7.66 (d, J=7.7 Hz, 1H), 7.46-7.40 (m, 1H), 7.39-7.31 (m, 2H), 3.93 (s, 2H), 3.71 (s, 3H), 2.45 (s, 3H). LCMS-A: rt 5.993 min; m/z 301 [M+H]⁺.

Example 1

Synthesis of 2-(2-(2-(2-((4-(piperazin-1-yl)phenyl)amino)pyrimidin-4-yl)ethyl)phenyl)acetamide (1)

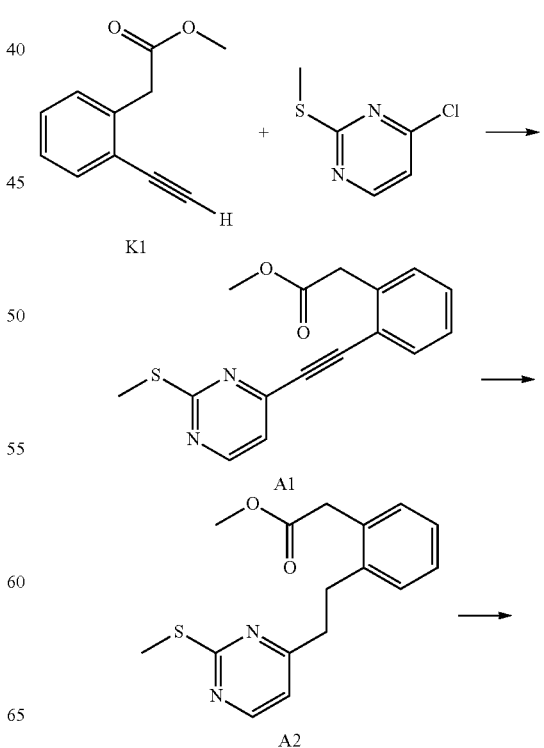

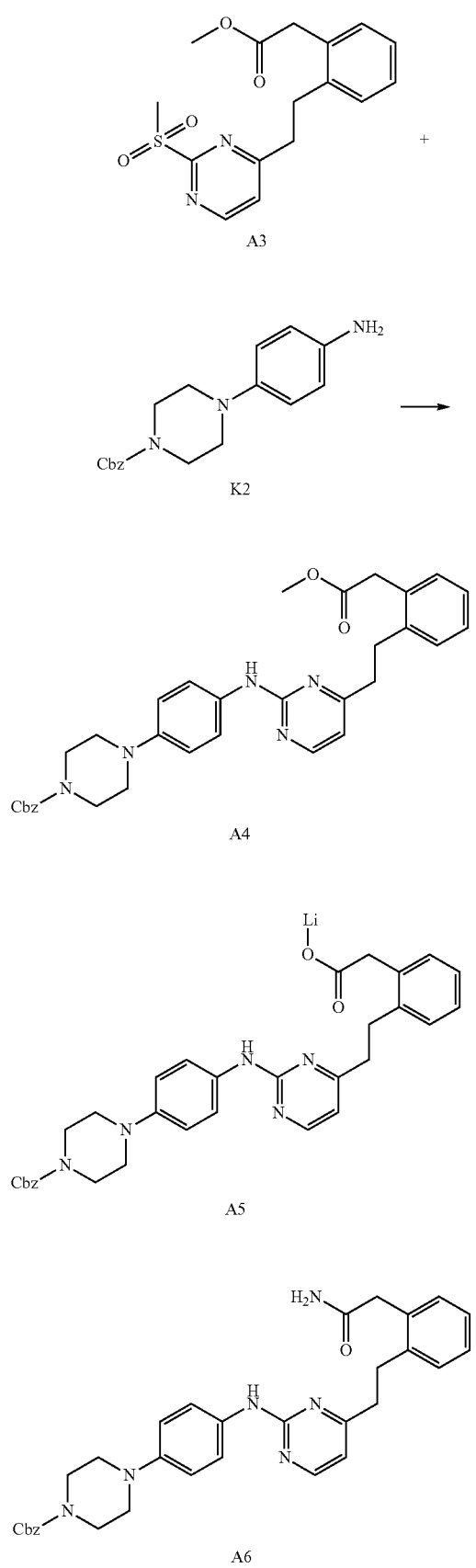

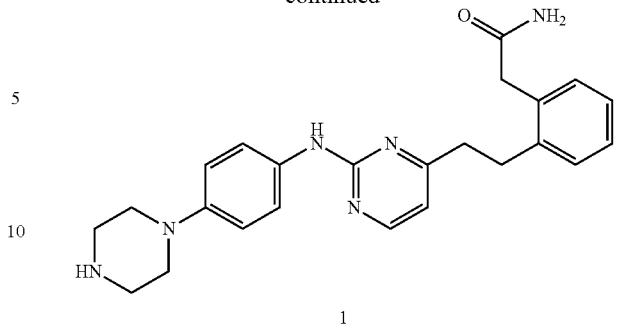

(a) Methyl 2-(2-((2-(methylthio)pyrimidin-4-yl)ethynyl)phenyl)acetate (A1)

A suspension of 4-chloro-2-methylthiopyrimidine (200 μL, 1.72 mmol), PdCl$_2$(PPh$_3$)$_2$ (121 mg, 0.172 mmol), CuI (33.0 mg, 0.172 mmol), PPh$_3$ (45.0 mg, 0.172 mmol), methyl 2-(2-ethynyl phenyl)acetate (K1) (359 mg, 1.08 mmol) and Et$_3$N (0.938 mL) in THF (6 mL) was heated at 100° C. under microwave irradiation for 10 minutes. The volatiles were removed in vacuo and the resultant residue adsorbed onto silica gel and purified by column chromatography (Biotage Isolera, SiO$_2$ cartridge, 0-40% EtOAc in petroleum benzine 40-60° C., then Biotage Isolera, SiO$_2$ cartridge, 0-40% EtOAc in DCM) to give the title compound A1 as a yellow oil (323 mg, 63%); $^1$H NMR (400 MHz, CDCl$_3$) δ 8.50 (d, J=5.0 Hz, 1H), 7.63 (dd, J=7.6, 1.1 Hz, 1H), 7.44-7.29 (m, 3H), 7.12 (d, J=5.0 Hz, 1H), 3.92 (s, 2H), 3.71 (s, 3H), 2.59 (s, 3H).

(b) Methyl 2-(2-(2-(2-(methylthio)pyrimidin-4-yl)ethyl)phenyl)acetate (A2)

A suspension of methyl 2-(2-((2-(methylthio)pyrimidin-4-yl)ethynyl)phenyl)acetate (A1) (323 mg, 1.08 mmol) and 10% Pd/C (300 mg) in DMF (15 mL) was stirred under a hydrogen atmosphere at room temperature for 20 hours. The resulting mixture was filtered through Celite, washing with EtOAc (100 mL). The filtrate was evaporated in vacuo to yield a brown oil which was dissolved in DMF (10 mL). A slurry of 10% Pd/C (330 mg) in DMF (5 ml) was added and the resulting suspension was stirred under a hydrogen atmosphere at room temperature for a further 20 hours. The resulting mixture was filtered through Celite, washing with EtOAc (100 mL) then the filtrate was evaporated in vacuo. The resulting residue was adsorbed onto silica gel and purified by column chromatography (Biotage Isolera, 12 g SiO$_2$ cartridge, 0-20% EtOAc in petroleum benzine 40-60° C.) to yield the title compound A2 as a clear oil (170 mg, 52%); $^1$H NMR (400 MHz, CDCl$_3$) δ 8.36 (d, J=5.0 Hz, 1H), 7.25-7.14 (m, 4H), 6.75 (d, J=5.1 Hz, 1H), 3.69 (m, 5H), 3.11-3.04 (m, 2H), 2.99-2.91 (m, 2H), 2.57 (s, 3H). LC-MS-A: rt 6.060 min; m/z 303.1 [M+H]$^+$.

(c) Methyl 2-(2-(2-(2-(methylsulfonyl)pyrimidin-4-yl)ethyl)phenyl)acetate (A3)

m-CPBA (70%; 174 mg, 1.01 mmol) was added to a solution of methyl 2-(2-(2-(2-(methylthio)pyrimidin-4-yl)ethyl)phenyl)acetate (A2) (170 mg, 0.458 mmol) in DCM (50 mL) at 0° C. The resulting mixture was stirred at 0° C. for 1 hour, then warmed to room temperature and stirred for a further 18 hours. The temperature was reduced to 0° C. and additional m-CPBA (70%; 174 mg, 1.01 mmol) was added. After warming to room temperature, stirring was continued for a further 3 hours then 10% aqueous NaHCO$_3$ (50 mL) was added. The layers were separated and the organics were dried (MgSO$_4$), evaporated under reduced pressure and adsorbed onto silica gel and purified by column chromatography (Biotage Isolera, SiO$_2$ cartridge, 0-100% EtOAc in petroleum benzine 40-60° C.) to give the title compound A3 as a clear oil (150 mg, 80%); $^1$H NMR (400 MHz, CDCl$_3$) δ 8.73 (d, J=5.1 Hz, 1H), 7.31 (d, J=5.1 Hz, 1H), 7.24-7.21 (m, 1H), 7.21-7.18 (m, 2H), 7.14-7.09 (m, 1H), 3.70 (s, 3H), 3.68 (s, 2H), 3.35 (s, 3H), 3.23-3.17 (m, 2H), 3.17-3.11 (m, 2H).

(d) Benzyl 4-(4-((4-(2-(2-methoxy-2-oxoethyl)phenethyl)pyrimidin-2-yl)amino)phenyl)piperazine-1-carboxylate (A4)

A solution of methyl 2-(2-(2-(2-(methylsulfonyl)pyrimidin-4-yl)ethyl)phenyl)acetate (A3) (150 mg, 449 μmol) and benzyl 4-(4-aminophenyl)piperazine-1-carboxylate (K2) (168 mg, 538 μmol) in TFE (5 mL) containing TFA (180 μL) was heated at 100° C. under microwave irradiation for 60 minutes. Additional TFA (200 μL) was added and the resulting solution heated at 120° C. under microwave irradiation for a further 40 minutes. Additional TFA (200 μL) was again added and the mixture was heated at 150° C. under microwave irradiation for a further 20 minutes. The resulting mixture was adsorbed onto silica gel and purified by column chromatography (Biotage Isolera, SiO$_2$ cartridge, 0-100% EtOAc in petroleum benzine 40-60° C.) to give the title compound A4 as a brown oil (76 mg, 30%). LCMS-A: rt 6.212 min; m/z 566.2 [M+H]$^+$.

(e) 2-(2-(2-(2-((4-(4-(Benzyloxy)carbonyl)piperazin-1-yl)phenyl)amino)pyrimidin-4-yl)ethyl)phenyl)acetic acid (A5)

LiOH.H$_2$O (40 mg, 0.93 mmol) was added to a solution of benzyl 4-(4-((4-(2-(2-methoxy-2-oxoethyl)phenethyl)pyrimidin-2-yl)amino)phenyl)piperazine-1-carboxylate (A4) (76 mg, 0.13 mmol) in THF (7 mL), water (1.5 mL) and MeOH (1 mL) and the resulting mixture was stirred at room temperature for 16 hours. The volatiles were removed in vacuo and the resultant residue was diluted with EtOAc (50 mL) and saturated aqueous NaHCO$_3$ (50 mL). The layers were separated and the aqueous layer was extracted with EtOAc (2×50 mL). The organic layers were combined, washed with brine (50 mL), dried over MgSO$_4$, filtered and concentrated under reduced pressure to give the title compound A5 as yellow oil; LCMS-A: rt 5.803 min; m/z 552.1 [M+H]$^+$.

(f) Benzyl 4-(4-((4-(2-(2-amino-2-oxoethyl)phenethyl)pyrimidin-2-yl)amino)phenyl)piperazine-1-carboxylate (A6)

HOBt (24 mg, 0.17 mmol), EDCl.HCl (33 mg, 0.17 mmol) and DIPEA (0.12 mL, 0.67 mmol) were added to a stirred solution of 2-(2-(2-(2-((4-(4-((benzyloxy)carbonyl)piperazin-1-yl)phenyl)amino)pyrimidin-4-yl)ethyl)phenyl)acetic acid (A5) (74 mg, 0.13 mmol) in dry THF (5 mL) and dry DMF (2 mL) under an atmosphere of nitrogen. After 10 minutes ammonium carbonate (65 mg, 0.67 mmol) was added and stirring was continued at room temperature for 18 hours. The volatiles were removed in vacuo and the residue was diluted with EtOAc (65 mL) and saturated NaHCO$_3$ (65 mL). The aqueous layer was extracted with EtOAc (2×50 mL) then the combined organic layers were washed with brine (50 mL) and dried over Na$_2$SO$_4$. After filtration the solvent was removed in vacuo to afford a pale yellow solid which was purified by silica gel column chromatography (Biotage Isolera, SiO$_2$ cartridge, 0-100% EtOAc in petroleum benzine 40-60° C.) to give the title compound A6 as brown oil (70 mg, 95%); $^1$H-NMR (400 MHz, CDCl$_3$) δ 8.20 (s, 1H), 7.64 (s, 1H), 7.48 (d, J=8.9 Hz, 2H), 7.37 (d, J=4.3 Hz, 4H), 7.32 (m, 1H), 7.25-7.17 (m, 4H), 6.91 (d, J=9.0 Hz, 2H), 6.51 (d, J=4.9 Hz, 1H), 5.77 (s, 1H), 5.51 (s, 1H), 5.16 (s, 2H), 3.69-3.64 (m, 4H), 3.64 (s, 2H), 3.11-3.06 (m, 4H), 3.05 (dd, J=9.6, 6.5 Hz, 2H), 2.91-2.84 (m, peak obscured), 2.07 (t, J=7.0 Hz 1H). LCMS-A: rt 5.646 min; m/z 551.2 [M+H]$^+$.

(g) 2-(2-(2-(2-((4-(piperazin-1-yl)phenyl)amino)pyrimidin-4-yl)ethyl)phenyl)acetamide (1)

To a solution of benzyl 4-(4-((4-(2-(2-amino-2-oxoethyl)phenethyl)pyrimidin-2-yl)amino)phenyl)piperazine-1-carboxylate (A6) (73 mg, 0.13 mmol) in DMF (5 mL) under nitrogen, was added a slurry of 10% Pd/C (20 mg) in DMF. The resulting mixture was stirred under an atmosphere of hydrogen at room temperature for 19 hours then filtered through a 2.0 PFTE filter. The filtrate was evaporated in vacuo and the residue was loaded onto a SCX (5 g) column using MeOH. The column was washed with 2 column volumes of MeOH followed by 3 column volumes of 1% MeNH$_2$ in MeOH. The 1% MeNH$_2$ in MeOH filtrate was evaporated in vacuo to give a pale brown oil which was taken up in DCM (0.5 mL) and cyclohexane (1 mL) and sonicated. The resulting precipitate was filtered and the filter cake dried in vacuo to give the title compound 1 as a white solid (1.4 mg, 90% purity). $^1$H-NMR: (400 MHz, d$_4$-MeOH) δ 8.22-8.16 (m, 1H), 7.57-7.48 (m, 2H), 7.20 (m, 4H), 7.01-6.93 (m, 2H), 6.60 (dd, J=5.0, 2.8 Hz, 1H), 3.63 (d, J=2.3 Hz, 2H), 3.18-3.12 (m, 4H), 3.09 (dd, J=9.2, 6.4 Hz, 5H), 2.93-2.83 (m, 3H). LC-MS Method A: rt 4.305 min; m/z 417.2 [m+H]$^+$.

Example 2

Synthesis of 2-(2-(2-(5-methyl-2-((4-(piperazin-1-yl)phenyl)amino)pyrimidin-4-yl)ethyl)phenyl)acetamide (2)

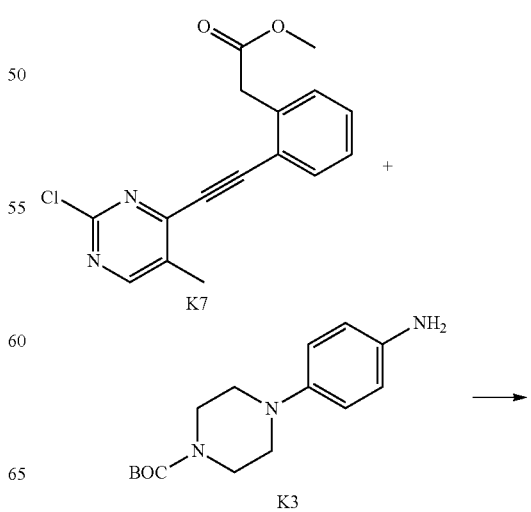

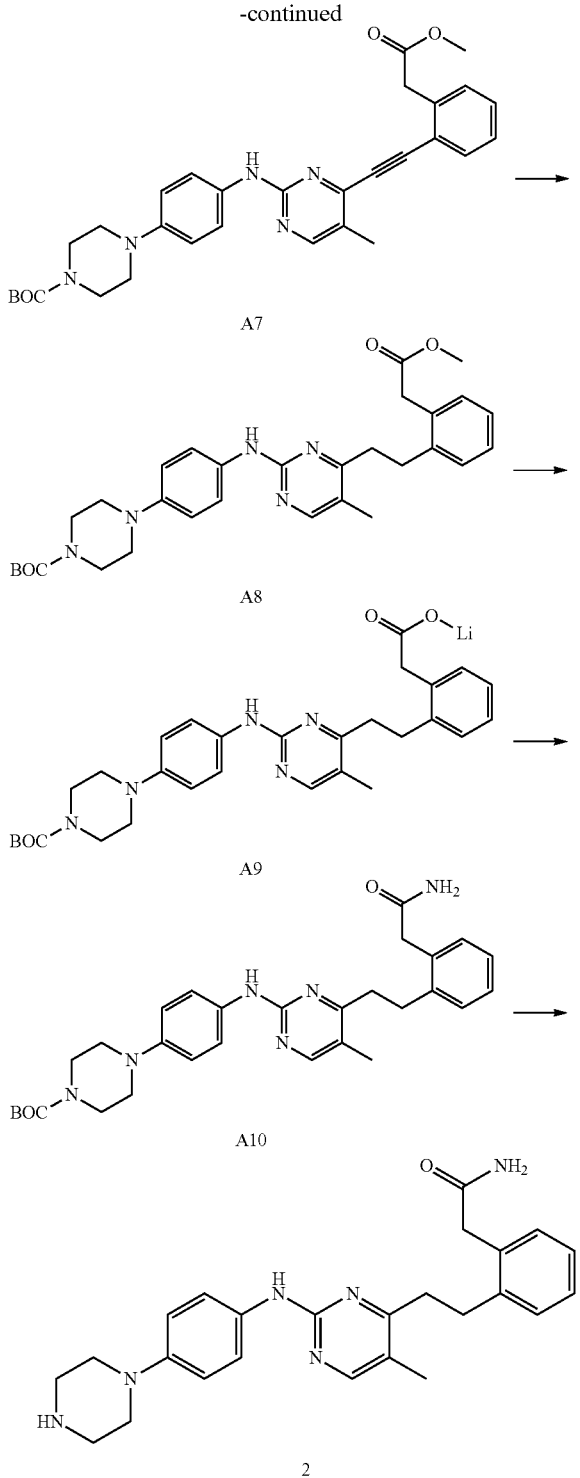

(a) tert-Butyl 4-(4-((4-((2-(2-methoxy-2-oxoethyl)phenyl)ethynyl)-5-methylpyrimidin-2-yl)amino)phenyl)piperazine-1-carboxylate (A7)

A mixture of tert-Butyl 4-(4-aminophenyl)piperazine-1-carboxylate (K3) (0.845 g, 3.06 mmol), methyl 2-(2-((2-chloro-5-methylpyrimidin-4-yl)ethynyl)phenyl)acetate (K7) (0.460 g, 1.53 mmol), Pd$_2$(dba)$_3$ (0.070 g, 0.076 mmol), Xantphos (0.089 g, 0.15 mmol), and Na$_2$CO$_3$ (0.648 g, 6.12 mmol) in DME (16 mL) was degassed with nitrogen before heating under microwave irradiation for 30 minutes at 110° C., then a further 60 minutes at 110° C. An additional 0.1 equivalent of Pd$_2$(dba)$_3$ and 0.1 equivalent of Xantphos were added before the solution was degassed with nitrogen for 5 minutes and heated under microwave irradiation for 60 minutes at 110° C. The resulting mixture was filtered and the filtrate evaporated in vacuo to give a dark brown residue which was adsorbed onto silica gel and purified by column chromatography (Biotage Isolera, 40 g SiO$_2$ cartridge, 0-100% MeOH in EtOAc), to yield the title compound A7 as brown oil (66 mg, 8%); $^1$H NMR (400 MHz, CDCl$_3$) δ 8.27 (s, 1H), 7.66 (d, J=7.6 Hz, 1H), 7.53-7.46 (m, 2H), 7.44-7.28 (m, 4H), 6.94 (dd, J=7.2, 5.1 Hz, 2H), 3.96 (s, 2H), 3.70 (s, 3H), 3.58 (dd, J=11.4, 6.2 Hz, 4H), 3.11-3.04 (m, 4H), 2.33 (s, 3H), 1.49 (s, 9H). LC-MS-A: rt 6.409 min; m/z 542 [M+H]$^+$.

(b) tert-Butyl 4-(4-((4-(2-(2-methoxy-2-oxoethyl)phenethyl)-5-methylpyrimidin-2-yl)amino)phenyl)piperazine-1-carboxylate (A8)

To a solution of tert-butyl 4-(4-((4-((2-(2-methoxy-2-oxoethyl)phenyl)ethynyl)-5-methylpyrimidin-2-yl)amino)phenyl)piperazine-1-carboxylate (A7) (60 mg, 0.11 mmol) in anhydrous DMF (10 mL) was added a slurry of 10% Pd/C (30 mg) in DMF (2 mL). The resulting mixture was stirred at room temperature under an atmosphere of hydrogen for 72 hours then diluted with EtOAc (30 mL) and filtered through a plug of Celite, washing with EtOAc (50 mL). The filtrate was evaporated to dryness to give the title compound A8 as a brown oily residue (44 mg, 73%); $^1$H NMR (400 MHz, CDCl$_3$) δ 8.06 (s, 1H), 7.52 (dt, J=8.0, 2.5 Hz, 2H), 7.25-7.17 (m, 4H), 6.92 (dd, J=7.2, 5.1 Hz, 2H), 6.88 (s, 1H), 3.72 (s, 2H), 3.68 (d, J=3.0 Hz, 3H), 3.61-3.56 (m, 4H), 3.07 (dd, J=9.3, 5.1 Hz, 6H), 2.06 (s, 3H), 1.48 (s, 9H). LC-MS-A: rt 6.260 min; m/z 546.2 [M+H]$^+$.

(c) 2-(2-(2-(2-((4-(4-(tert-Butoxycarbonyl)piperazin-1-yl)phenyl)amino)-5-methylpyrimidin-4-yl)ethyl)phenyl)acetic acid (A9)

LiOH.H$_2$O (24 mg, 0.56 mmol) was added to a solution of tert-butyl 4-(4-((4-(2-(2-methoxy-2-oxoethyl)phenethyl)-5-methylpyrimidin-2-yl)amino)phenyl)piperazine-1-carboxylate (A8) (44 mg, 0.081 mmol) in THF (7 mL), water (1.5 mL) and MeOH (1 mL) and the resulting mixture was stirred at room temperature for 24 hours. The volatiles were removed in vacuo and the resulting residue was diluted with EtOAc (50 mL) and saturated aqueous NaHCO$_3$ (50 mL). The layers were separated and the aqueous layer was extracted with EtOAc (2×50 mL). The organic layers were combined, washed with brine (50 mL), dried over MgSO$_4$, filtered and concentrated under reduced pressure to give the title compound A9 as brown oily residue (36 mg, 84%); LCMS-A: rt 5.737 min; m/z 532.2 [M+H]$^+$.

(d) tert-Butyl 4-(4-((4-(2-(2-amino-2-oxoethyl)phenethyl)-5-methylpyrimidin-2-yl)amino)phenyl)piperazine-1-carboxylate (A10)

HOBt (15 mg, 0.11 mmol), EDCl.HCl (21 mg, 0.11 mmol) and DIPEA (72 μL, 0.41 mmol) were added to a solution of 2-(2-(2-(2-((4-(4-(tert-butoxycarbonyl)piperazin-1-yl)phenyl)amino)-5-methylpyrimidin-4-yl)ethyl)phenyl)acetic acid (A9) (44 mg, 0.083 mmol) in dry DMF (10 mL) under an atmosphere of nitrogen. After 10 minutes ammonium carbonate (40 mg, 0.41 mmol) was added and the resulting mixture was stirred at room temperature for 18 hours. A solution of HOBt (15 mg, 0.11 mmol), EDCl.HCl (21 mg, 0.11 mmol) and DIPEA in DMF (3 mL) was then added and after 10 minutes ammonium carbonate (40 mg, 0.41 mmol) was added in one portion. The resulting mixture was stirred at 26° C. for a further 24 hours before the volatiles were removed in vacuo and the residue partitioned between EtOAc (65 mL) and saturated NaHCO$_3$ (65 mL). The aqueous layer was extracted with EtOAc (2×50 mL) then the combined organics were washed with brine (50 mL) and dried over Na$_2$SO$_4$. After filtration the solvent was removed in vacuo to afford a pale yellow solid which was adsorbed onto silica gel and purified by column chromatography (Biotage Isolera, SiO$_2$ cartridge, 0-100% EtOAc in petroleum benzine 40-60° C. then 0-100% MeOH in EtOAc). After removing the solvent in vacuo the resulting residue was taken up in EtOAc, filtered through cotton wool and the filtrate evaporated to dryness to give the title compound A10 as a light brown solid (28 mg, 64%); $^1$H NMR (400 MHz, CDCl$_3$) δ 8.05 (s, 1H), 7.47-7.41 (m, 2H), 7.25-7.17 (m, 4H), 7.13 (s, 1H), 6.93-6.88 (m, 2H), 5.59 (s, 1H), 5.53 (s, 1H), 3.65 (s, 2H), 3.61-3.55 (m, 4H), 3.10-3.01 (m, 6H), 2.92-2.88 (m, 2H), 2.08 (s, 3H), 1.48 (s, 9H). LCMS-A: rt 5.525 min; m/z 531.2 [M+H]$^+$ (e) 2-(2-(2-(5-Methyl-2-((4-(piperazin-1-yl)phenyl)amino)pyrimidin-4-yl)ethyl)phenyl)acetamide (2)

To a solution of tert-butyl 4-(4-((4-(2-(2-amino-2-oxoethyl)phenethyl)-5-methylpyrimidin-2-yl)amino)phenyl)piperazine-1-carboxylate (A10) (28 mg, 0.053 mmol) in DCM (8 mL) was added TFA (2 mL) and the resulting solution was stirred at 25° C. for 24 hours. The volatiles were removed in vacuo and the residue was partitioned between EtOAc (10 mL) and 2 M NaOH (20 mL). The aqueous layer was extracted with EtOAc (2×10 mL) then the combined organic layers washed with brine (10 mL) and dried (MgSO$_4$). The solvent was removed in vacuo to give a brown solid which was taken up in MeOH and purified by SCX cartridge (5 g, MeOH followed by 0.5 M NH$_3$ in MeOH). The volatiles from the ammoniacal filtrate were removed in vacuo and the resulting solid residue suspended in cyclohexane and sonicated. The resulting suspension was filtered and the filter cake dried to give the title compound 2 as a light brown solid (8 mg, 35%); $^1$H NMR (400 MHz, d$_6$-DMSO) δ 9.08 (s, 1H), 8.11 (s, 1H), 7.60 (dd, J=9.2, 2.2 Hz, 2H), 7.41 (s, 1H), 7.26-7.20 (m, 1H), 7.19-7.13 (m, 3H), 6.92 (s, 1H), 6.85 (d, J=9.1 Hz, 2H), 4.02 (s, 1H), 3.50 (s, 2H), 3.03 (dd, J=10.1, 5.7 Hz, 2H), 2.97 (m, 2H), 2.85 (m, 4H), 2.69-2.64 (m, 2H), 2.36-2.30 (m, 2H), 2.05 (s, 3H). LCMS-A: rt 4.364 min; m/z 431.1 [M+H]$^+$.

Example 3

Synthesis of 2-(2-(2-(2-((4-(aminomethyl)phenyl)amino)-5-(trifluoromethyl)pyrimidin-4-yl)ethyl)phenyl)acetamide (3)

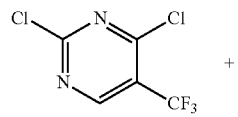

+

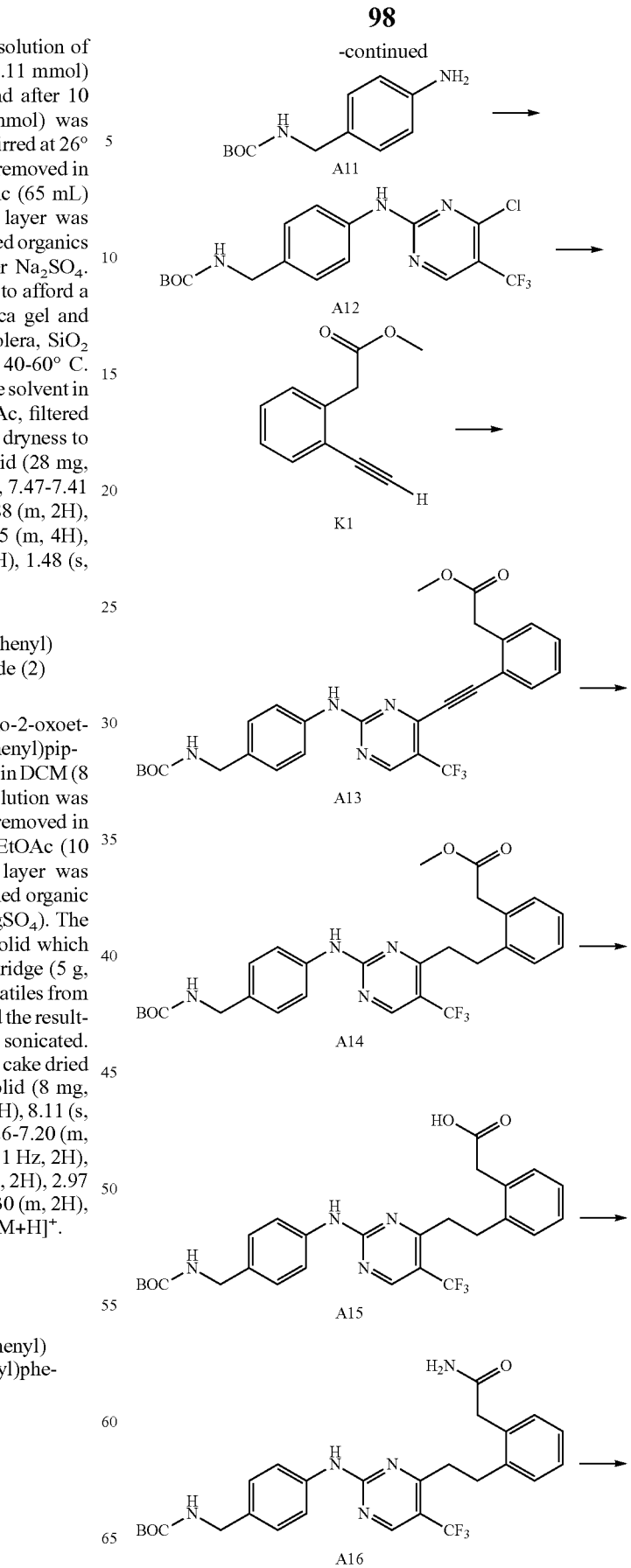

-continued

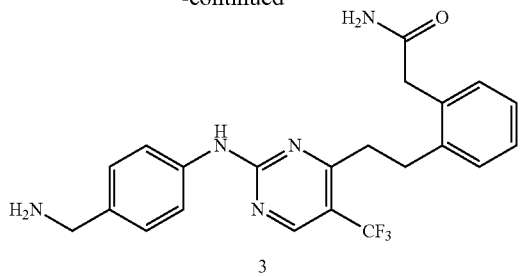

3

(a) tert-Butyl 4-aminobenzylcarbamate (A11)

Boc anhydride (4.46 g, 20.5 mmol) was added to a stirred solution of 4-aminobenzylamine (2.50 g, 20.5 mmol) and Et$_3$N (5.70 mL, 40.9 mmol) in DCM (100 mL) at room temperature. The resulting mixture was stirred overnight before the volatiles were removed in vacuo. The residue was adsorbed onto silica gel and purified by column chromatography (Biotage Isolera, SiO$_2$ cartridge, 0-100% EtOAc in petroleum benzine 40-60° C.) to yield the title compound A11 as a yellow solid (4.28 g, 94%); $^1$H NMR (400 MHz, CDCl$_3$) δ 7.09 (d, J=8.2 Hz, 2H), 6.69-6.64 (m, 2H), 4.73 (s, 1H), 4.21 (d, J=5.4 Hz, 2H), 3.66 (s, 2H), 1.48 (s, 9H). LCMS-A: rt 4.363 min.

(b) tert-Butyl 4-((4-chloro-5-(trifluoromethyl)pyrimidin-2-yl)amino)benzylcarbamate (A12)

A 1.0 M ZnCl$_2$ solution in Et$_2$O (5.40 mL, 5.40 mmol) was added cautiously to a stirred suspension of 2,4-dichloro-5-(trifluoromethyl)pyrimidine (1.03 g, 4.72 mmol) in 1:1 t-BuOH:DCE (200 mL) at room temperature. After stirring for 20 minutes, tert-butyl 4-aminobenzylcarbamate (A11) (1.00 g, 4.50 mmol) was added followed by Et$_3$N (752 µL, 5.40 mmol) and the resulting mixture stirred at room temperature overnight. The volatiles were removed in vacuo and the resulting tan solid was suspended in water (500 mL). The suspension was sonicated for 10 minutes, filtered and the filter cake was washed with water (2×100 mL) then dried under high vacuum to give the title compound A12 as a tan solid (1.77 g, 97%); $^1$H NMR (400 MHz, d$_6$-DMSO) δ 10.63 (s, 1H), 8.79 (s, 1H), 7.61 (d, J=8.1 Hz, 2H), 7.36 (t, J=7.6 Hz, 1H), 7.22 (d, J=8.4 Hz, 2H), 4.10 (d, J=6.0 Hz, 2H), 1.40 (s, 9H). LCMS-A: rt 6.356 min; m/z 401 [M−1]$^−$.

(c) Methyl 2-(2-((2-((4-(((tert-butoxycarbonyl)amino)methyl)phenyl)amino)-5-(trifluoromethyl)pyrimidin-4-yl)ethynyl)phenyl)acetate (A13)

A suspension of tert-butyl 4-((4-chloro-5-(trifluoromethyl)pyrimidin-2-yl)amino)benzylcarbamate (A12) (500 mg, 1.24 mmol), CuI (12 mg, 0.06 mmol), PPh$_3$ (16 mg, 0.06 mmol), and Et$_3$N (346 µL, 2.28 mmol) in DMF (3 mL) was sonicated for 5 minutes before the addition of PdCl$_2$(PPh$_3$)$_2$ (44 mg, 0.06 mmol) and methyl 2-(2-ethynylphenyl)acetate (K1) (324 mg, 1.86 mmol). The resulting mixture was heated under microwave irradiation at 120° C. for 20 minutes then adsorbed onto silica gel and purified by column chromatography (Biotage Isolera, SiO$_2$ cartridge, 0-100% EtOAc in petroleum benzine 40-60° C.) to yield a yellow solid. The solid was suspended in toluene and the resulting suspension was sonicated for 10 minutes. The suspension was filtered and the filter cake dried to give the title compound A13 as a yellow solid (412 mg, 61%); $^1$H NMR (400 MHz, d$_6$-DMSO) δ 10.44 (s, 1H), 8.82 (s, 1H), 7.68 (d, J=8.4 Hz, 2H), 7.63 (d, J=7.6 Hz, 1H), 7.58-7.52 (m, 1H), 7.50-7.40 (m, 2H), 7.36 (t, J=6.0 Hz, 1H), 7.22 (d, J=8.5 Hz, 2H), 4.10 (d, J=6.0 Hz, 2H), 3.96 (s, 2H), 3.62 (s, 3H), 1.40 (s, 9H). LCMS-A: rt 6.497 min; m/z 539 [M−1]$^−$.

(d) Methyl 2-(2-(2-(2-((4-(((tert-butoxycarbonyl)amino)methyl)phenyl)amino)-5-(trifluoromethyl)pyrimidin-4-yl)ethyl)phenyl)acetate (A14)

A suspension of 10% Pd/C (200 mg) and methyl 2-(2-((2-((4-(((tert-butoxycarbonyl)amino)methyl)phenyl)amino)-5-(trifluoromethyl)pyrimidin-4-yl)ethynyl)phenyl)acetate (A13) (412 mg, 0.762 mmol) in DMF (5 mL) and Et$_3$N (1 mL) was stirred under a hydrogen atmosphere at room temperature for 16 h. The resulting mixture was filtered through Celite, washing with EtOAc (200 mL) then the combined filtrates were evaporated in vacuo to give the title compound A14 as a white solid (306 mg, 74%); $^1$H NMR (400 MHz, d$_6$-DMSO) δ 10.19 (s, 1H), 8.68 (s, 1H), 7.68 (d, J=8.5 Hz, 2H), 7.34 (t, J=6.0 Hz, 1H), 7.27-7.16 (m, 6H), 4.09 (d, J=6.0 Hz, 2H), 3.76 (s, 2H), 3.59 (s, 3H), 3.11-2.95 (m, 4H), 1.40 (s, 9H). LCMS-A: rt 6.637 min; m/z 545 [M+H]$^+$.

(e) 2-(2-(2-(2-((4-(((tert-Butoxycarbonyl)amino)methyl)phenyl)amino)-5-(trifluoromethyl)pyrimidin-4-yl)ethyl)phenyl)acetic acid (A15)

LiOH.H$_2$O (94 mg, 2.2 mmol) was added to a solution of methyl 2-(2-(2-(2-((4-(((tert-butoxycarbonyl)amino)methyl)phenyl)amino)-5-(trifluoromethyl)pyrimidin-4-yl)ethyl)phenyl)acetate (A14) (306 mg, 0.562 mmol) in MeOH (1 mL), water (1 mL) and THF (10 mL) and the resulting mixture was stirred at room temperature overnight. The volatiles were removed in vacuo and the resultant oil partitioned between EtOAc (150 mL) and 2 M aqueous NaOH (100 mL). The organic layer was separated, washed with water (2×100 mL), brine (50 mL) and dried over MgSO$_4$. The volatiles were removed in vacuo to yield the title compound A15 as a yellow oil (0.25 g, 83%); LCMS-A: rt 6.267 min; m/z 531 [M+H]$^+$.

(f) tert-Butyl 4-((4-(2-(2-amino-2-oxoethyl)phenethyl)-5-(trifluoromethyl)pyrimidin-2-yl)amino)benzylcarbamate (A16)

HOBt (76 mg, 0.56 mmol) and EDCl.HCl (108 mg, 0.561 mmol) were added to a solution of 2-(2-(2-(2-((4-(((tert-butoxycarbonyl)amino)methyl)phenyl)amino)-5-(trifluoromethyl)pyrimidin-4-yl)ethyl)phenyl)acetic acid (A15) (251 mg, 0.468 mmol) and DIPEA (326 µL, 1.87 mmol) in DMF (2 mL) and THF (10 mL). The resulting mixture was stirred at room temperature overnight then the volatiles were removed in vacuo and the residue partitioned between EtOAc (150 mL) and saturated aqueous NaHCO$_3$ (100 mL). The layers were separated and the organic layer was washed with water (100 mL), brine (50 mL) and dried over MgSO$_4$. The volatiles were removed in vacuo and the residue adsorbed onto silica gel and purified by silica gel column chromatography (Biotage Isolera, SiO$_2$ cartridge, 0-100% EtOAc in petroleum benzine 40-60° C.) to give the title compound A16 as a tan solid (0.22 g, 89%); $^1$H NMR (400 MHz, d$_6$-DMSO) δ 10.18 (s, 1H), 8.67 (s, 1H), 7.68 (d, J=8.5 Hz, 2H), 7.43 (s, 1H), 7.33 (t, J=6.0 Hz, 1H), 7.27-7.10 (m, 6H), 6.91 (s, 1H), 3.50 (s, 2H), 3.18 (d, J=5.3 Hz, 2H), 3.14-2.99 (m, 4H), 1.40 (s, 9H). LCMS-A: rt 6.086 min; m/z 530 [M+H]$^+$.

(g) 2-(2-(2-(2-((4-(Aminomethyl)phenyl)amino)-5-(trifluoromethyl)pyrimidin-4-yl)ethyl)phenyl)acetamide (3)

TFA (954 μL, 12.5 mmol) was added to a solution of tert-butyl 4-((4-(2-(2-amino-2-oxoethyl)phenethyl)-5-(trifluoromethyl)pyrimidin-2-yl)amino)benzylcarbamate (A16) (220 mg, 0.415 mmol) in DCM (10 mL) and the resulting mixture stirred for 20 hours at room temperature. The volatiles were removed in vacuo and the resulting residue partitioned between EtOAc (100 mL) and 2 M aqueous NaOH (100 mL). The layers were separated and the organic layer washed with water (100 mL), brine (50 mL), dried (MgSO$_4$) then evaporated in vacuo to yield a white solid. The solid was taken up in DCM (10 mL) and sonicated for 2 minutes then petroleum benzine 40-60° C. (100 mL) was added and sonication continued for a further 10 minutes. The resulting suspension was filtered and the filter cake dried to give the title compound 3 as a white solid (135 mg, 76%); $^1$H NMR (400 MHz, d$_4$-MeOH) δ 8.57 (s, 1H), 7.68 (d, J=8.6 Hz, 2H), 7.33 (d, J=8.8 Hz, 2H), 7.31-7.17 (m, 4H), 3.81 (s, 2H), 3.69 (s, 2H), 3.22-3.06 (m, 4H). LCMS-A: rt 4.722 min; m/z 428 [M−1]$^−$.

Example 4

Synthesis of 2-(2-(2-(5-methyl-2-((6-(piperidin-4-yl)pyridin-3-yl)amino)pyrimidin-4-yl)ethyl)phenyl)acetamide (4)

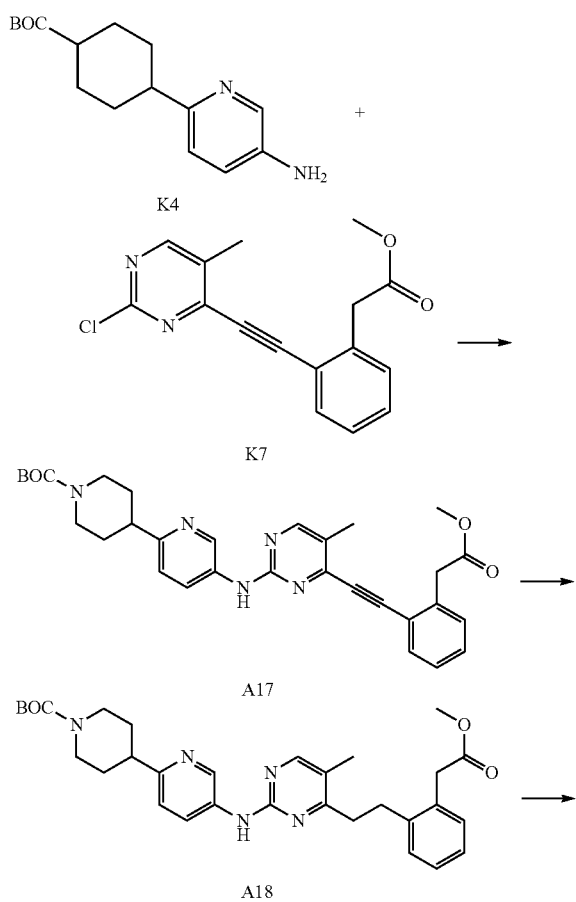

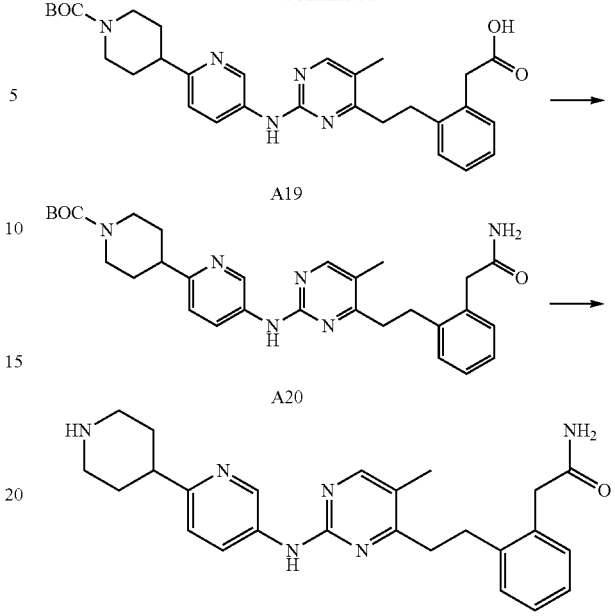

(a) tert-Butyl 4-(5-((4-((2-(2-methoxy-2-oxoethyl)phenyl)ethynyl)-5-methylpyrimidin-2-yl)amino)pyridin-2-yl)piperidine-1-carboxylate (A17)

To a solution of methyl 2-(2-((2-chloro-5-methylpyrimidin-4-yl)ethynyl)phenyl)acetate (K7) (100 mg, 0.333 mmol) in 1,4-dioxane (8 mL) was added tert-butyl 4-(5-aminopyridin-2-yl)piperidine-1-carboxylate (K4) (92.2 mg, 0.333 mmol), Cs$_2$CO$_3$ (433 mg, 1.33 mmol), Pd$_2$(dba)$_3$ (30 mg, 0.033 mmol) and Xantphos (58 mg, 0.10 mmol). The resulting mixture was degassed with nitrogen for 5 minutes before heating under microwave irradiation for 30 minutes at 120° C. The resulting mixture was diluted with EtOAc (100 mL) then washed with water (2×25 mL), brine (25 mL), dried (Na$_2$SO$_4$) and concentrated under reduced pressure. The residue was purified by silica gel column chromatography (Biotage Isolera, 40 g SiO$_2$ cartridge, 0-100% EtOAc in hexanes) to give the title compound A17 as a yellow foam (112 mg, 62%); $^1$H NMR (400 MHz, CDCl$_3$) δ 8.62 (d, J=2.4 Hz, 1H), 8.32 (d, J=0.6 Hz, 1H), 8.16 (dd, J=8.5, 2.7 Hz, 1H), 7.66 (dd, J=7.6, 0.9 Hz, 1H), 7.43-7.30 (m, 3H), 7.14 (d, J=8.5 Hz, 1H), 7.10 (s, 1H), 4.25 (br. s, 2H), 3.95 (s, 2H), 3.70 (s, 3H), 2.86-2.78 (m, 3H), 2.35 (d, J=0.4 Hz, 3H), 1.91 (d, J=13.3 Hz, 2H), 1.75-1.63 (m, 2H), 1.47 (s, 9H). LCMS-A: rt 5.462 min; m/z 542 [M+H]$^+$.

(b) tert-Butyl 4-(5-((4-(2-(2-methoxy-2-oxoethyl)phenethyl)-5-methylpyrimidin-2-yl)amino)pyridin-2-yl)piperidine-1-carboxylate (A18)

A suspension of 10% Pd/C (53% water; 30 mg) and tert-butyl 4-(5-((4-((2-(2-methoxy-2-oxoethyl)phenyl)ethynyl)-5-methylpyrimidin-2-yl)amino)pyridin-2-yl)piperidine-1-carboxylate (A17) (125 mg, 0.231 mmol) in DMF (5 mL) and Et$_3$N (1 mL) was stirred under a hydrogen atmosphere at room temperature for 44 hours. The resulting mixture was filtered through Celite, washing with EtOAc (200 mL). The combined filtrates were evaporated in vacuo and the resulting oil purified by silica gel chromatography (Biotage Isolera, 12 g SiO₂ cartridge, 0-100% EtOAc in hexanes) to give the title compound A18 as a yellow foam (115 mg, 91%); ¹H NMR (400 MHz, CDCl₃) δ 8.62 (d, J=2.5 Hz, 1H), 8.16 (dd, J=8.5, 2.7 Hz, 1H), 8.11 (d, J=0.5 Hz, 1H), 7.25-7.16 (m, 5H), 7.11 (d, J=8.5 Hz, 1H), 4.25 (br. s, 2H), 3.71 (s, 2H), 3.67 (s, 3H), 3.09 (dd, J=9.6, 6.1 Hz, 2H), 2.93 (dd, J=9.4, 6.0 Hz, 2H), 2.88-2.76 (m, 3H), 2.08 (s, 3H), 1.91 (d, J=11.8 Hz, 2H), 1.75-1.61 (m, 2H), 1.47 (s, 9H). LCMS-A: rt 5.401 min; m/z 546 [M+H]⁺.

(c) 2-(2-(2-(2-((6-(1-(tert-Butoxycarbonyl)piperidin-4-yl)pyridin-3-yl)amino)-5-methylpyrimidin-4-yl)ethyl)phenyl)acetic acid (A19)

LiOH·H₂O (442 mg, 10.5 mmol) was added to a stirred solution of tert-butyl 4-(5-((4-(2-(2-methoxy-2-oxoethyl)phenethyl)-5-methylpyrimidin-2-yl)amino)pyridin-2-yl)piperidine-1-carboxylate (A18) (115 mg, 0.211 mmol) in water (4 mL) and THF (40 mL) and the resulting mixture heated at 40° C. for 18 hours. On cooling the volatiles were removed in vacuo and the residue taken up in EtOAc (100 mL). The resulting solution was washed with water (100 mL), brine (50 mL) and dried over MgSO₄. The volatiles were removed in vacuo to give the title compound A19 as a clear oil (96 mg, 86%); LCMS-A: rt 5.137 min; m/z 532 [M+H]⁺.

(d) tert-Butyl 4-(5-((4-(2-(2-amino-2-oxoethyl)phenethyl)-5-methylpyrimidin-2-yl)amino)pyridin-2-yl)piperidine-1-carboxylate (A20)

HOBt (71 mg, 0.52 mmol), EDCl·HCl (0.11 g, 0.59 mmol) and DIPEA (0.16 mL, 0.90 mmol) were added to a stirred solution of 2-(2-(2-(2-((6-(1-(tert-butoxycarbonyl)piperidin-4-yl)pyridin-3-yl)amino)-5-methylpyrimidin-4-ylethyl)phenyl)acetic acid (A19) (96 mg, 0.18 mmol) in dry DMF (5 mL) under an atmosphere of nitrogen. After 10 minutes ammonium carbonate (174 mg, 1.81 mmol) was added in one portion and the resulting mixture was stirred for 18 hours at room temperature. The volatiles were removed in vacuo and the residue was partitioned between EtOAc (10 mL) and saturated aqueous NaHCO₃ (10 mL). The aqueous layer was extracted with EtOAc (2×10 mL) then the combined organic layers were washed with brine (10 mL) and dried over Na₂SO₄. The volatiles were removed in vacuo and the residue adsorbed onto silica gel and purified by chromatography (Biotage Isolera, 40 g SiO₂ cartridge, 0-100% EtOAc in petroleum benzine 40-60° C. followed by 0-25% MeOH in DCM) to give the title compound A20 as a clear oil (72 mg, 75%). ¹H NMR (400 MHz, CDCl₃) δ 8.82 (d, J=2.4 Hz, 1H), 8.14-8.06 (m, 1H), 7.93 (dd, J=8.5, 2.7 Hz, 1H), 7.37 (s, 1H), 7.26-7.22 (m, 4H), 7.10 (d, J=8.5 Hz, 1H), 5.91 (s, 1H), 5.73 (s, 1H), 4.24 (s, 2H), 3.69 (s, 2H), 3.09 (dd, J=9.7, 6.0 Hz, 2H), 2.97-2.90 (m, 2H), 2.86-2.72 (m, 3H), 2.12 (s, 3H), 1.90 (d, J=12.8 Hz, 2H), 1.68 (m, 2H), 1.47 (s, 9H). LCMS-A: rt 5.018 min; m/z 531 [M+H]⁺.

(e) 2-(2-(2-(5-Methyl-2-((6-(piperidin-4-yl)pyridin-3-yl)amino)pyrimidin-4-yl)ethyl)phenyl)acetamide (4)

TFA (0.5 mL) was added to a solution of tert-butyl 4-(5-((4-(2-(2-amino-2-oxoethyl)phenethyl)-5-methylpyrimidin-2-yl)amino)pyridin-2-yl)piperidine-1-carboxylate (A20) (70 mg, 0.13 mmol) in DCM (5 mL) and the resulting mixture stirred for 18 hours at room temperature. The volatiles were removed in vacuo and the residue partitioned between 2 M aqueous NaOH (10 mL) and EtOAc (25 mL). The organic layer was separated then washed with water (25 mL), brine (25 mL), dried (Na₂SO₄) and concentrated under reduced pressure to give the title compound 4 as an off white solid (45 mg, 79%); ¹H NMR (400 MHz, d₄-MeOH) δ 8.79 (dd, J=2.6, 0.5 Hz, 1H), 8.15 (dd, J=8.6, 2.7 Hz, 1H), 8.13 (d, J=0.6 Hz, 1H), 7.28-7.22 (m, 2H), 7.21-7.14 (m, 3H), 3.64 (s, 2H), 3.20-3.10 (m, 4H), 3.02-2.95 (m, 2H), 2.88-2.68 (m, 3H), 2.11 (s, 3H), 1.95-1.84 (m, 2H), 1.71 (qd, J=12.7, 4.0 Hz, 2H). LCMS-A: rt 4.241 min; m/z 431 [M+H]⁺.

Example 5

Synthesis of 2-(2-(2-(5-methyl-2-((6-(1-methylpiperidin-4-yl)pyridin-3-yl)amino)pyrimidin-4-yl)ethyl)phenyl)acetamide (5)

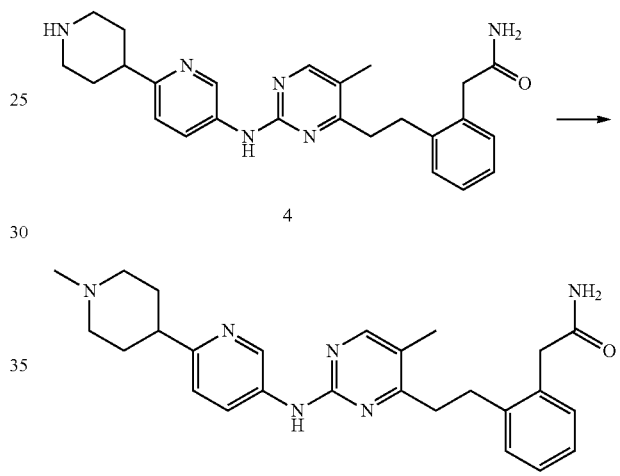

Formaldehyde (37% wt. in H₂O; 0.017 mL, 0.22 mmol) was added to a solution of 2-(2-(2-(5-methyl-2-((6-(piperidin-4-yl)pyridin-3-yl)amino)pyrimidin-4-yl)ethyl)phenyl)acetamide (4) (32 mg, 0.07 mmol) in MeOH (4 mL) under an atmosphere of nitrogen. The resulting solution was stirred for 15 minutes at room temperature then sodium triacetoxyborohydride (63 mg, 0.30 mmol) was added in one portion. After stirring at room temperature for 18 hours a further portion of formaldehyde (37 wt. % in H₂O; 0.017 mL, 0.22 mmol) was added and after 15 minutes sodium triacetoxyborohydride (63 mg, 0.30 mmol) was added in one portion. The resulting mixture was stirred at room temperature for 20 hours then the volatiles were removed in vacuo and the residue partitioned between EtOAc (50 mL) and saturated aqueous NaHCO₃ (50 mL). The layers were separated and the aqueous layer was extracted with EtOAc (2×25 mL). The combined organic layers were washed with water (25 mL), brine (25 mL) and dried over Na₂SO₄. The volatiles were removed under reduced pressure to give the title compound 5 as an off white solid (20 mg, 61%); ¹H NMR (400 MHz, d₄-MeOH) δ 8.79 (d, J=2.2 Hz, 1H), 8.15 (dd, J=8.6, 2.7 Hz, 1H), 8.12 (d, J=0.6 Hz, 1H), 7.27-7.23 (m, 2H), 7.20-7.15 (m, 3H), 3.64 (s, 2H), 3.16-3.06 (m, 4H), 2.98 (dd, J=9.2, 6.0 Hz, 2H), 2.72 (tt, J=12.0, 3.9 Hz, 1H), 2.40 (s, 3H), 2.32 (td, J=12.0, 2.4 Hz, 2H), 2.11 (s, 3H), 1.97 (d, J=11.9 Hz, 2H), 1.92-1.80 (m, 2H). LCMS-A: rt 4.237 min; m/z 445 [M+H]⁺.

Example 6

Synthesis of 2-(2-(2-(2-((4-(piperazine-1-carbonyl)phenyl)amino)-5-(trifluoromethyl)pyrimidin-4-yl)ethyl)phenyl)acetamide (6)

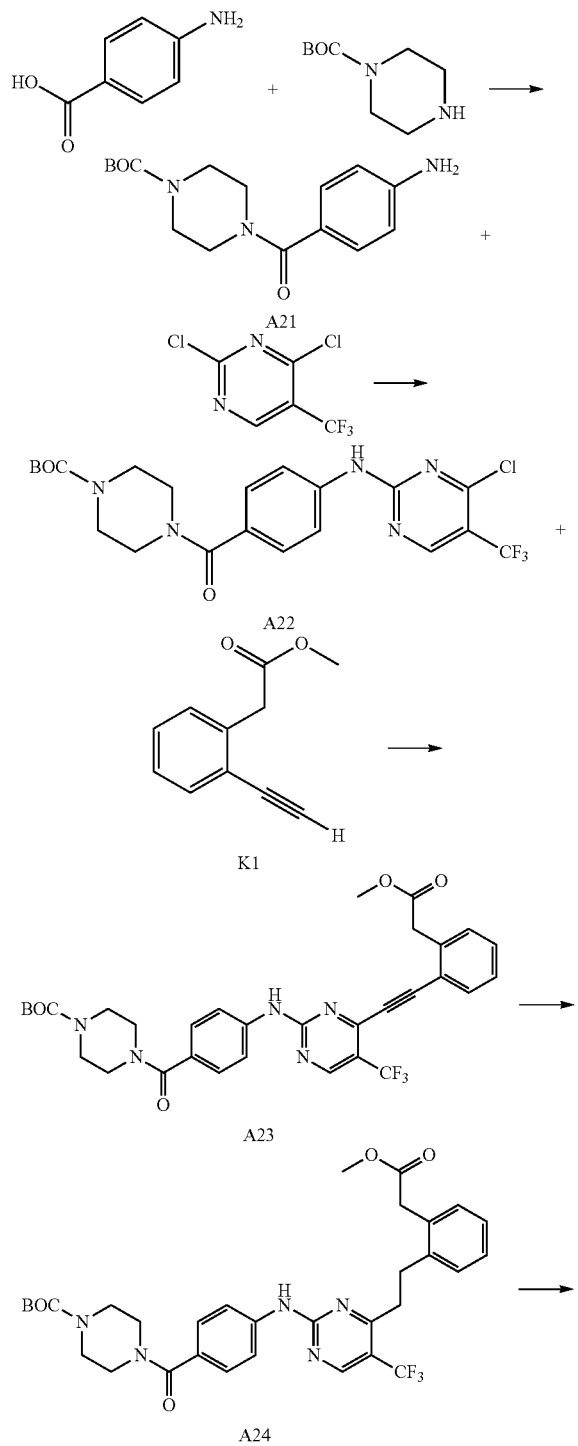

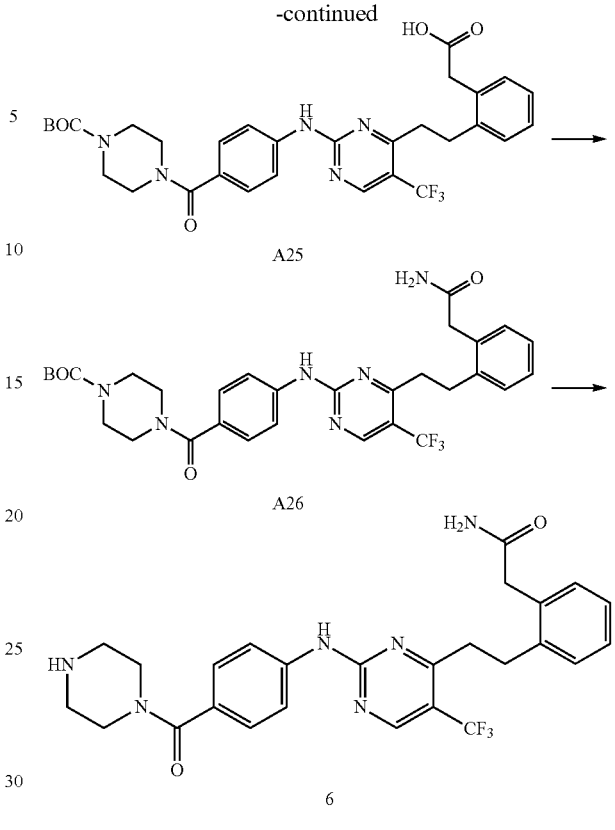

(a) tert-Butyl 4-(4-aminobenzoyl)piperazine-1-carboxylate (A21)

To a solution of 4-aminobenzoic acid (0.411 g, 3.00 mmol) in DMF (5.0 mL) at room temperature was added EDCl.HCl (0.862 g, 4.50 mmol), HOBt (0.608 g, 4.50 mmol), Et₃N (0.835 mL, 6.00 mmol) and N-Boc piperazine (0.671 g, 3.60 mmol). The resulting mixture was stirred at room temperature for 21 hours then 2 M aqueous NaOH was added to adjust the pH to >10. EtOAc was added then the layers separated and the organic layer dried over MgSO₄. The volatiles were removed under reduced pressure and the residue was purified by silica gel chromatography (Biotage Isolera, 40 g SiO₂ cartridge, 50-90% EtOAc in petroleum benzine 40-60° C.) to give the title compound A21 as a white solid (0.530 g, 56%); LCMS-A: rt 5.079 min; m/z 250.1 [(M-t-Bu)+H]⁺, 206.1 [(M-Boc)+H]⁺.

(b) tert-Butyl 4-(4-((4-chloro-5-(trifluoromethyl)pyrimidin-2-yl)amino)benzoyl)piperazine-1-carboxylate (A22)

Zinc(II) chloride (1.0 M in Et₂O; 2.00 mL, 2.00 mmol) was added to a solution of 2,4-dichloro-5-(trifluoromethyl)pyrimidine (0.399 g, 1.84 mmol) in 1:1 DCE/t-BuOH (15 mL) at 0° C. under a nitrogen atmosphere. The resulting mixture was stirred for 1 hour at 0° C. and then tert-butyl 4-(4-aminobenzoyl)piperazine-1-carboxylate (A21) (0.510 g, 1.67 mmol) in 1:1 DCE/tBuOH (15 mL) was added. A solution of Et₃N (0.256 mL, 1.84 mmol) in 1:1 DCE/t-BuOH (15 mL) was added dropwise at 0° C. and the resulting mixture was vigorously stirred for a further 30 minutes at 0° C. then at room temperature for 16 hours. The volatiles were removed in vacuo to afford a brown residue which was purified by silica gel column chromatography (Biotage Isolera, 25 g SiO$_2$ cartridge, 0-100% EtOAc in petroleum benzine 40-60° C.) to yield a pale yellow solid. The solid was suspended in MeOH (15 mL) and water (15 mL) and the resulting suspension filtered to give the title compound A22 as a white solid (0.561 g, 69%); $^1$H NMR (400 MHz, CDCl$_3$) δ 8.61 (s, 1H), 7.68 (d, J=8.7 Hz, 2H), 7.64 (s, 1H), 7.45 (d, J=8.6 Hz, 2H), 3.87-3.30 (m, 8H), 1.47 (s, 9H). LCMS-A: rt 6.206 min; m/z 484.1 [M−H]$^−$.

(c) tert-Butyl 4-(4-((4-((2-(2-methoxy-2-oxoethyl)phenyl)ethynyl)-5-(trifluoromethyl)pyrimidin-2-yl)amino)benzoyl)piperazine-1-carboxylate (A23)

A solution of methyl 2-(2-ethynylphenyl)acetate (K1) (0.129 g, 0.741 mmol) in DMF (3 mL) and Et$_3$N (344 µL, 2.47 mmol) was added to a mixture of tert-butyl 4-(4-((4-chloro-5-(trifluoromethyl)pyrimidin-2-yl)amino)benzoyl)piperazine-1-carboxylate (A22) (0.300 g, 0.617 mmol), PdCl$_2$(PPh$_3$)$_2$ (0.065 g, 0.093 mmol), CuI (0.018 g, 0.093 mmol) and PPh$_3$ (0.016 g, 0.062 mmol) in DMF (3 mL). The resulting mixture was heated under microwave irradiation at 120° C. for 15 minutes, diluted with EtOAc and passed through a plug of Celite, washing with EtOAc (60 mL). The filtrates were combined and the volatiles were removed in vacuo to give a residue that was purified by silica gel column chromatography (Biotage Isolera, 25 g SiO$_2$ cartridge, 0-80% EtOAc in petroleum benzine 40-60° C.) to give the title compound A23 as a yellow oil (0.337 g, 88%); $^1$H NMR (400 MHz, CDCl$_3$) δ 8.67 (s, 1H), 7.73 (d, J=8.6 Hz, 2H), 7.68 (dd, J=7.7, 1.0 Hz, 1H), 7.61 (s, 1H), 7.48-7.41 (m, 3H), 7.40-7.31 (m, 2H), 3.96 (s, 2H), 3.71 (s, 3H), 3.67-3.37 (m, 8H), 1.47 (s, 9H). LCMS-A: rt 6.393 min; m/z 624.1 [M+H]$^+$.

(d) tert-Butyl 4-(4-((4-(2-(2-methoxy-2-oxoethyl)phenethyl)-5-(trifluoromethyl)pyrimidin-2-yl)amino)benzoyl)piperazine-1-carboxylate (A24)

A suspension of 10% Pd/C (53% water; 0.660 g), tert-butyl 4-(4-((4-((2-(2-methoxy-2-oxoethyl)phenyl)ethynyl)-5-(trifluoromethyl)pyrimidin-2-yl)amino)benzoyl)piperazine-1-carboxylate (A23) (0.337 g, 0.540 mmol) and Et$_3$N (1 mL) was stirred at room temperature for 16 hours under an atmosphere of hydrogen. The mixture was filtered through a pad of Celite, washing with EtOAc (80 mL). The filtrates were evaporated in vacuo affording a yellow oil which was purified by silica gel column chromatography (Biotage Isolera, 40 g SiO$_2$ cartridge, 0-80% EtOAc in petroleum benzine 40-60° C.) to yield the title compound A24 as a pale yellow oil (0.245 g, 72%); $^1$H NMR (400 MHz, CDCl$_3$) δ 8.54 (s, 1H), 8.19 (s, 1H), 7.72 (d, J=8.7 Hz, 2H), 7.41 (d, J=8.6 Hz, 2H), 7.25-7.13 (m, 4H), 3.73 (s, 2H), 3.65 (s, 3H), 3.84-3.30 (m, 8H), 3.18-3.00 (m, 4H), 1.46 (s, 9H). LCMS-A: rt 6.500 min; m/z 628 [M+H]$^+$.

(e) tert-Butyl 4-(4-((4-(2-(2-methoxy-2-oxoethyl)phenethyl)-5-(trifluoromethyl)pyrimidin-2-yl)amino)benzoyl)piperazine-1-carboxylate (A25)

LiOH.H$_2$O (0.050 g, 1.2 mmol) was added to a solution of tert-butyl 4-(4-((4-(2-(2-methoxy-2-oxoethyl)phenethyl)-5-(trifluoromethyl)pyrimidin-2-yl)amino)benzoyl)piperazine-1-carboxylate (A24) (0.25 g, 0.39 mmol) in THF (7 mL), water (1.5 mL) and MeOH (1 mL) and the resulting mixture was stirred at room temperature for 18 hours. The volatiles were removed in vacuo and the residue was partitioned between EtOAc (50 mL) and saturated aqueous NaHCO$_3$ (50 mL). The layers were separated and the aqueous layer was extracted with EtOAc (2×50 mL). The combined organic layers were washed with brine (50 mL), dried over MgSO$_4$ and the volatiles removed in vacuo to give the title compound A25 as a white solid (0.24 g, 99%). LCMS-A: rt 6.281 min; m/z 558 [(M-t-Bu)+H]$^+$, 514 ([M-Boc]+H]$^+$.

(f) tert-Butyl 4-(4-((4-(2-(2-amino-2-oxoethyl)phenethyl)-5-(trifluoromethyl)pyrimidin-2-yl)amino)benzoyl)piperazine-1-carboxylate (A26)

HOBt (0.068 g, 0.50 mmol), EDCl.HCl (0.096 g, 0.50 mmol) and DIPEA (0.34 mL, 1.9 mmol) were added to a stirred solution of tert-butyl 4-(4-((4-(2-(2-methoxy-2-oxoethyl)phenethyl)-5-(trifluoromethyl)pyrimidin-2-yl)amino)benzoyl)piperazine-1-carboxylate (A25) (0.28 g, 0.39 mmol) in dry THF (6 mL) and dry DMF (1 mL) under an atmosphere of nitrogen. After 10 minutes ammonium carbonate (0.19 g, 1.9 mmol) was added in one portion and the resulting solution was stirred at room temperature for 17 hours. The volatiles were removed in vacuo and the residue was partitioned between EtOAc (65 mL) and saturated aqueous NaHCO$_3$ (65 mL). The aqueous layer was extracted with EtOAc (2×50 mL) then the combined organic layers were washed with brine (50 mL) and dried over MgSO$_4$. The volatiles were removed in vacuo and the residue was purified by silica gel column chromatography (Biotage Isolera, 25 g SiO$_2$ cartridge, 0-100% EtOAc in petroleum benzine 40-60° C. then 0-20% MeOH in EtOAc) to give the title compound A26 as a white solid (0.18 g, 77%); $^1$H NMR (400 MHz, CDCl$_3$) δ 8.58 (s, 1H), 7.91 (s, 1H), 7.72 (d, J=8.4 Hz, 2H), 7.44 (d, J=8.3 Hz, 2H), 7.31-7.21 (m, obscured), 5.43 (br. s, 2H), 3.74 (s, 2H), 3.71-3.35 (m, 8H), 3.18-3.03 (m, 4H), 1.47 (s, 9H). LCMS-A: rt 6.120 min; m/z 613.3 [M+H]$^+$.

(g) 2-(2-(2-(2-((4-(piperazine-1-carbonyl)phenyl)amino)-5-(trifluoromethyl)pyrimidin-4-yl)ethyl)phenyl)acetamide (6)

To a solution of tert-butyl 4-(4-((4-(2-(2-amino-2-oxoethyl)phenethyl)-5-(trifluoromethyl)pyrimidin-2-yl)amino)benzoyl)piperazine-1-carboxylate (A26) (0.182 g, 0.297 mmol) in DCM (4 mL) was added TFA (1 mL) and the resulting mixture was stirred at room temperature for 16 hours. The volatiles were removed in vacuo and the residue partitioned between EtOAc (10 mL) and 2 M aqueous NaOH (10 mL). The aqueous layer was extracted with EtOAc (2×10 mL) then the combined organic fractions were washed with water (10 mL), brine (10 mL) and dried over MgSO$_4$. The volatiles were removed in vacuo to give a yellow solid, which was suspended in cyclohexane and then filtered to give the title compound 6 as a white solid (0.132 g, 87%); $^1$H NMR (400 MHz, d$_4$-MeOH) δ 8.62 (s, 1H), 7.83 (d, J=8.7 Hz, 2H), 7.42 (d, J=8.8 Hz, 2H), 7.27 (d, J=6.3 Hz, 1H), 7.23-7.15 (m, 3H), 3.68 (s, 2H), 3.82-3.46 (m, 4H), 3.23-3.15 (m, 2H), 3.12 (dd, J=9.8, 5.4 Hz, 2H), 3.02-2.71 (m, 4H). LCMS-A: rt 4.676 min; m/z 513.3 [M+H]$^+$.

Example 7

Synthesis of 2-(2-(2-(2-((3-fluoro-4-(piperidin-4-yl)phenyl)amino)-5-(trifluoromethyl)pyrimidin-4-yl)ethyl)phenyl)acetamide (7)

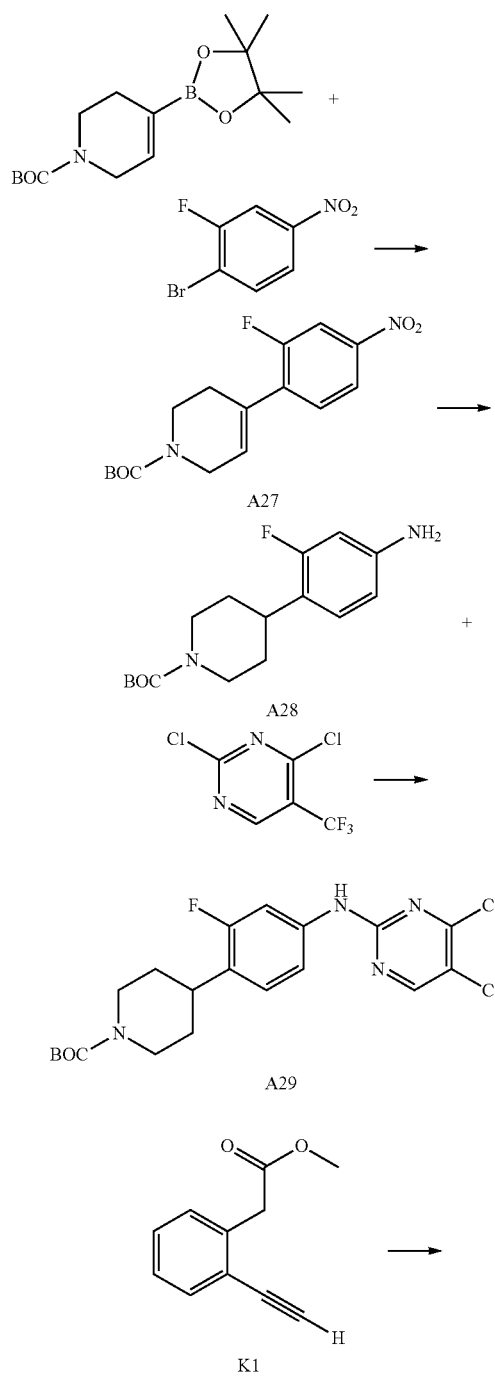

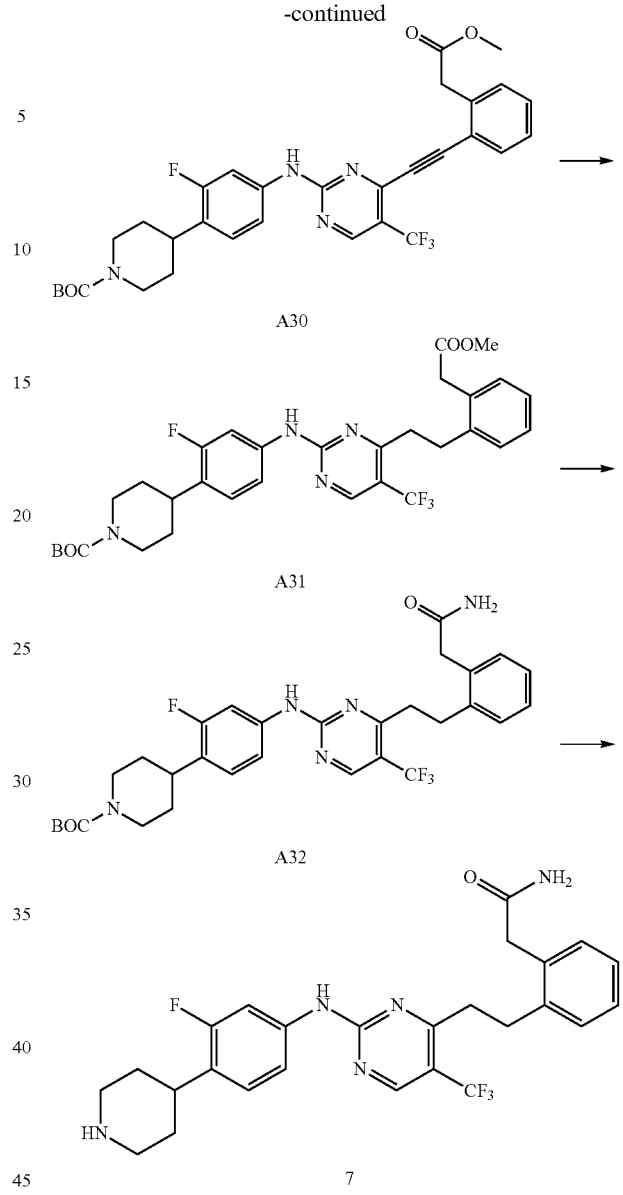

tert-Butyl 4-(2-fluoro-4-nitrophenyl)-5,6-dihydropyridine-1(2H)-carboxylate (A27)

To a mixture of 3,6-dihydro-2H-pyridine-1-tert-butoxycarbonyl-4-boronic acid pinacol ester (0.555 g, 1.80 mmol), 4-bromo-3-fluoronitrobenzene (0.294 g, 1.33 mmol) and PdCl$_2$(PPh$_3$)$_2$ (0.051 g, 0.072 mmol) under nitrogen was added 1,4-dioxane (5.0 mL) and 3 M aqueous Na$_2$CO$_3$ (1.4 mL, 4.2 mmol). The resulting solution was degassed with a stream of nitrogen for 10 minutes then heated at reflux for 16 hours. The volatiles were evaporated under reduced pressure and the residue purified using silica gel column chromatography (Biotage Isolera, SiO$_2$ cartridge, 0-25% EtOAc in petroleum benzine 40-60° C.) to give the title compound A27 (0.391 g, 91%); $^1$H NMR (400 MHz, CDCl$_3$) δ 8.01 (m, 1H), 7.93 (dd, J=10.6, 2.2 Hz, 1H), 7.42 (dd, J=8.5, 7.6 Hz, 1H), 6.11 (s, 1H), 4.12 (m, 2H), 3.64 (t, J=5.6 Hz, 2H), 2.52 (brs, 2H), 1.50 (s, 9H).

(b) tert-Butyl 4-(4-amino-2-fluorophenyl)piperidine-1-carboxylate (A28)

To a solution of tert-butyl 4-(2-fluoro-4-nitrophenyl)-5,6-dihydropyridine-1(2H)-carboxylate (A27) (0.391 g, 1.20 mmol) in EtOAc (10 mL) was added 10% Pd/C (0.118 g) in EtOAc (1 mL) and the resulting suspension was stirred at 30° C. under a hydrogen atmosphere for 16 hours. The resulting mixture was filtered through Celite and the filtrate concentrated under reduced pressure to give the title compound A28 (0.339 g, 96%); $^1$H NMR (400 MHz, CDCl$_3$) δ 6.94 (dd, J=8.3 Hz, 1H), 6.41 (dd, J=8.2, 2.4 Hz, 1H), 6.36 (dd, J=12.1, 2.3 Hz, 1H), 4.21 (brs, 2H), 3.65 (s, 2H), 2.84 (m, 3H), 1.75 (bd, J=13.3 Hz, 2H), 1.47 (s, 9H).

(c) tert-Butyl 4-(4-((4-chloro-5-(trifluoromethyl)pyrimidin-2-yl)amino)-2-fluorophenyl)piperidine-1-carboxylate (A29)

Zinc(II) chloride (1.0 M in Et$_2$O; 1.08 mL, 1.08 mmol) was added to a solution of 2,4-dichloro-5-(trifluoromethyl)pyrimidine (0.216 g, 0.994 mmol) in 1:1 DCE/t-BuOH (8 mL) at 0° C. under a nitrogen atmosphere. The resulting mixture was stirred for 1 hour at 0° C. then tert-butyl 4-(4-amino-2-fluorophenyl)piperidine-1-carboxylate (A28) (0.266 g, 0.904 mmol) in 1:1 DCE/t-BuOH (8 mL) was added. A solution of Et$_3$N (0.139 mL, 0.994 mmol) in 1:1 DCE/t-BuOH (5 mL) was then added dropwise at 0° C. and the resulting mixture was vigorously stirred for a further 30 minutes at 0° C., then at room temperature for 18 hours. The volatiles removed in vacuo to afford a brown residue which was purified by silica gel column chromatography (Biotage Isolera, 25 g SiO$_2$ Cartridge, 0-20% EtOAc in petroleum benzine 40-60° C.) to yield a pale yellow solid. The solid was suspended in MeOH (15 mL) and water (15 mL) and the resulting suspension filtered to afford the title compound A29 as a white solid (0.363 g, 85%); $^1$H NMR (400 MHz, CDCl$_3$) δ 8.59 (s, 1H), 7.59-7.47 (m, 2H), 7.20-7.14 (m, 1H), 4.37-4.14 (m, 2H), 2.98 (tt, J=12.1, 3.4 Hz, 1H), 2.83 (t, J=11.7 Hz, 2H), 1.80 (d, J=12.8 Hz, 2H), 1.71-1.55 (m, 3H), 1.48 (s, 9H). LCMS-A: rt 6.902 min; m/z 473.1 [M−H]$^−$.

(d) tert-Butyl 4-(4-((4-chloro-5-(trifluoromethyl)pyrimidin-2-yl)amino)-2-fluorophenyl)piperidine-1-carboxylate (A30)

A solution of methyl 2-(2-ethynylphenyl)acetate (K1) (0.15 g, 0.87 mmol) in DMF (3 mL) and Et$_3$N (0.40 mL, 2.9 mmol) were added to a mixture of tert-butyl 4-(4-((4-chloro-5-(trifluoromethyl)pyrimidin-2-yl)amino)-2-fluorophenyl)piperidine-1-carboxylate (A29) (0.34 g, 0.72 mmol), PdCl$_2$(PPh$_3$)$_2$ (0.076 g, 0.11 mmol), CuI (0.021 g, 0.072 mmol) and PPh$_3$ (0.019 g, 0.072 mmol) in DMF (3 mL). The resulting mixture was heated under microwave irradiation at 120° C. for 15 minutes then diluted with EtOAc and passed through a plug of Celite, washing with EtOAc (60 mL). The filtrates were combined and the volatiles were removed in vacuo to give a brown residue. The residue was purified by silica gel column chromatography (Biotage Isolera, 40 g SiO$_2$ cartridge, 0-40% EtOAc in petroleum benzine 40-60° C.) to give the title compound A30 as a yellow oil (0.40 g, 90%); $^1$H NMR (400 MHz, CDCl$_3$) δ 8.65 (s, 1H), 7.70-7.60 (m, 2H), 7.50 (s, 1H), 7.47-7.41 (m, 1H), 7.40-7.31 (m, 2H), 7.22-7.12 (m, 2H), 4.36-4.18 (m, 2H), 3.96 (s, 2H), 3.71 (s, 3H), 2.98 (tt, J=12.1, 3.4 Hz, 1H), 2.83 (t, J=12.0 Hz, 2H), 1.81 (d, J=12.4 Hz, 2H), 1.70-1.55 (m, obscured), 1.49 (s, 9H). LCMS-A: rt 7.010 min; m/z 613.1 [M+H]$^+$.

(e) tert-Butyl 4-(2-fluoro-4-((4-(2-(2-methoxy-2-oxoethyl)phenethyl)-5-(trifluoromethyl)pyrimidin-2-yl)amino)phenyl)piperidine-1-carboxylate (A31)

To a solution of tert-butyl 4-(4-((4-chloro-5-(trifluoromethyl)pyrimidin-2-yl)amino)-2-fluorophenyl)piperidine-1-carboxylate (A30) (0.399 g, 0.651 mmol) in DMF (6 mL) and Et$_3$N (1 mL) was added a slurry of 10% Pd/C (53% water; 0.500 g) in DMF (3 mL). The resulting mixture was stirred at room temperature for 21 hours under an atmosphere of hydrogen then filtered through a pad of Celite, washing with EtOAc (80 mL). The filtrates were concentrated in vacuo and the residue purified by silica gel chromatography (Biotage Isolera, 25 g SiO$_2$ cartridges, 0-40% EtOAc in petroleum benzine 40-60° C.) to yield the title compound A31 as a pale yellow solid (0.312 g, 78%); $^1$H NMR (400 MHz, CDCl$_3$) δ 8.56 (s, 1H), 7.66 (dd, J=12.7, 2.0 Hz, 1H), 7.45 (s, 1H), 7.29-7.12 (m, obscured by solvent), 4.41-4.16 (m, 2H), 3.77 (s, 2H), 3.68 (s, 3H), 3.18-3.06 (m, 4H), 2.97 (tt, J=11.9, 3.3 Hz, 1H), 2.83 (t, J=12.8 Hz, 2H), 1.81 (d, J=12.1 Hz, 2H), 1.71-1.52 (m, obscured), 1.49 (s, 9H). LCMS-A: rt 7.221 min; m/z 617.1 [M+H]$^+$.

(f) tert-Butyl 4-(4-((4-(2-(2-amino-2-oxoethyl)phenethyl)-5-(trifluoromethyl)pyrimidin-2-yl)amino)-2-fluorophenyl)piperidine-1-carboxylate (A32)

LiOH.H$_2$O (0.063 g, 1.5 mmol) was added to a solution of tert-butyl 4-(2-fluoro-4-((4-(2-(2-methoxy-2-oxoethyl)phenethyl)-5-(trifluoromethyl)pyrimidin-2-yl)amino)phenyl)piperidine-1-carboxylate (A31) (0.30 g, 0.49 mmol) in THF (10 mL), water (2 mL) and MeOH (1.5 mL) and the resulting mixture was stirred at room temperature for 18 hours. The volatiles were removed in vacuo and the residue was partitioned between EtOAc (50 mL) and saturated aqueous NaHCO$_3$ (50 mL). The layers were separated and the aqueous layer was extracted with EtOAc (2×50 mL). The combined organic layers were washed with brine (50 mL), dried (MgSO$_4$) and the volatiles removed in vacuo to give a white solid. The solid was dissolved in dry THF (12 mL) and dry DMF (2 mL) under an atmosphere of nitrogen and HOBt (0.086 g, 0.64 mmol), EDCl.HCl (0.12 g, 0.64 mmol) and DIPEA (0.43 mL, 2.4 mmol) were added. After 10 minutes ammonium carbonate (0.24 g, 2.4 mmol) was added in one portion and the resulting mixture was stirred at room temperature for 18 hours. The volatiles were removed in vacuo and the residue was partitioned between EtOAc (65 mL) and saturated aqueous NaHCO$_3$ (65 mL). The aqueous layer was extracted with EtOAc (2×50 mL) then the combined organic layers were washed with brine (50 mL) and dried over MgSO$_4$. The volatiles were removed in vacuo to afford a pale yellow oil which was purified by silica gel column chromatography (Biotage Isolera, SiO$_2$ cartridge, 0-80% EtOAc in petroleum benzine 40-60° C.) to give the title compound A32 as a white solid (0.209 g, 69%); $^1$H NMR (400 MHz, CDCl$_3$) δ 8.50 (s, 1H), 8.44 (s, 1H), 7.61 (dd, J=12.8, 2.2 Hz, 1H), 7.30-7.18 (m, 5H), 7.09 (t, J=8.4 Hz, 1H), 6.31 (s, 1H), 5.69 (s, 1H), 4.39-4.16 (m, 2H), 3.72 (s, 2H), 3.14-3.00 (m, 4H), 2.94 (tt, J=12.1, 3.3 Hz, 1H), 2.81 (t, J=11.4 Hz, 2H), 1.78 (d, J=12.2 Hz, 2H), 1.69-1.53 (m, 2H), 1.49 (s, 9H). LCMS-A: rt 6.710 min; m/z 602.3 [M+H]$^+$.

(g) 2-(2-(2-(2-((3-Fluoro-4-(piperidin-4-yl)phenyl)amino)-5-(trifluoromethyl)pyrimidin-4-yl)ethyl)phenyl)acetamide (7)

To a solution of tert-butyl 4-(4-((4-(2-(2-amino-2-oxoethyl)phenethyl)-5-(trifluoromethyl)pyrimidin-2-yl)amino)-

2-fluorophenyl)piperidine-1-carboxylate (A32) (0.209 g, 0.347 mmol) in DCM (4 mL) was added TFA (1.0 mL) and the resulting mixture was stirred at room temperature for 16 hours. The volatiles were removed in vacuo and the residue partitioned between EtOAc (10 mL) and 2 M aqueous NaOH (10 mL). The aqueous layer was extracted with EtOAc (2×10 mL) then the combined organic layers washed with water (10 mL), brine (10 mL) and dried over $MgSO_4$. The volatiles were removed in vacuo to give a yellow solid which was suspended in DCM/cyclohexane and the resulting suspension filtered to give the title compound 7 as a white solid (0.107 g, 61%); $^1$H NMR (400 MHz, $d_4$-MeOH) δ 8.59 (s, 1H), 7.66 (dd, J=13.2, 2.1 Hz, 1H), 7.39 (dd, J=8.5, 2.1 Hz, 1H), 7.28-7.15 (m, 5H), 3.68 (s, 2H), 3.23-3.14 (m, 4H), 3.10 (dd, J=10.6, 5.4 Hz, 2H), 2.99 (tt, J=11.7, 3.8 Hz, 1H), 2.80 (td, J=12.4, 2.9 Hz, 2H), 1.87-1.68 (m, 4H). LCMS-A: rt 4.851 min; m/z 502.2 [M+H]$^+$.

Example 8

Synthesis of 2-(2-(2-(2-((3-fluoro-4-(1-methylpiperidin-4-yl)phenyl)amino)-5-(trifluoromethyl)pyrimidin-4-yl)ethyl)phenyl)acetamide (8)

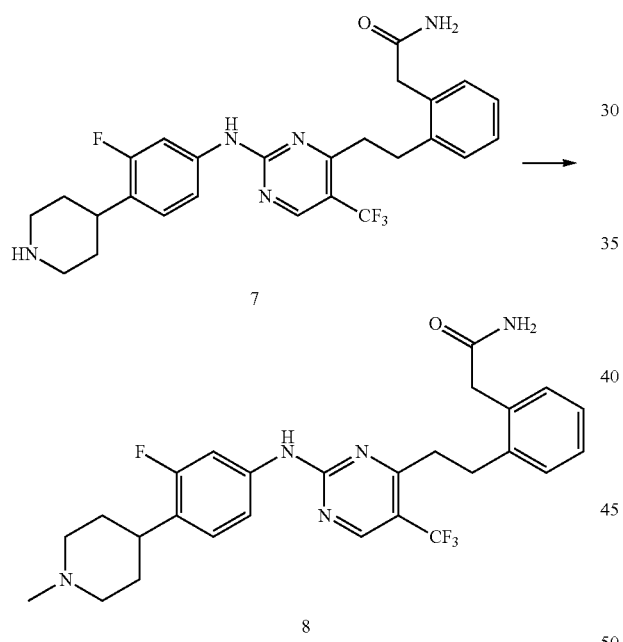

Formaldehyde (37 wt. % in $H_2O$; 0.041 mL, 0.50 mmol) was added to a suspension of 2-(2-(2-(2-((3-fluoro-4-(piperidin-4-yl)phenyl)amino)-5-(trifluoromethyl)pyrimidin-4-yl)ethyl)phenyl)acetamide (7) (0.046 g, 0.092 mmol) in anhydrous MeOH (5 mL) under an atmosphere of nitrogen. Sodium triacetoxyborohydride (0.19 g, 0.10 mmol) was then added in one portion and the resulting mixture stirred at room temperature for 3 hours. The volatiles were removed in vacuo and the residue was partitioned between EtOAc (10 mL) and saturated aqueous $NaHCO_3$ (10 mL). Solid $NaHCO_3$ was added until the formation of gas ceased, then the layers were separated and the aqueous layer was extracted with EtOAc (2×100 mL). The organic layers were combined, washed with water (10 mL), brine (10 mL) and dried over $Na_2SO_4$. The volatiles were removed under reduced pressure to yield the title compound 8 as a white solid (0.043 g, 92%); $^1$H NMR (400 MHz, $d_4$-MeOH) δ 8.58 (s, 1H), 7.66 (dd, J=13.2, 2.0 Hz, 1H), 7.37 (dd, J=8.5, 2.0 Hz, 1H), 7.28-7.14 (m, 5H), 3.68 (s, 2H), 3.20-3.12 (m, 2H), 3.13-3.04 (m, 2H), 3.01 (d, J=12.0 Hz, 2H), 2.90-2.76 (m, 1H), 2.34 (s, 3H), 2.24-2.12 (m, 2H), 1.90-1.77 (m, 4H). LCMS-A rt 4.888 min; m/z 516.3 [M+H]$^+$.

Example 9

Synthesis of 2-(5-fluoro-2-(2-(2-((4-(piperidin-4-yl)phenyl)amino)-5-(trifluoromethyl)pyrimidin-4-yl)ethyl)phenyl)acetamide (9)

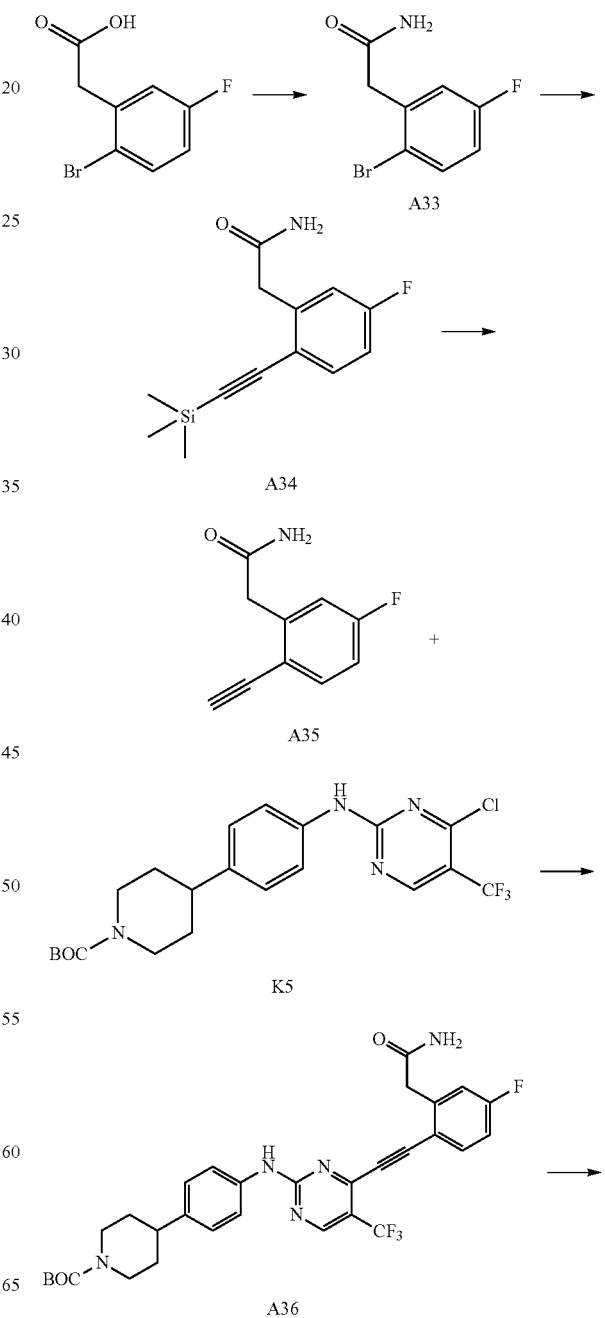

-continued

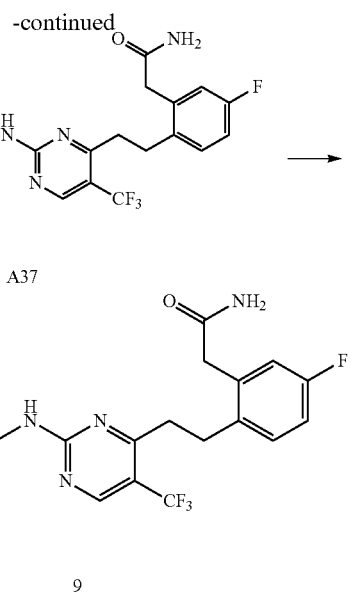

A37

9

(a) 2-(2-Bromo-5-fluorophenyl)acetamide (A33)

HOBt (0.435 g, 3.22 mmol), EDCl.HCl (0.617 g, 3.22 mmol) and DIPEA (1.87 mL, 10.7 mmol) were added to a stirred solution of 2-(2-bromo-5-phenyl)acetic acid (0.500 g, 2.15 mmol) in dry THF (6 mL) and dry DMF (1 mL) under an atmosphere of nitrogen. After 10 minutes ammonium carbonate (1.03 g, 10.7 mmol) was added in one portion and the resulting mixture stirred at room temperature for 16 hours. The volatiles were removed in vacuo and the residue was partitioned between DCM (50 mL) and saturated aqueous NaHCO$_3$ (50 mL). The aqueous phase was extracted with DCM (2×50 mL) then the combined organics washed with brine and dried over MgSO$_4$. The volatiles were removed under reduced pressure, then the residue purified by silica gel column chromatography (Biotage Isolera, SiO$_2$ cartridge, 20-100% EtOAc in petroleum benzine 40-60° C.) to give the title compound A33 as a white solid (0.250 g, 50%); $^1$H NMR (400 MHz, d$_6$-DMSO) δ 7.61 (dd, J=8.8, 5.5 Hz, 1H), 7.48 (s, 1H), 7.25 (dd, J=9.8, 3.1 Hz, 1H), 7.07 (td, J=8.6, 3.2 Hz, 1H), 7.02 (s, 1H), 3.58 (s, 2H).

(b) 2-(5-Fluoro-2-((trimethylsilyl)ethynyl)phenyl)acetamide (A34)

Under inert conditions a suspension of 2-(2-bromo-5-fluorophenyl)acetamide (A33) (0.242 g, 1.04 mmol), PdCl$_2$(PPh$_3$)$_2$ (0.037 g, 0.052 mmol), t-Bu$_3$PH.BF$_4$ (0.015 g, 0.052 mmol), CuI (0.010 g, 0.052 mmol) and (trimethylsilyl)acetylene (0.177 mL, 1.25 mmol) in anhydrous DMF (9 mL) was degassed with nitrogen for 10 minutes. Et$_3$N (3 mL) was added and the resulting mixture was stirred at 65° C. under nitrogen for 16 hours. The volatiles were removed under reduced pressure, then the residue adsorbed onto silica gel and purified by column chromatography (Biotage Isolera, SiO$_2$ cartridge, 0-50% EtOAc in petroleum benzine 40-60° C.) to give the title compound A34 as a tan coloured solid (0.242 g, 93%); $^1$H NMR (400 MHz, d$_6$-DMSO) δ 7.46 (dd, J=8.6, 5.9 Hz, 1H), 7.38 (s, 1H), 7.15 (dd, J=10.0, 2.7 Hz, 1H), 7.08 (td, J=8.6, 2.7 Hz, 1H), 6.99 (s, 1H), 3.60 (s, 2H), 0.23 (s, 9H).

(c) 2-(2-Ethynyl-5-fluorophenyl)acetamide (A35)

To a solution of 2-(5-fluoro-2-((trimethylsilyl)ethynyl)phenyl)acetamide (A34) (0.239 g, 0.958 mmol) in DCM (10 mL) at 0° C. was added TBAF (1.0 M in THF; 1.44 mL, 1.44 mmol). The resulting mixture was stirred at 0° C. for 10 minutes, then poured into water (50 mL). The organic phase was separated and the aqueous layer was extracted with DCM (2×50 mL). The combined organic layers were washed with brine, dried (MgSO$_4$) and the volatiles removed in vacuo. The residue was adsorbed onto silica gel then purified by column chromatography (Biotage Isolera, SiO$_2$, 0-100% EtOAc in petroleum benzine 40-60° C.) to give the title compound A35 as a white solid (0.114 g, 67%); $^1$H NMR (400 MHz, d$_6$-DMSO) δ 7.50 (dd, J=8.6, 5.9 Hz, 1H), 7.44 (s, 1H), 7.17 (dd, J=10.0, 2.7 Hz, 1H), 7.10 (td, J=8.6, 2.8 Hz, 1H), 6.99 (s, 1H), 4.32 (s, 1H), 3.61 (s, 2H). LCMS-A: rt 4.843 min; m/z 178 [M+H]$^+$.

(d) tert-Butyl 4-(4-((4-((2-(2-amino-2-oxoethyl)-4-fluorophenyl)ethynyl)-5-(trifluoromethyl)pyrimidin-2-yl)amino)phenyl)piperidine-1-carboxylate (A36)

A suspension of 2-(2-ethynyl-5-fluorophenyl)acetamide (A35) (0.114 g, 0.643 mmol), tert-butyl 4-(4-((4-chloro-5-(trifluoromethyl)pyrimidin-2-yl)amino)phenyl)piperidine-1-carboxylate (K5) (0.267 g, 0.585 mmol), PdCl$_2$(PPh$_3$)$_2$ (0.021 g, 0.029 mmol), t-Bu$_3$PH.BF$_4$ (8 mg, 0.03 mmol) and CuI (6 mg, 0.03 mmol) in anhydrous DMF (4 mL) was degassed with nitrogen for 10 minutes. Et$_3$N (1 mL) was added and the resulting mixture was heated under microwave irradiation at 120° C. for 20 minutes. The volatiles were removed under reduced pressure, then the residue adsorbed onto silica gel and purified by column chromatography (Biotage Isolera, SiO$_2$ cartridge, 0-100% EtOAc in petroleum benzine 40-60° C.) to give the title compound A36 as a yellow solid (0.198 g, 57%); $^1$H NMR (400 MHz, d$_6$-DMSO) δ 10.41 (s, 1H), 8.81 (s, 1H), 7.69-7.62 (m, 3H), 7.47 (s, 1H), 7.31-7.19 (m, 4H), 7.07 (s, 1H), 4.05 (s, 2H), 3.72 (s, 2H), 2.80 (s, 2H), 2.69-2.59 (m, 1H), 1.74 (d, J=13.5 Hz, 2H), 1.55-1.44 (m, 2H), 1.42 (s, 9H). LCMS-A: rt 6.554 min; m/z 596 [M−H]$^-$.

(e) tert-Butyl 4-(4-((4-(2-(2-amino-2-oxoethyl)-4-fluorophenethyl)-5-(trifluoromethyl)pyrimidin-2-yl)amino)phenyl)piperidine-1-carboxylate (A37)

A suspension of 10% Pd/C (0.175 g) and tert-butyl 4-(4-((4-((2-(2-amino-2-oxoethyl)-4-fluorophenyl)ethynyl)-5-(trifluoromethyl)pyrimidin-2-yl)amino)phenyl)piperidine-1-carboxylate (A36) (0.191 g, 0.320 mmol) in DMF (10 mL) and Et$_3$N (1 mL) was stirred under an atmosphere of hydrogen for 16 hours. The resulting mixture was diluted with EtOAc (60 mL), filtered through Celite and the volatiles were removed under reduced pressure. The residue was adsorbed onto silica gel, then purified by column chromatography (Biotage Isolera, SiO$_2$ cartridge, 0-100% EtOAc in petroleum benzine 40-60° C.) to give the title compound A37 as a yellow solid (0.168 g, 87%); $^1$H NMR (400 MHz, d$_6$-DMSO) δ 10.14 (s, 1H), 8.65 (s, 1H), 7.65 (d, J=8.6 Hz, 2H), 7.48 (s, 1H), 7.23-7.15 (m, 3H), 7.08 (dd, J=10.2, 2.8 Hz, 1H), 7.00 (td, J=8.4, 2.7 Hz, 2H), 4.07 (d, J=11.8 Hz, 2H), 3.50 (s, 2H), 3.13-3.04 (m, 2H), 3.04-2.95 (m, 2H), 2.79 (brs, 2H), 2.69-2.57 (m, 1H), 1.74 (d, J=12.9 Hz, 2H), 1.54-1.43 (m, 2H), 1.42 (s, 9H). LCMS-A: rt 6.612 min; m/z 602 [M+H]$^+$.

(f) 2-(5-Fluoro-2-(2-(2-((4-(piperidin-4-yl)phenyl) amino)-5-(trifluoromethyl)pyrimidin-4-yl)ethyl)phenyl)acetamide (9)

TFA (0.825 mL, 10.8 mmol) was added to a solution of tert-butyl 4-(4-((4-(2-(2-amino-2-oxoethyl)-4-fluorophenethyl)-5-(trifluoromethyl)pyrimidin-2-yl)amino)phenyl)piperidine-1-carboxylate (A37) (0.162 g, 0.269 mmol) in DCM (20 mL) under nitrogen and the resulting solution stirred for 24 hours at room temperature. The volatiles were removed in vacuo and the residue was taken up in MeOH and loaded onto an SCX cartridge (10 g). The column was eluted with 5 column volumes of MeOH and then 6 column volumes of 5% v/v aqueous ammonia in MeOH. The volatiles from the ammoniacal eluent were evaporated under reduced pressure to give the title compound 9 as a yellow solid (0.117 g, 87%); $^1$H NMR (400 MHz, d$_6$-DMSO) δ 10.12 (s, 1H), 8.65 (s, 1H), 7.64 (d, J=8.6 Hz, 2H), 7.48 (s, 1H), 7.23-7.13 (m, 3H), 7.08 (dd, J=10.2, 2.8 Hz, 1H), 7.04-6.95 (m, 2H), 3.50 (s, 2H), 3.14-2.95 (m, 6H), 2.63-2.52 (m, 3H), 1.67 (d, J=10.8 Hz, 2H), 1.49 (qd, J=12.4, 3.9 Hz, 2H). LCMS-A: rt 4.853 min; m/z 502 [M+H]$^+$.

Example 10

Synthesis of 2-(5-fluoro-2-(2-(2-((4-(1-methylpiperidin-4-yl)phenyl)amino)-5-(trifluoromethyl)pyrimidin-4-yl)ethyl)phenyl)acetamide (10)

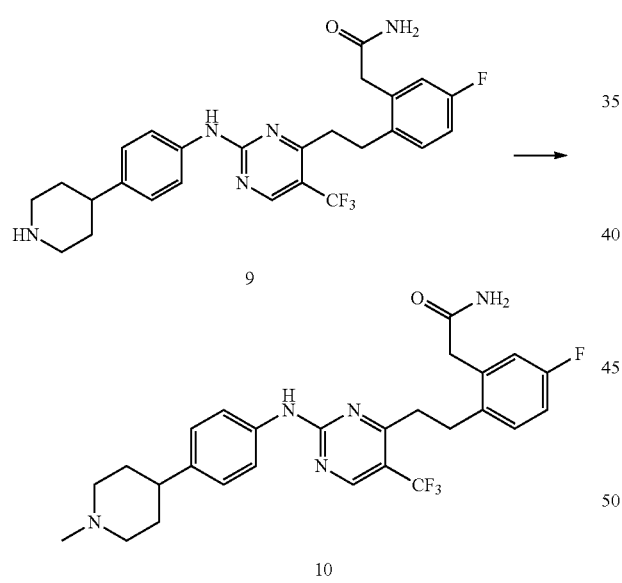

Formaldehyde (37 wt. % in H$_2$O; 29 μL, 0.39 mmol) was added to a suspension of 2-(5-fluoro-2-(2-(2-((4-(piperidin-4-yl)phenyl)amino)-5-(trifluoromethyl)pyrimidin-4-yl) ethyl)phenyl)acetamide (9) (0.065 g, 0.13 mmol) in MeOH (8 mL) under an atmosphere of nitrogen. The resulting mixture was stirred for 10 minutes at room temperature then sodium triacetoxyborohydride (0.110 g, 0.518 mmol) was added in one portion and stirring continued for 3 hours The volatiles were removed in vacuo, then the residue was partitioned between EtOAc (20 mL) and saturated aqueous NaHCO$_3$ (20 mL). The layers were separated and the aqueous layer was extracted with EtOAc (2×20 mL). The combined organic layers were washed with brine (20 mL) and dried over Na$_2$SO$_4$. The volatiles were removed under reduced pressure to yield the title compound 10 as an off-white solid (58 mg, 87%); $^1$H NMR (400 MHz, d$_6$-DMSO) δ 10.13 (s, 1H), 8.65 (s, 1H), 7.64 (d, J=8.6 Hz, 2H), 7.49 (s, 1H), 7.22-7.16 (m, 3H), 7.08 (dd, J=10.2, 2.8 Hz, 1H), 7.04-6.95 (m, 2H), 3.50 (s, 2H), 3.12-3.04 (m, 2H), 3.04-2.95 (m, 2H), 2.87 (d, J=11.3 Hz, 2H), 2.46-2.36 (m, 1H), 2.20 (s, 3H), 2.02-1.92 (m, 2H), 1.76-1.58 (m, 4H). LCMS-A: rt 4.867 min; m/z 516 [M+H]$^+$.

Example 11

Synthesis of 2-(2-(2-(2-((3-methyl-4-(piperidin-4-yl) phenyl)amino)-5-(trifluoromethyl)pyrimidin-4-yl) ethyl)phenyl)acetamide (11)

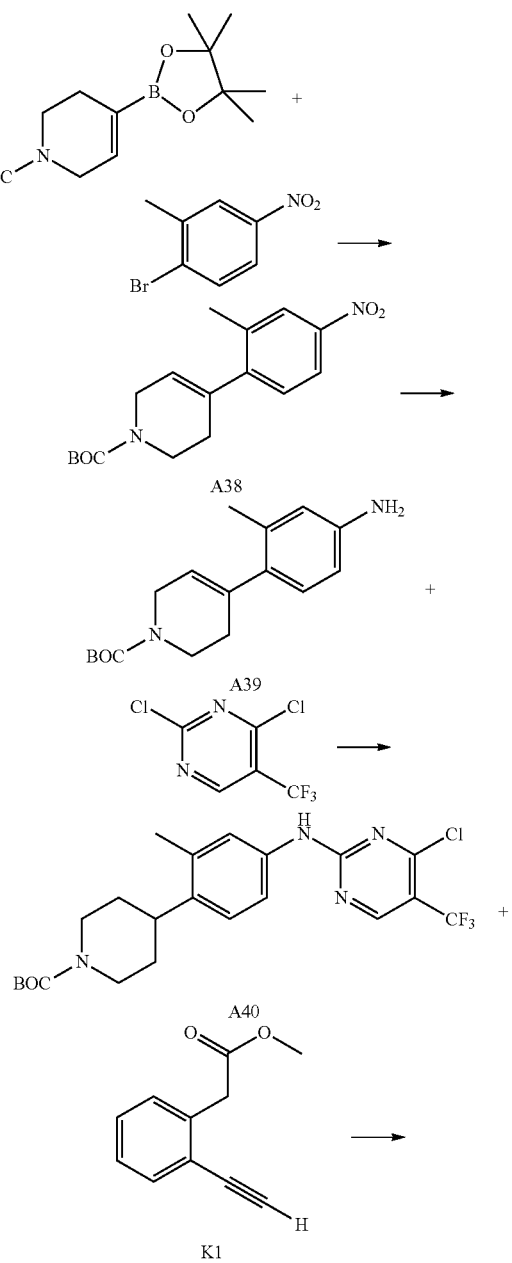

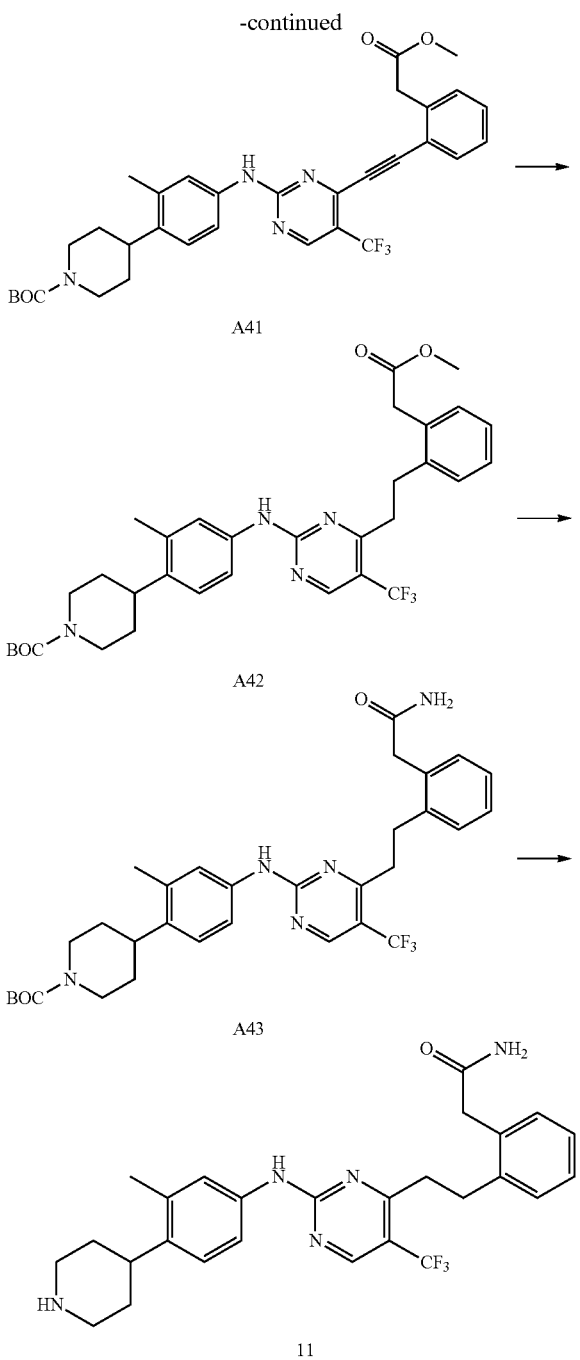

NMR (400 MHz, CDCl₃) δ 8.05 (d, J=2.4 Hz, 1H), 8.03-7.98 (m, 1H), 7.22 (d, J=8.4 Hz, 1H), 5.63 (s, 1H), 4.09-4.04 (m, 2H), 3.64 (t, J=5.6 Hz, 2H), 2.38 (s, 3H), 2.35 (s, 2H), 1.51 (s, 9H).

(b) tert-Butyl 4-(4-amino-2-methylphenyl)piperidine-1-carboxylate (A39)

To a solution of tert-butyl 4-(2-methyl-4-nitrophenyl)-5,6-dihydropyridine-1(2H)-carboxylate (A38) (211 mg, 0.663 mmol) in DMF (7.5 mL) was added a slurry of 10% Pd/C (100 mg) in DMF (0.5 mL) and the resulting mixture was stirred for 16 hours under a hydrogen atmosphere at room temperature. The resulting mixture was filtered through Celite then the volatiles were removed under reduced pressure. The residue was purified by silica gel column chromatography (Biotage Isolera, SiO₂ cartridge, 0-60% EtOAc in petroleum benzine 40-60° C.) to give the title compound A39 as a pale orange solid (185 mg, 96%); ¹H NMR (400 MHz, CDCl₃) δ 6.95 (d, J=8.0 Hz, 1H), 6.56-6.48 (m, 2H), 3.51 (s, 2H), 2.88-2.65 (m, 3H), 2.26 (s, 3H), 1.74-1.66 (m, 2H), 1.63-1.51 (m, obscured by solvent), 1.48 (s, 9H).

(c) tert-Butyl 4-(4-((4-chloro-5-(trifluoromethyl)pyrimidin-2-yl)amino)-2-methylphenyl)piperidine-1-carboxylate (A40)

Zinc(II) chloride (1.0 M in Et₂O; 0.661 mL, 0.661 mmol) was added to a solution of 2,4-dichloro-5-(trifluoromethyl)pyrimidine (0.132 g, 0.606 mmol) in 1:1 DCE/t-BuOH (5 mL) at 0° C. under nitrogen. The resulting mixture was stirred for 1 hour at 0° C. then tert-butyl 4-(4-amino-2-methylphenyl)piperidine-1-carboxylate (A39) (0.160 g, 0.551 mmol) in 1:1 DCE/t-BuOH (5 mL) was added. A solution of Et₃N (840 μL, 0.606 mmol) in 1:1 DCE/t-BuOH (5 mL) at 0° C. was then added and the resulting mixture was vigorously stirred for a further 30 minutes at 0° C. then at room temperature for 16 hours. The volatiles were removed in vacuo to afford a brown residue which was purified by silica gel column chromatography (Biotage Isolera, 25 g SiO₂ cartridge, 0-50% EtOAc in petroleum benzine 40-60° C.) to yield a pale yellow solid. The solid was suspended in MeOH (10 mL) and water (10 mL) and the resulting suspension filtered to give the title compound A40 as a white solid (0.231 g, 89%); ¹H NMR (400 MHz, CDCl₃) δ 8.48 (s, 1H), 7.35 (d, J=8.2 Hz, 1H), 7.27 (brs, 1H), 7.24 (d, J=2.3 Hz, 1H), 7.11 (d, J=8.4 Hz, 1H), 4.32-4.04 (m, 2H), 2.79-2.73 (m, 3H), 2.30 (s, 3H), 1.67 (d, J=13.0 Hz, 2H), 1.62-1.45 (m, obscured), 1.42 (s, 9H). LCMS-A: rt 6.895 min; m/z 469.1 [M−H]⁻.

(d) tert-Butyl 4-(4-((4-((2-(2-methoxy-2-oxoethyl)phenyl)ethynyl)-5-(trifluoromethyl)pyrimidin-2-yl)amino)-2-methylphenyl)piperidine-1-carboxylate (A41)

A solution of methyl 2-(2-ethynylphenyl)acetate (K1) (0.103 g, 0.589 mmol) in DMF (1.5 mL) and Et₃N (0.273 mL, 1.96 mmol) were added to a suspension of tert-butyl 4-(4-((4-chloro-5-(trifluoromethyl)pyrimidin-2-yl)amino)-2-methylphenyl)piperidine-1-carboxylate (A40) (0.231 g, 0.491 mmol), PdCl₂(PPh₃)₂ (0.052 g, 0.074 mmol), CuI (0.014 g, 0.074 mmol) and PPh₃ (0.013 g, 0.049 mmol) in DMF (2 mL). The resulting mixture was heated under microwave irradiation at 120° C. for 15 minutes, then diluted with EtOAc and passed through a plug of Celite, washing with EtOAc (60 mL). The filtrate was washed with water (50 mL) and the aqueous layer was extracted with EtOAc (2×50 mL). The (a) tert-Butyl 4-(2-methyl-4-nitrophenyl)-5,6-dihydropyridine-1(2H)-carboxylate (A38)

A suspension of N-Boc-1,2,3,6-tetrahydropyridine-4-boronic acid pinacol ester (0.29 g, 0.93 mmol), 1-bromo-2-methyl-4-nitrobenzene (0.20 g, 0.93 mmol), PdCl₂(PPh₃)₂ (0.03 g, 0.05 mmol) and 3 M aqueous Na₂CO₃ (0.93 mL, 2.8 mmol) in 1,4-dioxane (10 mL) was degassed with nitrogen for 10 minutes then heated at reflux for 16 hours. The resulting mixture was concentrated under reduced pressure and purified using silica gel column chromatography (Biotage Isolera, SiO₂ cartridge, 0-30% EtOAc in petroleum benzine 40-60° C.) to give the title compound A38 (0.25 g, 83%); ¹H combined organics were washed with water (50 mL), brine (50 mL) and dried (Na$_2$SO$_4$). The volatiles were removed in vacuo and the residue was purified by silica gel column chromatography (Biotage Isolera, 25 g SiO$_2$ cartridge, 0-40% EtOAc in petroleum benzine 40-60° C.) to give the title compound A41 as a yellow oil (0.248 g, 83%); $^1$H NMR (400 MHz, CDCl$_3$) δ 8.62 (s, 1H), 7.68 (dd, J=7.6, 0.9 Hz, 1H), 7.47 (d, J=7.2 Hz, 1H), 7.45-7.40 (m, 1H), 7.39-7.29 (m, 4H), 7.18 (d, J=8.4 Hz, 1H), 4.38-4.21 (m, 2H), 3.96 (s, 2H), 3.70 (s, 3H), 2.92-2.71 (m, 3H), 2.38 (s, 3H), 1.75 (d, J=12.7 Hz, 2H), 1.69-1.54 (m, peak obscured), 1.49 (s, 9H). LCMS-A: rt 6.992 min; m/z 609.1 [M+H]$^+$.

(e) tert-Butyl 4-(4-((4-(2-(2-methoxy-2-oxoethyl) phenethyl)-5-(trifluoromethyl)pyrimidin-2-yl) amino)-2-methylphenyl)piperidine-1-carboxylate (A42)

A solution of tert-butyl 4-(4-((4-((2-(2-methoxy-2-oxoethyl)phenyl)ethynyl)-5-(trifluoromethyl)pyrimidin-2-yl) amino)-2-methylphenyl)piperidine-1-carboxylate (A41) (0.248 g, 0.407 mmol) in EtOH (10 mL) was added to a solution of 10% Pd/C (53% water; 0.680 g) in DMF (6 mL). The resulting mixture was stirred at room temperature for 16 hours under an atmosphere of hydrogen then filtered through a pad of Celite, washing with EtOAc (80 mL). The volatiles were removed in vacuo to afford a yellow oil which was purified by silica gel column chromatography (Biotage Isolera, 25 g SiO$_2$ cartridge, 0-40% EtOAc in petroleum benzine 40-60° C.) to yield the title compound A42 as a clear oil (0.196 g, 79%); $^1$H NMR (400 MHz, CDCl$_3$) δ 8.53 (s, 1H), 7.61 (s, 1H), 7.51 (dd, J=7.9, 1.5 Hz, 1H), 7.39 (d, J=2.2 Hz, 1H), 7.29-7.19 (m, obscured by solvent), 7.17 (d, J=8.4 Hz, 1H), 4.42-4.18 (m, 2H), 3.75 (s, 2H), 3.67 (s, 3H), 3.19-3.03 (m, 4H), 2.90-2.73 (m, 3H), 2.37 (s, 3H), 1.75 (d, J=12.6 Hz, 2H), 1.62 (m, 2H), 1.50 (s, 9H). LCMS-A: rt 7.094 min; m/z 613.2 [M+H]$^+$.

(f) tert-Butyl 4-(4-((4-(2-(2-amino-2-oxoethyl)phenethyl)-5-(trifluoromethyl)pyrimidin-2-yl)amino)-2-methylphenyl)piperidine-1-carboxylate (A43)

LiOH.H$_2$O (41.0 mg, 0.960 mmol) was added to a solution of tert-butyl 4-(4-((4-(2-(2-methoxy-2-oxoethyl)phenethyl)-5-(trifluoromethyl)pyrimidin-2-yl)amino)-2-methylphenyl) piperidine-1-carboxylate (A42) (0.196 g, 0.320 mmol) in THF (7 mL), water (1.5 mL) and MeOH (1 mL) and the resulting mixture stirred at room temperature for 19 hours. The volatiles were removed in vacuo, then the residue was partitioned between EtOAc (50 mL) and saturated aqueous NaHCO$_3$ (50 mL). The layers were separated and the aqueous layer was extracted with EtOAc (2×50 mL). The combined organic layers were washed with brine (50 mL), dried over MgSO$_4$ and the volatiles removed under reduced pressure. The residue was dissolved in dry THF (6 mL) and dry DMF (1 mL) under an atmosphere of nitrogen then HOBt (0.056 g, 0.41 mmol), EDCl.HCl (0.079 g, 0.41 mmol) and DIPEA (0.28 mL, 1.3 mmol) were added. After 10 minutes ammonium carbonate (0.15 g, 1.6 mmol) was added in one portion and the resulting mixture stirred at room temperature for 19 hours. The volatiles were removed in vacuo and the residue was partitioned between EtOAc (65 mL) and saturated NaHCO$_3$ (65 mL). The aqueous layer was extracted with EtOAc (2×50 mL) then the combined organic layers were washed with brine (50 mL) and dried over MgSO$_4$. The solvent was removed in vacuo and the residue purified by silica gel column chromatography (Biotage Isolera, 25 g SiO$_2$ cartridge, 0-80% EtOAc in petroleum benzine 40-60° C.) to give the title compound A43 as a white solid (0.16 g, 84%); $^1$H NMR (400 MHz, CDCl$_3$) δ 8.49 (s, 1H), 8.20 (s, 1H), 7.46 (dd, J=8.4, 2.0 Hz, 1H), 7.37 (d, J=1.9 Hz, 1H), 7.28-7.18 (m, obscured by solvent), 7.13 (d, J=8.4 Hz, 1H), 6.33 (s, 1H), 5.68 (s, 1H), 4.40-4.16 (m, 2H), 3.68 (s, 2H), 3.17-2.95 (m, 4H), 2.91-2.68 (m, 3H), 2.34 (s, 3H), 1.73 (d, J=12.3 Hz, 2H), 1.68-1.53 (m, 2H), 1.50 (s, 9H). LCMS-A: rt 6.670 min; m/z 598.1 [M+H]$^+$.

(g) 2-(2-(2-(2-((3-methyl-4-(piperidin-4-yl)phenyl) amino)-5-(trifluoromethyl)pyrimidin-4-yl)ethyl)phenyl)acetamide (11)

TFA (1 mL) was added to a stirred solution of tert-butyl 4-(4-((4-(2-(2-amino-2-oxoethyl)phenethyl)-5-(trifluoromethyl)pyrimidin-2-yl)amino)-2-methylphenyl)piperidine-1-carboxylate (A43) (0.16 g, 0.27 mmol) in DCM (4 mL) and the resulting solution was stirred at room temperature for 16 hours. The volatiles were removed in vacuo and the residue was partitioned between EtOAc (10 mL) and 2 M aqueous NaOH (10 mL). The aqueous layer was extracted with EtOAc (2×10 mL) then and the combined organic layers were washed with water (10 mL), brine (10 mL) and dried over MgSO$_4$. The volatiles were removed in vacuo to give a pale yellow solid. The solid was suspended in cyclohexane and the resulting suspension filtered to give the title compound 11 as a white solid (0.085 g, 64%); $^1$H NMR (400 MHz, d$_4$-MeOH) δ 8.52 (s, 1H), 7.54 (dd, J=8.4, 2.2 Hz, 1H), 7.44 (d, J=2.1 Hz, 1H), 7.29-7.23 (m, 1H), 7.23-7.15 (m, 4H), 3.67 (s, 2H), 3.23-3.11 (m, 4H), 3.10-3.01 (m, 2H), 2.91 (tt, J=11.7, 3.8 Hz, 1H), 2.80 (td, J=12.3, 2.8 Hz, 2H), 2.35 (s, 3H), 1.84-1.59 (m, 4H). LCMS-A: rt 4.962 min; m/z 498.3 [M+H]$^+$.

Example 12

Synthesis of 2-(2-(2-(2-((3-methyl-4-(1-methylpiperidin-4-yl)phenyl)amino)-5-(trifluoromethyl)pyrimidin-4-yl)ethyl)phenyl)acetamide (12)

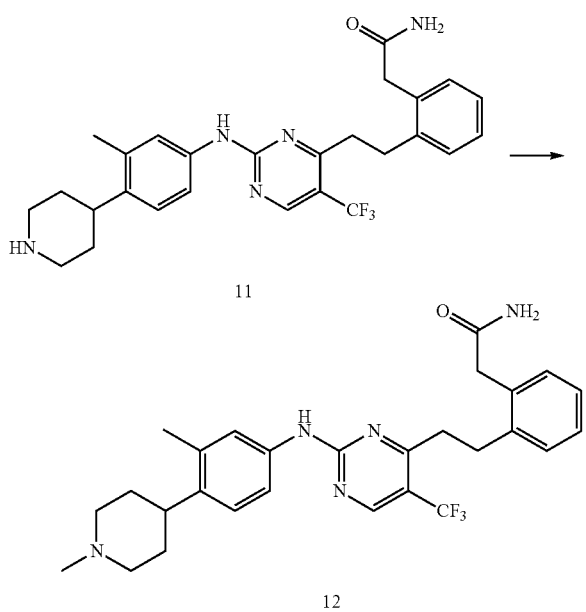

Formaldehyde (37 wt. % in H₂O; 0.040 mL, 0.50 mmol) was added to a suspension of 2-(2-(2-(2-((3-methyl-4-(piperidin-4-yl)phenyl)amino)-5-(trifluoromethyl)pyrimidin-4-yl)ethyl)phenyl)acetamide (11) (0.035 g, 0.070 mmol) in MeOH (5 mL) under an atmosphere of nitrogen. Sodium triacetoxyborohydride (0.19 g, 0.10 mmol) was added in one portion and the resulting mixture stirred at room temperature for 3 hours. The volatiles were removed in vacuo and the residue was partitioned between EtOAc (10 mL) and saturated aqueous NaHCO₃ (10 mL). Solid NaHCO₃ was added until the formation of gas ceased then the layers were separated and the aqueous layer was extracted with EtOAc (2×100 mL). The combined organic layers were washed with water (10 mL), brine (10 mL) and dried over Na₂SO₄. The volatiles were removed under reduced pressure to yield the title compound 12 as a white solid (0.032 g, 89%); ¹H NMR (400 MHz, d₄-MeOH) δ 8.52 (s, 1H), 7.53 (dd, J=8.4, 2.3 Hz, 1H), 7.44 (d J=2.2 Hz, 1H), 7.28-7.22 (m, 1H), 7.24-7.15 (m, 4H), 3.67 (s, 2H), 3.20-3.11 (m, 2H), 3.11-2.95 (m, 4H), 2.81-2.70 (m, 1H), 2.35 (s, 3H), 2.34 (s, 3H), 2.28-2.13 (m, 2H), 1.87-1.70 (m, 4H). LCMS-A: rt 4.908 min; m/z 512.3 [M+H]⁺.

Example 13

Synthesis of 2-(2-(2-(2-((6-(piperidin-4-yl)pyridin-3-yl)amino)-5-(trifluoromethyl)pyrimidin-4-yl)ethyl)phenyl)acetamide (13)

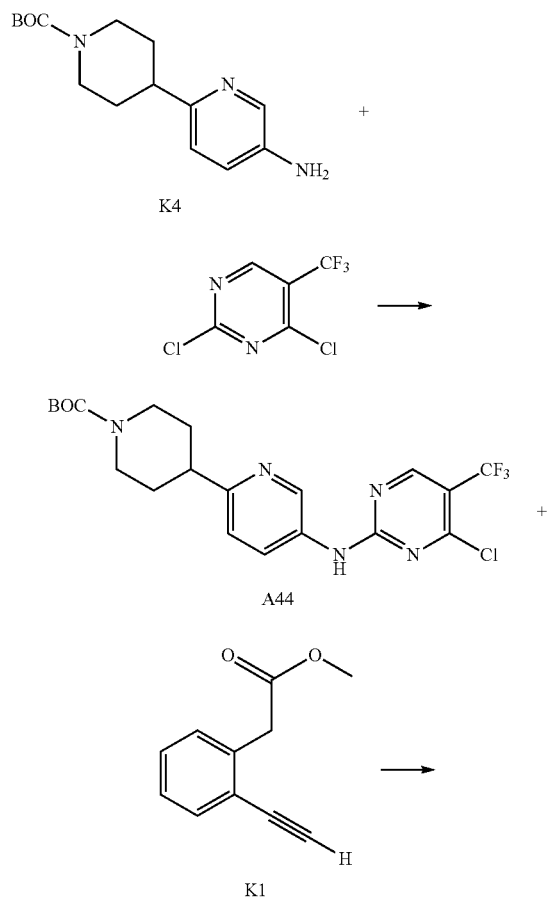

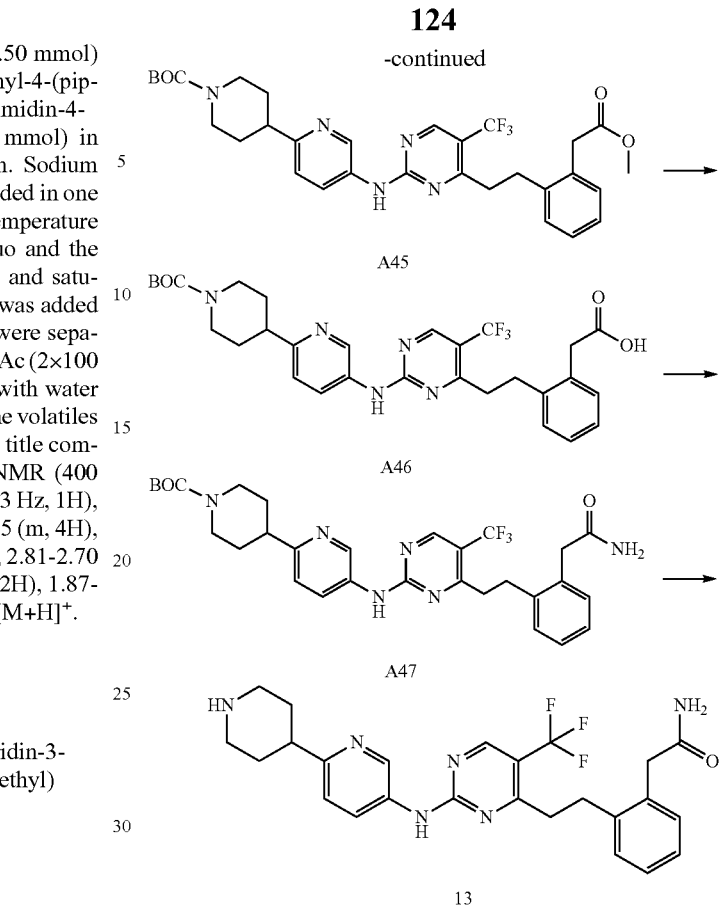

(a) tert-Butyl 4-(5-((4-chloro-5-(trifluoromethyl)pyrimidin-2-yl)amino)pyridin-2-yl)piperidine-1-carboxylate (A44)

A 1.0 M ZnCl₂ solution in Et₂O (2.16 mL, 2.16 mmol) was added cautiously to a solution of 2,4-dichloro-5-(trifluoromethyl)pyrimidine (411 mg, 1.89 mmol) in 1:1 t-BuOH:DCE (100 mL) at room temperature and the resulting mixture stirred at room temperature for 20 minutes. tert-Butyl 4-(5-aminopyridin-2-yl)piperidine-1-carboxylate (K4) (500 mg, 1.80 mmol) was added followed by Et₃N (0.30 mL, 2.16 mmol) then stirring was continued for 44 hours at room temperature. The volatiles were removed in vacuo and the residue was suspended in water (250 mL). The resulting suspension was sonicated for 10 minutes then filtered, washing the filter cake with water (2×100 mL). The filter cake was adsorbed onto silica gel and purified by column chromatography (Biotage Isolera, 40 g SiO₂ cartridge, 0-100% EtOAc in petroleum benzine 40-60° C.) to give the title compound A44 as an off white solid (346 mg, 42%); ¹H NMR (400 MHz, d₆-DMSO) δ 10.74 (s, 1H), 8.81 (s, 1H), 8.73 (d, J=2.4 Hz, 1H), 8.00 (dd, J=8.5, 2.5 Hz, 1H), 7.30 (d, J=8.5 Hz, 1H), 4.05 (d, J=11.8 Hz, 2H), 2.82 (m, 3H), 1.81 (d, J=11.1 Hz, 2H), 1.55 (m, 2H), 1.41 (s, 9H). LCMS-A: rt 5.949 min; m/z 458 [M+H]⁺.

(b) tert-Butyl 4-(5-((4-(2-(2-methoxy-2-oxoethyl)phenethyl)-5-(trifluoromethyl)pyrimidin-2-yl)amino)pyridin-2-yl)piperidine-1-carboxylate (A45)

A suspension of tert-butyl 4-(5-((4-chloro-5-(trifluoromethyl)pyrimidin-2-yl)amino)pyridin-2-yl)piperidine-1-carboxylate (A44) (340 mg, 0.74 mmol), CuI (7 mg, 0.04 mmol), PPh₃ (10 mg, 0.04 mmol) and Et₃N (207 μL, 1.49 mmol) in DMF (2.5 mL) was sonicated for 5 minutes. PdCl₂(PPh₃)₂ (26 mg, 0.04 mmol) and methyl 2-(2-ethynylphenyl)acetate (K1) (194 mg, 1.11 mmol) in DMF (1 mL) were added and the resulting mixture degassed with nitrogen for 5 minutes before heating under microwave irradiation at 120° C. for 20 minutes. The resulting mixture was adsorbed on silica gel and purified by column chromatography (Biotage Isolera, 40 g SiO₂ cartridge, 0-100% EtOAc in hexanes) to give a brown oil that was taken up in DMF (25 mL) and Et₃N (2 mL) before 10% Pd/C (53% water; 75 mg) was added. The resulting mixture was stirred at room temperature for 44 hours under a hydrogen atmosphere then filtered through Celite, washing with EtOAc (200 mL). Activated charcoal (ca. 2.5 g) was added to the filtrate and the resulting suspension stirred at room temperature for 4 hours before filtration through Celite, washing with EtOAc (100 mL). The filtrate was washed with water (100 mL), brine (100 mL), dried (Na₂SO₄) and concentrated under reduced pressure to give a brown oil. A suspension of 10% Pd/C (53% water; 200 mg) in DMF (100 mL) and Et₃N (10 mL) was added and the resulting mixture stirred under a hydrogen atmosphere at room temperature for 4.5 days. The resulting mixture was filtered through Celite, washing with EtOAc (250 mL) then the combined filtrates were washed with water (3×100 mL) then brine (3×100 mL). The organic layer was dried (Na₂SO₄), filtered and concentrated under reduced pressure. The residue was purified by silica gel column chromatography (Biotage Isolera, 40 g SiO₂ cartridge, 0-100% EtOAc in petroleum benzine 40-60° C.) to give the title compound A45 as a yellow oil (96 mg, 21%); ¹H NMR (400 MHz, CDCl₃) δ 8.65 (d, J=2.4 Hz, 1H), 8.55 (d, J=0.5 Hz, 1H), 8.14 (dd, J=8.5, 2.7 Hz, 1H), 7.55 (s, 1H), 7.25-7.18 (m, 4H), 7.16 (d, J=8.5 Hz, 1H), 4.26 (s, 2H), 3.74 (s, 2H), 3.68 (s, 3H), 3.11 (s, 4H), 2.88-2.79 (m, 3H), 1.92 (d, J=12.0 Hz, 2H), 1.77-1.64 (m, 2H), 1.47 (s, 9H). LCMS-A: rt 6.137 min; m/z 600 [M+H]⁺.

(c) 2-(2-(2-(2-((6-(1-(tert-Butoxycarbonyl)piperidin-4-yl)pyridin-3-yl)amino)-5-(trifluoromethyl)pyrimidin-4-yl)ethyl)phenyl)acetic acid (A46)

LiOH.H₂O (297 mg, 7.1 mmol) was added to a stirred solution of tert-butyl 4-(5-((4-(2-(2-methoxy-2-oxoethyl)phenethyl)-5-(trifluoromethyl)pyrimidin-2-yl)amino)pyridin-2-yl)piperidine-1-carboxylate (A45) (85 mg, 0.14 mmol) in H₂O (2 mL) and THF (20 mL) and the resulting mixture heated at 40° C. for 18 hours. The volatiles were removed in vacuo and the residue was partitioned between EtOAc (100 mL), and aqueous 2 M HCl (50 mL). The layers were separated and the organics washed with water (100 mL), brine (50 mL) and dried over MgSO₄. The volatiles were removed in vacuo to give the title compound A46 as an orange foam (74 mg, 89%); ¹H NMR (400 MHz, d₄-MeOH) δ 9.00 (d, J=1.8 Hz, 1H), 8.66 (s, 1H), 8.36 (dd, J=8.7, 2.6 Hz, 1H), 7.54 (d, J=8.7 Hz, 1H), 7.28-7.10 (m, 4H), 4.25 (d, J=13.4 Hz, 2H), 3.72 (s, 2H), 3.19-3.09 (m, 4H), 3.07-2.83 (m, 3H), 1.94 (d, J=12.7 Hz, 2H), 1.72 (m, 2H), 1.48 (s, 9H). LCMS-A: rt 5.707 min; m/z 586 [M+H]⁺.

(d) tert-Butyl 4-(5-((4-(2-(2-amino-2-oxoethyl)phenethyl)-5-(trifluoromethyl)pyrimidin-2-yl)amino)pyridin-2-yl)piperidine-1-carboxylate (A47)

HOBt (50 mg, 0.37 mmol), EDCl.HCl (78 mg, 0.41 mmol) and DIPEA (0.11 mL, 0.63 mmol) were added to a stirred solution of 2-(2-(2-(2-((6-(1-(tert-butoxycarbonyl)piperidin-4-yl)pyridin-3-yl)amino)-5-(trifluoromethyl)pyrimidin-4-yl)ethyl)phenyl)acetic acid (A46) (74 mg, 0.13 mmol) in dry DMF (5 mL) under an atmosphere of nitrogen. After 10 minutes ammonium carbonate (121 mg, 1.26 mmol) was added in one portion and the resulting mixture was stirred for 18 hours at room temperature. The volatiles were removed in vacuo and the residue was partitioned between EtOAc (10 mL) and saturated aqueous NaHCO₃ (10 mL). The aqueous layer was extracted with EtOAc (2×10 mL) then the combined organic layers were washed with brine (10 mL) and dried over Na₂SO₄. The volatiles were removed in vacuo and the residue purified by silica gel column chromatography (Biotage Isolera, 40 g SiO₂ cartridges, 0-100% EtOAc in petroleum benzine 40-60° C. followed by 0-25% MeOH in EtOAc) to give the title compound A47 as clear oil (58 mg, 78%); ¹H NMR (400 MHz, CDCl₃) δ 8.83 (s, 1H), 8.54 (s, 1H), 7.97 (s, 1H), 7.80 (s, 1H), 7.30-7.22 (m, 4H), 7.17 (d, J=8.5 Hz, 1H), 5.78 (s, 1H), 5.62 (s, 1H), 4.25 (s, 2H), 3.74 (s, 2H), 3.11 (s, 4H), 2.83 (m, 3H), 1.92 (d, J=12.3 Hz, 2H), 1.79-1.60 (m, 2H, peak obscured), 1.48 (s, 9H). LCMS-A: rt 5.549 min; m/z 585 [M+H]⁺.

(e) 2-(2-(2-(2-((6-(Piperidin-4-yl)pyridin-3-yl)-amino)-5-(trifluoromethyl)pyrimidin-4-yl)ethyl)phenyl)acetamide (13)

TFA (0.5 mL) was added to a solution of tert-butyl 4-(5-((4-(2-(2-amino-2-oxoethyl)phenethyl)-5-(trifluoromethyl)pyrimidin-2-yl)amino)pyridin-2-yl)piperidine-1-carboxylate (A47) (58 mg, 0.099 mmol) in DCM (5 mL) and the resulting solution stirred for 18 hours at room temperature. The volatiles were evaporated under reduced pressure and the residue partitioned between 2 M aqueous NaOH (10 mL) and EtOAc (25 mL). The organic layer was separated and washed with water (25 mL), brine (25 mL), dried (Na₂SO₄) and concentrated under reduced pressure to give the title compound 13 as a white solid (41 mg, 85%); ¹H NMR (400 MHz, d₄-MeOH) δ 8.78 (d, J=2.1 Hz, 1H), 8.61 (d, J=0.6 Hz, 1H), 8.19 (dd, J=8.6, 2.6 Hz, 1H), 7.31 (d, J=8.5 Hz, 1H), 7.26 (d, J=6.3 Hz, 1H), 7.24-7.15 (m, 3H), 3.67 (s, 2H), 3.22-3.15 (m, 4H), 3.14-3.05 (m, 2H), 2.90-2.70 (m, 3H), 1.93 (d, J=13.9 Hz, 2H), 1.75 (m, 2H). LCMS-A: rt 4.552 min; m/z 485 [M+H]⁺.

Example 14

Synthesis of 2-(2-(2-(2-((6-(1-methylpiperidin-4-yl)pyridin-3-yl)amino)-5-(trifluoromethyl)pyrimidin-4-yl)ethyl)phenyl)acetamide (14)

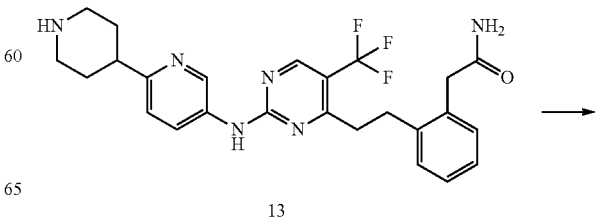

13

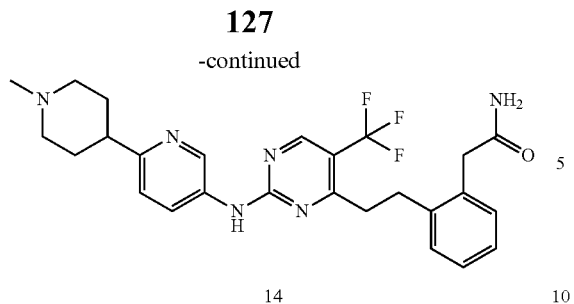

Formaldehyde (37 wt. % in H$_2$O; 0.012 mL, 0.17 mmol) was added to a solution of 2-(2-(2-(2-((6-(piperidin-4-yl)pyridin-3-yl)amino)-5-(trifluoromethyl)pyrimidin-4-yl)ethyl)phenyl)acetamide (13) (27 mg, 0.056 mmol) in MeOH (2 mL) under an atmosphere of nitrogen. The resulting mixture was stirred for 15 minutes at room temperature before sodium triacetoxyborohydride (47 mg, 0.22 mmol) was added in one portion and stirring was continued at room temperature for 18 hours. The volatiles were removed in vacuo and the residue was partitioned between EtOAc (50 mL) and saturated aqueous NaHCO$_3$ (50 mL). The layers were separated and the aqueous layer was extracted with EtOAc (2×25 mL). The combined organic layers were washed with water (25 mL), brine (25 mL) then dried over Na$_2$SO$_4$. The solvent was removed under reduced pressure to give the title compound 14 as a white solid (25 mg, 90%); $^1$H NMR (400 MHz, d$_4$-MeOH) δ 8.77 (d, J=2.4 Hz, 1H), 8.60 (s, 1H), 8.18 (dd, J=8.6, 2.6 Hz, 1H), 7.31 (d, J=8.6 Hz, 1H), 7.26 (d, J=6.3 Hz, 1H), 7.21-7.15 (m, 3H), 3.67 (s, 2H), 3.20-3.14 (m, 2H), 3.14-3.08 (m, 2H), 3.04 (d, J=11.7 Hz, 2H), 2.71 (tt, J=11.9, 3.9 Hz, 1H), 2.35 (s, 3H), 2.21 (td, J=12.0, 2.5 Hz, 2H), 1.96 (d, J=11.0 Hz, 2H), 1.92-1.80 (m, 2H). LCMS-A: rt 4.635 min; m/z 499 [M+H]$^+$.

Example 15

Synthesis of 2-(4-fluoro-2-(2-(2-((4-(piperidin-4-yl)phenyl)amino)-5-(trifluoromethyl)pyrimidin-4-yl)ethyl)phenyl)acetamide (15)

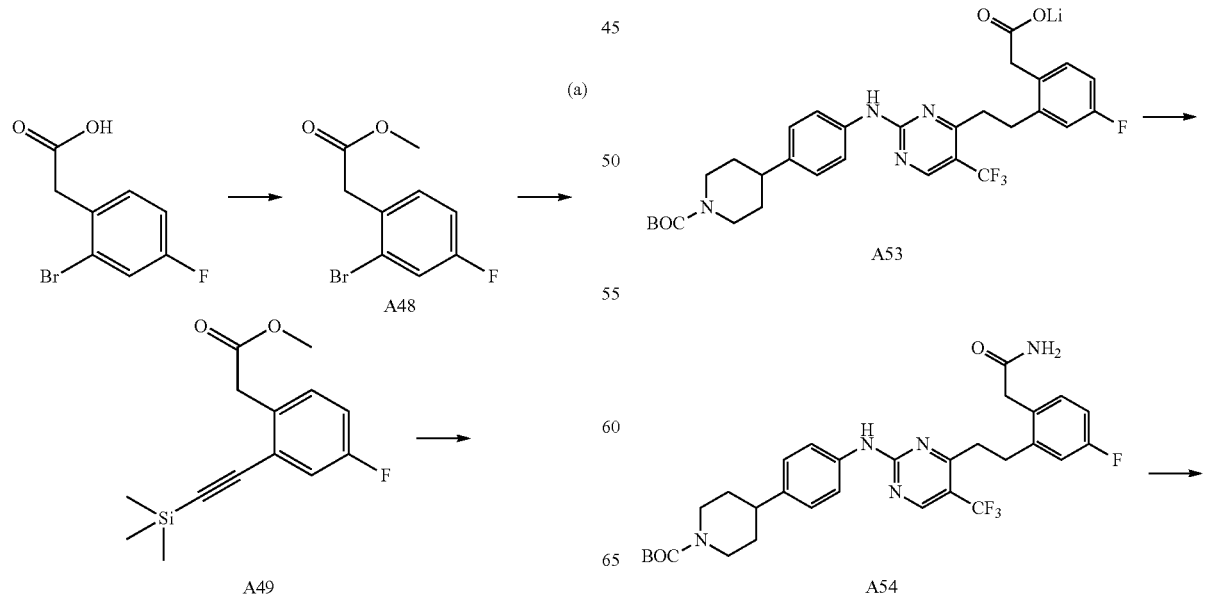

-continued

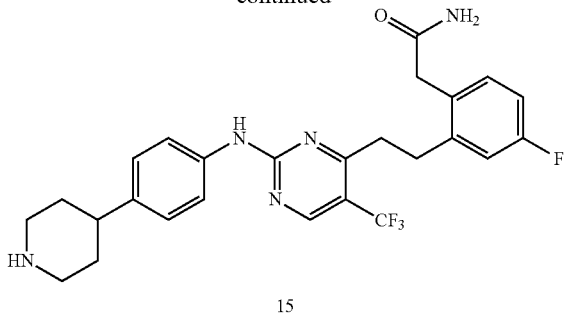

Methyl 2-(2-bromo-4-fluorophenyl)acetate (A48)

Sulfuric acid (1.50 mL) was added cautiously to a solution of 2-bromo-4-fluorophenylacetic acid (1.00 g, 4.29 mmol) in MeOH (25 mL) and the resulting mixture stirred overnight at room temperature. Saturated aqueous $Na_2CO_3$ solution was added until the pH of the mixture was 14, then the aqueous layer was extracted with DCM (2×100 mL). The combined organics were dried over $MgSO_4$ then the volatiles were removed in vacuo to yield the title compound A48 as a clear oil (1.00 g, 94%); $^1$H NMR (400 MHz, $CDCl_3$) δ 7.34 (dd, J=8.2, 2.6 Hz, 1H), 7.29 (dd, J=8.5, 6.0 Hz, 1H), 7.03 (td, J=8.3, 2.6 Hz, 1H), 3.79 (s, 2H), 3.74 (s, 3H). LCMS-A: rt 5.911 min.

(b) Methyl 2-(4-fluoro-2-((trimethylsilyl)-ethynyl) phenyl)acetate (A49)

A suspension of (trimethylsilyl)acetylene (0.696 g, 7.08 mmol), methyl 2-(2-bromo-4-fluorophenyl)acetate (A48) (0.500 g, 2.02 mmol), $PPh_3$ (0.053 g, 0.202 mmol), CuI (39 mg, 0.202 mmol), $Et_3N$ (1.41 mL, 10.1 mmol) and $PdCl_2(PPh_3)_2$ (0.142 g, 0.202 mmol) in THF (25 mL) was heated at 35° C. for 16 hours. The resulting mixture was adsorbed onto silica gel and purified using column chromatography (Biotage Isolera, 40 g $SiO_2$ cartridge, 0-40% EtOAc in petroleum benzine 40-60° C.) to yield the title compound A49 as a clear oil (0.212 g, 40%); LCMS-A: rt 6.830 min.

(c) Methyl 2-(2-ethynyl-4-fluorophenyl)acetate (A50)

A solution of TBAF (1.0 M in THF; 2.0 mL, 2.0 mmol) was added to a stirred solution of methyl 2-(4-fluoro-2-((trimethylsilyl)ethynyl)phenyl)acetate (A49) (0.212 g, 0.802 mmol) in DCM (5 mL). After 2 minutes the resulting mixture was diluted with water (100 mL) and DCM (50 mL). The organic fraction was separated and adsorbed onto silica gel then purified using column chromatography (Biotage Isolera, 12 g $SiO_2$ Cartridge, 0-20% EtOAc in petroleum benzine 40-60° C.) to give the title compound A50 as a brown oil (0.106 g, 69%); $^1$H NMR (400 MHz, $CDCl_3$) δ 7.37-7.26 (m, 1H), 7.23 (dd, J=9.0, 2.8 Hz, 1H), 7.06 (m, 1H), 3.84 (s, 2H), 3.73 (s, 3H), 3.33 (s, 1H). LCMS-A: rt 5.838 min; m/z 193 [M+H]$^+$.

(d) tert-Butyl 4-(4-((4-((5-fluoro-2-(2-methoxy-2-oxoethyl)phenyl)ethynyl)-5-(trifluoromethyl)pyrimidin-2-yl)amino)phenyl)piperidine-1-carboxylate (A51)

A suspension of tert-butyl 4-(4-((4-chloro-5-(trifluoromethyl)pyrimidin-2-yl)amino)phenyl)piperidine-1-carboxylate (K5) (0.252 g, 0.552 mmol), methyl 2-(2-ethynyl-4-fluorophenyl)acetate (A50) (0.106 g, 0.552 mmol), $PPh_3$ (0.007 g, 0.03 mmol), CuI (0.005 g, 0.03 mmol) and $PdCl_2(PPh_3)_2$ (0.019 g, 0.028 mmol) in DMF (3 mL) and $Et_3N$ (1.0 mL) was heated under microwave irradiation for 20 minutes at 120° C. The resulting mixture was diluted with EtOAc (100 mL) then washed with water (100 mL), brine (25 mL) and dried over $MgSO_4$. The volatiles were evaporated in vacuo and the residue was adsorbed onto silica gel and purified using column chromatography (Biotage Isolera, 40 g $SiO_2$ cartridge, 0-80% EtOAc in petroleum benzine 40-60° C.) to give the title compound A51 as a yellow solid (0.158 g, 47%); $^1$H NMR (400 MHz, $CDCl_3$) δ 8.64 (d, J=1.0 Hz, 1H), 7.75 (s, 1H), 7.62-7.55 (m, 2H), 7.38-7.27 (m, 2H), 7.25-7.19 (m, 2H), 7.14 (td, J=8.3, 2.7 Hz, 1H), 4.36-4.20 (m, 2H), 3.92 (s, 2H), 3.72 (s, 3H), 2.82 (t, J=12.8 Hz, 2H), 2.66 (td, J=8.5, 4.2 Hz, 1H), 1.89-1.78 (m, 2H), 1.70-1.54 (m, 2H), 1.51 (s, 9H). LCMS-A: rt 1.852 min; m/z 613 [M+H]$^+$.

(e) tert-Butyl 4-(4-((4-(5-fluoro-2-(2-methoxy-2-oxoethyl)phenethyl)-5-(trifluoromethyl)pyrimidin-2-yl)amino)phenyl)piperidine-1-carboxylate (A52)

A suspension of Pd/C 10% (0.100 g) and tert-butyl 4-(4-((4-((5-fluoro-2-(2-methoxy-2-oxoethyl)phenyl)ethynyl)-5-(trifluoromethyl)pyrimidin-2-yl)amino)phenyl)piperidine-1-carboxylate (A51) (0.158 g, 0.258 mmol) in EtOAc (20 mL) was stirred under a hydrogen atmosphere at room temperature overnight. The resulting mixture was filtered through a Celite plug, washing with EtOAc (100 mL) then the combined organic washings were evaporated in vacuo to yield the title compound A52 as a yellow oil (0.092 g, 58%); $^1$H NMR (400 MHz, $CDCl_3$) δ 8.46 (s, 1H), 7.48 (d, J=8.5 Hz, 2H), 7.17-7.10 (m, 3H), 6.91-6.78 (m, 2H), 4.18 (s, 2H), 3.62 (s, 2H), 3.60 (s, 3H), 3.01 (s, 4H), 2.73 (t, J=11.9 Hz, 2H), 2.57 (tt, J=12.0, 3.4 Hz, 1H), 1.75 (d, J=12.8 Hz, 2H), 1.54 (qd, J=12.8, 4.2 Hz, 2H), 1.41 (s, 9H). LCMS-A: rt 6.727/6.998 min; m/z 617 [M+H]$^+$.

(f) Lithium 2-(2-(2-(2-((4-(1-(tert-butoxycarbonyl) piperidin-4-yl)phenyl)amino)-5-(trifluoromethyl) pyrimidin-4-yl)ethyl)-4-fluorophenyl)acetate (A53)

$LiOH.H_2O$ (0.063 g, 1.5 mmol) was added to a stirred solution of tert-butyl 4-(4-((4-((5-fluoro-2-(2-methoxy-2-oxoethyl)phenethyl)-5-(trifluoromethyl)pyrimidin-2-yl) amino)phenyl)piperidine-1-carboxylate (A52) (0.092 g, 0.15 mmol) in $H_2O$ (0.5 mL) and THF (5 mL) and the resulting mixture heated at 40° C. overnight. The volatiles were removed in vacuo and the residue was taken up in DCM (50 mL). The resulting solution was washed with saturated aqueous $Na_2CO_3$ (25 mL) then the aqueous phase was then extracted with DCM (2×25 mL). The organic layers were combined, dried over $MgSO_4$ and the volatiles were removed in vacuo to yield the title compound A53 (0.089 g, 98%); LCMS-A: rt 6.596 min; m/z 603 [(M-Li)+H]$^+$.

(g) tert-Butyl 4-(4-((4-(2-(2-amino-2-oxoethyl)-5-fluorophenethyl)-5-(trifluoromethyl)pyrimidin-2-yl) amino)phenyl)piperidine-1-carboxylate (A54)

HOBt (0.024 g, 0.175 mmol) and EDCl.HCl (0.034 g, 0.175 mmol) were added to a solution of lithium 2-(2-(2-(2-((4-(1-(tert-butoxycarbonyl)piperidin-4-yl)phenyl)amino)-5-(trifluoromethyl)pyrimidin-4-yl)ethyl)-4-fluorophenyl) acetate (A53) (0.089 g, 0.146 mmol) and $Et_3N$ (0.082 mL, 0.585 mmol) in DMF (5 mL) and the resulting mixture stirred at 40° C. overnight. Saturated aqueous NaHCO₃ (25 mL) and DCM (25 mL) were added then the layers separated and the aqueous phase extracted with CHCl₃ (3×25 mL). The organics were combined then the volatiles were evaporated in vacuo. The residue was adsorbed onto silica gel and purified using column chromatography (Biotage Isolera, 12 g SiO₂ cartridge, 0-100% EtOAc in petroleum benzine 40-60° C.) to yield a clear oil. The oil was triturated with water and the resulting precipitate collected by filtration to give the title compound A54 as a white solid (0.065 g, 74%); ¹H NMR (400 MHz, CDCl₃) δ 8.47 (d, J=1.0 Hz, 1H), 7.46 (d, J=8.2 Hz, 3H), 7.18-7.09 (m, 3H), 6.95-6.84 (m, 2H), 5.24 (d, J=21.9 Hz, 2H), 4.18 (s, 2H), 3.60 (s, 2H), 3.02 (s, 4H), 2.74 (t, J=10.2 Hz, 2H), 2.58 (m, 1H), 1.76 (d, J=11.7 Hz, 2H), 1.64-1.51 (m, 2H), 1.42 (s, 9H). LCMS-A: rt 6.477 min; m/z 602 [M+H]⁺.

(h) 2-(4-Fluoro-2-(2-(2-((4-(piperidin-4-yl)phenyl) amino)-5-(trifluoromethyl)pyrimidin-4-yl)ethyl)phenyl)acetamide (15)

TFA (0.5 mL) was added to a solution of tert-butyl 4-(4-((4-(2-(2-amino-2-oxoethyl)-5-fluorophenethyl)-5-(trifluoromethyl)pyrimidin-2-yl)amino)phenyl)piperidine-1-carboxylate (A54) (0.065 g, 0.108 mmol) in DCM (5.0 mL) and the resulting mixture stirred at room temperature overnight. The volatiles were removed in vacuo to yield an orange oil to which 2 M aqueous NaOH (25 mL) was cautiously added. The resulting suspension was sonicated for 10 minutes then filtered. The white filter cake was washed with water (50 mL), petroleum benzine 40-60° C. (50 mL) then air dried to yield the title compound 15 as a white solid (0.036 g, 66%); ¹H NMR (400 MHz, d₆-DMSO) δ 10.13 (s, 1H), 8.66 (s, 1H), 7.65 (d, J=8.6 Hz, 2H), 7.45 (s, 1H), 7.26 (dd, J=8.3, 6.2 Hz, 1H), 7.18 (d, J=8.6 Hz, 2H), 7.06-6.96 (m, 2H), 6.94 (s, 1H), 3.47 (s, 2H), 3.17-2.95 (m, 6H), 2.56 (m, 3H), 1.67 (d, J=13.6 Hz, 2H), 1.49 (qd, J=12.1, 2.8 Hz, 2H). LCMS-A: rt 4.687 min; m/z 502 [M+H]⁺.

Example 16

Synthesis of 2-(2-(2-(5-methyl-2-((4-(piperidin-4-yl) phenyl)amino)pyrimidin-4-yl)ethyl)phenyl)acetamide (16)

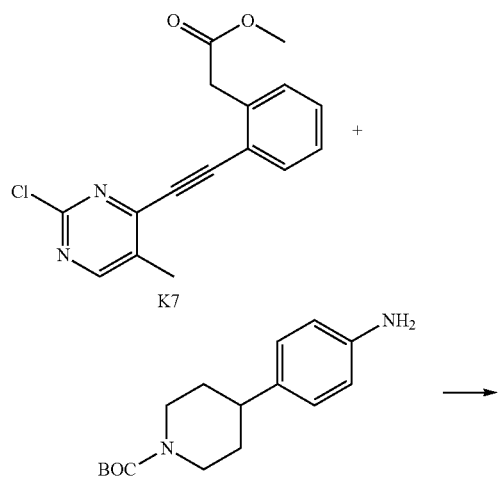

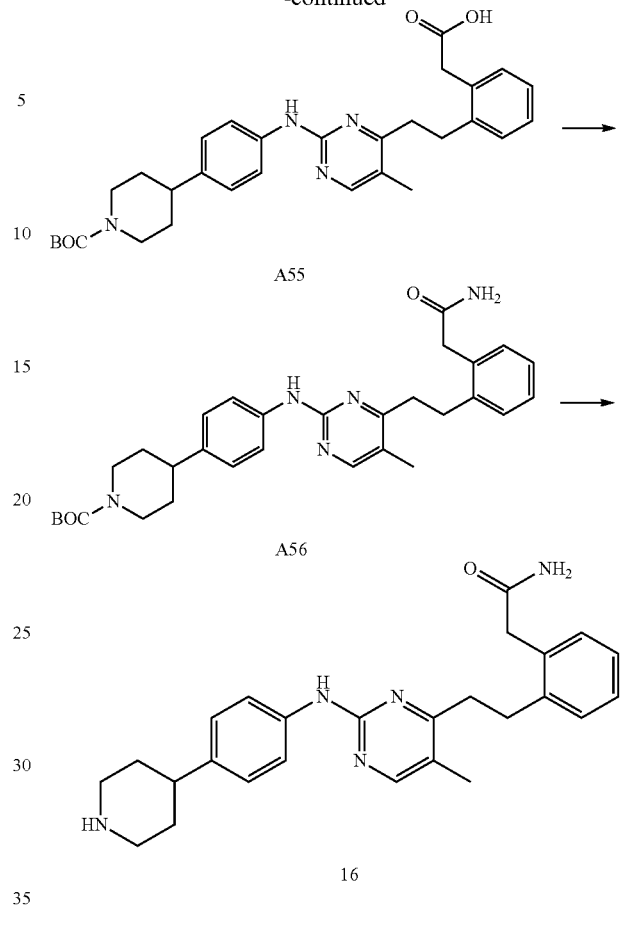

(a) 2-(2-(2-(2-((4-(1-(tert-Butoxycarbonyl)piperidin-4-yl)phenyl)amino)-5-methylpyrimidin-4-yl)ethyl) phenyl)acetic acid (A55)

To a suspension of methyl 2-(2-((2-chloro-5-methylpyrimidin-4-yl)ethynyl)phenyl)acetate (K7) (110 mg, 0.366 mmol) in 1,4-dioxane (5 mL) was added tert-butyl 4-(4-aminophenyl)piperidine-1-carboxylate (101 mg, 0.366 mmol), Cs₂CO₃ (477 mg, 1.46 mmol), Pd₂(dba)₃ (33 mg, 0.037 mmol) and Xantphos (63 mg, 0.11 mmol). The resulting suspension was degassed with nitrogen for 5 minutes then heated under microwave irradiation for 30 minutes at 120° C. The volatiles were removed under reduced pressure and the residue was adsorbed onto silica gel and purified by column chromatography (Biotage Isolera, SiO₂ cartridge, 0-50% EtOAc in petroleum benzine 40-60° C.) to give a yellow oil. A suspension of 10% Pd/C (100 mg) in DMF (10 mL) and Et₃N (1 mL) was added and the resulting mixture stirred under an atmosphere of hydrogen for 16 hours. EtOAc (60 mL) was added and the resulting mixture filtered through Celite. The filtrate was evaporated under reduced pressure and the residue was adsorbed onto silica gel and purified by column chromatography (Biotage Isolera, SiO₂ cartridges, 0-60% EtOAc in petroleum benzine 40-60° C.) to give a yellow oil. This was taken up in THF (7 mL), MeOH (7 mL) and H₂O (1.5 mL) to which LiOH.H₂O (115 mg, 2.74 mmol) was added. The resulting mixture was stirred at room temperature overnight then the volatiles were removed under

133 reduced pressure. The residue was partitioned between EtOAc (50 mL) and aqueous HCl (2 M; 50 mL) then the layers were separated. The aqueous phase was extracted with EtOAc (2×50 mL) then the organics were combined, washed with brine and dried over MgSO₄. The volatiles were removed in vacuo to give the title compound A55 as yellow oil (127 mg, 87%); LCMS-A: rt 6.272 min; m/z 531 [M+H]⁺.

(b) tert-Butyl 4-(4-((4-(2-(2-amino-2-oxoethyl)phenethyl)-5-methylpyrimidin-2-yl)amino)phenyl)piperidine-1-carboxylate (A56)

HOBt (49 mg, 0.36 mmol), EDCl.HCl (69 mg, 0.36 mmol) and DIPEA (0.21 mL, 1.2 mmol) were added to a stirred solution of 2-(2-(2-(2-((4-(1-(tert-butoxycarbonyl)piperidin-4-yl)phenyl)amino)-5-methylpyrimidin-4-yl)ethyl)phenyl) acetic acid (A55) (127 mg, 0.239 mmol) in dry THF (6 mL) and dry DMF (1 mL) under an atmosphere of nitrogen. After 10 minutes ammonium carbonate (115 mg, 1.20 mmol) was added in one portion and the resulting mixture was stirred at room temperature for 24 hours. The volatiles were removed in vacuo then the residue was partitioned between EtOAc (50 mL) and saturated aqueous NaHCO₃ (50 mL). The layers were separated and the aqueous phase was extracted with EtOAc (2×50 mL). The organic extracts were combined, washed with brine and dried over MgSO₄. The volatiles were removed under reduced pressure and the residue purified by column chromatography (0-100% EtOAc in petroleum benzine 40-60° C.) to give the title compound A56 as an off-white solid (66 mg, 52%); ¹H NMR (400 MHz, d₆-DMSO) δ 9.36 (s, 1H), 8.25-8.16 (m, 1H), 7.74 (d, J=8.7 Hz, 2H), 7.49 (s, 1H), 7.28 (m, 1H), 7.25-7.14 (m, 5H), 7.00 (s, 1H), 4.14 (m, 2H), 3.56 (s, 2H), 3.17-3.04 (m, 2H), 2.98-2.91 (m, 2H), 2.84 (m, 2H), 2.71-2.60 (m, 1H), 2.13 (s, 3H), 1.79 (d, J=11.7 Hz, 2H), 1.59-1.43 (m, 11H). LCMS-A: rt 6.078 min; m/z 530 [M+H]⁺.

(c) 2-(2-(2-(5-Methyl-2-((4-(piperidin-4-yl)phenyl) amino)pyrimidin-4-yl)ethyl)phenyl)acetamide (16)

TFA (0.37 mL, 4.8 mmol) was added to a solution of tert-butyl 4-(4-((4-(2-(2-amino-2-oxoethyl)phenethyl)-5-methylpyrimidin-2-yl)amino)phenyl)piperidine-1-carboxylate (A56) (64 mg, 0.12 mmol) in DCM (20 mL) under nitrogen and the resulting mixture stirred for 24 hours at room temperature. The volatiles were removed in vacuo and the residue was taken up in MeOH and loaded onto an SCX cartridge (10 g). The column was eluted with 5 column volumes of MeOH and then 5 column volumes of 5% v/v aqueous ammonia in MeOH. The volatiles from the ammoniacal filtrate were evaporated under reduced pressure and the resulting solid dried under high vacuum to give the title compound 16 as a white solid (36 mg, 69%); ¹H NMR (400 MHz, d₆-DMSO) δ 9.28 (s, 1H), 8.15 (s, 1H), 7.67 (d, J=8.6 Hz, 2H), 7.44 (s, 1H), 7.25-7.13 (m, 4H), 7.10 (d, J=8.6 Hz, 2H), 6.93 (s, 1H), 3.50 (s, 2H), 3.10-2.98 (m, 4H), 2.94-2.82 (m, 2H), 2.65-2.53 (m, 3H), 2.06 (s, 3H), 1.67 (d, J=10.6 Hz, 2H), 1.49 (qd, J=12.4, 3.7 Hz, 2H). LCMS-A: rt 4.463 min; m/z 430 [M+H]⁺.

134

Example 17

Synthesis of 2-(2-(2-(2-((4-(1-methylpiperidin-4-yl) phenyl)amino)-5-(trifluoromethyl)pyrimidin-4-yl) ethyl)-4-(trifluoromethyl)phenyl)acetamide (17)

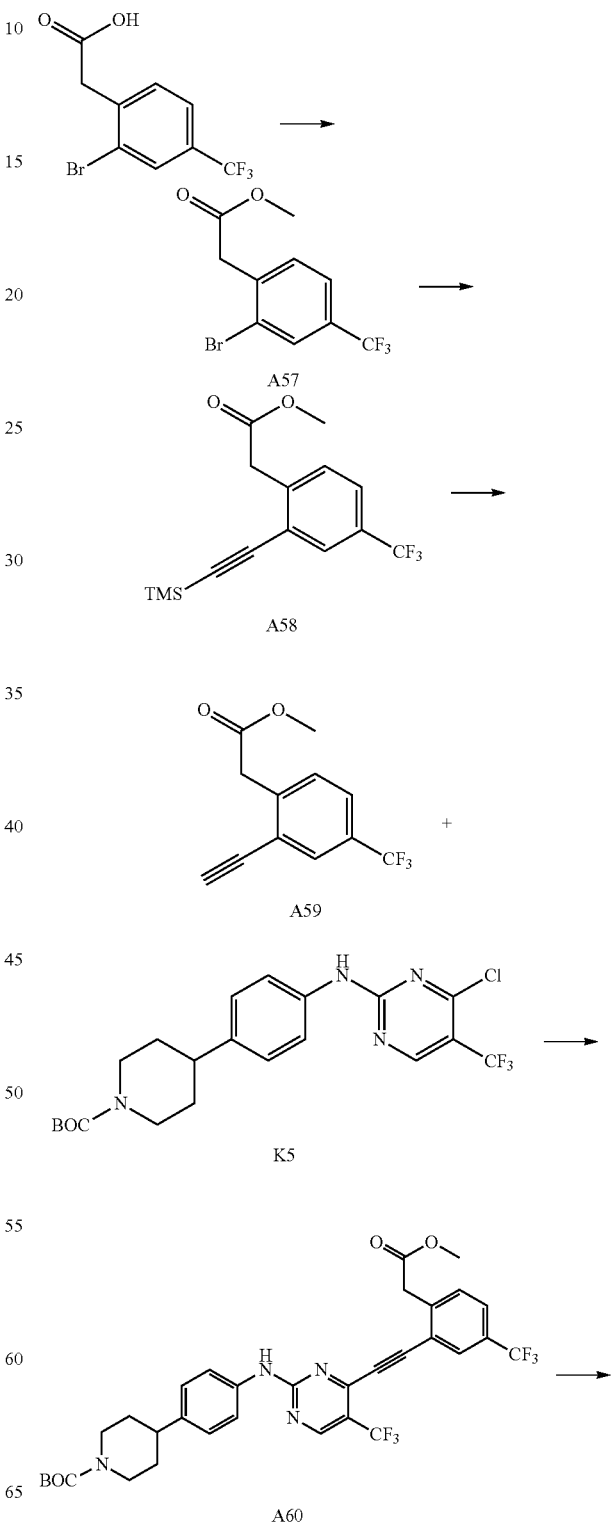

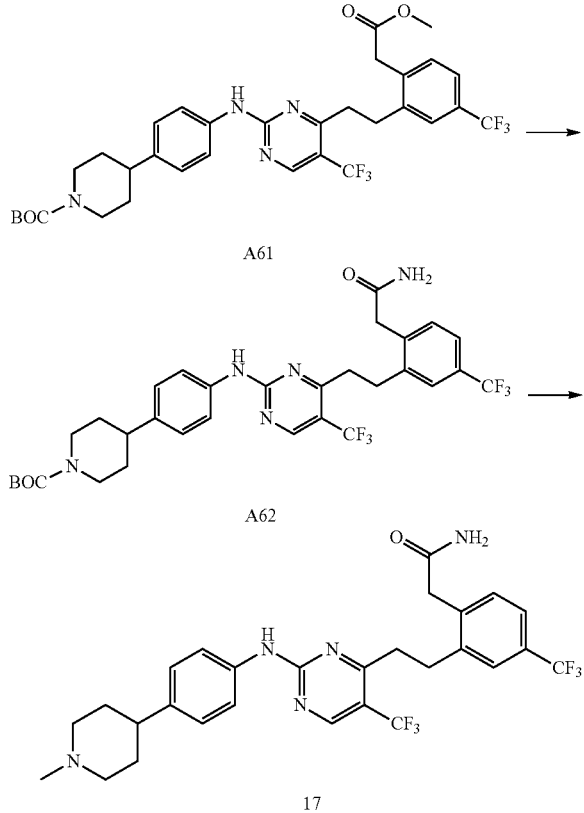

(a) Methyl 2-(2-bromo-4-(trifluoromethyl)phenyl) acetate (A57)

A solution of 2-bromo-4-trifluoromethylphenylacetic acid (2.00 g, 7.07 mmol) and concentrated aqueous $H_2SO_4$ (1 mL) in MeOH (30 mL) was heated at reflux for 16 hours. The volatiles were removed under reduced pressure then the residue taken up in EtOAc. The resulting solution was washed with 10% $NaHCO_3$, dried ($MgSO_4$) and evaporated under reduced pressure to give the title compound A57 as a clear liquid (2.07 g, 98%); $^1$H NMR (400 MHz, $CDCl_3$) δ 7.83 (d, J=1.1 Hz, 1H), 7.53 (dd, J=8.0, 1.1 Hz, 1H), 7.41 (d, J=8.0 Hz, 1H), 3.84 (s, 2H), 3.72 (s, 3H). LCMS-A: rt 6.236 min; m/z 297/299 [M+H]$^+$.

(b) Methyl 2-(4-(trifluoromethyl)-2-((trimethylsilyl) ethynyl)phenyl)acetate (A58)

A suspension of methyl 2-(2-bromo-4-(trifluoromethyl) phenyl)acetate (A57) (1.60 g, 5.38 mmol), $PdCl_2(PPh_3)_2$ (189 mg, 269 μmmol), t-$Bu_3PH.BF_4$ (78.1 mg, 269 μmmol), CuI (51.3 mg, 269 μmol) and TMS-acetylene (1.52 mL, 10.8 mmol) in $Et_3N$ (10 mL) and anhydrous, degassed DMF (10 mL) was stirred at 80° C. for 16 hours. The resulting mixture was adsorbed onto silica gel and purified using column chromatography (Biotage Isolera, $SiO_2$ cartridge, 0-10% EtOAc in petroleum benzine 40-60° C.) to give the title compound A58 as an orange liquid (1.56 g, 92%); $^1$H NMR (400 MHz, $CDCl_3$) δ 7.73 (d, J=1.1 Hz, 1H), 7.53 (dd, J=8.1, 1.3 Hz, 1H), 7.39 (d, J=8.1 Hz, 1H), 3.87 (s, 2H), 3.71 (s, 3H), 0.26 (s, 9H). LCMS-A: rt 6.979 min; m/z 315 [M+H]$^+$.

(c) Methyl 2-(2-ethynyl-4-(trifluoromethyl)phenyl) acetate (A59)

TBAF (1.0 M in THF; 7.16 mL, 7.15 mmol) was added to a stirred solution of methyl 2-(4-(trifluoromethyl)-2-((trimethylsilyl)ethynyl)phenyl)acetate (A58) (1.50 g, 4.77 mmol) in THF (50 mL) at 0° C. After 5 minutes the resulting mixture was diluted with EtOAc (50 mL) then washed with 10% $NaHCO_3$ (50 mL). The organic layer was dried ($MgSO_4$) and evaporated under reduced pressure. The residue was adsorbed onto silica gel and purified by column chromatography (Biotage Isolera, $SiO_2$ cartridge, 0-10% EtOAc in petroleum benzine 40-60° C.) to give the title compound A59 as a dark red liquid (956 mg, 83%); $^1$H NMR (400 MHz, $CDCl_3$) δ 7.77 (d, J=1.2 Hz, 1H), 7.57 (dd, J=8.1, 1.4 Hz, 1H), 7.43 (d, J=8.1 Hz, 1H), 3.90 (s, 2H), 3.72 (s, 3H), 3.36 (s, 1H). LCMS-A: rt 6.099 min; m/z 243.1 [M+H]$^+$.

(d) tert-Butyl 4-(4-((4-((2-(2-methoxy-2-oxoethyl)-5-(trifluoromethyl)phenyl)ethynyl)-5-(trifluoromethyl)pyrimidin-2-yl)amino)phenyl)piperidine-1-carboxylate (A60)

A stirred suspension of tert-butyl 4-(4-((4-chloro-5-(trifluoromethyl)pyrimidin-2-yl)amino)phenyl)piperidine-1-carboxylate (K5) (0.200 g, 0.438 mmol), $PdCl_2(PPh_3)_2$ (0.031 g, 0.044 mmol), t-$Bu_3PH.BF_4$ (0.013 mg, 0.044 mmol), CuI (0.008 g, 0.044 mmol) and methyl 2-(2-ethynyl-4-(trifluoromethyl)phenyl)acetate (A59) (0.212 g, 0.875 mmol) in anhydrous, degassed DMF (6 mL) and $Et_3N$ (6 mL) was heated at 120° C. for 20 minutes under nitrogen. The volatiles were evaporated under reduced pressure then the residue adsorbed onto silica gel and purified by column chromatography (Biotage Isolera, $SiO_2$ cartridge, 0-100% EtOAc in petroleum benzine 40-60° C.) to give the title compound A60 as a brown solid (0.176 g, 61%); $^1$H NMR (400 MHz, $CDCl_3$) δ 8.64 (s, 1H), 7.93 (d, J=0.8 Hz, 1H), 7.67 (dd, J=8.2, 1.3 Hz, 1H), 7.56 (d, J=8.5 Hz, 2H), 7.51-7.49 (m, 2H), 7.23 (d, J=8.5 Hz, 2H), 4.36-4.18 (m, 2H), 4.01 (s, 2H), 3.72 (s, 3H), 2.91-2.74 (m, 2H), 2.72-2.58 (m, 1H), 1.83 (d, J=12.6 Hz, 2H), 1.64-1.56 (m, 2H), 1.50 (s, 9H). LCMS-A: rt 7.227 min; m/z 661 [M−H]$^-$.

(e) tert-Butyl 4-(4-((4-(2-(2-methoxy-2-oxoethyl)-5-(trifluoromethyl)phenethyl)-5-(trifluoromethyl)pyrimidin-2-yl)amino)phenyl)piperidine-1-carboxylate (A61)

A suspension of 10% Pd/C (0.050 g) and tert-butyl 4-(4-((4-((2-(2-methoxy-2-oxoethyl)-5-(trifluoromethyl)phenyl) ethynyl)-5-(trifluoromethyl)pyrimidin-2-yl)amino)phenyl) piperidine-1-carboxylate (A60) (0.200 g, 0.302 mmol) in DMF (10 mL) and $Et_3N$ (1 mL) was stirred at room temperature for 16 hours under an atmosphere of hydrogen. The resulting mixture was filtered through Celite, washing with MeOH. The volatiles were removed under reduced pressure then the residue was adsorbed onto silica gel and purified by column chromatography (Biotage Isolera, $SiO_2$ cartridge, 0-100% EtOAc in petroleum benzine 40-60° C.; repeated twice) to give the title compound A61 (170 mg, 84%); $^1$H NMR (400 MHz, $CDCl_3$) δ 8.54 (s, 1H), 7.55 (d, J=8.6 Hz, 2H), 7.49 (s, 1H), 7.47-7.45 (m, 1H), 7.41 (s, 1H), 7.37 (d, J=8.0 Hz, 1H), 7.20 (d, J=8.5 Hz, 2H), 4.37-4.17 (m, 2H), 3.79 (s, 2H), 3.69 (s, 3H), 3.24-3.14 (m, 2H), 3.21-3.06 (m, 2H), 2.92-2.72 (m, 2H), 2.71-2.52 (m, 1H), 1.90-1.74 (m, 2H), 1.68-1.60 (m, 2H), 1.48 (s, 9H). LCMS-A: rt 7.149 min; m/z 667 [M+H]$^+$.

(f) tert-Butyl 4-(4-((4-(2-(2-amino-2-oxoethyl)-5-(trifluoromethyl)phenethyl)-5-(trifluoromethyl)pyrimidin-2-yl)amino)phenyl)piperidine-1-carboxylate (A62)

A suspension of tert-butyl 4-(4-((4-(2-(2-methoxy-2-oxoethyl)-5-(trifluoromethyl)phenethyl)-5-(trifluoromethyl)pyrimidin-2-yl)amino)phenyl)piperidine-1-carboxylate (A61) (0.100 g, 0.150 mmol) and LiOH.H₂O (0.051 g, 1.21 mmol) in MeOH (2 mL), water (2 mL) and THF (2 mL) was heated at 40° C. for 16 hours. In a separate flask, a suspension of tert-butyl 4-(4-((4-(2-(2-methoxy-2-oxoethyl)-5-(trifluoromethyl)phenethyl)-5-(trifluoromethyl)pyrimidin-2-yl)amino)phenyl)piperidine-1-carboxylate (A61) (0.070 g, 0.105 mmol) and LiOH.H₂O (0.036 g, 0.858 mmol) in MeOH (2 mL), water (2 mL) and THF (2 mL) was heated at 40° C. for 16 hours. The resulting mixtures were combined and the volatiles were removed under reduced pressure. The resulting solid was dissolved in dry DMF (5 mL) and dry THF (5 mL) and HOBt (0.053 g, 0.398 mmol), EDCl.HCl (0.061 g, 0.398 mmol), DIPEA (0.260 mL, 1.53 mmol) and ammonium carbonate (0.144 g, 1.53 mmol) were added. The resulting mixture was stirred at room temperature for 16 hours then HOBt (0.053 g, 0.398 mmol), EDCl.HCl (0.061 g, 0.398 mmol), DIPEA (0.260 mL, 1.53 mmol) and ammonium carbonate (0.144 g, 1.53 mmol) were added and stirring was continued overnight. The resulting mixture was diluted with EtOAc, then washed with 10% aqueous NaHCO₃. The organic layer was dried (MgSO₄) and the volatiles were removed in vacuo. The resulting solid was adsorbed onto silica gel then purified by column chromatography (Biotage Isolera, SiO₂ cartridge, 0-50% EtOAc in petroleum benzine 40-60° C.) to give the title compound A62 as a yellow solid (0.086 g, 43%); ¹H NMR (400 MHz, CDCl₃) δ 8.54 (s, 1H), 7.55-7.47 (m, 5H), 7.38 (d, J=8.3 Hz, 1H), 7.21 (d, J=8.5 Hz, 2H), 5.48-5.28 (m, 2H), 4.39-4.15 (m, 2H), 3.74 (s, 2H), 3.22-3.13 (m, 2H), 3.12-3.05 (m, 2H), 2.88-2.73 (m, 2H), 2.70-2.56 (m, 1H), 1.85-1.80 (m, 2H), 1.70-1.61 (m, 2H), 1.49 (s, 9H). LCMS-A: rt 6.646 min; m/z 652 [M+H]⁺.

(g) 2-(2-(2-(2-((4-(1-methylpiperidin-4-yl)phenyl)amino)-5-(trifluoromethyl)pyrimidin-4-yl)ethyl)-4-(trifluoromethyl)phenyl)acetamide (17)

TFA (0.1 mL) was added to a solution of tert-butyl 4-(4-((4-(2-(2-amino-2-oxoethyl)-5-(trifluoromethyl)phenethyl)-5-(trifluoromethyl)pyrimidin-2-yl)amino)phenyl)piperidine-1-carboxylate (A62) (0.170 g, 0.261 mmol) in DCM (4 mL) and the resulting mixture stirred for 24 hours at room temperature. The volatiles were evaporated under reduced pressure then the residue adsorbed onto silica gel and purified by column chromatography (SiO₂, 1-50% MeOH in DCM). The volatiles were removed in vacuo and the residue dissolved in dry MeOH (5 mL). Formaldehyde (37 wt. % in H₂O; 0.030 mL, 0.36 mmol) was added and the resulting mixture was stirred for 30 minutes at room temperature. Sodium triacetoxyborohydride (0.077 g, 0.362 mmol) was added under nitrogen and the resulting mixture stirred at room temperature for 2 hours. The volatiles were evaporated under reduced pressure then the residue dissolved in EtOAc and washed with 10% NaHCO₃ (20 mL). The organics were dried (MgSO₄) and the volatiles removed under reduced pressure. The residue was adsorbed onto silica gel, then purified by silica gel column chromatography (Biotage Isolera, SiO₂ cartridge, 50-100% MeOH in EtOAc then 10% NH₃ in EtOH). Further purification by semi preparative HPLC was required to give the title compound 17 as a pale cream solid (0.011 g, 26%); ¹H NMR (400 MHz, d₄-MeOH) δ 8.55 (s, 1H), 7.67-7.60 (m, 2H), 7.50-7.40 (m, 3H), 7.28-7.19 (m, 2H), 3.74 (s, 2H), 3.54-3.40 (m, 2H), 3.31-3.25 (m, 2H), 3.14-3.12 (m, 2H), 2.95 (t, J=11.5 Hz, 2H), 2.80 (m, 4H), 2.08 (d, J=13.8 Hz, 2H), 1.97-1.92 (m, 2H). LCMS-B: rt 4.52 min; m/z 566 [M+H]⁺.

Example 18

Synthesis of 2-(2-(2-(2-(4-(1-aminoethyl)phenylamino)-5-(trifluoromethyl)pyrimidin-4-yl)ethyl)phenyl)acetamide (18)

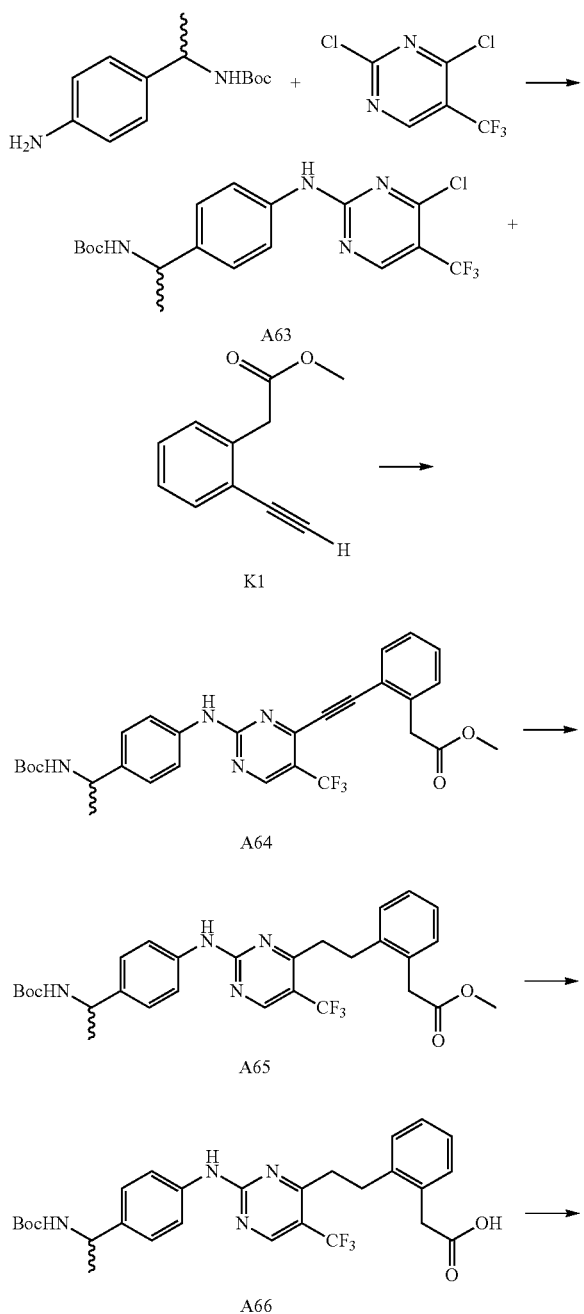

-continued

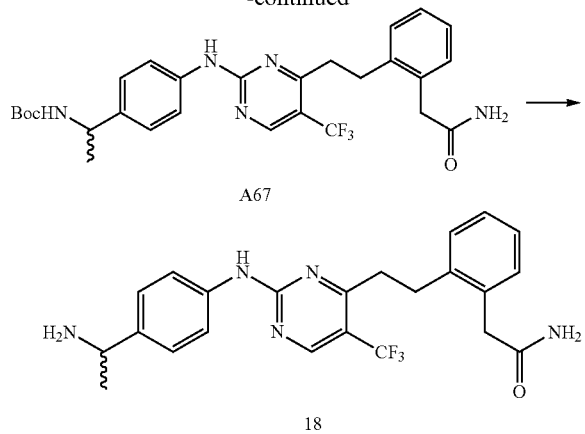

(a) tert-Butyl 1-(4-(4-chloro-5-(trifluoromethyl)pyrimidin-2-ylamino)phenyl)ethylcarbamate (A63)

ZnCl$_2$ (1.0 M in Et$_2$O; 3.27 mL, 3.27 mmol) was added to a stirred solution of 2,4-dichloro-5-(trifluoromethyl)pyrimidine (620 mg, 2.86 mmol) in a 1:1 t-BuOH:DCE mixture (120 mL) at room temperature. After stirring for 20 minutes tert-butyl 1-(4-aminophenyl)ethylcarbamate (0.643 g, 2.72 mmol) (prepared according to Bioorganic and Medicinal Chemistry Letters, 14(7), 1751-1755; 2004) followed by Et$_3$N (455 µL, 3.27 mmol) was added and the resulting mixture stirred at room temperature overnight. The volatiles were evaporated to dryness and the resulting residue purified by silica gel column chromatography (CombiFlash Rf, SiO$_2$ cartridge, 0-10% EtOAc in cyclohexane) to give the title compound A63 (480 mg, 42%); $^1$H NMR (300 MHz, CDCl$_3$) δ 8.57 (s, 1H), 7.56 (m, 1H), 7.56 (d, J=8.61 Hz, 2H), 7.33 (d, J=8.61 Hz, 2H), 4.81 (m, 2H), 1.46 (m, 12H). LCMS-B: rt 8.47 min; m/z 417 [M+H]$^+$.

(b) Methyl 2-(2-((2-(4-(1-(tert-butoxycarbonylamino)ethyl)phenylamino)-5-(trifluoromethyl)pyrimidin-4-yl)ethynyl)phenyl)acetate (A64)

A suspension of tert-butyl 1-(4-(4-chloro-5-(trifluoromethyl)pyrimidin-2-ylamino)phenyl)ethylcarbamate (A63) (487 mg, 1.17 mmol), Et$_3$N (760 µL), methyl 2-(2-ethynylphenyl)acetate (K1) (244 mg, 1.40 mmol), PdCl$_2$(PPh$_3$)$_2$ (41 mg, 0.058 mmol), CuI (22.0 mg, 0.117 mmol) and PPh$_3$ (36.0 mg, 0.117 mmol) in DMF (4.6 mL) was heated under microwave irradiation at 120° C. for 15 minutes. The volatiles were evaporated in vacuo and the residue purified by silica gel column chromatography (CombiFlash Rf, SiO$_2$ cartridge, 0-25% EtOAc in cyclohexane) to give the title compound A64 as a yellow solid (400 mg, 62%); $^1$H NMR (300 MHz, CDCl$_3$) δ 8.66 (s, 1H), 7.70 (dd, J=7.83, 1.17 Hz, 1H), 7.61 (d, J=8.61 Hz, 2H), 7.43 (m, 3H), 7.34 (d, J=8.40 Hz, 2H), 4.78 (m, 2H), 3.98 (s, 2H), 3.73 (s, 3H), 1.61 (s, 1H, peak obscured), 1.46 (m, 12H). LCMS-B: rt 8.90 min; m/z 555 [M+H]$^+$.

(c) Methyl 2-(2-(2-(2-(4-(1-(tert-butoxycarbonylamino)ethyl)phenylamino)-5-(trifluoromethyl)pyrimidin-4-yl)ethyl)phenyl)acetate (A65)

A suspension of methyl 2-(2-((2-(4-(1-(tert-butoxycarbonylamino)ethyl)phenylamino)-5-(trifluoromethyl)pyrimidin-4-yl)ethynyl)phenyl)acetate (A64) (353 mg, 0.637 mmol) and Pd/C (10%; 250 mg) in EtOAc (13 mL) was stirred under a hydrogen atmosphere at room temperature overnight. The resulting mixture was filtered through a pad of Celite then the filtrate evaporated under reduced pressure to give the title compound A65 as an off white solid (320 mg, 90%); $^1$H NMR (300 MHz, CDCl$_3$) δ 8.56 (s, 1H), 7.61 (d, J=8.64 Hz, 2H), 7.52 (s, 1H), 7.28 (m, 5H), 4.81 (m. s, 2H), 3.77 (s, 2H), 3.70 (s, 3H), 3.13 (m, 4H), 1.66 (m, 1H, peak obscured), 1.48 (d, J=6.54 Hz, 3H), 1.45 (s, 9H). LCMS-B: rt 9.07 min; m/z 559.5 [M+H]$^+$.

(d) 2-(2-(2-(2-(4-(1-(tert-Butoxycarbonylamino)ethyl)phenylamino)-5-(trifluoromethyl)pyrimidin-4-yl)ethyl)phenyl)acetic acid (A66)

LiOH (69.0 mg, 2.86 mmol) was added to a solution of methyl 2-(2-(2-(2-(4-(1-(tert-butoxycarbonylamino)ethyl)phenylamino)-5-(trifluoromethyl)pyrimidin-4-yl)ethyl)phenyl)acetate (A65) (320 mg, 0.573 mmol) in THF (7.5 mL) and water (2.5 mL) and the resulting mixture stirred at room temperature overnight. The resulting mixture was evaporated in vacuo then the residue was partitioned between EtOAc (15 mL) and 1 M aqueous HCl. The phases were separated and the aqueous phase was extracted with EtOAc. The combined organic phases were washed with brine, dried with Na$_2$SO$_4$ and concentrated to give the title compound A66 (310 mg, 99%); LCMS-B: rt 8.30 min; m/z 545.4 [M+H]$^+$.

(e) 2-(2-(2-(2-(4-(1-(tert-Butoxycarbonylamino)ethyl)phenylamino)-5-(trifluoromethyl)pyrimidin-4-yl)ethyl)phenyl)acetic acid (A67)

HOBt (119 mg, 0.881 mmol), EDCl.HCl (169 mg, 0.881 mmol) and DIPEA (512 µL, 2.94 mmol) were added to a stirred solution of 2-(2-(2-(2-(4-(1-(tert-butoxycarbonylamino)ethyl)phenylamino)-5-(trifluoromethyl)pyrimidin-4-yl)ethyl)phenyl)acetic acid (A66) (320 mg, 0.588 mmol) in dry THF (7.0 mL) and dry DMF (1.5 mL) under an atmosphere of nitrogen. After 10 minutes ammonium carbonate (282 mg, 2.94 mmol) was added in one portion and the resulting mixture was stirred at 40° C. overnight. The volatiles were removed in vacuo, then the residue was partitioned between EtOAc (50 mL) and saturated NaHCO$_3$ (50 mL). After separating the organic layer, the aqueous phase was extracted with EtOAc (2×50 mL). The combined organics were concentrated under reduced pressure then purified by silica gel column chromatography (CombiFlash Rf, SiO$_2$ cartridge, 0-60% EtOAc in cyclohexane) to give the title compound A67 (307 mg, 96%); $^1$H NMR (300 MHz, CDCl$_3$) δ 8.51 (s, 1H), 7.95 (br.s, 1H), 7.56 (d, J=8.52 Hz, 2H), 7.27 (m, 5H), 5.91 (m, 1H), 5.53 (br.s, 1H), 5.03 (m, 1H), 4.78 (m, 1H), 3.70 (s, 2H), 3.10 (m, 4H), 2.00 (br.s, 1H), 1.44 (m, 12H). LCMS-B: rt 7.85 min; m/z 544.4 [M+H]$^+$.

(f) tert-Butyl 1-(4-(4-(2-(2-amino-2-oxoethyl)phenethyl)-5-(trifluoromethyl)pyrimidin-2-ylamino)phenyl)ethylcarbamate (18)

A solution of 2-(2-(2-(2-(4-(1-(tert-butoxycarbonylamino)ethyl)phenylamino)-5-(trifluoromethyl)pyrimidin-4-yl)ethyl)phenyl)acetic acid (A67) (143 mg, 0.263 mmol) and TFA (806 µL, 1.20 mmol) in DCM (40 mL) was stirred at room temperature overnight. The volatiles were removed under reduced pressure and the residue azeotroped with toluene (×3). The residue was then dissolved in MeOH and applied to an SCX cartridge which was washed with MeOH followed by ethanolic ammonia solution (5 M). The ethanolic ammonia fractions were evaporated in vacuo to give the title compound 18 as a light yellow solid (114 mg, 98%); $^1$H NMR (300 MHz, $d_6$-DMSO) δ 10.13 (s, 1H), 8.66 (s, 1H), 7.66 (d, J=8.61 Hz, 2H), 7.44 (brs, 1H), 7.31 (d, J=8.40 Hz, 2H), 7.24 (m, 1H), 7.18 (m, 3H), 6.92 (brs, 1H), 3.95 (q, J=6.48 Hz, 1H), 3.51 (s, 2H), 3.33 (peak obscured), 3.11 (m, 4H), 1.24 (d, J=6.60 Hz, 2H). LCMS-B: rt 5.28 min; m/z 444.3 [M+H]$^+$.

Example 19

Synthesis of 2-(2-(2-(2-((4-(((2-hydroxyethyl)amino) methyl)phenyl)amino)-5-(trifluoromethyl)pyrimidin-4-yl)ethyl)phenyl)acetamide (19)

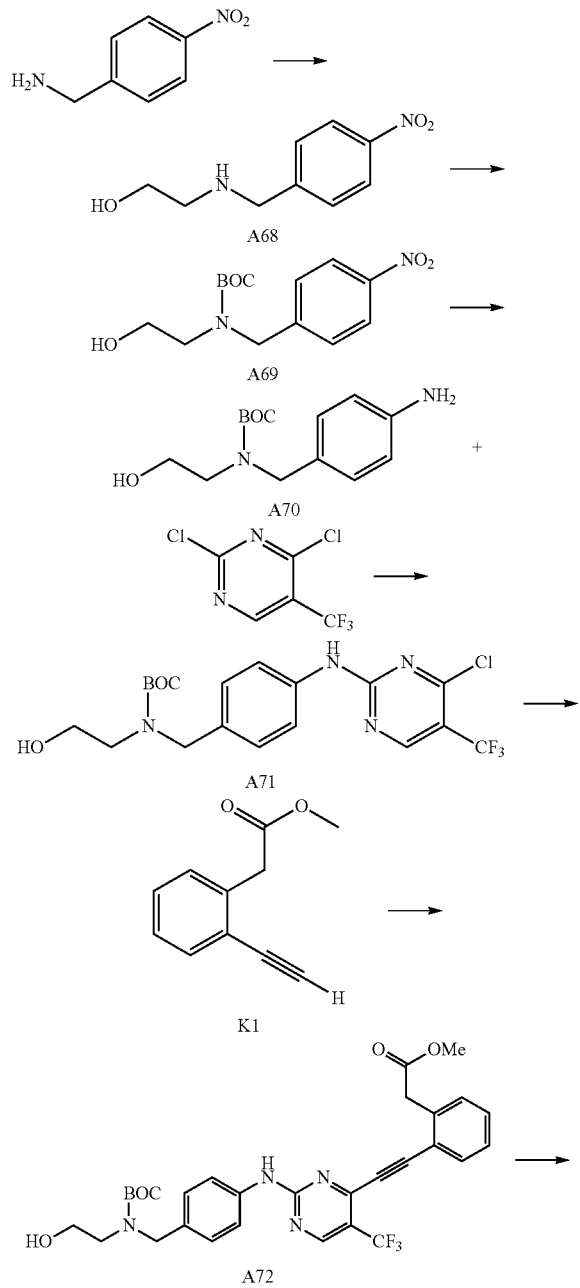

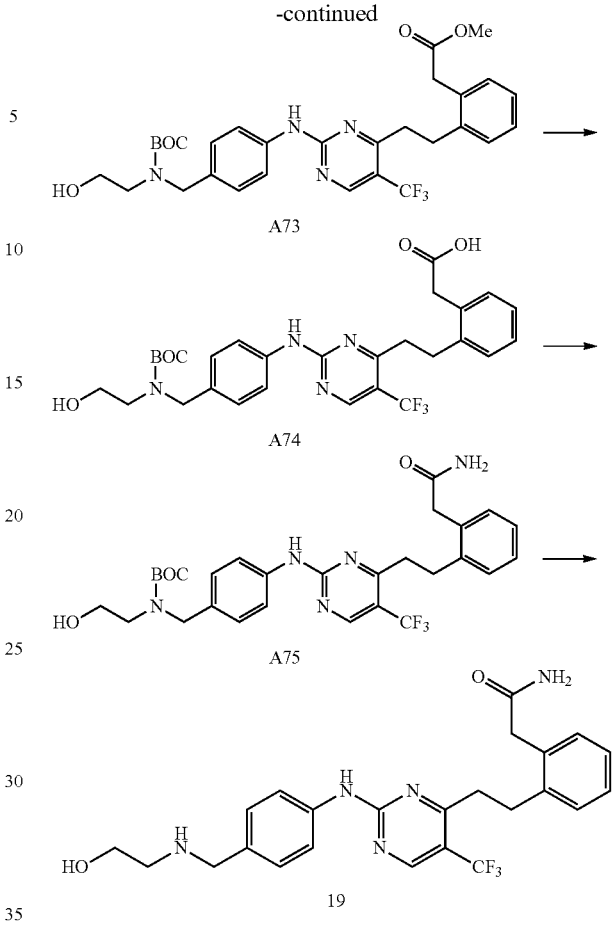

(a) 2-((4-Nitrobenzyl)amino)ethanol (A68)

A solution of ethanolamine (10.05 mL, 166.6 mmol), DIPEA (5.08 mL, 29.2 mmol) and 4-nitrobenzyl bromide (6.00 g, 27.8 mmol) in DCM (50 mL) was stirred at room temperature for 4 hours. The volatiles were removed in vacuo and the resulting residue partitioned between water and EtOAc. The aqueous phase was separated and extracted with EtOAc (3×30 mL). The combined organic fractions were washed with brine, dried (Na$_2$SO$_4$), filtered and concentrated in vacuo to give the title compound A68 as a light yellow solid (3.34 g, 61%); $^1$H NMR (300 MHz, $d_6$-DMSO) δ 8.18 (d, J=8.7 Hz, 2H), 7.62 (d, J=8.7 Hz, 2H), 4.49 (t, J=5.4 Hz, 1H), 3.84 (s, 2H), 3.47 (q, J=5.6 Hz, 2H), 2.56 (t, J=5.8 Hz, 2H), 2.28 (s, 1H).

(b) tert-Butyl (2-hydroxyethyl)(4-nitrobenzyl)carbamate (A69)

A solution of di-tert-butyl dicarbonate (1.79 g, 8.23 mmol) in DCM (17 mL) was added slowly to a solution of 2-((4-nitrobenzyl)amino)ethanol (A68) (1.60 g, 8.15 mmol) and 2 M aqueous sodium hydroxide (6.11 mL, 12.23 mmol) in DCM (17 mL). The resulting mixture was stirred at room temperature for 18 hours then diluted with water and DCM. The layers separated and the aqueous phase was extracted with DCM (3×20 mL). The combined organic fractions were washed with brine, dried (Na$_2$SO$_4$), filtered and concentrated in vacuo to give the title compound A69 as a viscous colourless oil (2.40 g, 99%); $^1$H NMR (300 MHz, CDCl$_3$) δ 8.22 (d, J=8.6 Hz, 2H), 7.42 (d, J=8.6 Hz, 2H), 4.61 (s, 2H), 3.77 (m, 2H), 3.46 (s, 2H), 2.72 (t, J=5.4 Hz, 1H), 1.44 (brs, 9H).

(c) tert-Butyl 4-aminobenzyl(2-hydroxyethyl)carbamate (A70)

A suspension of tert-butyl (2-hydroxyethyl)(4-nitrobenzyl)carbamate (A69) (2.40 g, 8.09 mmol) and 10% Pd/C (0.240 g) in EtOAc (12 mL) was stirred under a hydrogen atmosphere for 18 hours. The resulting mixture was filtered through a pad of Celite, washing with EtOAc and the filtrate concentrated in vacuo. The residue was purified using silica gel column chromatography (CombiFlash Rf, 40 g $SiO_2$ cartridge, 20-50% EtOAc in cyclohexane) to give the title compound A70 as a viscous light yellow oil (1.99 g, 92%); $^1$H NMR (300 MHz, $CDCl_3$) δ 7.05 (d, J=7.5 Hz, 2H), 6.66 (d, J=8.0 Hz, 2H), 4.37 (s, 2H), 3.67 (m, 4H), 3.37 (s, 2H), 3.10 (s, 1H), 1.50 (s, 9H).

(d) tert-Butyl 4-((4-chloro-5-(trifluoromethyl)pyrimidin-2-yl)amino)benzyl(2-hydroxyethyl)carbamate (A71)

Zinc(II) chloride (1.0 M in $Et_2O$; 3.30 mL, 3.30 mmol) was added to a solution of 2,4-dichloro-5-(trifluoromethyl)pyrimidine (0.658 g, 3.03 mmol) in 1:1 DCE/t-BuOH (20 mL) at 0° C. under nitrogen. After stirring for 1 hour at 0° C., a solution of tert-butyl 4-aminobenzyl(2-hydroxyethyl)carbamate (A70) (0.734 g, 2.75 mmol) in 1:1 DCE/t-BuOH (20 mL) was added followed by a solution of $Et_3N$ (0.423 mL, 3.03 mmol) in 1:1 DCE/t-BuOH (5 mL) at 0° C. The resulting mixture was vigorously stirred at 0° C. for 30 minutes, then at room temperature for 20 hours. The volatiles were evaporated in vacuo and the residue adsorbed onto silica gel then purified by column chromatography (CombiFlash Rf, 80 g $SiO_2$ cartridge, 10-40% EtOAc in cyclohexane) to give the title compound A71 as a white solid (1.06 g, 85%); $^1$H NMR (300 MHz, $CDCl_3$) δ 8.60 (s, 1H), 7.59-7.52 (m, 3H), 7.28 (m, 2H), 4.49 (s, 2H), 3.74 (s, 2H), 3.43-3.20 (m, 3H), 1.50 (s, 9H). LCMS-B: rt 7.856 min; m/z 447 $[M+H]^+$.

(e) Methyl 2-(2-((2-((4-(((tert-butoxycarbonyl)(2-hydroxyethyl)amino)methyl)phenyl)amino)-5-(trifluoromethyl)pyrimidin-4-yl)ethynyl)phenyl)acetate (A72)

A suspension of tert-butyl 4-((4-chloro-5-(trifluoromethyl)pyrimidin-2-yl)amino)benzyl(2-hydroxyethyl)carbamate (A71) (0.518 g, 1.15 mmol), $Et_3N$ (0.75 mL), methyl 2-(2-ethynylphenyl)acetate (K1) (0.242 g, 1.39 mmol), $PdCl_2(PPh_3)_2$ (0.041 g, 0.058 mmol), CuI (0.022 g, 0.116 mmol) and $PPh_3$ (0.030 g, 0.12 mmol) in DMF (4.5 mL) was heated under microwave irradiation at 120° C. for 15 minutes. The volatiles were evaporated in vacuo and the residue purified using silica gel column chromatography (CombiFlash Rf, 40 g $SiO_2$ cartridge, 20-50% EtOAc in cyclohexane) to give the title compound A72 as an orange foam (0.589 g, 86%); $^1$H NMR (300 MHz, $CDCl_3$) δ 8.65 (s, 1H), 7.70 (d, J=7.0 Hz, 1H), 7.63 (d, J=8.3 Hz, 2H), 7.48-7.28 (m, 6H), 4.49 (brs, 2H), 3.97 (s, 2H), 3.72 (m, 5H), 3.47 (brs, 2H), 3.01 (brs, 1H), 1.51 (s, 9H). LCMS-B: rt 8.350 min; m/z 585 $[M+H]^+$.

(f) Methyl 2-(2-(2-(2-((4-(((tert-butoxycarbonyl)(2-hydroxyethyl)amino)methyl)phenyl)amino)-5-(trifluoromethyl)pyrimidin-4-yl)ethyl)phenyl)acetate (A73)

A suspension of methyl 2-(2-((2-((4-(((tert-butoxycarbonyl)(2-hydroxyethyl)amino)methyl)phenyl)amino)-5-(trifluoromethyl)pyrimidin-4-yl)ethynyl)phenyl)acetate (A72) (0.589 g, 1.00 mmol) and 10% Pd/C (0.300 g) in EtOAc (13 mL) was stirred under a hydrogen atmosphere for 18 hours. A further portion of 10% Pd/C (0.300 g) was added and the resulting mixture stirred under a hydrogen atmosphere for 20 hours. The resulting mixture was filtered through a pad of Celite, washing with EtOAc and the filtrate concentrated in vacuo. The residue was purified using silica gel column chromatography (CombiFlash Rf, 24 g $SiO_2$ Cartridge, 20-60% EtOAc in cyclohexane) to give the title compound A73 as a light yellow gum (0.443 g, 74%); $^1$H NMR (300 MHz, $CDCl_3$) δ 8.56 (s, 1H), 7.63 (d, J=8.3 Hz, 2H), 7.44 (s, 1H), 7.28-7.25 (m, 6H), 4.49 (brs, 2H), 3.77-3.70 (m, 7H), 3.42 (brs, 2H), 3.15-2.95 (m, 5H), 1.51 (s, 9H). LCMS-B: rt 8.469 min; m/z 589 $[M+H]^+$.

(g) 2-(2-(2-(2-((4-(((tert-Butoxycarbonyl)(2-hydroxyethyl)amino)methyl)phenyl)amino)-5-(trifluoromethyl)pyrimidin-4-yl)ethyl)phenyl)acetic acid (A74)

LiOH (143 mg, 5.98 mmol) was added to a solution of methyl 2-(2-(2-(2-((4-(((tert-butoxycarbonyl)(2-hydroxyethyl)amino)methyl)phenyl)amino)-5-(trifluoromethyl)pyrimidin-4-yl)ethyl)phenyl)acetate (A73) (0.440 g, 0.748 mmol) in THF (10 mL), MeOH (1 mL) and water (1 mL) and the resulting mixture stirred at room temperature for 20 hours. Additional LiOH (107 mg, 4.48 mmol) was added and the mixture heated to 40° C. for 24 hours. The volatiles were removed in vacuo. The residue was diluted with a 10% citric acid solution (20 mL) and 1 M HCl (0.5 mL) until pH 3 was obtained. The resulting precipitate was collected by filtration and dried to give the title compound A74 as a pale yellow solid (0.421 g, 98%); $^1$H NMR (300 MHz, $d_6$-DMSO) δ 10.21 (s, 1H), 8.67 (s, 1H), 7.71 (d, J=8.0 Hz, 2H), 7.24-7.17 (m, 6H), 4.38 (brs, 2H), 3.64 (brs, 2H), 3.47-3.03 (m, 8H), 1.42 (s, 9H). LCMS-B: rt 7.786 min; m/z 575 $[M+H]^+$.

(h) tert-Butyl 4-((4-(2-(2-amino-2-oxoethyl)phenethyl)-5-(trifluoromethyl)pyrimidin-2-yl)amino)benzyl(2-hydroxyethyl)carbamate (A75)

HOBt (0.119 g, 0.879 mmol) and EDCl.HCl (0.169 g, 0.879 mmol) were added to a solution of 2-(2-(2-(2-((4-(((tert-butoxycarbonyl)(2-hydroxyethyl)amino)methyl)phenyl)amino)-5-(trifluoromethyl)pyrimidin-4-yl)ethyl)phenyl)acetic acid (A74) (0.421 g, 0.733 mmol) and $Et_3N$ (0.408 mL, 0.297 mmol) in DMF (10 mL). After 10 minutes ammonium carbonate (1.34 g, 14.65 mmol) was added and the resulting mixture was stirred at 40° C. for 22 hours. Saturated aqueous saturated $NaHCO_3$ solution (25 mL) was added the resulting mixture extracted with EtOAc (3×15 mL). The combined organic fractions were dried ($Na_2SO_4$), filtered and evaporated in vacuo. The residue was adsorbed onto silica gel then purified using column chromatography (CombiFlash Rf, 24 g $SiO_2$ cartridge, 40-100% EtOAc in cyclohexane) to give the title compound A75 as a white solid (0.301 g, 76%); $^1$H NMR (300 MHz, $CDCl_3$) δ 8.56 (s, 1H), 7.61-7.58 (m, 3H), 7.30-7.26 (m, 6H), 5.48 (brs, 2H), 4.49 (brs, 2H), 3.74 (brs, 4H), 3.42 (brs, 2H), 3.15-3.12 (m, 4H), 1.50 (s, 9H). LCMS-B: rt 7.344 min; m/z 574 $[M+H]^+$.

(i) 2-(2-(2-(2-((4-(((2-Hydroxyethyl)amino)methyl)phenyl)amino)-5-(trifluoromethyl)pyrimidin-4-yl)ethyl)phenyl)acetamide (19)

A solution of tert-butyl 4-((4-(2-(2-amino-2-oxoethyl)phenethyl)-5-(trifluoromethyl)pyrimidin-2-yl)amino)benzyl (2-hydroxyethyl)carbamate (A75) (0.301 g, 0.525 mmol) and trifluoroacetic acid (1.0 mL) in DCM (10 mL) was stirred at room temperature for 22 hours. The volatiles were removed in vacuo and 2 M aqueous sodium hydroxide solution (20 mL) added to the residue. The resulting suspension was sonicated for several minutes then filtered, washing the filter cake with water. Semi preparative HPLC of the filter cake gave the title compound 19 as a white solid (58 mg, 23%); $^1$H NMR (300 MHz, d$_4$-MeOH) δ 8.61 (s, 1H), 8.53 (s, 1H), 7.83 (d, J=8.5 Hz, 2H), 7.46 (d, J=8.6 Hz, 2H), 7.29-7.19 (m, 4H), 4.19 (s, 2H), 3.82 (t, J=5.2 Hz, 2H), 3.68 (s, 2H), 3.22-3.10 (m, 6H). LCMS-B: rt 5.313 min; m/z 474 [M+H]$^+$.

Example 20

Synthesis of 2-(2-(2-(2-((4-(azetidin-3-yl)phenyl)amino)-5-(trifluoromethyl)pyrimidin-4-yl)ethyl)phenyl)acetamide (20)

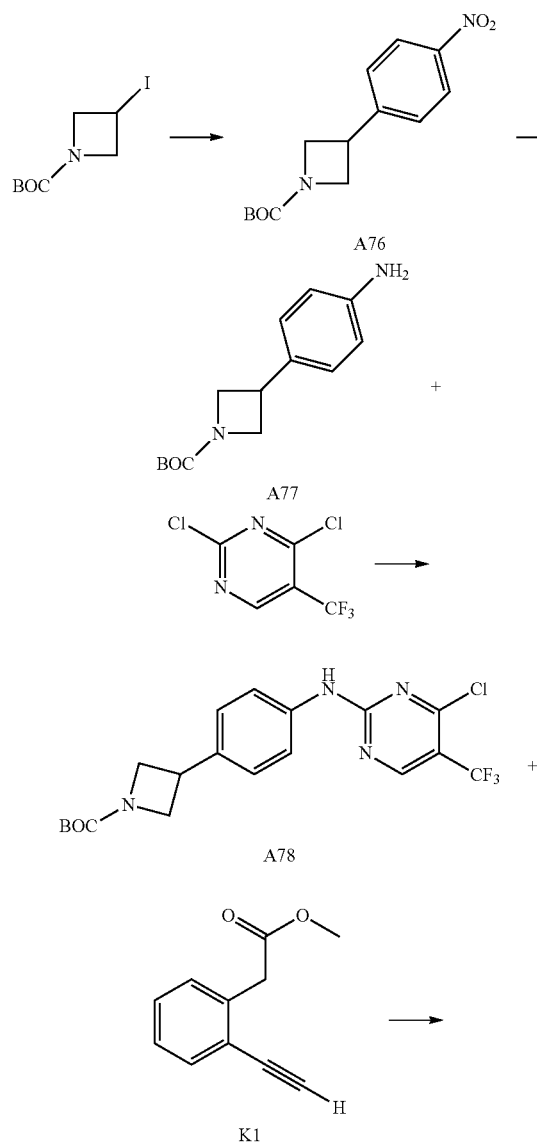

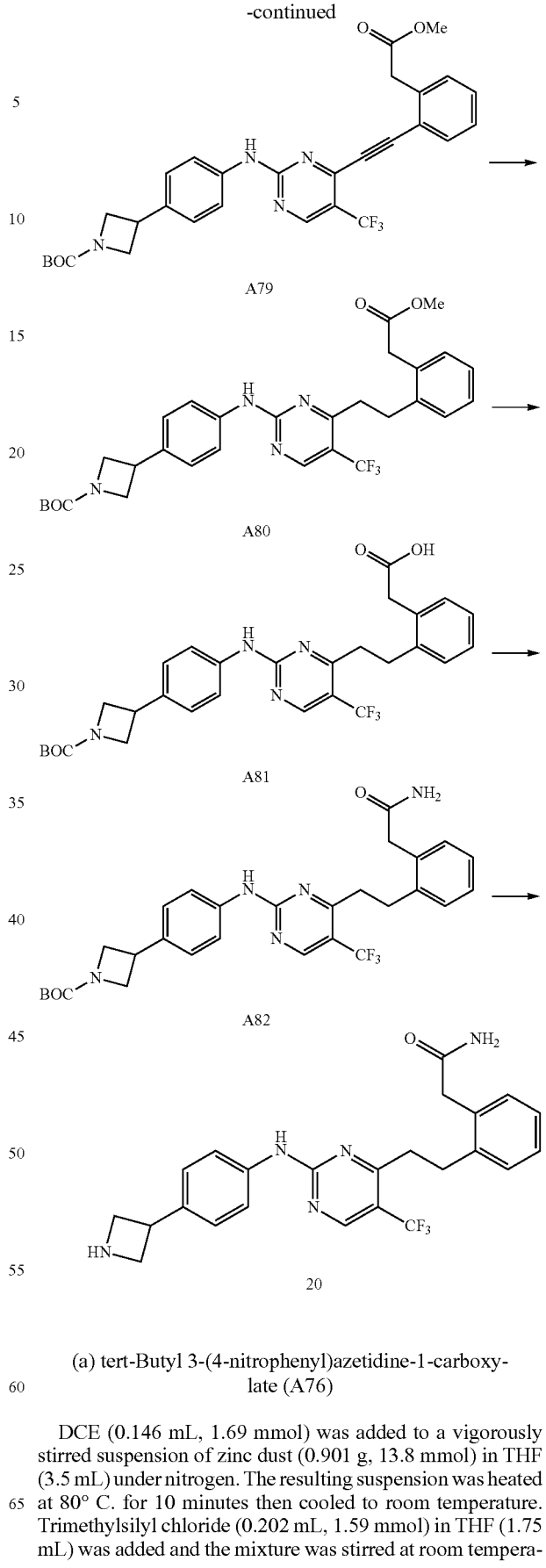

(a) tert-Butyl 3-(4-nitrophenyl)azetidine-1-carboxylate (A76)

DCE (0.146 mL, 1.69 mmol) was added to a vigorously stirred suspension of zinc dust (0.901 g, 13.8 mmol) in THF (3.5 mL) under nitrogen. The resulting suspension was heated at 80° C. for 10 minutes then cooled to room temperature. Trimethylsilyl chloride (0.202 mL, 1.59 mmol) in THF (1.75 mL) was added and the mixture was stirred at room temperature for 4 minutes. A solution of tert-butyl 3-iodoazetidine-1-carboxylate (3.00 g, 10.6 mmol) in THF (3.5 mL) was added dropwise over 15 minutes and the resulting mixture stirred at room temperature for 2 hours. $Pd_2(dba)_3$ (0.155 g, 0.170 mmol) and tri-2-furylphosphine (0.143 g, 0.615 mmol) were added followed by 1-iodo-4-nitrobenzene (2.90 g, 11.7 mmol) in THF (18 mL). The resulting mixture was then heated at 55° C. for 3 hours then quenched with an aqueous saturated sodium chloride solution (15 mL). After filtration through a pad of Celite, the layers were separated and the aqueous phase extracted with DCM (2×15 mL). The combined organic fractions were dried ($MgSO_4$), filtered and evaporated in vacuo. The residue was purified using silica gel column chromatography (CombiFlash Rf, 40 g $SiO_2$ cartridge, 10-40% EtOAc in cyclohexane) to give the title compound A76 as an orange oil (2.14 g, 72%); $^1$H NMR (300 MHz, $CDCl_3$) δ 8.24 (dd, J=6.8, 1.9 Hz, 2H), 7.51 (d, J=8.6 Hz, 2H), 4.41 (t, J=8.7 Hz, 2H), 3.98 (dd, J=8.5, 5.7 Hz, 2H), 3.89-3.81 (s, 1H), 1.49 (s, 9H).

(b) tert-Butyl 3-(4-aminophenyl)azetidine-1-carboxylate (A77)

A suspension of tert-butyl 3-(4-nitrophenyl)azetidine-1-carboxylate (A76) (2.14 g, 7.68 mmol) and 10% Pd/C (0.320 g) in EtOAc (16 mL) was stirred under a hydrogen atmosphere for 18 hours. Additional 10% Pd/C (1.00 g) was added and the mixture stirred under a hydrogen atmosphere for a further 20 hours. The resulting mixture was filtered through a pad of Celite, washing with EtOAc and the filtrate concentrated in vacuo to give the title compound A77 as a light yellow/cream solid (1.80 g, 94%); $^1$H NMR (300 MHz, $CDCl_3$) δ 7.12 (d, J=8.3 Hz, 2H), 6.69 (dd, J=6.5, 1.9 Hz, 2H), 4.29 (t, J=8.7 Hz, 2H), 3.93 (dd, J=8.4, 6.1 Hz, 2H), 3.69-3.61 (s, 2H), 1.55-1.68 (m, 1H), 1.48 (s, 9H). LCMS-B: rt 4.964 min; m/z 249 $[M+H]^+$.

(c) tert-Butyl 3-(4-((4-chloro-5-(trifluoromethyl)pyrimidin-2-yl)amino)phenyl)azetidine-1-carboxylate (A78)

Zinc(II) chloride (1.0 M in $Et_2O$; 4.83 mL, 4.83 mmol) was added to a solution of 2,4-dichloro-5-(trifluoromethyl)pyrimidine (0.769 g, 3.54 mmol) in DCE/t-BuOH (64 mL) at room temperature under nitrogen. After stirring for 10 minutes, tert-butyl 3-(4-aminophenyl)azetidine-1-carboxylate (A77) (0.800 g, 3.22 mmol) was added followed by $Et_3N$ (1.08 mL, 7.73 mmol). The resulting mixture was stirred at room temperature for 20 hours then the volatiles removed in vacuo. Water was added to the residue and the resulting suspension sonicated for 2 minutes. The suspension was filtered and the filter cake dried then adsorbed onto silica gel and purified using column chromatography (CombiFlash Rf, 40 g $SiO_2$ cartridge, 10-40% EtOAc in cyclohexane) to give a white solid. The solid was suspended in MeOH (7 mL) and the resulting suspension sonicated for 30 seconds. The suspension was filtered and the filter cake washed with MeOH (3 mL), then dried to give the title compound A78 as a white solid (0.777 g, 56%); $^1$H NMR (300 MHz, $d_6$-DMSO) δ 10.6 (s, 1H), 8.79 (s, 1H), 7.66 (d, J=8.4 Hz, 2H), 7.33 (d, J=8.4 Hz, 2H), 4.23 (t, J=7.6 Hz, 2H), 3.85-3.74 (m, 3H), 1.40 (s, 9H). LCMS-B: rt 8.810 min; m/z 429 $[M+H]^+$.

(d) tert-Butyl 3-(4-((4-((2-(2-methoxy-2-oxoethyl)phenyl)ethynyl)-5-(trifluoromethyl)pyrimidin-2-yl)amino)phenyl)azetidine-1-carboxylate (A79)

A suspension of tert-butyl 3-(4-((4-chloro-5-(trifluoromethyl)pyrimidin-2-yl)amino)phenyl)azetidine-1-carboxylate (A78) (500 mg, 1.16 mmol), methyl 2-(2-ethynylphenyl)acetate (K1) (244 mg, 1.39 mmol), $Et_3N$ (0.60 mL), $PdCl_2(PPh_3)_2$ (0.041 g, 0.058 mmol), CuI (0.022 g, 0.117 mmol) and $PPh_3$ (0.031 g, 0.117 mmol) in DMF (4 mL) were heated under microwave irradiation at 120° C. for 15 minutes. The resulting mixture was adsorbed onto silica gel and purified using column chromatography (CombiFlash Rf, 40 g $SiO_2$ cartridge, 0-30% EtOAc in cyclohexane) to give the title compound A79 as a yellow foam (0.570 g, 86%); $^1$H NMR (300 MHz, $d_6$-DMSO) δ 8.65 (s, 1H), 7.70 (d, J=7.7 Hz, 1H), 7.64 (d, J=8.5 Hz, 2H), 7.48-7.33 (m, 6H), 4.35 (t, J=8.6 Hz, 2H), 4.01-3.96 (m, 4H), 3.75-3.72 (m, 4H), 1.49 (s, 9H). LCMS-B: rt 9.160 min; m/z 567 $[M+H]^+$.

(e) tert-Butyl 3-(4-((4-(2-(2-methoxy-2-oxoethyl)phenethyl)-5-(trifluoromethyl)pyrimidin-2-yl)amino)phenyl)azetidine-1-carboxylate (A80)

A suspension of tert-butyl 3-(4-((4-((2-(2-methoxy-2-oxoethyl)phenyl)ethynyl)-5-(trifluoromethyl)pyrimidin-2-yl)amino)phenyl)azetidine-1-carboxylate (A79) (570 mg, 1.00 mmol) and 10% Pd/C (0.600 g) in EtOAc (13 mL) was stirred under a hydrogen atmosphere for 18 hours. The resulting mixture was filtered through a pad of Celite, washing with EtOAc and the filtrate concentrated in vacuo to give the title compound A80 as a light yellow foam (521 mg, 90%); $^1$H NMR (300 MHz, $d_6$-DMSO) δ 8.56 (s, 1H), 7.64 (d, J=8.5 Hz, 2H), 7.57 (s, 1H), 7.33 (d, J=8.5 Hz, 2H), 7.28-7.25 (m, 4H), 4.35 (t, J=8.7 Hz, 2H), 3.99 (dd, J=8.4, 6.7 Hz, 2H), 3.77 (m, 3H), 3.70 (brs, 3H), 3.13 (m, 4H), 1.44 (s, 9H). LCMS-B: rt 9.374 min; m/z 571 $[M+H]^+$.

(f) 2-(2-(2-(2-((4-(1-(tert-Butoxycarbonyl)azetidin-3-yl)phenyl)amino)-5-(trifluoromethyl)pyrimidin-4-yl)ethyl)phenyl)acetic acid (A81)

$LiOH.H_2O$ (0.219 g, 9.131 mmol) was added to a solution of tert-butyl 3-(4-((4-(2-(2-methoxy-2-oxoethyl)phenethyl)-5-(trifluoromethyl)pyrimidin-2-yl)amino)phenyl)azetidine-1-carboxylate (A80) (0.521 g, 0.913 mmol) in THF (10 mL), MeOH (1 mL) and water (1 mL) and the resulting mixture stirred at 40° C. for 20 hours. Additional $LiOH.H_2O$ (0.087 g, 3.65 mmol) was added and the mixture heated at 40° C. for a further 24 hours. The volatiles were removed in vacuo and the residue was diluted with 10% citric acid solution (20 mL). Aqueous 1 M HCl (ca 0.5 mL) was then added until a pH of 3 was obtained. EtOAc was added, the layers separated and the aqueous phase extracted with EtOAc (3×20 mL). The combined organics were washed with brine, dried ($MgSO_4$), filtered and evaporated in vacuo to give the title compound A81 as a viscous yellow oil (0.500 g, 98%); $^1$H NMR (300 MHz, $d_6$-DMSO) δ 9.26 (brs, 1H), 8.52 (s, 1H), 7.57 (d, J=8.5 Hz, 2H), 7.32-7.24 (m, 6H), 4.31 (t, J=8.7 Hz, 2H), 3.97-3.68 (m, 5H), 3.08 (m, 4H), 1.48 (s, 9H). LCMS-B: rt 8.649 min; m/z 557 $[M+H]^+$.

(g) tert-Butyl 3-(4-((4-(2-(2-amino-2-oxoethyl)phenethyl)-5-(trifluoromethyl)pyrimidin-2-yl)amino)phenyl)azetidine-1-carboxylate (A82)

HOBt (146 mg, 1.07 mmol) and EDCl.HCl (207 mg, 1.07 mmol) were added to a solution of 2-(2-(2-(2-((4-(1-(tert-butoxycarbonyl)azetidin-3-yl)phenyl)amino)-5-(trifluoromethyl)pyrimidin-4-yl)ethyl)phenyl)acetic acid (A81) (0.500 g, 0.898 mmol) and $Et_3N$ (455 µL, 4.49 mmol) in DMF (13 mL). After 10 minutes ammonium carbonate (1.65 g, 18.0 mmol) was added and the resulting mixture was stirred at 40°

C. for 22 hours. Additional HOBt (0.072 g, 0.539 mmol), EDCl.HCl (0.103 g, 0.539 mmol) and ammonium carbonate (0.413 g, 4.49 mmol) were added and the mixture stirred at 45° C. for 24 hours. The volatiles were removed in vacuo and water (25 mL) added to the residue resulting in the formation of a precipitate. The resulting suspension was sonicated for several minutes, filtered and the filter cake dried to give a solid which was adsorbed onto silica gel and purified by column chromatography (CombiFlash Rf, 40 g SiO$_2$ cartridge, 25-70% EtOAc in cyclohexane) to give the title compound A82 as a white solid (346 mg, 69%); $^1$H NMR (300 MHz, d$_6$-DMSO) δ 10.21 (s, 1H), 8.68 (s, 1H), 7.74 (d, J=8.6 Hz, 2H), 7.42 (s, 1H), 7.30 (d, J=8.6 Hz, 2H), 7.24-7.16 (m, 4H), 6.91 (s, 1H), 4.23 (t, J=8.0 Hz, 2H), 3.85-3.71 (m, 3H), 3.50 (s, 2H), 3.12-3.04 (m, 4H), 1.40 (s, 9H). LCMS-B: rt 8.187 min; m/z 556 [M+H]$^+$.

(h) 2-(2-(2-(2-((4-(azetidin-3-yl)phenyl)amino)-5-(trifluoromethyl)pyrimidin-4-yl)ethyl)phenyl)acetamide (20)

A solution of tert-butyl 3-(4-((4-(2-(2-amino-2-oxoethyl)phenethyl)-5-(trifluoromethyl)pyrimidin-2-yl)amino)phenyl)azetidine-1-carboxylate (A82) (0.346 g, 0.623 mmol) and trifluoroacetic acid (1 mL) in DCM (10 mL) was stirred at room temperature for 22 hours. The volatiles were removed in vacuo and 2 M aqueous NaOH (15 mL) was added to the residue. Water (20 mL) was added and the resulting suspension sonicated for 2 minutes, filtered and the filter cake washed with water and dried to give the title compound 20 as a white solid (0.283 g, 99%); $^1$H NMR (300 MHz, d$_6$-DMSO) δ 10.26 (s, 1H), 8.69 (s, 1H), 7.78 (d, J=8.6 Hz, 2H), 7.43 (s, 1H), 7.36 (d, J=8.6 Hz, 2H), 7.25-7.15 (m, 4H), 6.92 (s, 1H), 4.21 (brs, 2H), 4.06-3.99 (m, 3H), 3.50 (s, 2H), 3.12-3.05 (m, 5H). LCMS-B: rt 5.442 min; m/z 456 [M+H]$^+$.

Example 21

Synthesis of 2-(4-methyl-2-(2-(2-((4-(piperidin-4-yl)phenyl)amino)-5-(trifluoromethyl)pyrimidin-4-yl)ethyl)phenyl)acetamide (21)

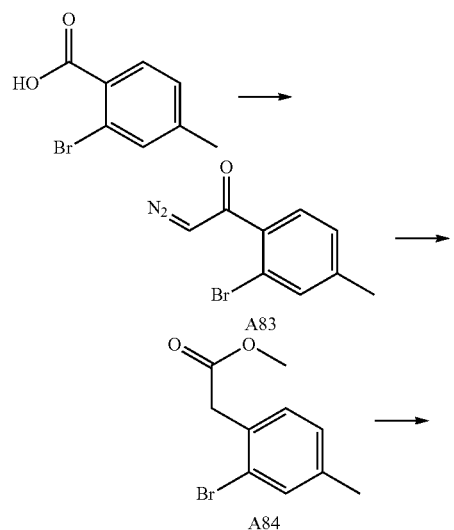

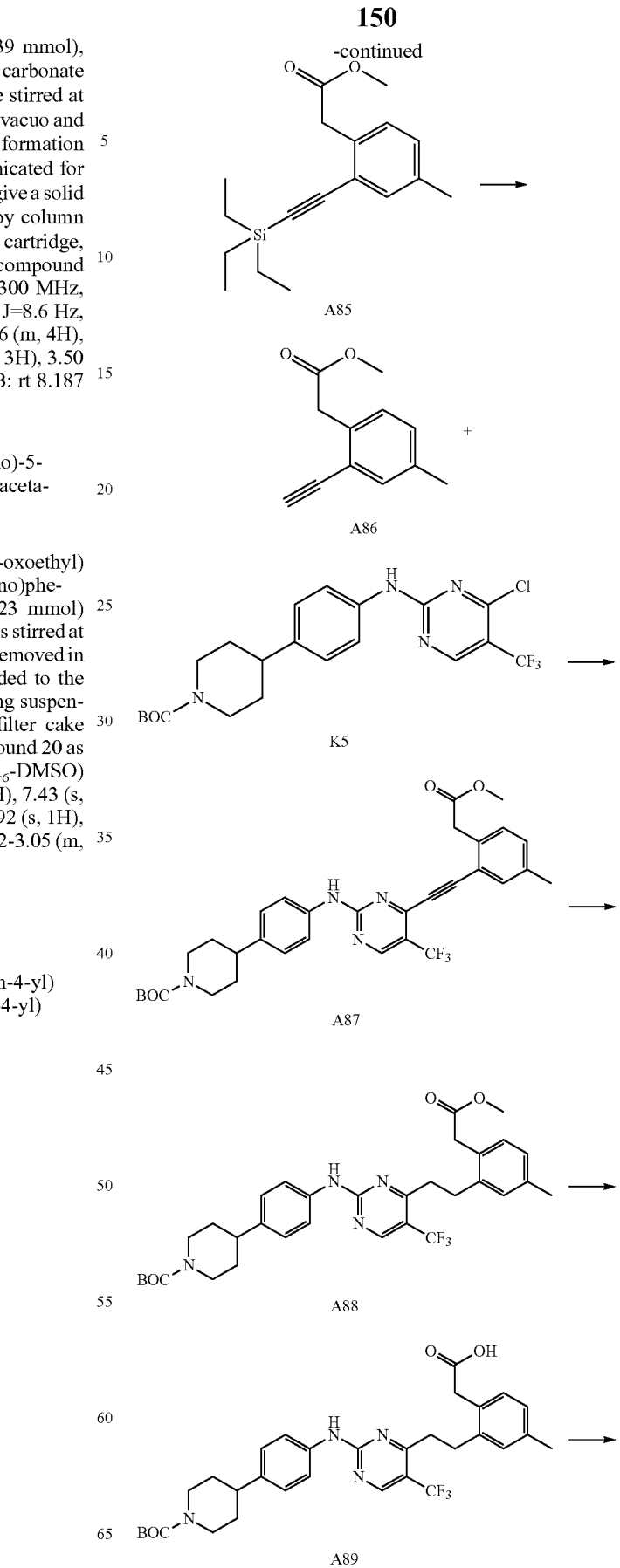

-continued

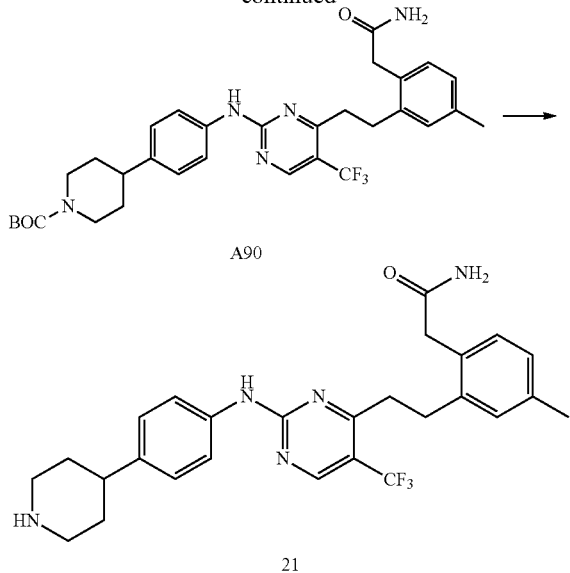

A90

21

(a) 1-(2-Bromo-4-methylphenyl)-2-diazoethanone (A83)

Oxalyl chloride (0.891 mL, 10.2 mmol) was slowly added to a solution of 2-bromo-4-methylbenzoic acid (813 mg, 3.78 mmol) and DMF (0.16 mL) in THF (35 mL) under nitrogen. The resulting mixture was stirred at room temperature for 30 minutes, then the volatiles were removed in vacuo and the residue azeotroped with toluene (2×20 mL). The resulting residue was taken up in anhydrous acetonitrile (40 mL) and chilled to 0° C. under a nitrogen atmosphere. A solution of TMS-diazomethane (2.0 M in Et$_2$O; 4.35 mL, 8.70 mmol) was rapidly added and the resulting mixture was stirred at room temperature for 1 hour. EtOAc (30 mL) and saturated aqueous NaHCO$_3$ (20 mL) were added and the layers separated. The aqueous layer was extracted with EtOAc (2×30 mL), then the combined organic extracts were washed with water (×2), brine, dried (MgSO$_4$), filtered and evaporated in vacuo. The residue was adsorbed onto silica gel and purified by column chromatography (Biotage Isolera, 25 g SiO$_2$ cartridge, 10-20% EtOAc in petroleum benzine 40-60° C.) to give the title compound A83 as a yellow oil (667 mg, 74%); $^1$H NMR (400 MHz, CDCl$_3$) δ 7.43 (d, J=0.6 Hz, 1H), 7.36 (d, J=7.5 Hz, 1H), 7.15 (dd, J=7.8, 0.7 Hz, 1H), 5.73 (s, 1H), 2.35 (s, 3H).

(b) Methyl 2-(2-bromo-4-methylphenyl)acetate (A84)

To a solution of 1-(2-bromo-4-methylphenyl)-2-diazoethanone (A83) (667 mg, 2.79 mmol) in THF (4.3 mL) and MeOH (4.3 mL) was added a solution of silver benzoate (96 mg, 0.42 mmol) in Et$_3$N (1.13 mL, 11.2 mmol). The resulting mixture was stirred for 2 hours at room temperature then passed through a plug of silica gel eluting with 50% EtOAc in petroleum benzine 40-60° C. The eluent was evaporated in vacuo and the residue was adsorbed onto silica gel and separated using silica gel column chromatography (Biotage Isolera, 25 g SiO$_2$ cartridge, 0-50% EtOAc in petroleum benzine 40-60° C.) to give the title compound A84 as a clear oil (678 mg, >99%); $^1$H NMR (400 MHz, CDCl$_3$) δ 7.39 (d, J=0.7 Hz, 1H), 7.16 (d, J=7.8 Hz, 1H), 7.07 (dd, J=7.7, 1.0 Hz, 1H), 3.76 (s, 2H), 3.70 (s, 3H), 2.30 (s, 3H). LCMS-A: rt 6.070 min.

(c) Methyl 2-(4-methyl-2-((triethylsilyl)ethynyl) phenyl)acetate (A85)

A solution of triethylsilyl acetylene (0.27 mL, 1.5 mmol) in degassed DMF (4 mL) and Et$_3$N (2.0 mL, 15 mmol) was added to a mixture of methyl 2-(2-bromo-4-methylphenyl) acetate (A84) (0.30 g, 1.2 mmol), PdCl$_2$(PPh$_3$)$_2$ (0.043 g, 0.062 mmol), CuI (0.012 g, 0.062 mmol) and t-Bu$_3$PH.BF$_4$ (0.018 g, 0.062 mmol) in degassed DMF (10 mL). The resulting mixture was heated at 70° C. for 17 hours then diluted with EtOAc and passed through a plug of Celite, washing with EtOAc (150 mL). The filtrate was concentrated under reduced pressure and adsorbed onto silica gel and purified by column chromatography (Biotage Isolera, 40 g SiO$_2$ cartridge, 0-15% EtOAc in petroleum spirits) to yield the title compound A85 as a yellow oil (0.326 g, 72% purity contaminated with starting material); $^1$H NMR (400 MHz, CDCl$_3$) δ 7.32 (s, 1H), 7.15 (d, J=7.8 Hz, 1H), 7.12-7.08 (m, 1H), 3.82 (s, 2H), 3.68 (s, 3H), 2.31 (s, 3H), 1.05 (t, J=7.9 Hz, 9H), 0.72-0.64 (m, 6H).

(d) Methyl 2-(2-ethynyl-4-methylphenyl)acetate (A86)

TBAF (1.0 M in THF; 1.16 mL, 1.16 mmol) was added to a solution of methyl 2-(4-methyl-2-((triethylsilyl)ethynyl) phenyl)acetate (A85) (0.326 g, 72% purity) in DCM (10 mL) at 0° C. and the resulting mixture stirred at room temperature for 5 minutes. Aqueous 10% NaHCO$_3$ was added and the layers separated. The organic layer was dried (MgSO$_4$) and the volatiles removed in vacuo to give a yellow oil which was adsorbed onto silica and purified by silica gel column chromatography (Biotage Isolera, 25 g SiO$_2$ cartridge, 0-10% EtOAc in petroleum benzine 40-60° C.) to give the title compound A86 (0.196 g, 71% pure: contaminated with methyl 2-(2-bromo-4-methylphenyl)acetate); $^1$H NMR (400 MHz, CDCl$_3$) δ 7.33 (s, 1H), 7.19-7.12 (m, 2H), 3.82 (s, 2H), 3.70 (s, 3H), 3.25 (s, 1H), 2.31 (s, 3H). LCMS-A: rt 5.900; m/z 189.2 [M+H]$^+$.

(e) tert-Butyl 4-(4-((4-((2-(2-methoxy-2-oxoethyl)-5-methylphenyl)ethynyl)-5-(trifluoromethyl)pyrimidin-2-yl)amino)phenyl)piperidine-1-carboxylate (A87)

A solution of methyl 2-(2-ethynyl-4-methylphenyl)acetate (A86) (0.196 g, 71% pure) in DMF (3 mL) and Et$_3$N (0.309 mL, 2.22 mmol) was added to a mixture of tert-butyl 4-(4-((4-chloro-5-(trifluoromethyl)pyrimidin-2-yl)amino)phenyl)piperidine-1-carboxylate (K5) (0.371 g, 0.812 mmol), PdCl$_2$(PPh$_3$)$_2$ (0.078 g, 0.11 mmol), CuI (0.021 g, 0.11 mmol) and PPh$_3$ (0.019 g, 0.074 mmol) in DMF (3 mL). The resulting mixture was heated under microwave irradiation at 120° C. for 15 minutes then diluted with EtOAc and passed through a plug of Celite, washing with EtOAc (50 mL). The filtrate was concentrated in vacuo and the residue purified by silica gel column chromatography (Biotage Isolera, 40 g cartridge, 0-35% EtOAc in petroleum benzine 40-60° C.) to give the title compound A87 as a yellow oil (133 mg, 30%); $^1$H NMR (400 MHz, CDCl$_3$) δ 8.61 (s, 1H), 7.74 (s, 1H), 7.56 (d, J=8.4 Hz, 2H), 7.44 (s, 1H), 7.24-7.16 (m, 4H), 4.43-4.14 (m, 2H), 3.90 (s, 2H), 3.69 (s, 3H), 2.80 (t, J=11.7 Hz, 2H), 2.63 (tt, J=12.0, 3.3 Hz, 1H), 2.34 (s, 3H), 1.81 (d, J=12.7 Hz, 2H), 1.69-1.54 (m, 2H), 1.49 (s, 9H). LCMS-A: rt 7.057 min; m/z 609.3 [M+H]$^+$.

(f) tert-Butyl 4-(4-((4-(2-(2-methoxy-2-oxoethyl)-5-methylphenethyl)-5-(trifluoromethyl)pyrimidin-2-yl)amino)phenyl)piperidine-1-carboxylate (A88)

A suspension of tert-butyl 4-(4-((4-((2-(2-methoxy-2-oxoethyl)-5-methylphenylethynyl)-5-(trifluoromethyl)pyrimidin-2-yl)amino)phenyl)piperidine-1-carboxylate (A87) (0.133 g, 0.219 mmol) and 10% Pd/C (53% water; 0.133 g) in DMF (7 mL) and Et$_3$N (1 mL) was stirred under an atmosphere of hydrogen at room temperature for 16 hours. The resulting mixture was filtered through a pad of Celite, washing with EtOAc (50 mL). The filtrate was evaporated in vacuo and the residue purified by silica gel column chromatography (Biotage Isolera, 25 g SiO$_2$ cartridge, 0-35% EtOAc in petroleum benzine 40-60° C.) to yield the title compound A88 as a clear oil (0.133 g, 99%); $^1$H NMR (400 MHz, CDCl$_3$) δ 8.54 (s, 1H), 7.57 (d, J=8.6 Hz, 2H), 7.53 (s, 1H), 7.20 (d, J=8.5 Hz, 2H), 7.15 (d, J=7.7 Hz, 1H), 7.07 (s, 1H), 7.02 (dd, J=7.7, 1.2 Hz, 1H), 4.40-4.15 (m, 2H), 3.71 (s, 2H), 3.67 (s, 3H), 3.08 (m, 4H), 2.81 (t, J=12.1 Hz, 2H), 2.65 (tt, J=12.0, 3.4 Hz, 1H), 2.32 (s, 3H), 1.83 (d, J=12.8 Hz, 2H), 1.62 (m, 2H), 1.49 (s, 9H). LCMS-A: rt 7.156 min; m/z 613.4 [M+H]$^+$.

(g) 2-(2-(2-(2-((4-(1-(tert-Butoxycarbonyl)piperidin-4-yl)phenyl)amino)-5-(trifluoromethyl)pyrimidin-4-yl)ethyl)-4-methylphenyl)acetic acid (A89)

LiOH.H$_2$O (0.028 g, 0.65 mmol) was added to a solution of tert-butyl 4-(4-((4-(2-(2-methoxy-2-oxoethyl)-5-methylphenethyl)-5-(trifluoromethyl)pyrimidin-2-yl)amino)phenyl)piperidine-1-carboxylate (A88) (0.133 g, 0.217 mmol) in THF (7 mL), water (1.5 mL) and MeOH (1 mL) and the resulting mixture stirred at room temperature for 27 hours. The volatiles were removed in vacuo and the residue was partitioned between EtOAc (50 mL) and saturated aqueous NaHCO$_3$ (50 mL). The layers were separated and the aqueous layer was extracted with EtOAc (2×50 mL). The combined organic layers were washed with brine (50 mL), dried over MgSO$_4$ and the volatiles removed in vacuo to give the title compound A89 as a white solid (0.124 g, 95%); $^1$H NMR (400 MHz, d$_4$-MeOH) δ 8.49 (s, 1H), 7.61 (d, J=8.5 Hz, 2H), 7.15 (d, J=8.5 Hz, 2H), 7.09 (d, J=7.7 Hz, 1H), 7.00 (s, 1H), 6.96 (d, J=7.7 Hz, 1H), 4.18 (d, J=13.1 Hz, 2H), 3.65 (s, 2H), 3.13-2.90 (m, 4H), 2.92-2.71 (m, 2H), 2.64 (tt, J=12.0, 3.1 Hz, 1H), 2.26 (s, 3H), 1.78 (d, J=12.5 Hz, 2H), 1.61-1.49 (m, 2H), 1.47 (s, 9H). LCMS-A: rt 6.736 min; m/z 599.3 [M+H]$^+$.

(h) tert-Butyl 4-(4-((4-(2-(2-amino-2-oxoethyl)-5-methylphenethyl)-5-(trifluoromethyl)pyrimidin-2-yl)amino)phenyl)piperidine-1-carboxylate (A90)

HOBt (0.036 g, 0.27 mmol), EDCl.HCl (0.052 g, 0.27 mmol) and DIPEA (0.18 mL, 1.0 mmol) were added to a solution of 2-(2-(2-(2-((4-(1-(tert-butoxycarbonyl)piperidin-4-yl)phenyl)amino)-5-(trifluoromethyl)pyrimidin-4-yl)ethyl)-4-methylphenyl)acetic acid (A89) (0.12 g, 0.21 mmol) in dry THF (6 mL) and dry DMF (1 mL) under a nitrogen atmosphere. After 10 minutes ammonium carbonate (0.10 g, 1.0 mmol) was added in one portion and the resulting mixture stirred at room temperature for 20 hours. The volatiles were removed in vacuo and the residue dried under high vacuum. The resulting residue was taken up in dry THF (5 mL) and dry DMF (4 mL) under a nitrogen atmosphere and HOBt (0.036 g, 0.27 mmol), EDCl.HCl (0.052 g, 0.27 mmol) and DIPEA (0.18 mL, 1.0 mmol) were added. After 10 minutes ammonium carbonate (0.10 g, 1.0 mmol) was added in one portion and the resulting mixture was stirred at 25° C. for 22 hours. The volatiles were removed in vacuo and the residue was partitioned between EtOAc (65 mL) and saturated aqueous NaHCO$_3$ (65 mL). The layers were separated and the aqueous layer was extracted with EtOAc (2×50 mL). The combined organic layers were washed with brine (50 mL), dried over MgSO$_4$, the volatiles removed in vacuo and the residue absorbed onto silica gel and purified by column chromatography (Biotage Isolera, 25 g SiO$_2$ cartridge, 0-100% EtOAc in petroleum benzine 40-60° C.) to give the title compound A90 as a white solid (0.106 g, 86%); $^1$H NMR (400 MHz, CDCl$_3$) δ 8.51 (s, 1H), 7.88 (s, 1H), 7.54 (d, J=8.5 Hz, 2H), 7.18 (d, J=8.5 Hz, 2H), 7.13 (d, J=7.6 Hz, 1H), 7.08-7.01 (m, 2H), 5.78 (s, 1H), 5.47 (s, 1H), 4.39-4.15 (m, 2H), 3.66 (s, 2H), 3.04 (apparent s, 4H), 2.79 (t, J=12.2 Hz, 2H), 2.62 (tt, J=12.0, 3.3 Hz, 1H), 2.32 (s, 3H), 1.81 (d, J=12.7 Hz, 2H), 1.60 (qd, J=12.8, 4.2 Hz, 2H), 1.48 (s, 9H). LCMS-A: rt 6.63 min; m/z 598.4 [M+H]$^+$.

(i) 2-(4-Methyl-2-(2-(2-((4-(piperidin-4-yl)phenyl)amino)-5-(trifluoromethyl)pyrimidin-4-yl)ethyl)phenyl)acetamide (21)

TFA (0.5 mL) was added to a solution of tert-butyl 4-(4-((4-(2-(2-amino-2-oxoethyl)-5-methylphenethyl)-5-(trifluoromethyl)pyrimidin-2-yl)amino)phenyl)piperidine-1-carboxylate (A90) (0.106 g, 0.177 mmol) in DCM (5 mL) and the resulting mixture stirred at room temperature for 17 hours. The solvent was removed in vacuo and the residue partitioned between EtOAc (20 mL) and 2 M aqueous NaOH (20 mL). The aqueous layer was extracted with EtOAc (2×10 mL) and the combined organic layers washed with water (20 mL), brine (20 mL) and dried over MgSO$_4$. The volatiles were removed in vacuo to give a solid which was suspended in DCM and cyclohexane. The resulting suspension was filtered to give the title compound 21 as a white solid (0.085 g, 96%); $^1$H NMR (400 MHz, d$_4$-MeOH) δ 8.54 (s, 1H), 7.62 (d, J=8.6 Hz, 2H), 7.22 (d, J=8.5 Hz, 2H), 7.14 (d, J=7.7 Hz, 1H), 7.06-6.98 (m, 2H), 3.62 (s, 2H), 3.28-3.21 (m, 2H), 3.15-3.08 (m, 2H), 3.08-3.01 (m, 2H), 2.86 (td, J=12.6, 2.6 Hz, 2H), 2.78-2.67 (m, 1H), 2.26 (s, 3H), 1.91 (d, J=12.0 Hz, 2H), 1.74 (qd, J=12.9, 4.0 Hz, 2H). LCMS-A: rt 4.94 min; m/z 498.3 [M+H]$^+$.

Example 22

Synthesis of 2-(2-(2-(2-((4-(piperidin-4-yl)phenyl)amino)-5-(trifluoromethyl)pyrimidin-4-yl)ethyl)-6-(trifluoromethyl)phenyl)acetamide (22)

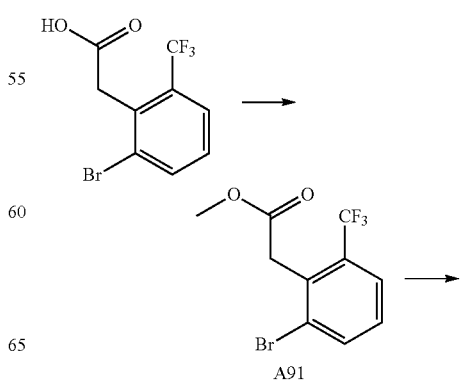

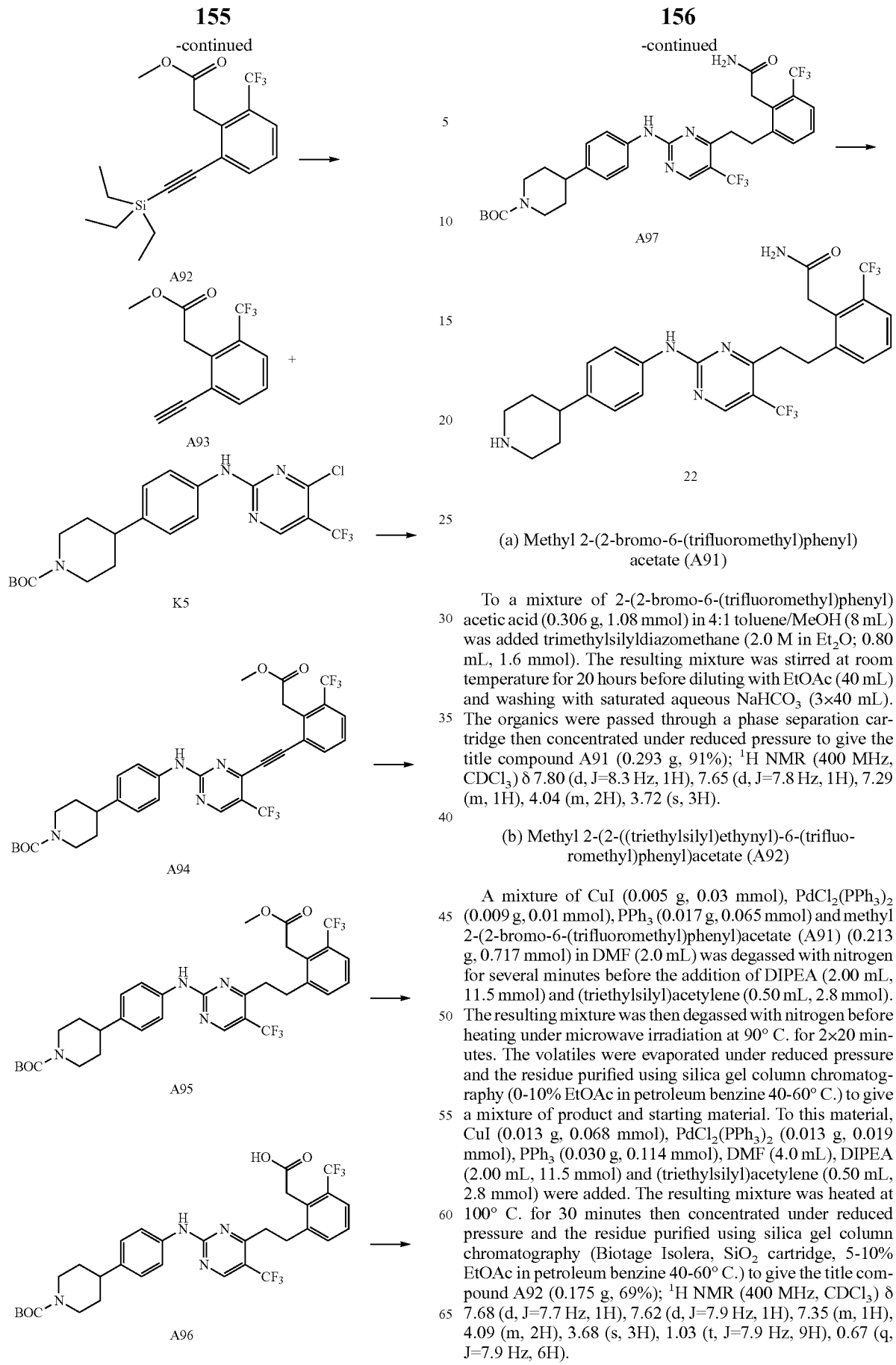

(a) Methyl 2-(2-bromo-6-(trifluoromethyl)phenyl)acetate (A91)

To a mixture of 2-(2-bromo-6-(trifluoromethyl)phenyl)acetic acid (0.306 g, 1.08 mmol) in 4:1 toluene/MeOH (8 mL) was added trimethylsilyldiazomethane (2.0 M in Et$_2$O; 0.80 mL, 1.6 mmol). The resulting mixture was stirred at room temperature for 20 hours before diluting with EtOAc (40 mL) and washing with saturated aqueous NaHCO$_3$ (3×40 mL). The organics were passed through a phase separation cartridge then concentrated under reduced pressure to give the title compound A91 (0.293 g, 91%); $^1$H NMR (400 MHz, CDCl$_3$) δ 7.80 (d, J=8.3 Hz, 1H), 7.65 (d, J=7.8 Hz, 1H), 7.29 (m, 1H), 4.04 (m, 2H), 3.72 (s, 3H).

(b) Methyl 2-(2-((triethylsilyl)ethynyl)-6-(trifluoromethyl)phenyl)acetate (A92)

A mixture of CuI (0.005 g, 0.03 mmol), PdCl$_2$(PPh$_3$)$_2$ (0.009 g, 0.01 mmol), PPh$_3$ (0.017 g, 0.065 mmol) and methyl 2-(2-bromo-6-(trifluoromethyl)phenyl)acetate (A91) (0.213 g, 0.717 mmol) in DMF (2.0 mL) was degassed with nitrogen for several minutes before the addition of DIPEA (2.00 mL, 11.5 mmol) and (triethylsilyl)acetylene (0.50 mL, 2.8 mmol). The resulting mixture was then degassed with nitrogen before heating under microwave irradiation at 90° C. for 2×20 minutes. The volatiles were evaporated under reduced pressure and the residue purified using silica gel column chromatography (0-10% EtOAc in petroleum benzine 40-60° C.) to give a mixture of product and starting material. To this material, CuI (0.013 g, 0.068 mmol), PdCl$_2$(PPh$_3$)$_2$ (0.013 g, 0.019 mmol), PPh$_3$ (0.030 g, 0.114 mmol), DMF (4.0 mL), DIPEA (2.00 mL, 11.5 mmol) and (triethylsilyl)acetylene (0.50 mL, 2.8 mmol) were added. The resulting mixture was heated at 100° C. for 30 minutes then concentrated under reduced pressure and the residue purified using silica gel column chromatography (Biotage Isolera, SiO$_2$ cartridge, 5-10% EtOAc in petroleum benzine 40-60° C.) to give the title compound A92 (0.175 g, 69%); $^1$H NMR (400 MHz, CDCl$_3$) δ 7.68 (d, J=7.7 Hz, 1H), 7.62 (d, J=7.9 Hz, 1H), 7.35 (m, 1H), 4.09 (m, 2H), 3.68 (s, 3H), 1.03 (t, J=7.9 Hz, 9H), 0.67 (q, J=7.9 Hz, 6H).

(c) Methyl 2-(2-ethynyl-6-(trifluoromethyl)phenyl) acetate (A93)

K$_2$CO$_3$ (0.210 g, 1.52 mmol) was added to a solution of methyl 2-(2-((triethylsilyl)ethynyl)-6-(trifluoromethyl)phenyl)acetate (A92) (0.175 g, 0.491 mmol) in MeOH (1 mL) and the mixture stirred for 10 minutes at room temperature. The resulting mixture was diluted with water (20 mL) and extracted with DCM (3×20 mL). The combined organic extracts were concentrated under reduced pressure and the residue dissolved in MeOH (1 mL). K$_2$CO$_3$ (0.204 g, 1.48 mmol) was added and the mixture stirred at room temperature for 30 minutes. The resulting mixture was diluted with water (20 mL) and extracted with DCM (3×20 mL) then the combined organic extracts were concentrated under reduced pressure. The residue was dissolved in MeOH (2 mL) to which K$_2$CO$_3$ (0.230 g, 1.66 mmol) was added and the resulting mixture stirred at room temperature for 30 minutes. Water (20 mL) was added and the mixture extracted with DCM (3×20 mL). The combined organic extracts were concentrated under reduced pressure to give the title compound A93 (0.113 g, 95%); $^1$H NMR (400 MHz, CDCl$_3$) δ 7.71 (d, J=7.7 Hz, 1H), 7.67 (d, J=8.0 Hz, 1H), 7.38 (m, 1H), 4.08 (m, 2H), 3.70 (s, 3H), 3.35 (s, 1H).

(d) tert-Butyl 4-(4-((4-((2-(2-methoxy-2-oxoethyl)-3-(trifluoromethyl)phenyl)ethynyl)-5-(trifluoromethyl)pyrimidin-2-yl)amino)phenyl)piperidine-1-carboxylate (A94)

A mixture of methyl 2-(2-ethynyl-6-(trifluoromethyl)phenyl)acetate (A93) (0.113 g, 0.468 mmol), tert-butyl 4-(4-((4-chloro-5-(trifluoromethyl)pyrimidin-2-yl)amino)phenyl)piperidine-1-carboxylate (K5) (0.222 g, 0.487 mmol), copper (I) iodide (0.005 g, 0.03 mmol), PdCl$_2$(PPh$_3$)$_2$ (0.021 g, 0.030 mmol) and t-Bu$_3$PH.BF$_4$ (0.011 g, 0.038 mmol) in DMF (2.0 mL) was degassed with nitrogen for several minutes before the addition of DIPEA (2.0 mL, 12 mmol) then further degassed with nitrogen for several minutes. The resulting mixture was heated under microwave irradiation 110° C. for 20 minutes and then a further 30 minutes. The volatiles were evaporated under reduced pressure and the residue purified using silica gel column chromatography (Biotage Isolera, SiO$_2$ cartridge, 0-30% EtOAc in petroleum benzine 40-60° C.) to give the title compound A94 (0.127 g, 41%); $^1$H NMR (400 MHz, CDCl$_3$) δ 8.63 (s, 1H), 7.88 (d, J=7.3 Hz, 1H), 7.76 (d, J=7.7 Hz, 1H), 7.55 (d, J=8.5 Hz, 2H), 7.47 (t, J=7.7 Hz, 1H), 7.41 (s, 1H), 7.22 (d, J=8.5 Hz, 2H), 4.25 (m, 2H), 4.17 (s, 2H), 3.69 (s, 3H), 2.81 (t, J=12.5 Hz, 2H), 2.65 (m, 1H), 1.83 (d, J=12.6 Hz, 2H), 1.63 (m, 2H), 1.49 (s, 9H). LCMS-A: rt 7.12 min; m/z 661.1 [M–H]$^+$.

(e) tert-Butyl 4-(4-((4-(2-(2-methoxy-2-oxoethyl)-3-(trifluoromethyl)phenethyl)-5-(trifluoromethyl)pyrimidin-2-yl)amino)phenyl)piperidine-1-carboxylate (A95)

A suspension of tert-butyl 4-(4-((4-((2-(2-methoxy-2-oxoethyl)-3-(trifluoromethyl)phenyl)ethynyl)-5-(trifluoromethyl)pyrimidin-2-yl)amino)phenyl)piperidine-1-carboxylate (A94) (0.127 g, 0.192 mmol) and 10% Pd/C (53% water; 0.234 g) in EtOAc (4.0 mL) and triethylamine (0.2 mL) was stirred under a hydrogen atmosphere for 20 hours. The resulting mixture was filtered through Celite and the filtrate concentrated under reduced pressure. The residue was purified by silica gel column chromatography (15-30% EtOAc in petroleum benzine 40-60° C.) to give the title compound A95 (0.106 g, 83%); $^1$H NMR (400 MHz, CDCl$_3$) δ 8.54 (s, 1H), 7.56 (m, 3H), 7.46 (d, J=7.3 Hz, 1H), 7.36 (m, 2H), 7.21 (d, J=8.5 Hz, 2H), 4.25 (m, 2H), 3.98 (s, 2H), 3.68 (s, 3H), 3.11 (m, 4H), 2.81 (m, 2H), 2.64 (m, 1H), 1.83 (m, 2H), 1.62 (m, 2H), 1.49 (s, 9H). LCMS-A: rt 7.19 min; m/z 665.1 [M–H]$^-$.

(f) 2-(2-(2-(2-((4-(1-(tert-Butoxycarbonyl)piperidin-4-yl)phenyl)amino)-5-(trifluoromethyl)pyrimidin-4-yl)ethyl)-6-(trifluoromethyl)phenyl)acetic acid (A96)

LiOH (31 mg, 1.3 mmol) was added to a solution of tert-butyl 4-(4-((4-(2-(2-methoxy-2-oxoethyl)-3-(trifluoromethyl)phenethyl)-5-(trifluoromethyl)pyrimidin-2-yl)amino)phenyl)piperidine-1-carboxylate (A95) (0.106 g, 0.159 mmol) in THF (2.0 mL), MeOH (1.0 mL) and water (1.0 mL) and the resulting mixture was stirred at room temperature for 16 hours. Water (20 mL) was added and the mixture extracted with EtOAc (2×20 mL). The combined organic extracts were concentrated under reduced pressure and the residue taken up in THF (2.0 mL), MeOH (1.0 mL) and water (1.0 mL). LiOH (0.103 g, 4.30 mmol) was added and the resulting mixture stirred for 136 hours at room temperature. The mixture was diluted with water (30 mL) then extracted with EtOAc (3×30 mL). The combined organic extracts were passed through a phase separation cartridge then concentrated under reduced pressure to give the title compound A96 (0.104 g, 99%); $^1$H NMR (400 MHz, d$_6$-DMSO) δ 10.27 (bs, 1H), 8.65 (s, 1H), 7.64 (d, J=8.6 Hz, 2H), 7.45 (d, J=7.7 Hz, 1H), 7.38 (d, J=7.6 Hz, 1H), 7.25 (dd, J=7.6, 7.6 Hz, 1H), 7.19 (d, J=8.6 Hz, 2H), 4.06 (m, 2H), 3.48 (s, 2H), 3.14 (m, 2H), 3.05 (m, 2H), 2.80 (m, 2H), 2.61 (m, 1H), 1.74 (m, 2H), 1.48 (m, 2H), 1.42 (s, 9H). LCMS-A: rt 6.78 min; m/z 653.3 [M+H]$^+$.

(g) tert-Butyl 4-(4-((4-(2-(2-amino-2-oxoethyl)-3-(trifluoromethyl)phenethyl)-5-(trifluoromethyl)pyrimidin-2-yl)amino)phenyl)piperidine-1-carboxylate (A97)

DIPEA (0.16 mL, 0.92 mmol) was added to a mixture of 2-(2-(2-(2-((4-(1-(tert-butoxycarbonyl)piperidin-4-yl)phenyl)amino)-5-(trifluoromethyl)pyrimidin-4-yl)ethyl)-6-(trifluoromethyl)phenyl)acetic acid (A96) (0.104 g, 0.160 mmol), HOBt (0.037 g, 0.27 mmol), and EDCl.HCl (0.056 g, 0.29 mmol) in DMF (5.0 mL) under a nitrogen atmosphere. After 15 minutes ammonium carbonate (0.077 g, 0.80 mmol) was added and stirring continued at room temperature for 24 hours. Additional HOBt (0.072 g, 0.53 mmol), EDCl.HCl (0.056 g, 0.29 mmol) and DIPEA (0.16 mL, 0.92 mmol) were added, then and after 15 minutes ammonium carbonate (0.121 g, 1.26 mmol) was also added and the resulting mixture stirred at room temperature for 16 hours. The resulting mixture was diluted with water (20 mL) then extracted with EtOAc (3×20 mL). The combined organic extracts were concentrated under reduced pressure and the residue purified using silica gel column chromatography (Biotage Isolera, SiO$_2$ cartridge, 0-50% EtOAc in petroleum benzine 40-60° C.) to give the title compound A97 (75 mg, 72%); $^1$H NMR (400 MHz, d$_6$-DMSO) δ 10.16 (s, 1H), 8.66 (s, 1H), 7.64 (d, J=8.6 Hz, 2H), 7.57 (d, J=7.9 Hz, 1H), 7.51 (d, J=7.4 Hz, 1H), 7.47 (s, 1H), 7.41 (dd, J=7.7, 7.7 Hz, 1H), 7.19 (d, J=8.6 Hz, 2H), 6.96 (s, 1H), 4.07 (m, 2H), 3.74 (s, 2H), 3.09 (m, 4H), 2.79 (m, 2H), 2.62 (m, 1H), 1.74 (m, 2H), 1.49 (m, 2H), 1.42 (s, 9H). LCMS-A: rt 6.63 min; m/z 652.3 [M+H]$^+$.

(h) 2-(2-(2-(2-((4-(Piperidin-4-yl)phenyl)amino)-5-(trifluoromethyl)pyrimidin-4-yl)ethyl)-6-(trifluoromethyl)phenyl)acetamide (22)

To a solution of tert-butyl 4-(4-((4-(2-(2-amino-2-oxoethyl)-3-(trifluoromethyl)phenethyl)-5-(trifluoromethyl)pyrimidin-2-yl)amino)phenyl)piperidine-1-carboxylate (A97) (0.075 g, 0.12 mmol) in DCM (5 mL) was added TFA (0.20 mL, 2.6 mmol) and the resulting mixture was stirred at room temperature for 16 hours. The volatiles were evaporated under reduced pressure and the residue partitioned between water (20 mL) and EtOAc. The layers were separated and the aqueous layer extracted with EtOAc (2×20 mL). The combined organic extracts were dried using a phase separation cartridge then the volatiles were removed under reduced pressure. The residue was triturated with $Et_2O$ and the resulting precipitate collected by filtration to give the title compound 22 (56 mg, 88%); $^1H$ NMR (400 MHz, $d_6$-DMSO) δ 10.22 (s, 1H), 8.67 (s, 1H), 8.29 (brs, 1H), 7.68 (d, J=8.6 Hz, 2H), 7.57 (d, J=7.9 Hz, 1H), 7.52 (d, J=7.6 Hz, 1H), 7.48 (s, 1H), 7.41 (t, J=7.8 Hz, 1H), 7.19 (d, J=8.6 Hz, 2H), 6.94 (s, 1H), 3.73 (s, 2H), 3.38 (m, 2H), 3.10 (m, 4H), 2.98 (td, J=12.8, 2.6 Hz, 2H), 2.79 (tt, J=11.7, 2.7 Hz, 1H), 1.93 (d, J=15.8 Hz, 2H), 1.74 (qd, J=13.8, 4.0 Hz, 2H). LCMS-A: rt 4.99 min; m/z 552.3 $[M+H]^+$.

Example 23

Synthesis of 2-(2-(2-(5-methoxy-2-((4-(piperidin-4-yl)phenyl)amino)pyrimidin-4-yl)ethyl)phenyl)acetamide (23)

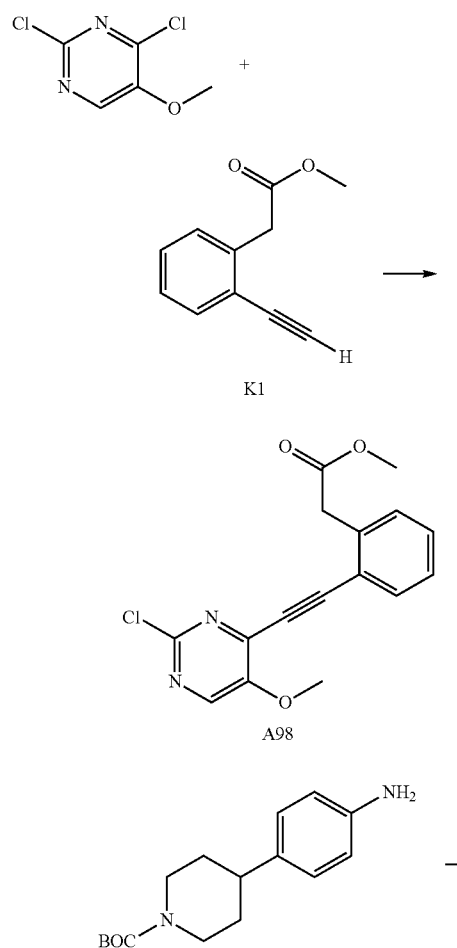

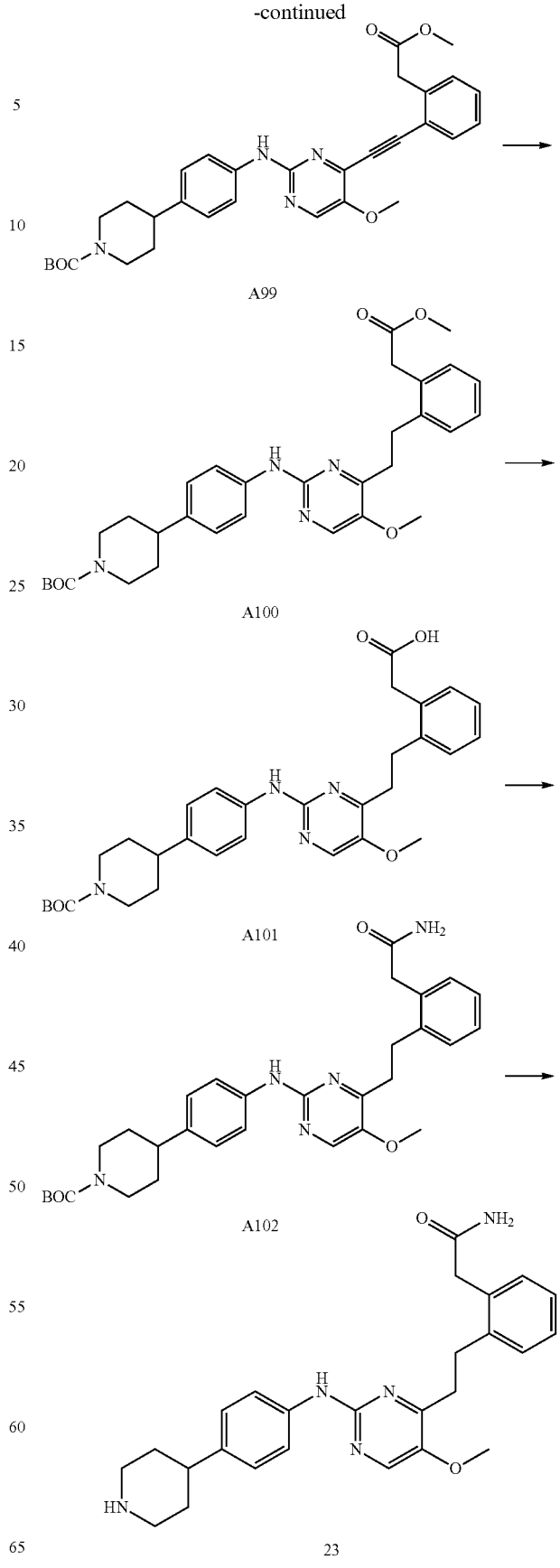

(a) Methyl 2-(2-((2-chloro-5-methoxypyrimidin-4-yl)ethynyl)phenyl)acetate (A98)

A solution of methyl 2-(2-ethynylphenyl)acetate (K1) (0.35 g, 2.0 mmol) in DMF (3 mL) and Et$_3$N (0.70 mL, 5.0 mmol) was added to a mixture of 2,4-dichloro-5-methoxypyrimidine (0.30 g, 1.7 mmol), PdCl$_2$(PPh$_3$)$_2$ (0.12 g, 0.17 mmol), CuI (0.032 g, 0.17 mmol) and PPh$_3$ (0.044 g, 0.17 mmol) in DMF (3 mL). The resulting mixture was heated under microwave irradiation at 120° C. for 15 minutes, then diluted with EtOAc and passed through a plug of Celite, washing with EtOAc (50 mL). The volatiles were removed in vacuo and the residue was purified by silica gel column chromatography (Biotage Isolera, 24 g SiO$_2$ cartridge, 0-25% EtOAc in hexanes) to give the title compound A98 as a pale yellow solid (0.38 g, 72%); $^1$H NMR (400 MHz, CDCl$_3$) δ 8.26 (s, 1H), 7.65 (dd, J=7.6, 1.0 Hz, 1H), 7.46-7.29 (m, 3H), 4.03 (s, 3H), 3.99 (s, 2H), 3.71 (s, 3H). LCMS-A: rt 5.92 min; m/z 317.1 [M+H]$^+$.

(b) tert-Butyl 4-(4-((5-methoxy-4-((2-(2-methoxy-2-oxoethyl)phenyl)ethynyl)pyrimidin-2-yl)amino)phenyl)piperidine-1-carboxylate (A99)

To a solution of methyl 2-(2-((2-chloro-5-methoxypyrimidin-4-yl)ethynyl)phenyl)acetate (A98) (0.10 g, 0.32 mmol) in 1,4-dioxane (6 mL) was added tert-butyl 4-(4-aminophenyl)piperidine-1-carboxylate (0.087 g, 0.32 mmol), Cs$_2$CO$_3$ (0.41 g, 1.3 mmol), Pd$_2$(dba)$_3$ (0.030 g, 0.032 mmol) and Xantphos (0.055 g, 0.095 mmol). The resulting mixture was degassed with nitrogen for 5 minutes, before heating under microwave irradiation for 30 minutes at 120° C., then for 60 minutes at 120° C. EtOAc (100 mL) was added and the mixture was washed with water (2×25 mL), brine (25 mL), dried (MgSO$_4$) and then concentrated under reduced pressure. The residue was purified by silica gel column chromatography (Biotage Isolera, 40 g SiO$_2$ cartridge, 0-25% EtOAc in petroleum benzine 40-60° C.) to give the title compound A99 as a yellow oil (0.11 g, 64%); $^1$H NMR (400 MHz, CDCl$_3$) δ 8.18 (s, 1H), 7.66 (d, J=7.6 Hz, 1H), 7.52 (d, J=8.5 Hz, 2H), 7.43-7.29 (m, 3H), 7.16 (d, J=8.5 Hz, 2H), 6.98 (s, 1H), 4.38-4.17 (m, 2H), 4.02 (s, 2H), 3.94 (s, 3H), 3.70 (s, 3H), 2.80 (t, J=11.9 Hz, 2H), 2.62 (tt, J=12.0, 3.3 Hz, 1H), 1.82 (d, J=13.0 Hz, 2H), 1.68-1.51 (m, peak obscured), 1.49 (s, 9H). LCMS-A: rt 6.69 min; m/z 557.3 [M+H]$^+$.

(c) tert-Butyl 4-(4-((5-methoxy-4-(2-(2-methoxy-2-oxoethyl)phenethyl)pyrimidin-2-yl)amino)phenyl)piperidine-1-carboxylate (A100)

A slurry of 10% Pd/C (53% water; 0.100 g) in DMF (2 mL) was added to a solution of tert-butyl 4-(4-((5-methoxy-4-((2-(2-methoxy-2-oxoethyl)phenyl)ethynyl)pyrimidin-2-yl)amino)phenyl)piperidine-1-carboxylate (A99) (0.112 g, 0.201 mmol) in DMF (8 mL) and TEA (1 mL), and the resulting mixture stirred under an atmosphere of hydrogen at room temperature for 16 hours. The resulting mixture was filtered through a pad of Celite, washing with EtOAc (50 mL). The solvent was removed in vacuo and the resultant residue purified by silica gel column chromatography (Biotage Isolera, 25 g SiO$_2$ cartridge, 0-65% EtOAc in petroleum benzine 40-60° C.) to yield the title compound A100 as a pale yellow oil (0.110 g, 98%); $^1$H NMR (400 MHz, CDCl$_3$) δ 7.95 (s, 1H), 7.50 (d, J=8.6 Hz, 2H), 7.24-7.14 (m, 4H), 7.11 (d, J=8.5 Hz, 2H), 7.02 (s, 1H), 4.34-4.13 (m, 2H), 3.76 (s, 3H), 3.73 (s, 2H), 3.65 (s, 3H), 3.06-2.98 (m, 2H), 2.98-2.90 (m, 2H), 2.77 (t, J=12.1 Hz, 2H), 2.58 (tt, J=11.9, 3.3 Hz, 1H), 1.78 (d, J=13.0 Hz, 2H), 1.57 (qd, J=12.9, 4.5 Hz, 2H), 1.46 (s, 9H). LCMS-A: rt 6.77 min; m/z 561.4 [M+H]$^+$.

(d) 2-(2-(2-(2-((4-(1-(tert-Butoxycarbonyl)piperidin-4-yl)phenyl)amino)-5-methoxypyrimidin-4-yl)ethyl)phenyl)acetic acid (A101)

LiOH.H$_2$O (0.025 g, 0.59 mmol) was added to a solution of tert-butyl 4-(4-((5-methoxy-4-(2-(2-methoxy-2-oxoethyl)phenethyl)pyrimidin-2-yl)amino)phenyl)piperidine-1-carboxylate (A100) (0.11 g, 0.20 mmol) in THF (7 mL), water (1.5 mL) and MeOH (1 mL) and the resulting mixture stirred at room temperature for 17 hours. The volatiles were removed in vacuo and the residue was partitioned between EtOAc (50 mL) and saturated aqueous NaHCO$_3$ (50 mL). The layers were separated and the aqueous layer was extracted with EtOAc (2×50 mL). The combined organic layers were washed with brine (50 mL), dried over MgSO$_4$ and the volatiles removed in vacuo to give the title compound A101 as a pale yellow oil (0.099 g, 92%); $^1$H NMR (400 MHz, d$_4$-MeOH) δ 7.98 (s, 1H), 7.52 (d, J=8.5 Hz, 2H), 7.22-7.04 (m, 6H), 4.16 (d, J=13.1 Hz, 2H), 3.76 (s, 3H), 3.71 (s, 2H), 2.96-2.88 (m, 4H), 2.88-2.70 (m, 2H), 2.65-2.55 (m, 1H), 1.76 (d, J=12.3 Hz, 2H), 1.59-1.49 (m, 2H), 1.46 (s, 9H). LCMS-A: rt 6.35 min; m/z 547.3 [M+H]$^+$.

(e) 2-(2-(2-(5-Methoxy-2-((4-(piperidin-4-yl)phenyl)amino)pyrimidin-4-yl)ethyl)phenyl)acetamide (A102)

HOBt (0.032 g, 0.24 mmol), EDCl.HCl (0.045 g, 0.24 mmol) and DIPEA (0.16 mL, 0.91 mmol) were added to a solution of 2-(2-(2-(2-((4-(1-(tert-butoxycarbonyl)piperidin-4-yl)phenyl)amino)-5-methoxypyrimidin-4-yl)ethyl)phenyl)acetic acid (A101) (0.099 g, 0.18 mmol) in dry THF (6 mL) and dry DMF (1 mL) under nitrogen. After 10 minutes ammonium carbonate (0.087 g, 0.91 mmol) was added in one portion and the resulting mixture was stirred at room temperature for 66 hours. The volatiles were removed in vacuo and the residue partitioned between EtOAc (50 mL) and saturated aqueous NaHCO$_3$ (50 mL). The aqueous layer was extracted with EtOAc (2×50 mL). The combined organic layers were washed with brine (50 mL) and dried over MgSO$_4$. The solvent was removed in vacuo and the residue purified by silica gel column chromatography (Biotage Isolera, 24 g SiO$_2$ cartridge, 0-100% EtOAc in petroleum benzine 40-60° C. followed by 0-20% MeOH in EtOAc) to give the title compound A102 as a clear oil (0.094 g, 92%); $^1$H NMR (400 MHz, d$_4$-MeOH) δ 8.00 (s, 1H), 7.53 (d, J=8.6 Hz, 2H), 7.22 (dd, J=7.0, 3.8 Hz, 1H), 7.20-7.13 (m, 3H), 7.10 (d, J=8.6 Hz, 2H), 4.18 (d, J=13.0 Hz, 2H), 3.78 (s, 3H), 3.65 (s, 2H), 3.10-3.00 (m, 2H), 3.00-2.92 (m, peak obscured, 2H), 2.90-2.71 (m, peak obscured, 2H), 2.62 (tt, J=11.9, 3.2 Hz, 1H), 1.78 (d, J=12.2 Hz, 2H), 1.60-1.49 (m, 2H), 1.47 (s, 9H). LCMS-A: rt 6.20 min; m/z 546.4 [M+H]$^+$.

(f) 2-(2-(2-(5-Methoxy-2-((4-(piperidin-4-yl)phenyl)amino)pyrimidin-4-yl)ethyl)phenyl)acetamide (23)

TFA (0.5 mL) was added to a solution of 2-(2-(2-(5-methoxy-2-((4-(piperidin-4-yl)phenyl)amino)pyrimidin-4-yl)ethyl)phenyl)acetamide (A102) (0.091 g, 0.17 mmol) in DCM (5 mL), and the resulting solution stirred at room temperature for 17 hours. The volatiles were removed in vacuo and the residue partitioned between EtOAc (30 mL) and 2 M aqueous NaOH (30 mL). The aqueous layer was extracted with EtOAc (2×30 mL) then the combined organic layers

163 washed with water (30 mL), brine (30 mL) and dried over MgSO$_4$. The volatiles were removed in vacuo to give a yellow solid. The solid was suspended in DCM and cyclohexane and the resulting suspension filtered to give the title compound 23 as a white solid (0.031 g, 42%); $^1$H NMR (400 MHz, d$_4$-MeOH) δ 8.04 (s, 1H), 7.54 (d, J=8.6 Hz, 2H), 7.27-7.21 (m, 1H), 7.22-7.10 (m, 5H), 3.82 (s, 3H), 3.67 (s, 2H), 3.25 (m, 2H obscured by solvent), 3.11-3.03 (m, 2H), 3.03-2.95 (m, 2H), 2.87 (td, J=12.6, 2.6 Hz, 2H), 2.70 (tt, J=12.0, 3.5 Hz, 1H), 1.91 (d, J=12.6 Hz, 2H), 1.81-1.67 (m, 2H). LCMS-A: rt 4.58 min; m/z 446.3 [M+H]$^+$.

Example 24

Synthesis of 2-(2-(2-(5-methyl-2-(pyridin-3-ylamino)pyrimidin-4-yl)ethyl)phenyl)acetamide (24)

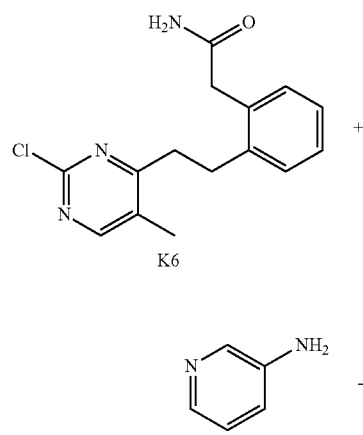

A mixture of 2-(2-(2-(2-chloro-5-methylpyrimidin-4-yl)ethyl)phenyl)acetamide (K6) (0.050 g, 0.17 mmol), 3-aminopyridine (0.019 g, 0.21 mmol), Pd(OAc)$_2$ (0.8 mg, 0.003 mmol), Cs$_2$CO$_3$ (0.169 g, 0.518 mmol) and Xantphos (4 mg, 0.007 mmol) in 1,4-dioxane (1 mL) was heated under microwave irradiation at 150° C. for 10 minutes. Water (30 mL) was added and the resulting suspension was sonicated for 1 minute. The precipitate was collected by filtration then adsorbed onto silica gel and purified by silica gel column chromatography (CombiFlash Rf, 12 g SiO$_2$ cartridge, 0-10% MeOH in DCM) to give the title compound 24 as a light pink solid (6 mg, 10%); $^1$H NMR (300 MHz, d$_4$-MeOH) δ 8.87 (s, 1H), 8.26 (d, J=7.4 Hz, 1H), 8.16 (s, 1H), 8.10 (s, 1H), 7.34 (dd, J=8.1, 4.6 Hz, 1H), 7.23-7.27 (m, 1H), 7.16-7.20 (m, 3H), 3.65 (s, 2H), 3.12-3.17 (m, 2H), 2.97-3.02 (m, 2H), 2.12 (s, 3H). LCMS-B: rt 4.649 min; m/z 348 [M+H]$^+$.

164

Example 25

Synthesis of 2-(2-(2-(2-((4-(piperidin-4-yl)phenyl)amino)-5-(trifluoromethyl)pyrimidin-4-yl)ethyl)-5-(trifluoromethyl)phenyl)acetamide (25)

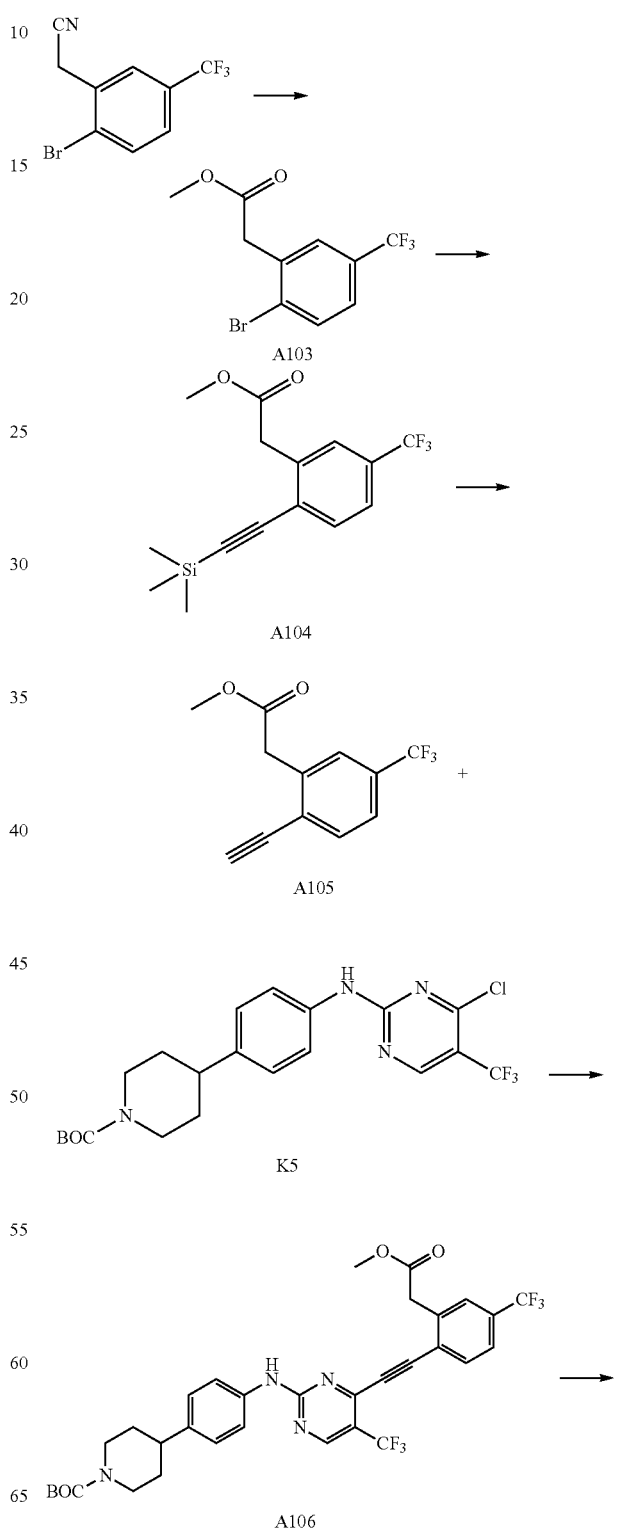

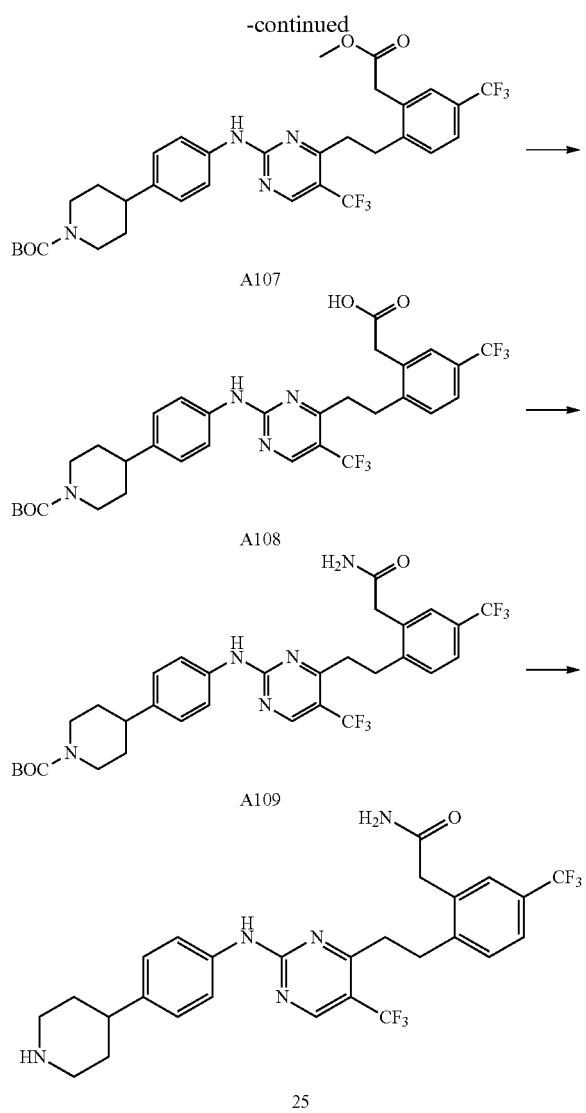

A107

A108

A109

25

(a) Methyl 2-(2-bromo-5-(trifluoromethyl)phenyl) acetate (A103)

Concentrated aqueous H₂SO₄ (1 mL) was added to a solution of 2-(2-bromo-5-(trifluoromethyl)phenyl)acetonitrile (2.00 g, 7.57 mmol) in MeOH (30 mL) and the resulting mixture heated at reflux for 14 days. The volatiles were removed in vacuo and the residue was taken up in EtOAc (100 mL). The resulting solution was washed with 10% aqueous NaHCO₃, dried (MgSO₄), and the volatiles removed under reduced pressure to give a clear liquid which was purified by silica gel column chromatography (Biotage Isolera, SiO₂ cartridge, 0-20% EtOAc in petroleum benzine 40-60° C.) to give the title compound A103 as a clear liquid (1.67 g, 74%); ¹H NMR (400 MHz, CDCl₃) δ 7.71 (d, J=8.3 Hz, 1H), 7.55 (d, J=2.0 Hz, 1H), 7.41 (dd, J=8.3, 2.0 Hz, 1H), 3.85 (s, 2H), 3.74 (s, 3H). LCMS-A: rt 6.223 min.

(b) Methyl 2-(5-(trifluoromethyl)-2-((trimethylsilyl)-ethynyl)phenyl)acetate (A104)

A suspension of methyl 2-(2-bromo-5-(trifluoromethyl) phenyl)acetate (A103) (1.00 g, 3.36 mmol), PdCl₂(PPh₃)₂ (0.118 g, 0.168 mmol), t-Bu₃PH.BF₄ (0.049 g, 0.17 mmol), CuI (0.032 g, 0.17 mmol) and trimethylsilylacetylene (0.951 mL, 6.73 mmol) in anhydrous degassed DMF (10 mL) and Et₃N (10 mL) was stirred at 80° C. for 16 hours. The resulting mixture was adsorbed onto silica gel and purified by column chromatography (Biotage Isolera, SiO₂ cartridge, 0-10% EtOAc in petroleum benzine 40-60° C.) to give the title compound A104 as an orange liquid (0.863 g, 82%); ¹H NMR (400 MHz, CDCl₃) δ 7.57 (d, J=8.0 Hz, 1H), 7.53 (d, J=0.5 Hz, 1H), 7.50-7.44 (m, 1H), 3.87 (s, 2H), 3.7s (s, 3H), 0.24 (s, 9H). LCMS: rt 6.931 min; m/z 315.1 [M+H]⁺.

(c) Methyl 2-(2-ethynyl-5-(trifluoromethyl)phenyl) acetate (A105)

TBAF (1.0 M in THF; 4.29 mL, 4.29 mmol) was added to a solution of methyl 2-(5-(trifluoromethyl)-2-((trimethylsilyl)ethynyl)phenyl)acetate (A104) (0.900 g, 2.86 mmol) in THF (25 mL) at 0° C. The resulting mixture was stirred at 0° C. for 5 minutes before the addition of EtOAc (50 mL) and 10% aqueous NaHCO₃ (50 mL). The layers were separated and the organic phase dried (MgSO₄) then the solvent was evaporated under reduced pressure. The residue was adsorbed onto silica gel and purified by silica gel column chromatography (Biotage Isolera, SiO₂ cartridge, 0-10% EtOAc in petroleum benzine 40-60° C.) to give the title compound A105 as a light brown coloured liquid (0.498 g, 72%); ¹H NMR (400 MHz, CDCl₃) δ 7.60 (d, J=8.1 Hz, 1H), 7.56 (s, 1H), 7.50 (d, J=8.1 Hz, 1H), 3.89 (s, 2H), 3.71 (s, 3H), 3.40 (s, 1H). LCMS-A: rt 6.094 min; m/z 243.1 [M+H]⁺.

(d) tert-Butyl 4-(4-((4-((2-(2-methoxy-2-oxoethyl)-4-(trifluoromethyl)phenyl)ethynyl)-5-(trifluoromethyl)pyrimidin-2-yl)amino)phenyl)piperidine-1-carboxylate (A106)

A suspension of tert-butyl 4-(4-((4-chloro-5-(trifluoromethyl)pyrimidin-2-yl)amino)phenyl)piperidine-1-carboxylate (K5) (0.300 g, 0.656 mmol), PdCl₂(PPh₃)₂ (0.046 g, 0.066 mmol), t-Bu₃PH.BF₄ (0.019 g, 0.066 mmol), CuI (0.013 g, 0.022 mmol) and methyl 2-(2-ethynyl-5-(trifluoromethyl)phenyl)acetate (A105) (0.191 g, 0.657 mmol) in dry degassed DMF (4 mL) and Et₃N (4 mL) was heated at 120° C. for 20 minutes under nitrogen. The volatiles were evaporated under reduced pressure and the residue adsorbed onto silica gel then purified by column chromatography (Biotage Isolera, SiO₂ cartridge, 0-50% EtOAc in petroleum benzine 40-60° C.) to give the title compound A106 as a yellow solid (0.196 g, 45%); ¹H NMR (400 MHz, CDCl₃) δ 8.64 (s, 1H), 7.75 (d, J=8.0 Hz, 1H), 7.62 (s, 1H), 7.60-7.53 (m, 4H), 7.21 (d, J=8.5 Hz, 2H), 4.25 (s, 2H), 3.99 (s, 2H), 3.72 (s, 3H), 2.80 (t, J=11.9 Hz, 2H), 2.64 (m, 1H), 1.82 (d, J=12.8 Hz, 2H), 1.68-1.53 (m, 2H), 1.49 (s, 9H). LCMS-A: rt 7.109 min; m/z 663.3 [M+H]⁺.

(e) tert-Butyl 4-(4-((4-(2-(2-methoxy-2-oxoethyl)-4-(trifluoromethyl)phenethyl)-5-(trifluoromethyl)pyrimidin-2-yl)amino)phenyl)piperidine-1-carboxylate (A107)

A suspension of 10% Pd/C (0.050 g) and tert-butyl 4-(4-((4-((2-(2-methoxy-2-oxoethyl)-4-(trifluoromethyl)phenyl)ethynyl)-5-(trifluoromethyl)pyrimidin-2-yl)amino)phenyl)piperidine-1-carboxylate (A106) (0.196 g, 0.295 mmol) in DMF (20 mL) was stirred under a hydrogen atmosphere at 50 Psi pressure for 24 hours. The resulting mixture was filtered through Celite, washing with MeOH (2×50 mL). The filtrate was adsorbed onto silica gel then purified by column chromatography (Biotage Isolera, SiO$_2$ cartridge, 0-30% EtOAc in petroleum benzine 40-60° C.) to give the title compound A107 as a light yellow liquid (0.157 g, 80%); $^1$H NMR (400 MHz, CDCl$_3$) δ 8.54 (s, 1H), 7.54 (d, J=8.5 Hz, 2H), 7.52-7.43 (m, 3H), 7.35 (d, J=7.8 Hz, 1H), 7.20 (d, J=8.5 Hz, 2H), 4.25 (brs, 2H), 3.79 (s, 2H), 3.70 (s, 3H), 3.17 (m, 2H), 3.09 (m, 2H), 2.81 (t, J=11.4 Hz, 2H), 2.70-2.56 (m, 1H), 1.83 (d, J=12.7 Hz, 2H), 1.72-1.55 (m, 2H), 1.49 (s, 9H). LCMS-A: rt 7.199 min; m/z 667.3 [M+H]$^+$.

(f) 2-(2-(2-(2-((4-(1-(tert-Butoxycarbonyl)piperidin-4-yl)phenyl)amino)-5-(trifluoromethyl)pyrimidin-4-yl)ethyl)-5-(trifluoromethyl)phenyl)acetic acid (A108)

tert-Butyl 4-(4-((4-(2-(2-methoxy-2-oxoethyl)-4-(trifluoromethyl)phenethyl)-5-(trifluoromethyl)pyrimidin-2-yl)amino)phenyl)piperidine-1-carboxylate (A107) (0.157 g, 0.236 mmol) and LiOH.H$_2$O (0.080 g, 0.711 mmol) were suspended in MeOH (2 mL), water (2 mL) and THF (2 mL) and the resulting mixture stirred for 16 hours at room temperature. The volatiles were evaporated under reduced pressure to give the title compound A108; LCMS-A: rt 6.828 min; m/z 653.3 [M+H]$^+$.

(g) tert-Butyl 4-(4-((4-(2-(2-amino-2-oxoethyl)-4-(trifluoromethyl)phenethyl)-5-(trifluoromethyl)pyrimidin-2-yl)amino)phenyl)piperidine-1-carboxylate (A109)

HOBt (0.042 g, 0.31 mmol), EDCl.HCl (0.049 g, 0.31 mmol) and DIPEA (0.204 mL, 1.20 mmol) were added to a solution of 2-(2-(2-(2-((4-(1-(tert-butoxycarbonyl)piperidin-4-yl)phenyl)amino)-5-(trifluoromethyl)pyrimidin-4-yl)ethyl)-5-(trifluoromethyl)phenyl)acetic acid (A108) (0.157 g, 0.240 mmol) in dry DMF (5 mL) and dry THF (5 mL). Ammonium carbonate (113 mg, 1.20 mmol) was then added and the resulting mixture was stirred at room temperature for 3 days. The mixture was diluted with EtOAc and washed with 10% aqueous NaHCO$_3$. The organic layer was dried (MgSO$_4$) and the volatiles removed under reduced pressure. The residue was adsorbed onto silica gel and purified by silica gel column chromatography (SiO$_2$, 0-100% EtOAc in petroleum benzine 40-60° C.) to give the title compound A109 as a colourless solid (0.121 g, 77%); $^1$H NMR (400 MHz, d$_4$-MeOH) δ 8.56 (s, 1H), 7.60 (m, 3H), 7.55-7.48 (m, 1H), 7.42 (m, 1H), 7.22 (d, J=8.5 Hz, 2H), 4.23 (d, J=13.3 Hz, 2H), 3.76 (s, 2H), 3.26 (m, 2H), 3.14 (m, 2H), 2.95-2.81 (m, 2H), 2.77-2.64 (m, 1H), 1.83 (m, 2H), 1.70-1.54 (m, 2H), 1.50 (s, 9H). LCMS-A: rt 6.671 min; m/z 652.3 [M+H]$^+$.

(h) 2-(2-(2-(2-((4-(Piperidin-4-yl)phenyl)amino)-5-(trifluoromethyl)pyrimidin-4-ylethyl)-5-(trifluoromethyl)phenyl)acetamide (25)

TFA (1.0 mL) was added to a solution of tert-butyl 4-(4-((4-(2-(2-amino-2-oxoethyl)-4-(trifluoromethyl)phenethyl)-5-(trifluoromethyl)pyrimidin-2-yl)amino)phenyl)piperidine-1-carboxylate (A109) (0.121 g, 0.185 mmol) in DCM (10 mL) and the resulting mixture stirred for 24 hours at room temperature. The volatiles were evaporated under reduced pressure and the residue was dissolved in DCM. Cyclohexane was added and the resultant precipitate was collected by vacuum filtration to give the title compound 25 as a cream solid (0.065 g, 68%); $^1$H NMR (400 MHz, d$_4$-MeOH) δ 8.55 (s, 1H), 7.61 (d, J=8.5 Hz, 2H), 7.57 (s, 1H), 7.50 (d, J=8.3 Hz, 1H), 7.39 (d, J=8.1 Hz, 1H), 7.22 (d, J=8.6 Hz, 2H), 4.73-4.49 (m, 2H), 3.74 (s, 2H), 3.28-3.21 (m, 2H), 3.17-3.09 (m, 2H), 2.95 (m, 2H), 2.84-2.71 (m, 1H), 1.96 (d, J=13.6 Hz, 2H), 1.79 (m, 2H). LCMS-A: rt 4.679 min; m/z 552.3 [M+H]$^+$.

Example 26

Synthesis of 2-(2-(2-(5-methyl-2-((4-(piperidin-4-yloxy)phenyl)amino)pyrimidin-4-yl)ethyl)phenyl)acetamide (26)

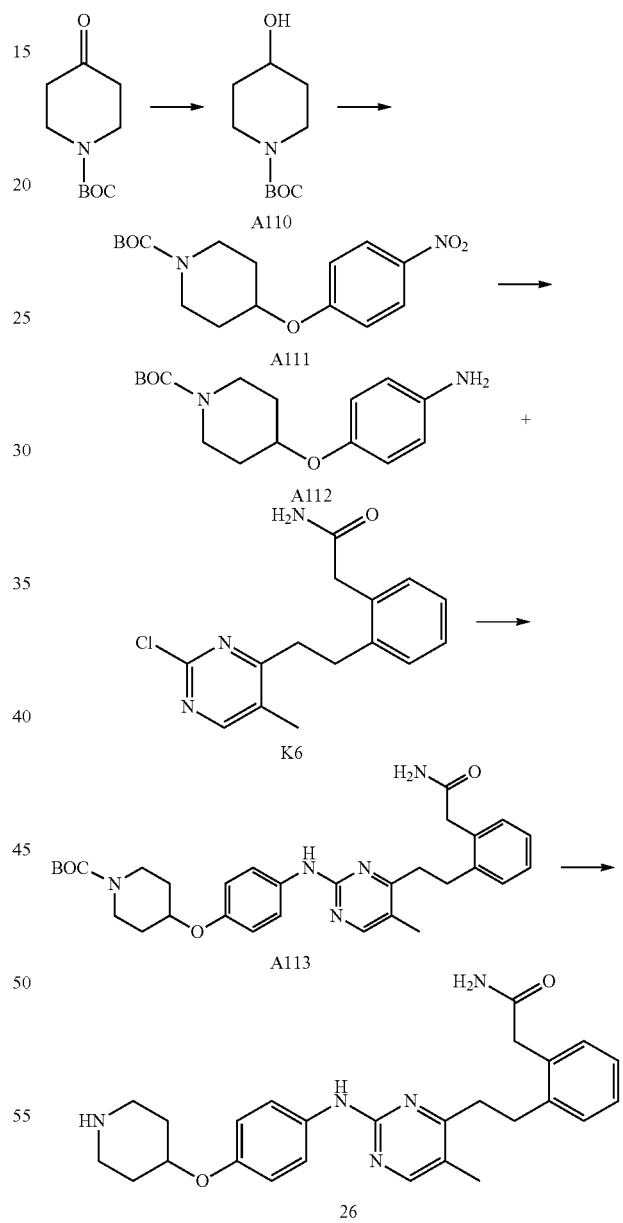

(a) tert-Butyl 4-hydroxypiperidine-1-carboxylate (A110)

Sodium borohydride (0.95 g, 25 mmol) was added to a solution of 1-Boc-4-piperidone (2.50 g, 12.5 mmol) in MeOH (25 mL) at 0° C. The resulting mixture was stirred at 0° C. for 2 hours, then room temperature for 2 hours. The mixture was diluted with water (100 mL) and brine (100 mL) then extracted with EtOAc (2×150 mL). The combined organic extracts were dried (Na$_2$SO$_4$), filtered and concentrated under reduced pressure to give the title compound A110 as a thick colorless oil (2.47 g, 98%); $^1$H NMR (400 MHz, CDCl$_3$) δ 3.91-3.79 (m, 3H), 3.02 (m, 2H), 1.93-1.78 (m, 2H), 1.56 (d, J=4.2 Hz, 1H), 1.52-1.40 (m, 11H).

(b) tert-Butyl 4-(4-nitrophenoxy)piperidine-1-carboxylate (A111)

4-Fluoro-nitrobenzene (0.728 mL, 6.96 mmol) was added to a solution of tert-butyl 4-hydroxypiperidine-1-carboxylate (A110) (1.40 g, 6.96 mmol) and potassium tert-butoxide (1.09 g, 9.74 mmol) in anhydrous DMSO (7.5 mL) and the resulting mixture was stirred for 2 hours at room temperature. Water and EtOAc were added to the mixture and the phases were separated. The aqueous phase was extracted with EtOAc, then the combined organic extracts were washed with water, brine and dried over Na$_2$SO$_4$. The volatiles were evaporated under reduced pressure and the residue was adsorbed onto silica gel and purified by column chromatography (SiO$_2$ cartridge, 0-15% EtOAc in cyclohexane) to give the title compound A111 as an oil (2.20 g, 98%); $^1$H NMR (300 MHz, CDCl$_3$); δ 8.09 (d, J=9.4 Hz, 2H), 6.91 (d, J=9.3 Hz, 2H), 4.58 (m, 1H), 3.65 (m, 2H), 3.33 (m, 2H), 1.92 (m, 2H), 1.72 (m, 2H), 1.41 (s, 9H). LCMS-B: rt 8.22 min; m/z 323.3 [M+H]$^+$.

(c) tert-Butyl 4-(4-aminophenoxy)piperidine-1-carboxylate (A112)

Pd/C (10%; 510 mg) was added to a solution of tert-butyl 4-(4-nitrophenoxy)piperidine-1-carboxylate (A111) (2.21 g, 6.86 mmol) in methanol (30 mL) and the resulting mixture was stirred under a hydrogen atmosphere overnight. The mixture was filtered through Celite and the filtrate concentrated under reduced pressure to afford the title compound A112 (1.13 g, 56%); $^1$H NMR (300 MHz, CDCl$_3$); δ 6.68 (d, J=8.8 Hz, 2H), 6.52 (d, J=8.7 Hz, 2H), 4.17 (m, 1H), 3.63 (m, 4H), 3.20 (m, 2H), 1.78 (m, 2H), 1.61 (m, 2H), 1.40 (s, 9H). LCMS-B: rt 5.05 min; m/z 293.2 [M+H]$^+$.

(d) tert-Butyl 4-(4-((4-(2-(2-amino-2-oxoethyl)phenethyl)-5-methylpyrimidin-2-yl)amino)phenoxy)piperidine-1-carboxylate (A113)

A suspension of 2-(2-(2-(2-chloro-5-methylpyrimidin-4-yl)ethyl)phenyl)acetamide (K6) (0.150 g, 0.518 mmol), tert-butyl 4-(4-aminophenoxy)piperidine-1-carboxylate (A112) (0.182 g, 0.621 mmol), Pd(OAc)$_2$ (2.3 mg, 0.010 mmol), Cs$_2$CO$_3$ (0.506 g, 1.55 mmol) and Xantphos (12 mg, 0.021 mmol) in 1,4-dioxane (2 mL) was heated under microwave irradiation at 100° C. for 45 minutes. Water (20 mL) and EtOAc (20 mL) were added and the resulting suspension sonicated for 1 minute and then filtered through Celite. The resulting mixture was extracted with EtOAc (×2) and the combined organic extracts were washed with brine, dried (MgSO$_4$), filtered and evaporated in vacuo. The residue was purified using silica gel column chromatography (Combi-Flash Rf, 12 g SiO$_2$ cartridge, 0-10% MeOH in DCM) to give the title compound A113 as a light pink colored foam (50 mg, 18%); $^1$H NMR (300 MHz, d$_4$-MeOH) δ 8.04 (s, 1H), 7.52 (d, J=8.9 Hz, 2H), 7.18-7.27 (m, 5H), 6.92 (d, J=9.0 Hz, 2H), 4.47-4.52 (m, 1H), 4.10-4.13 (m, 2H), 3.67-3.77 (m, 2H), 3.65 (s, 3H), 3.37 (m, 2H), 3.09-3.15 (m, 2H), 2.93-2.98 (m, 2H), 1.91-2.03 (m, 2H), 1.64-1.78 (m, 2H), 1.51 (s, 9H). LCMS-B: rt 7.302 min; m/z 546 [M+H]$^+$.

(e) 2-(2-(2-(5-methyl-2-((4-(piperidin-4-yloxy)phenyl)amino)pyrimidin-4-yl)ethyl)phenyl)acetamide (26)

TFA (0.5 mL) was added to a cooled (water/ice bath 6° C.) solution of tert-butyl 4-(4-((4-(2-(2-amino-2-oxoethyl)phenethyl)-5-methylpyrimidin-2-yl)amino)phenoxy)piperidine-1-carboxylate (A113) (0.050 g, 0.092 mmol) in DCM (2 mL) and the resulting mixture was stirred at room temperature for 4 hours. The volatiles were removed in vacuo then 2 M aqueous K$_2$CO$_3$ solution (10 mL) and water (10 mL) were added to the residue. The resulting suspension was sonicated for 1 minute, filtered and the filter cake dried to give the title compound 26 as a light pink solid (0.034 g, 83%); $^1$H NMR (300 MHz, d$_6$-DMSO) δ 9.17 (s, 1H), 8.12 (s, 1H), 7.62 (d, J=8.9 Hz, 2H), 7.43 (s, 1H), 7.12-7.27 (m, 4H), 6.93 (s, 1H), 6.84 (d, J=8.9 Hz, 2H), 4.23-4.29 (m, 1H), 3.49 (s, 2H), 3.30-3.34 (m, 2H), 2.83-3.05 (m, 7H), 2.05 (s, 3H), 1.86-1.90 (m, 2H), 1.39-1.42 (m, 2H). LCMS-B: rt 4.717 min; m/z 446 [M+H]$^+$.

Example 27

Synthesis of 2-(2-(2-(2-((4-(aminomethyl)phenyl)amino)-5-methylpyrimidin-4-yl)ethyl)phenyl)acetamide (27)

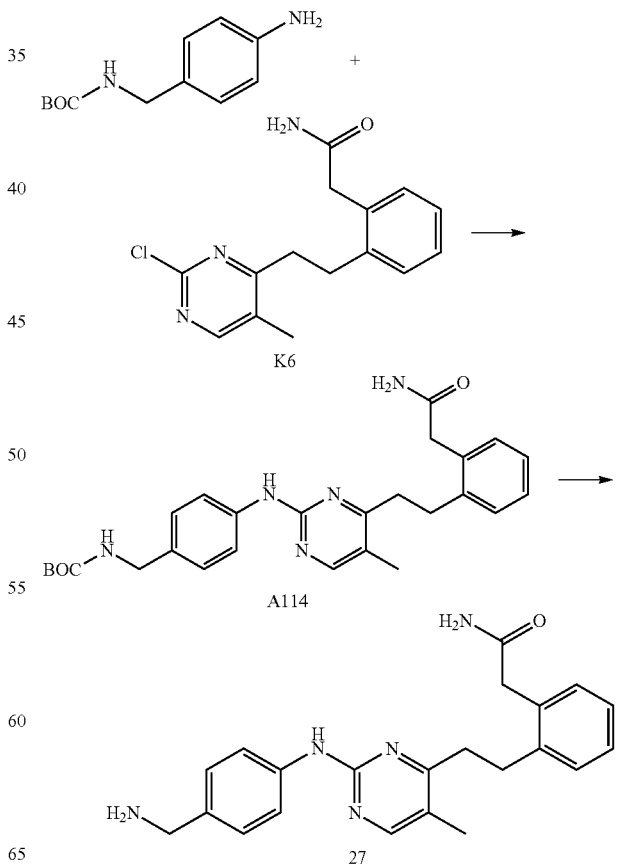

(a) tert-Butyl 4-((4-(2-(2-amino-2-oxoethyl)phenethyl)-5-methylpyrimidin-2-yl)amino)benzylcarbamate (A114)

A suspension of 2-(2-(2-(2-chloro-5-methylpyrimidin-4-yl)ethyl)phenyl)acetamide (K6) (0.150 g, 0.518 mmol), 4-(N-Boc-aminomethyl)aniline (0.145 g, 0.621 mmol), Pd(OAc)$_2$ (2.3 mg, 0.010 mmol), Cs$_2$CO$_3$ (0.506 g, 1.55 mmol) and Xantphos (12 mg, 0.021 mmol) in 1,4-dioxane (2 mL) was heated under microwave irradiation at 100° C. for 1.5 hours. The resulting mixture was filtered through a plug of silica gel, washing with 10% MeOH in DCM. The volatiles were removed in vacuo and the residue was adsorbed onto silica gel and the product purified using silica gel column chromatography (CombiFlash Rf, 12 g SiO$_2$ cartridge, 0-5% MeOH in DCM) to give the title compound A114 as a white solid (0.043 g, 17%); $^1$H NMR (300 MHz, d$_4$-MeOH) δ 8.07 (brs, 1H), 7.59 (brs, 2H), 7.19 (m, 6H), 4.19 (brs, 2H), 3.64 (brs, 2H), 3.11 (brs, 2H), 2.95-2.98 (m, 2H), 2.08 (brs, 3H), 1.46 (brs, 9H). LCMS-B: rt 6.636 min; m/z 476 [M+H]$^+$.

(b) 2-(2-(2-(2-((4-(Aminomethyl)phenyl)amino)-5-methylpyrimidin-4-yl)ethyl)phenyl)acetamide (27)

TFA (1 mL) was added to a solution of tert-butyl 4-((4-(2-(2-amino-2-oxoethyl)phenethyl)-5-methylpyrimidin-2-yl)amino)benzylcarbamate (A114) (0.043 g, 0.090 mmol) in DCM (3 mL) and the resulting solution stirred at room temperature for 4 hours. The volatiles were removed in vacuo then 2 M aqueous K$_2$CO$_3$ (5 mL) and water (15 mL) were added to the residue. The resulting suspension was sonicated for 1 minute, filtered and the filter cake dried to give the title compound 27 as a light tan solid (0.028 g, 82%); $^1$H NMR (300 MHz, d$_6$-DMSO) δ 9.30 (s, 1H), 8.16 (s, 1H), 7.70 (d, J=8.5 Hz, 2H), 7.43 (s, 1H), 7.12-7.27 (m, 6H), 6.93 (s, 1H), 3.64 (s, 2H), 3.49 (s, 2H), 3.34 (brs, 2H), 3.02-3.07 (m, 2H), 2.85-2.90 (m, 2H), 2.06 (s, 3H). LCMS-B: rt 4.666 min; m/z 376 [M+H]$^+$.

Example 28

Synthesis of 2-(2-(2-(5-methyl-2-((1-methyl-1H-pyrazol-4-yl)amino)pyrimidin-4-yl)ethyl)phenyl)acetamide (28)

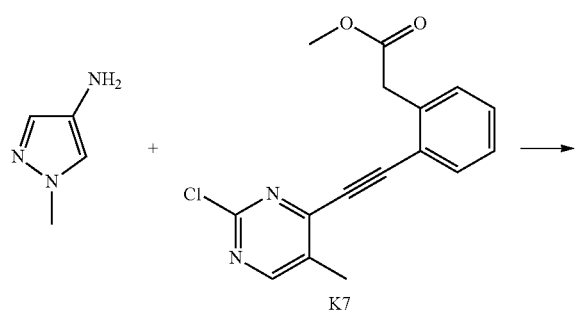

(a) Methyl 2-(2-((5-methyl-2-((1-methyl-1H-pyrazol-4-yl)amino)pyrimidin-4-yl)ethynyl)phenyl)acetate (A115)

To a solution of methyl 2-(2-((2-chloro-5-methylpyrimidin-4-yl)ethynyl)phenyl)acetate (K7) (0.200 g, 0.665 mmol) in 1,4-dioxane (8 mL) was added 1-methyl-1H-pyrazol-4-amine (0.065 g, 0.665 mmol), Cs$_2$CO$_3$ (0.867 g, 2.66 mmol), Pd$_2$(dba)$_3$ (0.061 g, 0.067 mmol) and Xantphos (0.115 g, 0.200 mmol). The resulting mixture was degassed with nitrogen for 5 minutes before heating under microwave irradiation for 30 minutes at 120° C. The mixture was diluted with EtOAc (100 mL), washed with water (2×25 mL), brine (25 mL), dried (Na$_2$SO$_4$) and concentrated under reduced pressure. The resulting brown oil was purified by silica gel column chromatography (Biotage Isolera, 40 g SiO$_2$ cartridge, 0-100% EtOAc in hexanes) to give the title compound A115 as a yellow solid (0.128 g, 53%); $^1$H NMR (400 MHz, d$_6$-DMSO) δ 9.47 (s, 1H), 8.39 (s, 1H), 7.89 (s, 1H), 7.67 (d, J=7.4 Hz, 1H) 7.51-7.44 (m, 3H), 7.43-7.37 (m, 1H), 3.98 (s, 2H), 3.81 (s, 3H), 3.61 (s, 3H), 2.25 (s, 3H). LCMS-A: rt 5.856 min; m/z 362 [M+H]$^+$.

(b) Methyl 2-(2-(2-(5-methyl-2-((1-methyl-1H-pyrazol-4-yl)amino)pyrimidin-4-yl)ethyl)phenyl)acetate (A116)

10% Pd/C (53% water; 0.020 g) was added to a solution of methyl 2-(2-((5-methyl-2-((1-methyl-1H-pyrazol-4-yl)amino)pyrimidin-4-ylethynyl)phenyl)acetate (A115) (0.115 g, 0.318 mmol) in DMF (5 mL) and Et$_3$N (0.5 mL) and the resulting suspension placed under a hydrogen atmosphere and stirred at room temperature for 18 hours. The mixture was filtered through Celite, washing with EtOAc (250 mL). The combined filtrates were washed with water (100 mL) then brine (100 mL) and the washing repeated 3 times. The organic layer was dried (Na$_2$SO$_4$), filtered and concentrated under reduced pressure and the resulting oil purified by silica gel column chromatography (Biotage Isolera, 24 g SiO$_2$ cartridge, 0-100% EtOAc in hexanes) to give the title compound A116 as a yellow solid (0.097 g, 83%); $^1$H NMR (400 MHz, CDCl$_3$) δ 8.07 (s, 1H), 7.83 (s, 1H), 7.46 (s, 1H), 7.25-7.17 (m, 4H), 6.75 (s, 1H), 3.89 (s, 3H), 3.72 (s, 2H), 3.67 (s, 3H), 3.09 (dd, J=9.5, 6.3 Hz, 2H), 2.91 (dd, J=9.5, 6.4 Hz, 2H), 2.07 (s, 3H). LCMS-A: rt 5.160 min; m/z 366 [M+H]$^+$.

(c) 2-(2-(2-(5-Methyl-2-((1-methyl-1H-pyrazol-4-yl)amino)pyrimidin-4-yl)ethyl)phenyl)acetic acid (A117)

LiOH.H$_2$O (0.534 g, 12.7 mmol) was added to a solution of methyl 2-(2-(2-(5-methyl-2-((1-methyl-1H-pyrazol-4-yl)amino)pyrimidin-4-yl)ethyl)phenyl)acetate (A116) (0.093 g, 0.25 mmol) in H$_2$O (1 mL) and THF (10 mL) and the resulting mixture heated at 40° C. for 18 hours. The volatiles were removed in vacuo and the residue was diluted with EtOAc (100 mL), washed with aqueous 2 M HCl (50 mL), water (100 mL), brine (50 mL) and dried over MgSO$_4$. The combined aqueous layers were additionally extracted with chloroform/isopropanol (4:1, 2×50 mL). The organic extracts were then combined, dried (Na$_2$SO$_4$), filtered and concentrated under reduced pressure to give the title compound A117 as a yellow solid (0.067 g, 75%); LCMS-A: rt 4.718 min; m/z 352 [M+H]$^+$.

(d) 2-(2-(2-(5-methyl-2-((1-methyl-1H-pyrazol-4-yl)-amino)pyrimidin-4-yl)ethyl)phenyl)acetamide (28)

HOBt (0.074 g, 0.55 mmol), EDCl.HCl (0.117 g, 0.610 mmol) and DIPEA (0.16 mL, 0.94 mmol) were added to a solution of 2-(2-(2-(5-methyl-2-((1-methyl-1H-pyrazol-4-yl)amino)pyrimidin-4-yl)ethyl)phenyl)acetic acid (A117) (0.066 g, 0.19 mmol) in dry DMF (5 mL) under an atmosphere of nitrogen. After 10 minutes ammonium carbonate (0.180 g, 1.88 mmol) was added in one portion and the resulting mixture stirred for 18 hours at room temperature. The volatiles were removed in vacuo and the residue partitioned between EtOAc (50 mL) and aqueous saturated NaHCO$_3$ (50 mL). The aqueous layer was extracted with EtOAc (2×25 mL). The combined organic layers were washed with brine (25 mL) and dried over Na$_2$SO$_4$. The solvent was removed in vacuo and the residue purified by silica gel column chromatography (Biotage Isolera, 24 g SiO$_2$ cartridge, 0-100% EtOAc in petroleum benzine 40-60° C. followed by 0-30% MeOH in EtOAc) to give the title compound 28 as a yellow solid (0.040 g, 61%); $^1$H NMR (400 MHz, d$_6$-DMSO) δ 9.18 (s, 1H), 8.10 (s, 1H), 7.86 (s, 1H), 7.43 (s, 2H), 7.28-7.10 (m, 4H), 6.93 (s, 1H), 3.78 (s, 3H), 3.49 (s, 2H), 3.07-2.98 (m, 2H), 2.90-2.81 (m, 2H), 2.04 (s, 3H). LCMS-A: rt 4.464 min; m/z 351 [M+H]$^+$.

Example 29

Synthesis of methyl 1-(4-(4-(2-(2-amino-2-oxoethyl)phenethyl)-5-methylpyrimidin-2-ylamino)phenyl)cyclobutylcarbamate (29)

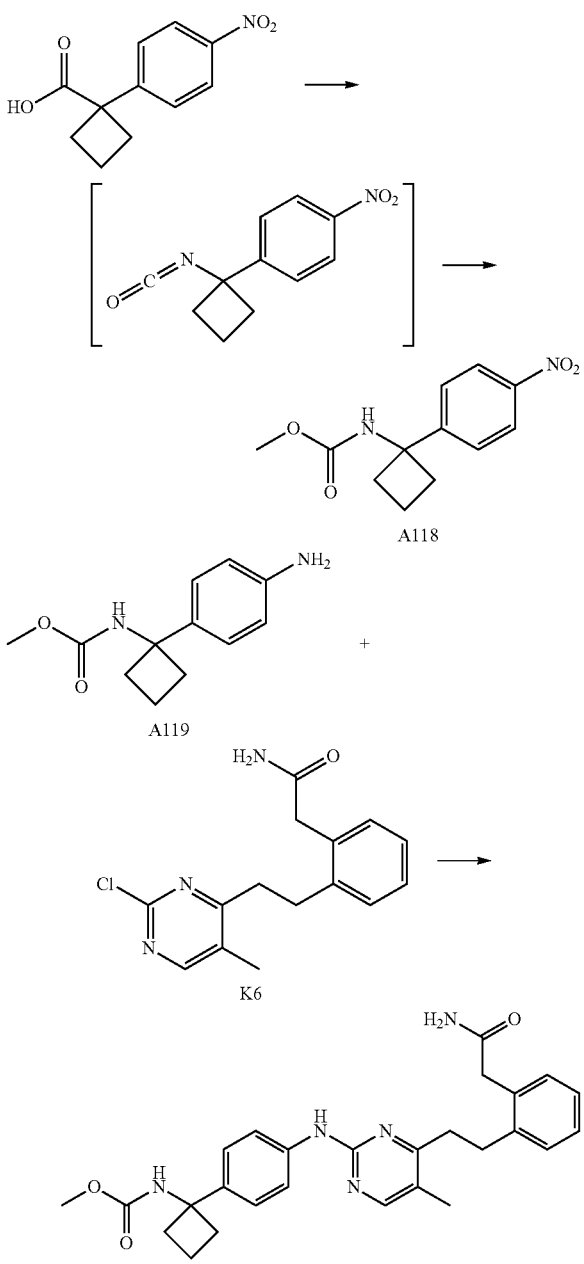

(a) Methyl 1-(4-nitrophenyl)cyclobutylcarbamate (A118)

A drop of DMF and oxalyl chloride (0.283 mL, 3.30 mmol) was added to a stirred solution of 1-(4-nitrophenyl)cyclobutanecarboxylic acid (503 mg, 2.27 mmol) in DCM (7 mL) under a nitrogen atmosphere and the resulting mixture was stirred for 25 minutes at room temperature. The volatiles were removed in vacuo and the residue was dissolved in acetone (4.50 mL). A solution of sodium azide (400 mg, 5.23 mmol) in water (4.50 mL) was added with the temperature maintained below 0° C. After stirring for 30 minutes, the mixture was diluted with chloroform and washed with cold water and saturated aqueous NaCl. The organics were dried with $Na_2SO_4$ and concentrated carefully. Toluene (10.0 mL) was added and the resulting solution was heated at 80° C. for 1 hour. MeOH (10 mL) was added and the resulting mixture heated at 60° C. for 1.5 hours under a nitrogen atmosphere. The volatiles were evaporated under reduced pressure then the residue adsorbed on silica gel and purified using silica gel column chromatography (CombiFlash Rf, $SiO_2$ cartridge, 0-20% EtOAc in cyclohexane) to give the title compound A118 (404 mg, 71%); $^1$H NMR (300 MHz, CDCl$_3$): δ 8.17 (d, J=9.0 Hz, 2H), 7.59 (d, J=8.9 Hz, 2H), 5.74 (br s, 1H), 3.57 (s, 3H), 2.52 (m, 4H), 2.15 (m, 1H), 1.92 (m, 1H); LCMS-B: rt 6.55 min; m/z 251.3 [M+H]$^+$.

(b) Methyl 1-(4-aminophenyl)cyclobutylcarbamate (A119)

A suspension of Pd/C (10%) (120 mg) and methyl 1-(4-nitrophenyl)cyclobutylcarbamate (A118) (404 mg, 1.61 mmol) in MeOH (17.0 mL) was vigorously stirred overnight under a hydrogen atmosphere. The resulting mixture was filtered through Celite then the filtrate concentrated in vacuo. The residue was purified using silica gel column chromatography (CombiFlash Rf, $SiO_2$ cartridge, 0-75% EtOAc in cyclohexane) to give the title compound A119 (237 mg, 67%); $^1$H NMR (300 MHz, CDCl$_3$): δ 7.21 (d, J=8.3 Hz, 2H), 6.63 (d, J=8.5 Hz, 2H), 5.57 (brs, 1H), 3.66 (s, 2H), 3.58 (s, 3H), 2.48 (m, 4H), 2.02 (m, 1H), 1.80 (m, 1H). LCMS-B: rt 2.35 min; m/z 221.2 [M+H]$^+$.

(c) Methyl 1-(4-(4-(2-(2-amino-2-oxoethyl)phenethyl)-5-methylpyrimidin-2-ylamino)phenyl)cyclobutylcarbamate (29)

A suspension of 2-(2-(2-(2-chloro-5-methylpyrimidin-4-yl)ethyl)phenyl)acetamide (K6) (150 mg, 0.518 mmol), Pd(OAc)$_2$ (11.6 mg, 0.052 mmol), Xantphos (45.0 mg, 0.078 mmol), Cs$_2$CO$_3$ (486 mg, 1.49 mmol) and methyl 1-(4-aminophenyl)cyclobutylcarbamate (A119) (125 mg, 0.569 mmol) in 1,4-dioxane (4.0 mL) was heated under microwave irradiation for 10 minutes at 150° C. The resulting mixture was filtered through Celite, and washed with EtOAc. The filtrate was concentrated under reduced pressure and the residue was purified by semi preparative HPLC to give the title compound 29 (86 mg, 35%); $^1$H NMR (300 MHz, CDCl$_3$): δ 8.17 (br s, 1H), 7.56 (m, 2H), 7.42 (m, 2H), 7.28 (4H, obscured by solvent peak), 5.65 (br s, 1H), 5.42 (br s, 1H), 5.30 (br s, 1H), 3.70 (s, 2H), 3.61 (s, 3H), 3.13 (m, 2H), 2.99 (m, 2H), 2.57 (s, 3H), 2.12-1.62 (m, 6H). LCMS-B: rt 6.28 min; m/z 474.2 [M+H]$^+$.

Example 30

Synthesis of 2-(2-(2-(2-((1-(azetidin-3-yl)-1H-pyrazol-4-yl)amino)-5-methylpyrimidin-4-yl)ethyl)phenyl)acetamide (30)

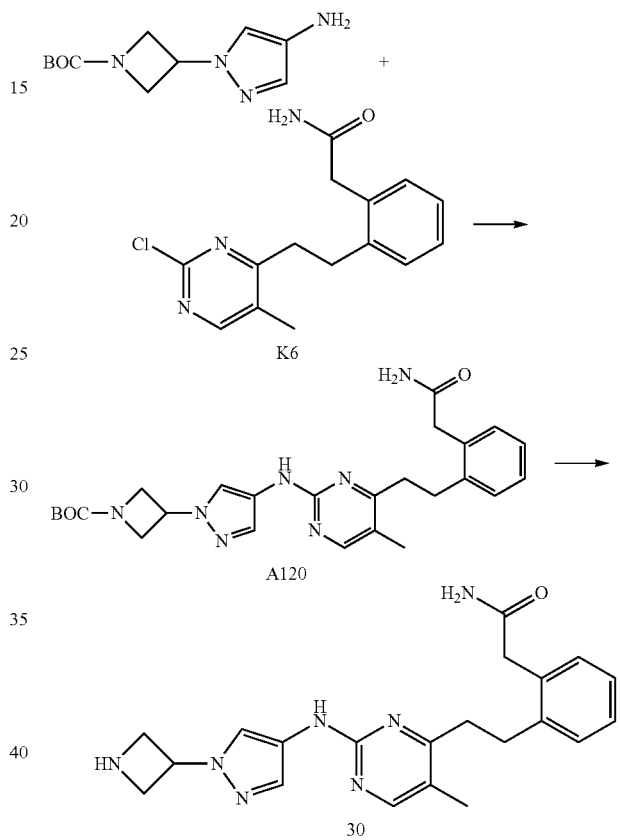

(a) tert-Butyl 3-(4-((4-(2-(2-amino-2-oxoethyl)phenethyl)-5-methylpyrimidin-2-yl)amino)-1H-pyrazol-1-yl)azetidine-1-carboxylate (A120)

A suspension of 2-(2-(2-(2-chloro-5-methylpyrimidin-4-yl)ethyl)phenyl)acetamide (K6) (0.150 g, 0.518 mmol), 4-amino-1-(1-Boc-azetidin-3-yl)-1H-pyrazole (0.195 g, 0.777 mmol), Pd(OAc)$_2$ (2.3 mg, 0.010 mmol), Cs$_2$CO$_3$ (0.506 g, 1.55 mmol) and Xantphos (11.9 mg, 0.021 mmol) in 1,4-dioxane (2 mL) was heated under microwave irradiation at 100° C. for 1.5 hours. 4-Amino-1-(1-Boc-azetidin-3-yl)-1H-pyrazole (65.0 mg, 0.259 mmol) was added and the mixture was heated for a further 1 hour at 100° C. The resulting mixture was adsorbed onto silica gel and purified using column chromatography (CombiFlash Rf, 12 g SiO$_2$ cartridge, 0-5% MeOH in DCM) to give the title compound A120 as a light pink colored foam (0.050 g, 19%); $^1$H NMR (300 MHz, d$_4$-MeOH) δ 8.06 (d, J=8.8 Hz, 2H), 7.66 (s, 1H), 7.16-7.27 (m, 4H), 5.12-5.21 (m, 1H), 4.39 (t, J=8.7 Hz, 2H), 4.25-4.30 (m, 2H), 3.65 (s, 2H), 3.32 (s, 1H), 3.10-3.16 (m, 2H), 2.95-3.00 (m, 2H), 2.10 (s, 3H), 1.48 (s, 9H). LCMS-B: rt 6.184 min; m/z 492 [M+H]$^+$.

(b) 2-(2-(2-(2-((1-(Azetidin-3-yl)-1H-pyrazol-4-yl)-amino)-5-methylpyrimidin-4-yl)ethyl)phenyl)acetamide (30)

TFA (1 mL) was added to a solution of tert-butyl 3-(4-((4-(2-(2-amino-2-oxoethyl)phenethyl)-5-methylpyrimidin-2-yl)amino)-1H-pyrazol-1-yl)azetidine-1-carboxylate (A120) (0.050 g, 0.102 mmol) in DCM (3 mL) and the resulting mixture stirred at room temperature for 3 hours. The volatiles were removed under reduced pressure then 2 M aqueous $K_2CO_3$ (5 mL) and water (15 mL) were added to the residue. The resulting aqueous solution was extracted with EtOAc (3×15 mL) then the combined organic extracts were dried ($MgSO_4$), filtered, evaporated in vacuo and adsorbed onto silica gel. The product was purified using column chromatography (CombiFlash Rf, 4 g $SiO_2$ Cartridge, 5-50% MeOH in DCM) to give the title compound 30 as a yellow oil (0.6 mg, 1.5%); $^1$H NMR (300 MHz, $d_4$-MeOH) δ 8.08 (d, J=2.0 Hz, 2H), 7.66 (s, 1H), 7.18-7.26 (m, 4H), 5.19-5.26 (m, 1H), 4.67 (t, J=9.0 Hz, 1H), 4.54 (dd, J=9.4, 5.3 Hz, 1H), 4.56 (t, J=9.8 Hz, 1H), 4.30 (dd, J=10.4, 5.5 Hz, 1H), 3.65 (s, 2H), 3.14 (t, J=2.9 Hz, 2H), 2.98-3.01 (m, 2H), 1.93 (s, 3H). LCMS-B: rt 4.426 min; m/z 392 [M+H]$^+$.

Example 31

Synthesis of 2-(2-(2-(2-(4-(3-aminooxetan-3-yl)phenylamino)-5-methylpyrimidin-4-yl)ethyl)phenyl)acetamide (31)

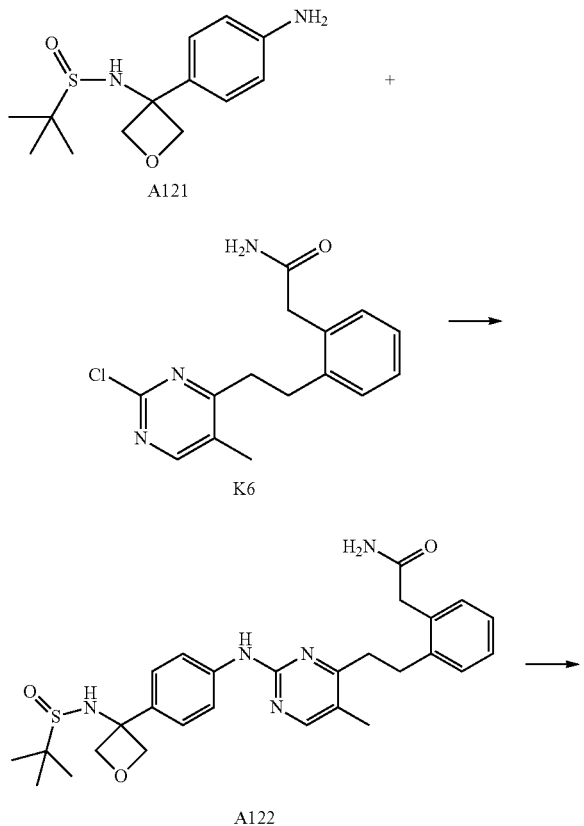

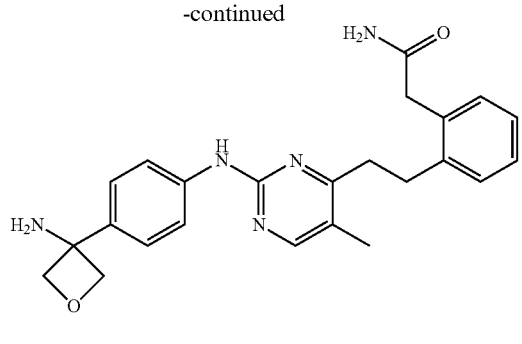

(a) N-(3-(4-Aminophenyl)oxetan-3-yl)-2-methylpropane-2-sulfinamide (A121)

Compound prepared using the procedure described in US2011/0172203 A1 (paragraphs 2413 to 2417, which are hereby incorporated by reference)

(b) 2-(2-(2-(2-(4-(3-(1,1-Dimethylethylsulfinamido)oxetan-3-yl)phenylamino)-5-methylpyrimidin-4-yl)ethyl)phenyl)acetamide (A122)

A suspension of 2-(2-(2-(2-chloro-5-methylpyrimidin-4-yl)ethyl)phenyl)acetamide (K6) (200 mg, 0.690 mmol), Pd(OAc)$_2$(16 mg, 0.069 mmol), Xantphos (59.9 mg, 0.104 mmol), $Cs_2CO_3$ (648 mg, 1.99 mmol) and N-(3-(4-aminophenyl)oxetan-3-yl)-2-methylpropane-2-sulfinamide (A121) (204 mg, 0.759 mmol) in 1,4-dioxane (1.73 mL) was heated under microwave irradiation for 10 minutes at 150° C. under nitrogen. The resulting mixture was filtered through Celite, washing with EtOAc. The volatiles were removed in vacuo and the residue was purified by silica gel column chromatography (CombiFlash Rf, $SiO_2$ cartridge, 0-30% MeOH in DCM) to give the title compound A122 (102 mg, 28%); $^1$H NMR (300 MHz, $d_4$-MeOH) δ 8.07 (s, 1H), 7.74 (d, J=8.6 Hz, 2H), 7.35 (d, J=8.7 Hz, 2H), 7.19 (m, 4H), 5.17 (d, J=6.6 Hz, 1H), 5.07 (d, J=6.5 Hz, 1H), 5.03 (d, J=6.7 Hz, 1H), 4.93 (d, J=6.4 Hz, 1H), 3.64 (s, 2H), 3.12 (m, 2H), 2.95 (m, 2H), 2.07 (s, 3H), 1.27 (s, 9H). LCMS-B: rt 5.80 min; 522.2 m/z [M+H]$^+$.

(c) 2-(2-(2-(2-(4-(3-Aminooxetan-3-yl)phenylamino)-5-methylpyrimidin-4-yl)ethyl)phenyl)acetamide (31)

TFA (0.5 mL) was added to a solution of 2-(2-(2-(2-(4-(3-(1,1-dimethylethylsulfinamido)oxetan-3-yl)phenylamino)-5-methylpyrimidin-4-yl)ethyl)phenyl)acetamide (A122) (30 mg, 0.058 mmol) in DCM (3.0 mL) under a nitrogen atmosphere and the resulting mixture stirred at room temperature for 30 minutes, then at 35° C. overnight. The volatiles were evaporated under reduced pressure, keeping the temperature below 30° C. The resulting oil was purified by semi preparative HPLC, to give the title compound 31 (5.0 mg, 21%); $^1$H NMR (300 MHz, $d_4$-MeOH) δ 8.24 (br s, 1H), 8.15 (s, 1H), 7.85 (d, J=8.8 Hz, 2H), 7.38 (d, J=8.8 Hz, 2H), 7.22 (m, 4H), 5.13 (d, J=7.7 Hz, 2H), 4.97 (d, J=7.7 Hz, 2H), 3.67 (s, 2H), 3.16 (m, 2H), 3.00 (m, 2H), 2.13 (s, 3H). LCMS: rt 4.72 min; m/z 418.2 [M+H]+.

Example 32

Synthesis of 2-(2-(2-(2-((4-(azetidin-3-yl)phenyl)amino)-5-methylpyrimidin-4-yl)ethyl)phenyl)acetamide (32)

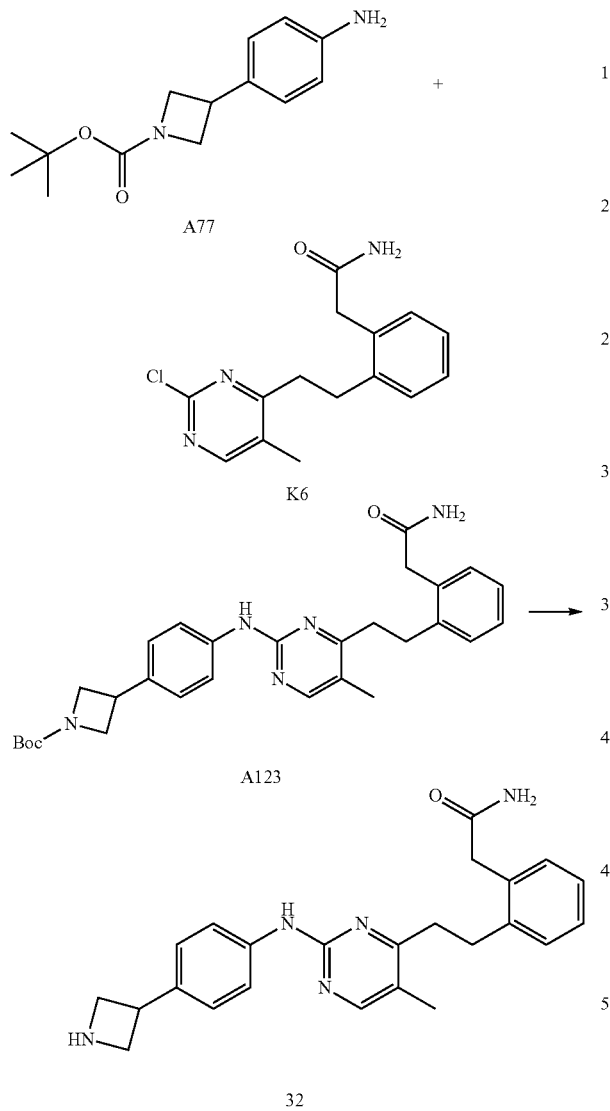

(a) tert-Butyl 3-(4-((4-(2-(2-amino-2-oxoethyl)phenethyl)-5-methylpyrimidin-2-yl)amino)phenyl)azetidine-1-carboxylate (A123)

A suspension of 2-(2-(2-(2-chloro-5-methylpyrimidin-4-yl)ethyl)phenyl)acetamide (K6) (0.150 g, 0.518 mmol), tert-butyl 3-(4-aminophenyl)azetidine-1-carboxylate (A77) (0.141 g, 0.569 mmol), Pd(OAc)$_2$ (2.3 mg, 0.010 mmol), Cs$_2$CO$_3$ (0.506 g, 1.55 mmol) and Xantphos (11.9 mg, 0.021 mmol) in 1,4-dioxane (2 mL) was heated under microwave irradiation at 100° C. for 1.5 hours. The resulting mixture was dry loaded onto silica gel and purified using silica gel column chromatography (CombiFlash Rf, 12 g SiO$_2$ Cartridge, 0-5% MeOH in DCM) to give the title compound A123 as a light orange foam (0.087 g, 33%); $^1$H NMR (300 MHz, CDCl$_3$) δ 8.12 (s, 1H), 7.59 (d, J=8.5 Hz, 2H), 7.53 (s, 1H), 7.26-7.28 (m, 6H), 5.59 (brs, 2H), 4.32 (t, J=8.7 Hz, 2H), 3.97 (dd, J=6.0, 8.4 Hz, 2H), 3.70-3.76 (m, 3H), 3.08-3.13 (m, 2H), 2.90-2.98 (m, 2H), 2.13 (s, 3H), 1.48 (s, 9H). LCMS-B: rt 7.208 min; m/z 502 [M+H]+.

(b) 2-(2-(2-(2-((4-(Azetidin-3-yl)phenyl)amino)-5-methylpyrimidin-4-yl)ethyl)phenyl)acetamide (32)

TFA (1 mL) was added to a solution of tert-butyl 3-(4-((4-(2-(2-amino-2-oxoethyl)phenethyl)-5-methylpyrimidin-2-yl)amino)phenyl)azetidine-1-carboxylate (A123) (0.087 g, 0.17 mmol) in DCM (3 mL) and the resulting mixture stirred at room temperature for 3 hours. The volatiles were removed in vacuo then 2 M aqueous K$_2$CO$_3$ solution (5 mL) and water (15 mL) were added to the residue. The resulting suspension was sonicated for 1 minute, filtered and the filter cake dried. The resulting residue was purified by semi preparative HPLC to give the title compound 32 as a light tan solid (7.6 mg, 10%); $^1$H NMR (300 MHz, d$_4$-MeOH) δ 8.12 (s, 1H), 7.74 (d, J=8.6 Hz, 2H), 7.33 (d, J=8.6 Hz, 2H), 7.18-7.28 (m, 4H), 4.31-4.39 (m, 2H), 4.19-4.27 (m, 3H), 3.66 (s, 2H), 3.13-3.18 (m, 2H), 2.96-3.01 (m, 2H), 2.12 (s, 3H). LCMS-B: rt 4.725 min; m/z 402 [M+H]+.

Example 33

Synthesis of 2-(2-(2-(5-Methyl-2-((1-(piperidin-4-yl)-1H-pyrazol-4-yl)amino)pyrimidin-4-yl)ethyl)phenyl)acetamide (33)

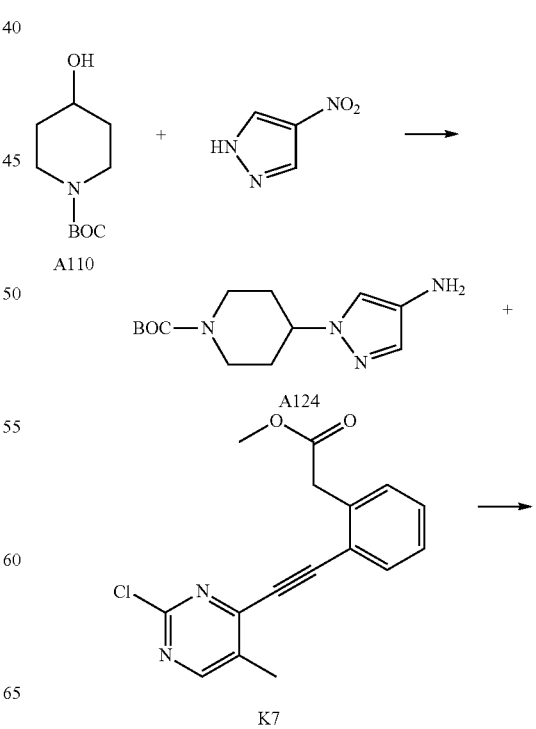

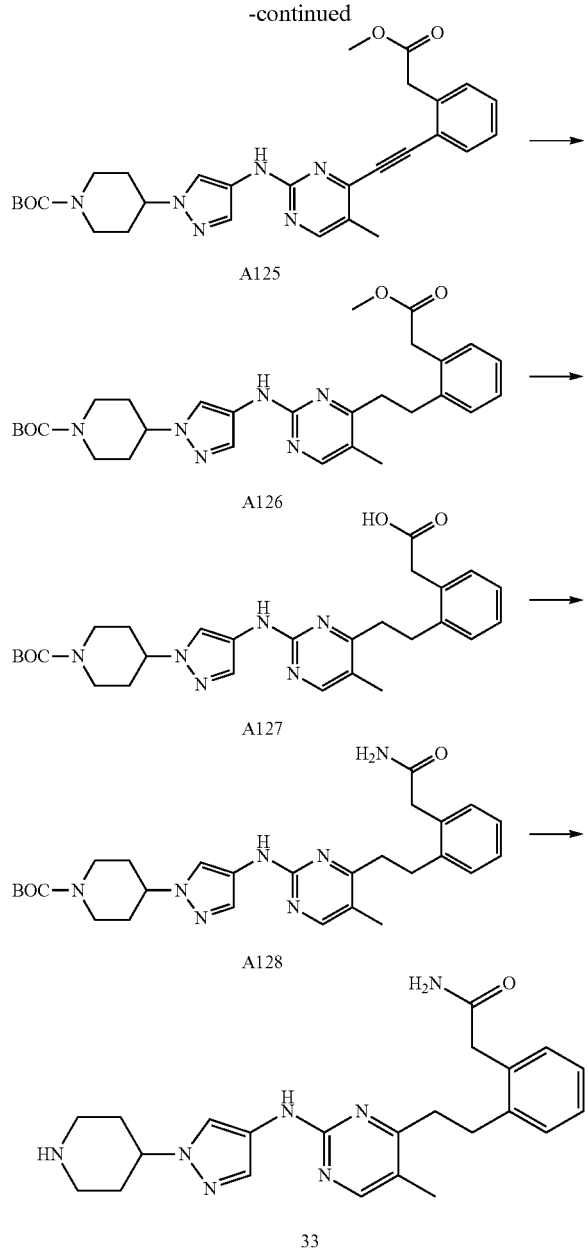

tert-Butyl 4-(4-amino-1H-pyrazol-1-yl)piperidine-1-carboxylate (A124)

Diisopropyl azodicarboxylate (3.60 mL, 18.3 mmol) was added dropwise to a solution of tert-butyl 4-hydroxypiperidine-1-carboxylate (A110) (2.45 g, 12.2 mmol), 4-nitro-1H-pyrazole (1.38 g, 12.2 mmol) and PPh$_3$ (4.79 g, 18.3 mmol) in THF (25 mL) at 0° C. The resulting mixture was maintained at this temperature for 10 minutes and then warmed to room temperature at which it was stirred for 6 days. The mixture was diluted with hexanes (80 mL) and EtOAc (20 mL) and stirred for 5 hours at room temperature before filtering, washing the filter cake with hexanes (50 mL) and concentrating the filtrate in vacuo. The resulting oil was purified by silica gel column chromatography (Biotage Isolera, 2×40 g SiO$_2$ cartridges, 0-50% EtOAc in cyclohexane) to give a residue that was dissolved in EtOH (200 mL). 10% Pd/C (53% water; 0.500 g) was added and the resulting suspension stirred under an atmosphere of hydrogen at room temperature for 18 hours. The mixture was filtered through Celite, washing with EtOAc (ca. 100 mL) and then the filtrate was concentrated under reduced pressure. The resulting oil was dissolved in EtOAc (200 mL) and washed with water (2×100 mL) and then aqueous 2 M HCl (100 mL). The acidic layer was basified with aqueous 2 M NaOH to pH 13 and extracted with EtOAc (2×100 mL). The combined organic layers from the basified extraction were washed with brine (50 mL), dried (Na$_2$SO$_4$), filtered and concentrated under reduced pressure to give the title compound A124 as a purple oil (1.39 g, 34%); $^1$H NMR (400 MHz, CDCl$_3$) δ 7.15 (d, J=0.9 Hz, 1H), 7.02 (d, J=0.9 Hz, 1H), 4.20 (s, 2H), 4.11 (m, 1H), 2.95-2.76 (m, 4H), 2.11-2.02 (m, 2H), 1.83 (qd, J=12.3, 4.5 Hz, 2H), 1.46 (s, 9H).

(b) tert-Butyl 4-(4-((4-((2-(2-methoxy-2-oxoethyl)phenyl)ethynyl)-5-methylpyrimidin-2-yl)amino)-1H-pyrazol-1-yl)piperidine-1-carboxylate (A125)

A suspension of methyl 2-(2-((2-chloro-5-methylpyrimidin-4-yl)ethynyl)phenyl)acetate (K7) (0.100 g, 0.333 mmol), tert-butyl 4-(4-amino-1H-pyrazol-1-yl)piperidine-1-carboxylate (A124) (0.089 g, 0.333 mmol), Cs$_2$CO$_3$ (0.433 g, 1.33 mmol), Pd$_2$(dba)$_3$ (0.030 g, 0.033 mmol) and Xantphos (0.058 g, 0.100 mmol) in 1,4-dioxane (6 mL) was degassed with nitrogen for 5 minutes before heating under microwave irradiation for 30 minutes at 120° C. The resulting mixture was diluted with EtOAc (100 mL) and washed with water (2×25 mL), brine (25 mL), dried (Na$_2$SO$_4$) then concentrated under reduced pressure. The resulting brown oil was purified by silica gel column chromatography (Biotage Isolera, 24 g SiO$_2$ cartridge, 0-100% EtOAc in hexanes) to give the title compound A125 as a yellow foam (0.096 g, 54%); $^1$H NMR (400 MHz, CDCl$_3$) δ 8.21 (s, 1H), 7.89 (s, 1H), 7.57 (dd, J=7.6, 1.3 Hz, 1H), 7.44 (s, 1H), 7.36-7.22 (m, 2H), 7.19 (s, 1H), 6.87 (s, 1H), 4.22-4.12 (m, 3H), 3.88 (s, 2H), 3.62 (s, 3H), 2.82 (t, J=11.9 Hz, 2H), 2.26 (s, 3H), 2.11-2.02 (m, 2H), 1.89 (qd, J=12.4, 4.4 Hz, 2H), 1.40 (s, 9H). LCMS-A: rt 6.358 min; m/z 531 [M+H]$^+$.

(c) tert-Butyl 4-(4-((4-(2-(2-methoxy-2-oxoethyl)phenethyl)-5-methylpyrimidin-2-yl)amino)-1H-pyrazol-1-yl)piperidine-1-carboxylate (A126)

A suspension of 10% Pd/C (53% water; 0.020 g) and tert-butyl 4-(4-((4-((2-(2-methoxy-2-oxoethyl)phenyl)ethynyl)-5-methylpyrimidin-2-yl)amino)-1H-pyrazol-1-yl)piperidine-1-carboxylate (A125) (0.092 g, 0.17 mmol) in DMF (5 mL) and Et$_3$N (0.5 mL) was stirred at room temperature for 18 hours under a hydrogen atmosphere. The resulting mixture was filtered through Celite, and the filter cake washed with EtOAc (250 mL). The combined filtrates were washed with water (3×100 mL) and brine (3×100 mL). The organic layer was dried (Na$_2$SO$_4$), filtered and concentrated under reduced pressure. The resulting oil was purified by silica gel column chromatography (Biotage Isolera, 40 g SiO$_2$ cartridge, 0-100% EtOAc in hexanes) to give the title compound A126 as a pale brown oil (80 mg, 86%); $^1$H NMR (400 MHz, CDCl$_3$) δ 8.06 (s, 1H), 7.89 (s, 1H), 7.51 (d, J=0.4 Hz, 1H), 7.25-7.15 (m, 4H), 6.92 (s, 1H), 4.31-4.15 (m, 3H), 3.70 (s, 2H), 3.66 (s, 3H), 3.08 (dd, J=9.4, 6.3 Hz, 2H), 2.90 (dd, J=9.5, 6.3 Hz, 4H), 2.15-2.07 (m, 2H), 2.05 (s, 3H), 2.00-1.85 (m, 2H), 1.46 (s, 9H). LCMS-A: rt 6.195 min; m/z 535.3 [M+H]$^+$.

(d) 2-(2-(2-(2-((1-(1-(tert-Butoxycarbonyl)piperidin-4-yl)-1H-pyrazol-4-yl)amino)-5-methylpyrimidin-4-yl)ethyl)phenyl)acetic acid (A127)

LiOH.H₂O (0.302 g, 7.20 mmol) was added to a solution of tert-butyl 4-(4-((4-(2-(2-methoxy-2-oxoethyl)phenethyl)-5-methylpyrimidin-2-yl)amino)-1H-pyrazol-1-yl)piperidine-1-carboxylate (A126) (0.077 g, 0.14 mmol) in H₂O (1 mL) and THF (10 mL) and the resulting mixture was heated to 40° C. for 18 hours. The volatiles were removed in vacuo and the residue was diluted with EtOAc (100 mL), washed with aqueous 2 M HCl (50 mL), water (100 mL), brine (50 mL) and dried over MgSO₄. The volatiles were removed in vacuo to give the title compound A127 as a pale yellow solid (0.068 g, 91%); LCMS-A: rt 5.366 min; m/z 521 [M+H]⁺.

(e) tert-Butyl 4-(4-((4-(2-(2-amino-2-oxoethyl)phenethyl)-5-methylpyrimidin-2-yl)amino)-1H-pyrazol-1-yl)piperidine-1-carboxylate (A128)

HOBt (0.051 g, 0.379 mmol), EDCl.HCl (0.081 g, 0.42 mmol) and DIPEA (0.11 mL, 0.65 mmol) were added to a solution of 2-(2-(2-(2-((1-(1-(tert-butoxycarbonyl)piperidin-4-yl)-1H-pyrazol-4-yl)amino)-5-methylpyrimidin-4-yl-ethyl)phenyl)acetic acid (A127) (0.068 g, 0.131 mmol) in dry DMF (5 mL) under an atmosphere of nitrogen. After 10 minutes ammonium carbonate (0.126 g, 1.31 mmol) was added in one portion and the resulting mixture stirred for 18 hours at room temperature. Additional HOBt (0.051 g, 0.38 mmol), EDCl.HCl (0.081 g, 0.42 mmol), DIPEA (0.11 mL, 0.65 mmol) and ammonium carbonate (0.126 g, 1.31 mmol) were added to the reaction mixture and the mixture stirred for 12 days at room temperature. The volatiles were removed in vacuo then the residue diluted with EtOAc (50 mL) and washed with saturated aqueous NaHCO₃ (50 mL). The aqueous layer was extracted with EtOAc (2×25 mL). The combined organic layers were washed with brine (25 mL) and dried over Na₂SO₄. The solvent was removed in vacuo to afford a yellow oil that was purified by silica gel column chromatography (Biotage Isolera, 25 g SiO₂ cartridge, 0-100% EtOAc in petroleum benzine 40-60° C. followed by 0-30% MeOH in EtOAc) to give the title compound A127 as an off white solid (0.044 g, 65%); ¹H NMR (400 MHz, CDCl₃) δ 8.05 (s, 1H), 7.85 (s, 1H), 7.50 (d, J=0.5 Hz, 1H), 7.26-7.17 (m, 5H), 5.79 (s, 1H), 5.62 (s, 1H), 4.26-4.19 (m, 3H), 3.65 (s, 2H), 3.07 (dd, J=9.5, 6.2 Hz, 2H), 2.93-2.82 (m, 4H), 2.15-2.08 (m, 2H), 2.04 (s, 3H), 1.91 (qd, J=12.3, 4.3 Hz, 2H), 1.46 (s, 9H). LCMS-A: rt 5.178 min; m/z 520 [M+H]⁺.

(f) 2-(2-(2-(5-methyl-2-((1-(piperidin-4-yl)-1H-pyrazol-4-yl)amino)pyrimidin-4-yl)ethyl)phenyl)acetamide (33)

TFA (0.5 mL) was added to a solution of tert-butyl 4-(4-((4-(2-(2-amino-2-oxoethyl)phenethyl)-5-methylpyrimidin-2-yl)amino)-1H-pyrazol-1-yl)piperidine-1-carboxylate (A128) (0.040 g, 0.077 mmol) in DCM (5 mL) and the resulting mixture stirred for 18 hours at room temperature. The volatiles were evaporated under reduced pressure and the residue partitioned between 2 M NaOH (10 mL) and EtOAc (25 mL). The organic layer was separated and washed with water (25 mL), brine (25 mL), dried (Na₂SO₄) and concentrated under reduced pressure to give the title compound 33 as an off white solid (0.015 g, 49%); ¹H NMR (400 MHz, d₄-MeOH) δ 8.05 (s, 1H), 7.99 (d, J=0.5 Hz, 1H), 7.56 (d, J=0.6 Hz, 1H), 7.27-7.22 (m, 1H), 7.22-7.15 (m, 3H), 4.23 (tt, J=11.7, 4.1 Hz, 1H), 3.64 (s, 2H), 3.23-3.09 (m, 4H), 3.02-2.91 (m, 2H), 2.76 (td, J=12.8, 2.5 Hz, 2H), 2.14-2.05 (m, 5H), 1.98-1.85 (m, 2H). LCMS-A: rt 3.968 min; m/z 420 [M+H]⁺.

Example 34

Synthesis of 2-(2-(2-(2-((4-(1-aminoethyl)phenyl)amino)-5-methylpyrimidin-4-yl)ethyl)phenyl)acetamide (34)

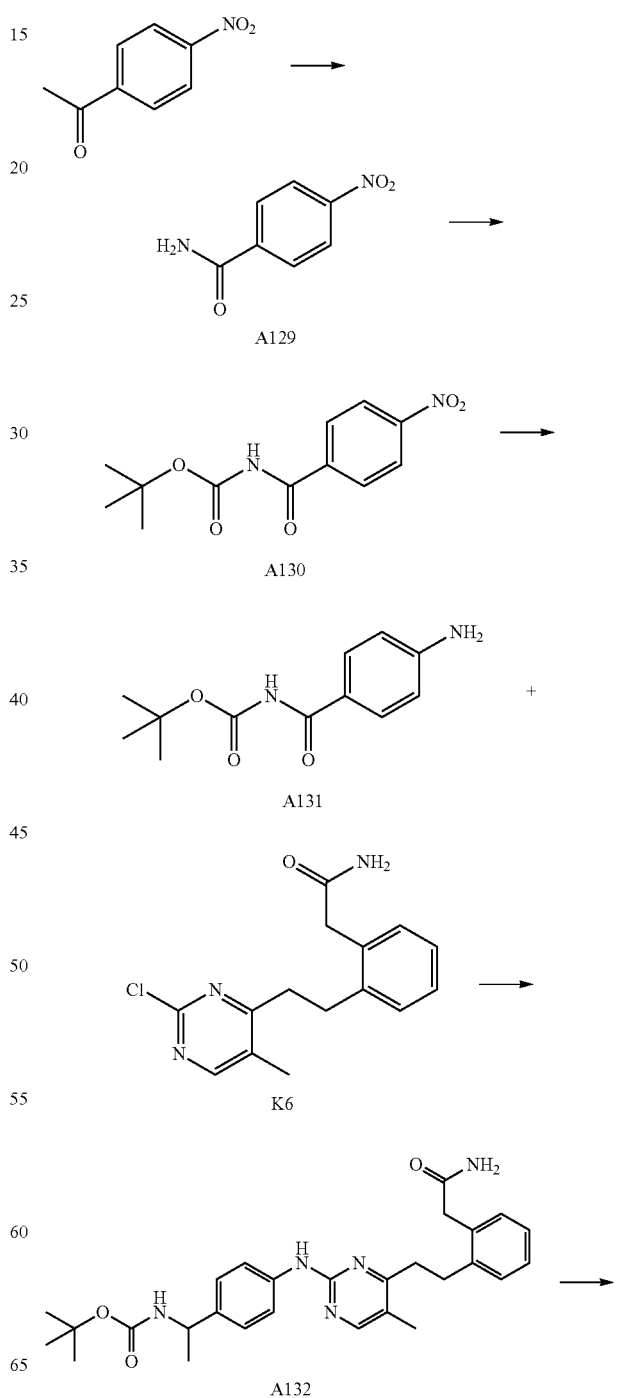

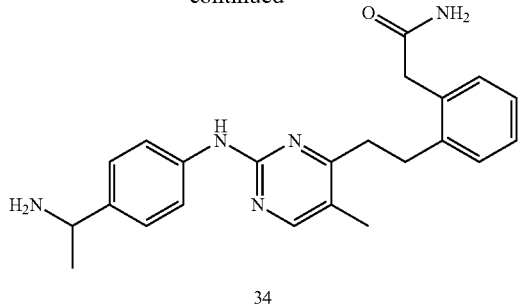

34

(a) 1-(4-Nitrophenyl)ethanamine (A129)

A suspension of 4'-nitroacetophenone (5.00 g, 30.3 mmol) and ammonium acetate (28.4 g, 378 mmol) in MeOH (75 mL) was stirred at room temperature for 20 minutes. Sodium cyanoborohydride (1.38 g, 21.2 mmol) was added and the resulting mixture stirred for 48 hours. Aqueous HCl (6 M, 40 mL) was added and the mixture was filtered. The filtrate was washed with Et$_2$O (3×40 mL) then the aqueous phase was basified to pH 10 using KOH. The basified aqueous layer was extracted with DCM (3×30 mL) and the combined organic phases were dried (MgSO$_4$), filtered and evaporated in vacuo to give the title compound A129 as an amorphous orange solid (3.00 g, 60%); $^1$H NMR (300 MHz, CDCl$_3$) δ 8.22 (d, J=8.6 Hz, 2H), 7.57 (d, J=8.6 Hz, 2H), 4.27-4.33 (m, 1H), 2.20 (brs, 2H), 1.45 (d, J=6.6 Hz, 3H).

(b) tert-Butyl (1-(4-nitrophenylethyl)carbamate (A130)

A solution of di-tert-butyl dicarbonate (3.94 g, 18.1 mmol) in DCM (50 mL) was slowly added over 1 hour by syringe pump to a solution of 1-(4-nitrophenyl)ethanamine (A129) (3.00 g, 18.05 mmol) and Et$_3$N (3.77 mL, 27.1 mmol) in DCM (120 mL). The resulting mixture was then stirred at room temperature for 20 hours. Water (50 mL) was added and the mixture extracted with DCM (×2). The combined organic extracts were washed with water, brine, dried (Na$_2$SO$_4$), filtered and the volatiles removed in vacuo. The residue was purified using silica gel column chromatography (CombiFlash Rf, 120 g SiO$_2$ cartridge, 10-20% EtOAc in cyclohexane) to give the title compound A130 as a white solid (3.78 g, 78%); $^1$H NMR (300 MHz, CDCl$_3$) δ 8.21 (d, J=8.6 Hz, 2H), 7.47 (d, J=8.7 Hz, 2H), 4.87 (s, 2H), 1.38-1.58 (m, 12H).

(c) tert-Butyl (1-(4-aminophenyl)ethyl)carbamate (A131)

A suspension of 10% Pd/C (1.25 g) and tert-butyl (1-(4-nitrophenyl)ethyl)carbamate (A130) (3.78 g, 14.2 mmol) in EtOAc (50 mL) was stirred under a hydrogen atmosphere for 3 hours. The resulting solution was filtered through a pad of Celite, washing with EtOAc, then the filtrate was concentrated in vacuo to give the title compound A131 as a viscous oil (3.01 g, 89%); $^1$H NMR (300 MHz, CDCl$_3$) δ 7.11 (d, J=8.1 Hz, 2H), 6.70 (d, J=8.0 Hz, 2H), 4.70 (brs, 2H), 1.44 (m, 14H). LCMS-B: 4.444 min; m/z 237 [M+H]$^+$.

(d) tert-Butyl (1-(4-((4-(2-(2-amino-2-oxoethyl) phenethyl)-5-methylpyrimidin-2-yl)amino)phenyl) ethyl)carbamate (A132)

A suspension of 2-(2-(2-(2-chloro-5-methylpyrimidin-4-yl)ethyl)phenyl)acetamide (K6) (0.200 g, 0.690 mmol), tert-butyl (1-(4-aminophenyl)ethyl)carbamate (A131) (0.326 g, 1.38 mmol), Pd(OAc)$_2$ (3 mg, 0.01 mmol), Cs$_2$CO$_3$ (0.675 g, 2.07 mmol) and Xantphos (16 mg, 0.028 mmol) in 1,4-dioxane (3 mL) was heated under microwave irradiation at 105° C. for 6 hours. The resulting mixture was filtered through a plug of silica gel, washing with 20% MeOH in K1 DCM and then the volatiles evaporated in vacuo. The residue was purified using silica gel column chromatography (CombiFlash Rf, 12 g SiO$_2$ Cartridge, 5-80% EtOAc in cyclohexane) to give the title compound A132 as a white solid (0.099 g, 29%); LCMS-B: rt 6.832 min; m/z 490 [M+H]$^+$.

A137

(e) 2-(2-(2-(2-((4-(1-Aminoethyl)phenyl)amino)-5-methylpyrimidin-4-yl)ethyl)phenyl)acetamide (34)

TFA (1 mL) was added to a solution of tert-butyl (1-(4-((4-(2-(2-amino-2-oxoethyl)phenethyl)-5-methylpyrimidin-2-yl)amino)phenyl)ethyl)carbamate (A132) (0.099 g, 0.20 mmol) in DCM (5 mL) and the resulting mixture stirred at room temperature for 3 hours. The volatiles were evaporated under reduced pressure then 2 M aqueous K$_2$CO$_3$ solution (10 mL) and water (15 mL) were added to the residue. The resulting suspension was sonicated for 1 minute, filtered and the filter cake dried to give the title compound 34 as a light tan solid (77 mg, 97%); $^1$H NMR (300 MHz, d$_6$-DMSO) δ 9.26 (s, 1H), 8.15 (s, 1H), 7.67 (d, J=8.6 Hz, 2H), 7.42 (s, 1H), 7.23 (d, J=8.6 Hz, 2H), 7.14-7.23 (m, 4H), 6.92 (s, 1H), 3.92 (d, J=6.4 Hz, 1H), 3.50 (s, 2H), 3.32 (brs, 2H), 3.02-3.07 (m, 2H), 2.88-2.90 (m, 2H), 2.06 (s, 3H), 1.23 (d, J=6.5 Hz, 3H). LCMS-B: rt 4.691 min; m/z 390 [M+H]$^+$.

Example 35

2-(2-(2-(2-((1-(piperidin-4-yl)-1H-pyrazol-4-yl) amino)-5-(trifluoromethyl)pyrimidin-4-yl)ethyl)phenyl)acetamide

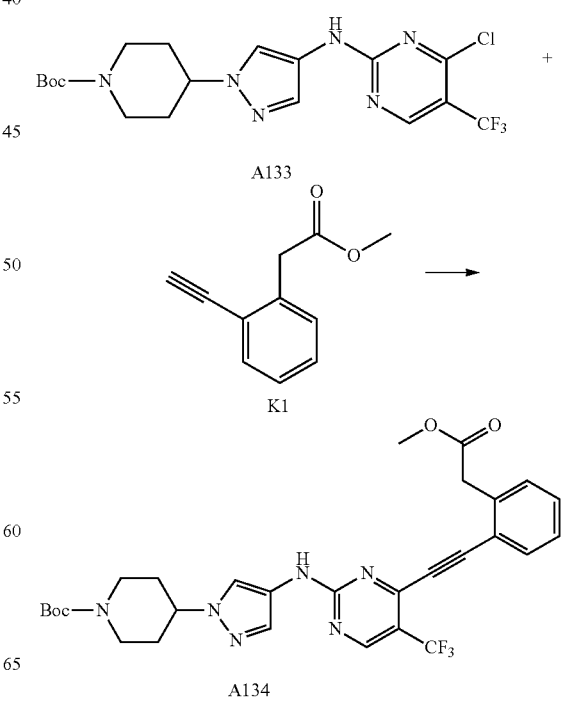

-continued

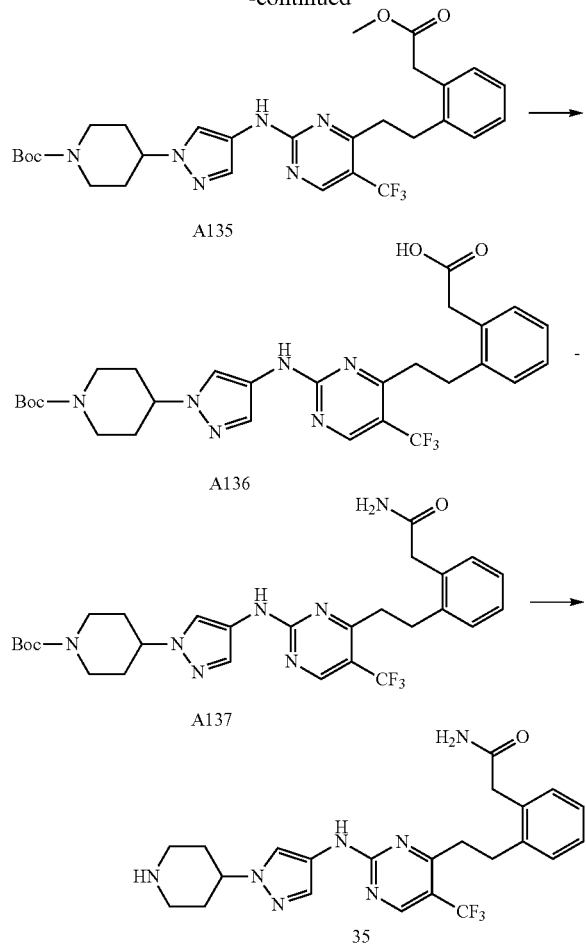

A135

A136

A137

35

(a) tert-Butyl 4-(4-((4-chloro-5-(trifluoromethyl) pyrimidin-2-yl)amino)-1H-pyrazol-1-yl)piperidine-1-carboxylate (A133)

A 1.0 M solution of ZnCl₂ in diethyl ether (20.7 mL, 20.7 mmol) was added to a solution of 2,4-dichloro-5-(trifluoromethyl)pyrimidine (4.48 g, 20.7 mmol) in t-BuOH (100 mL) and DCE (100 mL). The mixture was stirred for 10 minutes then diluted with t-BuOH (100 mL) and DCE (100 mL) before tert-butyl 4-(4-amino-1H-pyrazol-1-yl)piperidine-1-carboxylate (5.00 g, 18.8 mmol) and Et₃N (10.4 mL) were added. The mixture was stirred at room temperature overnight, the volatiles were removed in vacuo and the resultant residue was suspended in water (500 mL) and sonicated for 15 minutes. The solid was isolated by vacuum filtration and the filter cake washed with water (100 mL) and acetone (25 mL) to give the title compound (A133) as a tan solid (5.92 g, 71%); LCMS-A: rt 6.895 min; m/z 445.1 [M−H]⁻.

(b) tert-butyl 4-(4-((4-((2-(2-methoxy-2-oxoethyl) phenyl)ethynyl)-5-(trifluoromethyl)pyrimidin-2-yl) amino)-1H-pyrazol-1-yl)piperidine-1-carboxylate (A134)

A suspension of tert-butyl 4-(4-((4-chloro-5-(trifluoromethyl)pyrimidin-2-yl)amino)-1H-pyrazol-1-yl)piperidine-1-carboxylate (A133) (700 mg, 1.57 mmol), KI (300 mg, 1.72 mmol), PPh₃ (21 mg, 0.078 mmol) and CuI (15 mg, 0.078 mmol) in Et₃N (1 mL) and DMF (4 mL) was sonicated for 10 minutes before PdCl₂(PPh₃)₂ (55 mg, 0.078 mmol) was added. The reaction mixture was irradiated in the microwave at 120° C. for 40 minutes. The resultant mixture was adsorbed onto silica gel and purified by column chromatography (Biotage Isolera, 40 g SiO₂ cartridge, 0-100% EtOAc in petroleum benzine 40-60° C.), a second silica gel column was run (Biotage Isolera, 40 g SiO₂ cartridge, 0-50% EtOAc in petroleum benzine 40-60° C.) to give the title compound (A134) as a yellow solid (392 mg, 43%). LCMS-A: rt 7.064 min; m/z 585 [M+H]⁺.

(c) tert-Butyl 4-(4-((4-(2-(2-methoxy-2-oxoethyl) phenethyl)-5-(trifluoromethyl)pyrimidin-2-yl) amino)-1H-pyrazol-1-yl)piperidine-1-carboxylate (RCF_013_72_A) (A135)

A solution of tert-butyl 4-(4-((4-((2-(2-methoxy-2-oxoethyl)phenyl)ethynyl)-5-(trifluoromethyl)pyrimidin-2-yl) amino)-1H-pyrazol-1-yl)piperidine-1-carboxylate (A134) (392 mg, 0.671 mmol) in EtOAc (40 mL) and DMF (2 mL) was stirred with 10% Pd/C (wetted with ca. 53% water, 100 mg) under a hydrogen atmosphere at room temperature overnight. The mixture was filtered through Celite and the filter cake was washed with EtOAc (50 mL). The volatiles were removed in vacuo and the resulting yellow oil was adsorbed onto silica gel and purified by silica gel column chromatography (Biotage Isolera, 40 g SiO₂ cartridge, 0-100% EtOAc in petroleum benzine 40-60° C. then 0-20% MeOH in EtOAc) to give the title compound (A135) as a yellow solid (300 mg, 76%), ¹H NMR (400 MHz, Chloroform-d) δ 8.44 (s, 1H), 7.85 (s, 1H), 7.64-7.46 (m, 1H), 7.22-7.06 (m, 4H), 4.32-4.04 (m, 3H), 3.67 (s, 2H), 3.60 (s, 3H), 3.14-2.94 (m, 4H), 2.87-2.75 (m, 2H), 2.14-1.99 (m, 2H), 1.97-1.79 (m, 2H), 1.40 (s, 9H).

(d) 2-(2-(2-(2-((1-(1-(tert-Butoxycarbonyl)piperidin-4-yl)-1H-pyrazol-4-yl)amino)-5-(trifluoromethyl) pyrimidin-4-yl)ethyl)phenyl)acetic acid (A136)

A mixture of tert-butyl 4-(4-((4-(2-(2-methoxy-2-oxoethyl)phenethyl)-5-(trifluoromethyl)pyrimidin-2-yl)amino)-1H-pyrazol-1-yl)piperidine-1-carboxylate (A135) (300 mg, 0.510 mmol) and LiOH.H₂O (855 mg, 20.4 mmol) in THF (20 mL) and H₂O (1 mL) was stirred at 40° C. overnight. The mixture was diluted with DCM (50 mL) and water (50 mL) and the aqueous layer was extracted with EtOAc (2×50 mL). The combined washings were dried (Na₂SO₄) and the volatiles were removed in vacuo to yield the title compound (A136) as a yellow oil (270 mg, 92%). LCMS-A: rt 6.679 min; m/z 575.2 [M+H]⁺.

(e) tert-Butyl 4-(4-((4-(2-(2-amino-2-oxoethyl)phenethyl)-5-(trifluoromethyl)pyrimidin-2-yl)amino)-1H-pyrazol-1-yl)piperidine-1-carboxylate (A137)

Ammonium carbonate (903 mg 9.40 mmol) was added to a suspension of 2-(2-(2-(2-((1-(1-(tert-butoxycarbonyl)piperidin-4-yl)-1H-pyrazol-4-yl)amino)-5-(trifluoromethyl)pyrimidin-4-yl)ethyl)phenyl)acetic acid (A136) (270 mg, 0.470 mmol), HOBt (317 mg, 2.35 mmol) and EDCl.HCl (450 mg, 2.35 mmol) in Et₃N (1.0 mL) and DMF (25 mL) and the resulting solution was stirred at 40° C. overnight. The volatiles were removed in vacuo and the resulting residue was dissolved in EtOAc (250 mL) and washed with water (250 mL). The organics were adsorbed onto silica gel and the product was purified by silica gel column chromatography (Biotage Isolera, 40 g SiO$_2$ cartridge, 0-100% EtOAc in petroleum benzine 40-60° C., then 0-20% MeOH in EtOAc) to yield the title compound (A137) as a white solid (171 mg, 63%). LCMS-A: rt 6.481 min; m/z 574.3 [M+H]$^+$.

(f) 2-(2-(2-(2-((1-(Piperidin-4-yl)-1H-pyrazol-4-yl)amino)-5-(trifluoromethyl)pyrimidin-4-yl)ethyl)phenyl)acetamide (35)

TFA (2 mL) was added to a solution of tert-butyl 4-(4-((4-(2-(2-amino-2-oxoethyl)phenethyl)-5-(trifluoromethyl)pyrimidin-2-yl)amino)-1H-pyrazol-1-yl)piperidine-1-carboxylate (A137) (171 mg, 0.298 mmol) in DCM (25 mL) and the mixture was stirred at room temperature overnight. The volatiles were removed in vacuo and the resultant solid was dissolved in CHCl$_3$ (1 mL). Cyclohexane (25 mL) was added and the resultant precipitate was removed by filtration, washed with cyclohexane (25 mL) and air dried to yield the title compound as a white solid (101 mg, 72%). LCMS-A: rt 4.717 min; m/z 474.2 [M+H]$^+$.

Example 36

Synthesis of 2-(2-(2-(2-((1-(1-methylpiperidin-4-yl)-1H-pyrazol-4-yl)amino)-5-(trifluoromethyl)pyrimidin-4-yl)ethyl)phenyl)acetamide (36)

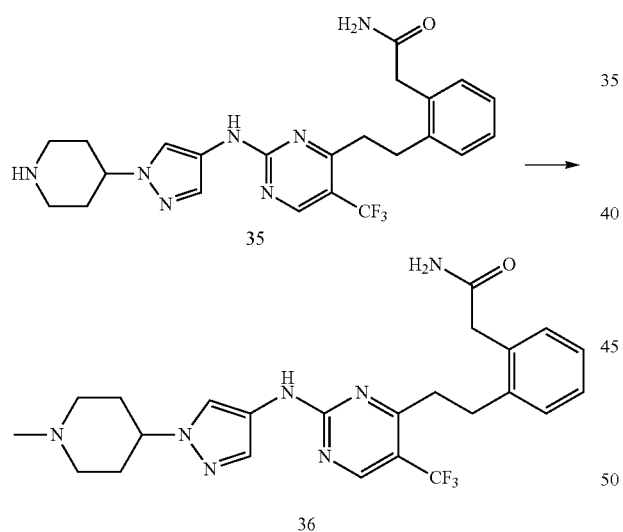

2-(2-(2-(2-((1-(1-Methylpiperidin-4-yl)-1H-pyrazol-4-yl)-amino)-5-(trifluoromethyl)pyrimidin-4-yl)ethyl)phenyl)acetamide (36)

NaHB(OAc)$_3$ (147 mg, 0.693 mmol) was added cautiously to a stirred solution of 2-(2-(2-(2-((1-(piperidin-4-yl)-1H-pyrazol-4-yl)amino)-5-(trifluoromethyl)pyrimidin-4-yl)ethyl)phenyl)acetamide (35) (82 mg, 0.17 mmol) in 37% aqueous formaldehyde solution (39 µL, 0.52 mmol) and MeOH (5.0 mL). The reaction mixture was stirred for 1 hr and then quenched with water (50 mL). The resultant precipitate was removed by filtration, washed with cyclohexane and dried under high vacuum to yield the title compound as a white solid (82 mg, 97%). LCMS-A: rt 4.751 min; m/z 488.3 [M+H]$^+$.

Example 37

Synthesis of 2-(2-(2-(2-(4-(1-aminoethyl)phenylamino)-5-chloropyrimidin-4-yl)ethyl)phenyl)acetamide (37)

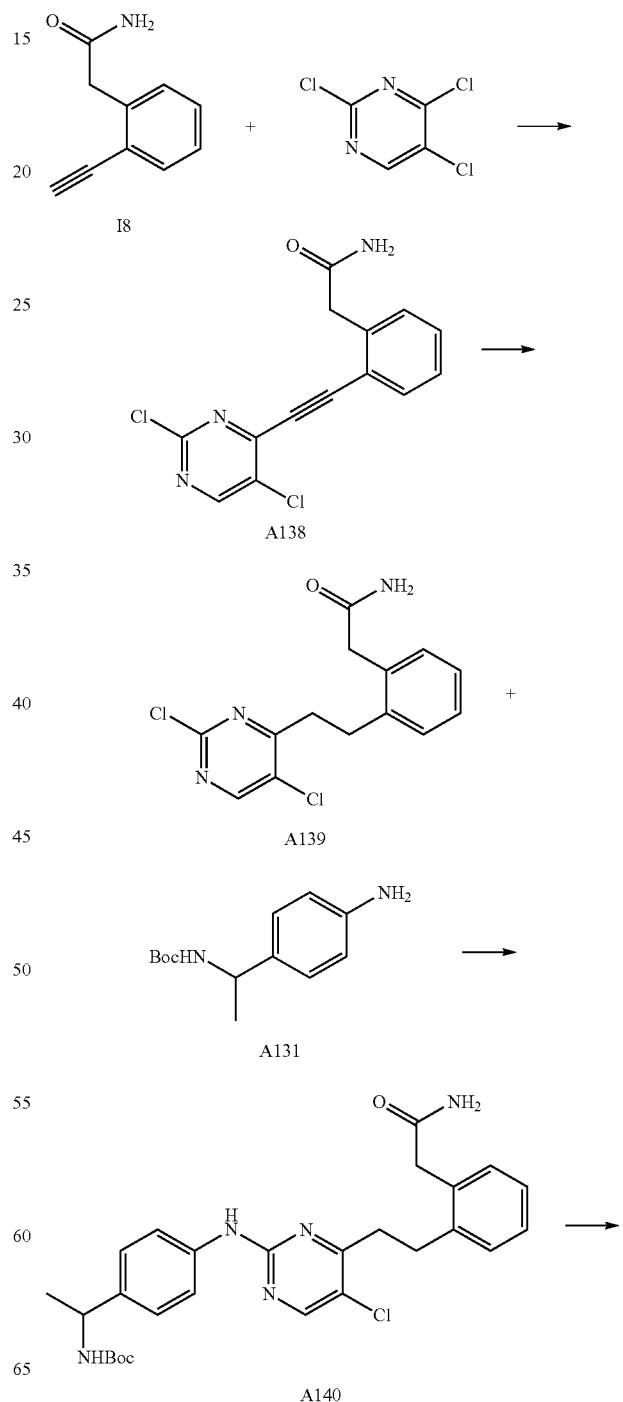

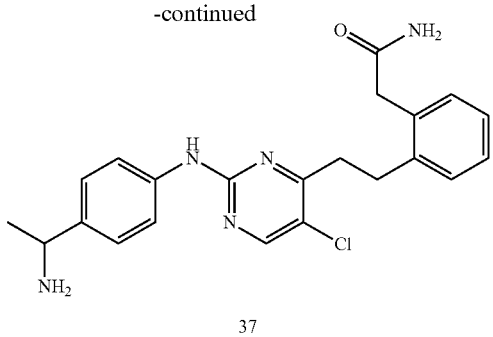

37

(a) 2-(2-((2,5-Dichloropyrimidin-4-yl)ethynyl)phenyl)acetamide (A138)

To a solution of 18 (0.75 g, 4.7 mmol) and 2,4,5-trichloropyrimidine (0.70 mL, 6.1 mmol) in 1,4-dioxane (10 mL) and Et₃N (2.6 mL, 19 mmol) containing CuI (0.018 g, 0.094 mmol) was added PdCl₂(PPh₃)₂ (0.033 g, 0.047 mmol). The reaction mixture was heated at 70° C. for 2 hours under a nitrogen atmosphere. The solvent was removed in vacuo and the residue was diluted with 20% diethyl ether in cyclohexane. The precipitate was filtered, washed with water and dried in vacuo to give the title compound (A138) as a light brown solid (1.22 g, 85%). LCMS-C: rt 4.88 min; m/z 306 [M+H]⁺.

(b) 2-(2-(2-(2,5-Dichloropyrimidin-4-yl)ethyl)phenyl)acetamide (A139)

A solution of 2-(2-((2,5-dichloropyrimidin-4-yl)ethynyl) phenyl)acetamide (A138) (1.2 g, 4.0 mmol) in DMF (40 mL) and MeOH (8 mL) was stirred with platinum(II)oxide (0.27 g, 1.2 mmol) under an atmosphere of hydrogen for 144 hours at ambient temperature. The reaction mixture was diluted with EtOAc and filtered through a plug of Celite. The solvents were removed in vacuo and the crude residue was purified by silica gel column chromatography (Combiflash Rf, 0-10% MeOH in DCM) to give the title compound (A139) as a light yellow solid (0.63 g, 51%). LCMS-C: rt 4.82 min; m/z 310 [M+H]⁺.

(c) tert-Butyl 1-(4-(4-(2-(2-amino-2-oxoethyl)phenethyl)-5-chloropyrimidin-2-ylamino)phenyl)ethylcarbamate (A140)

A mixture of 2-(2-(2-(2,5-dichloropyrimidin-4-yl)ethyl) phenyl)acetamide (A139) (0.050 g, 0.16 mmol), (A131) (0.046 g, 0.19 mmol), Xantphos (0.014 g, 0.024 mmol) and Cs₂CO₃ (0.16 g, 0.48 mmol) in 1,4-dioxane (1 mL) was bubbled with nitrogen for 10 minutes. Palladium (II) acetate (0.0036 g, 0.016 mmol) was added and the mixture was heated at 90° C. under microwave irradiation for 90 minutes. The mixture was portioned between water and EtOAc. The layers were separated and the water layer was extracted with EtOAc (twice). The combined organic extracts were washed with brine, dried (Na₂SO₄) and the solvent evaporated in vacuo to give the crude product. Purification by silica gel column chromatography (3 times) (Combiflash Rf, 0-10% MeOH in DCM twice then 0-100% EtOAc in cyclohexane) to give the title compound (A140) as a colourless oil (0.007 g, 9%). LCMS-C: rt 5.54 min; m/z 510 [M+H]⁺

(d) 2-(2-(2-(2-(4-(1-Aminoethyl)phenylamino)-5-chloropyrimidin-4-yl)ethyl)phenyl)acetamide (37)

To a solution of tert-butyl 1-(4-(4-(2-(2-amino-2-oxoethyl) phenethyl)-5-chloropyrimidin-2-ylamino)phenyl)ethylcarbamate (A140) (0.0070 g, 0.014 mmol) in DCM (1 mL) was added TFA (0.50 mL). The mixture was stirred at ambient temperature for 2 hours before the volatiles were removed in vacuo. The crude residue was purified using an SCX cartridge, (MeOH then 2 N ammonia in EtOH eluent) to give the title compound (37) as a grey solid (0.005 g, 89%). LCMS-C: rt 4.29 min; m/z 410 [M+H]⁺

Example 38

Synthesis of 2-(2-(2-(2-((3-(1-aminoethyl)phenyl) amino)-5-chloropyrimidin-4-yl)ethyl)phenyl)acetamide (38)

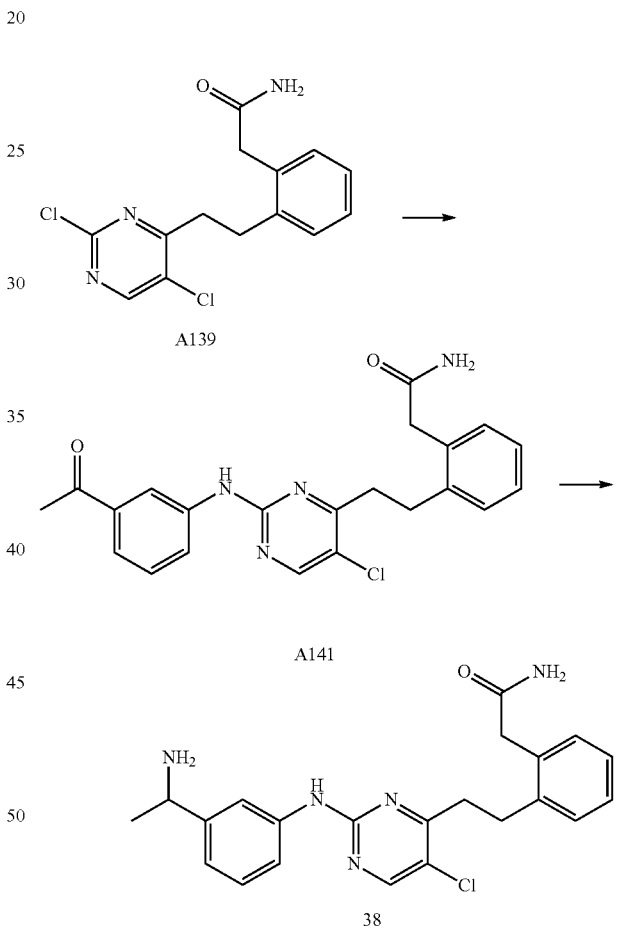

(a) 2-(2-(2-(2-((3-Acetylphenyl)amino)-5-chloropyrimidin-4-ylethyl)phenyl)acetamide (A141)

A solution of 2-(2-(2-(2,5-dichloropyrimidin-4-yl) ethyl) phenyl)acetamide (A139) (0.158 g, 0.509 mmol) in 2-propanol (2 mL) containing 1-(3-aminophenyl)ethanone (0.138 g, 1.01 mmol) was heated under microwave irradiation at 150° C. for 2 hours. The reaction mixture was adsorbed onto silica gel and the product was purified using silica gel column chromatography (CombiFlash Rf, 12 g SiO₂ Cartridge, 10-65% EtOAc in cyclohexane) to give the title compound (A141) as a white solid (0.125 g, 60%). LCMS-B: rt 6.804 min; m/z 409 [M+H]+.

(b) 2-(2-(2-(2-((3-(1-Aminoethyl)phenyl)amino)-5-chloropyrimidin-4-yl)ethyl)phenyl)acetamide (38)

Ammonium acetate (0.339 g, 4.40 mmol) was added to a solution of 2-(2-(2-(2-((3-acetylphenyl)amino)-5-chloropyrimidin-4-yl)ethyl)phenyl)acetamide (A141) (0.120 g, 0.293 mmol) in MeOH (5 mL) and the mixture was stirred for 20 minutes under a nitrogen atmosphere. Sodium cyanoborohydride (0.013 g, 0.21 mmol) was added and the mixture was stirred for 6 hours. Additional sodium cyanoborohydride (0.013 g, 0.21 mmol) was added and the mixture was stirred for 16 hours at room temperature. The mixture was diluted with water (10 mL), acidified with 20% aqueous HCl (10 mL) and washed with Et2O (2×30 mL). The aqueous phase was basified with solid potassium hydroxide to pH 10 and extracted with DCM (3×30 mL). The combined organic phases were washed with water, brine, dried (Na2SO4) and the solvent evaporated in vacuo. The crude product was adsorbed onto silica gel and purified by column chromatography (CombiFlash Rf, 12 g SiO2 Cartridge, 0-30% MeOH in DCM) to give the title compound (38) as a white foam (0.057 g, 47%). LCMS-B: rt 5.45 min; m/z 410 [M+H]+.

Example 39

Synthesis of 2-(2-(2-(2-((3-(1-acetamidoethyl)phenyl)amino)-5-chloropyrimidin-4-yl)ethyl)phenyl)acetamide (39)

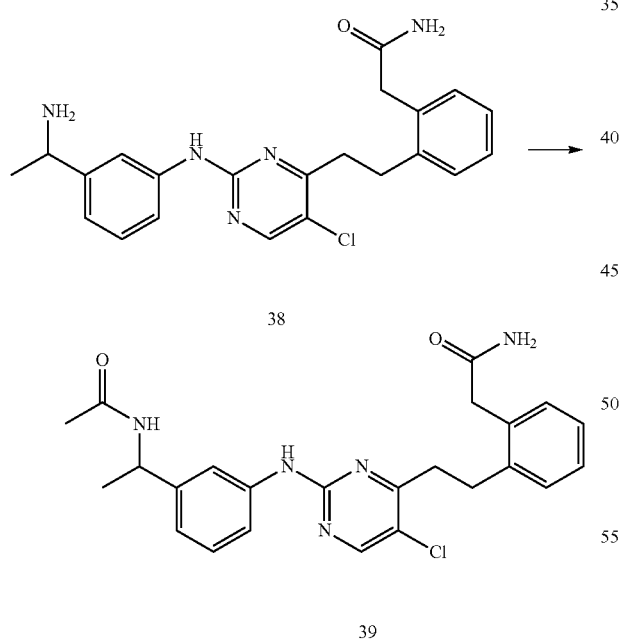

A solution of 2-(2-(2-(2-((3-(1-aminoethyl)phenyl)amino)-5-chloropyrimidin-4-yl)ethyl)phenyl)acetamide (38) (0.045 g, 0.11 mmol) in pyridine (3 mL) containing acetic anhydride (62 µL, 0.66 mmol) and 4-dimethylaminopyridine (2.6 mg, 0.022 mmol) was stirred at room temperature for 22 hours under a nitrogen atmosphere. The mixture was acidified with 1 M hydrochloric acid (30 mL) and extracted with DCM (3×20 mL). The combined organic phases were washed with water, brine, dried (Na2SO4) and the solvent evaporated in vacuo. The crude product was adsorbed onto silica gel and the product was purified by column chromatography (CombiFlash Rf, 4 g SiO2 Cartridge, 0-10% MeOH in DCM) to yield the title compound (39) as a white solid (0.035 g, 70%). LCMS-B: rt 6.20 min; m/z 452 [M+H]+.

Example 40

Synthesis of 2-(2-(2-(2-((6-(1-aminoethyl)pyridin-3-yl)amino)-5-chloropyrimidin-4-yl)ethyl)phenyl)acetamide (40)

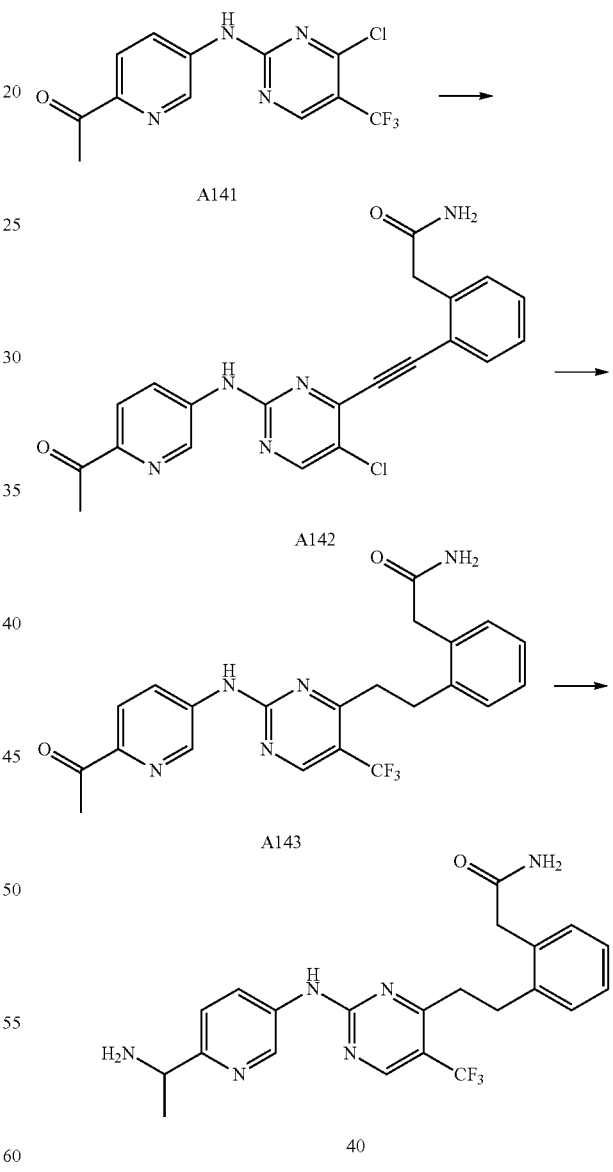

(a) 1-(5-((4-Chloro-5-(trifluoromethyl)pyrimidin-2-yl)amino)pyridin-2-yl)ethanone (A141)

A suspension of 1-(5-aminopyridin-2-yl)ethanone (2.08 g, 15.3 mmol) in DMF (30 mL) and DIPEA (6.65 mL, 38.2 mmol) was stirred at room temperature for 15 minutes. 2,4-Dichloro-5-(trifluoromethyl)pyrimidine (2.47 mL, 18.33 mmol) was added in 4 portions over 5 minutes. The reaction mixture was stirred at 60° C. for 2 hours under a nitrogen atmosphere before it was diluted with water and EtOAc. The aqueous was extracted several times with EtOAc and the combined organic phases were washed with water, brine, dried ($Na_2SO_4$), filtered and the solvent evaporated in vacuo. The crude product was adsorbed onto silica gel and purified by column chromatography (CombiFlash Rf, 40 g $SiO_2$ Cartridge, 0-30% EtOAc in cyclohexane) to give 2.17 g of a white solid. The 1:1 regiosiomeric mixture was dissolved in a minimum volume of cold (5° C.) acetonitrile (4-8 mL), sonicated for 10 seconds then filtered and dried to give the title compound (A141) as a white solid (1.14 g, 23%). LCMS-B: rt 7.34 min; m/z 317 [M+H]$^+$.

(b) 2-(2-((2-((6-Acetylpyridin-3-yl)amino)-5-(trifluoromethyl)pyrimidin-4-yl)ethynyl)phenyl)acetamide (A142)

1-(5-((4-Chloro-5-(trifluoromethyl)pyrimidin-2-yl)amino)pyridin-2-yl)ethanone (A141) (0.313 g, 0.988 mmol) and I8 (0.189 g, 1.18 mmol) were added to a solution of $PdCl_2(PPh_3)_2$ (0.017 g, 0.025 mmol), CuI (0.010 g, 0.049 mmol) and $PPh_3$ (0.013 g, 0.049 mmol) in DMF (3 mL) and $Et_3N$ (0.552 mL, 3.95 mmol). The reaction mixture was heated under microwave irradiation at 120° C. for 15 minutes. The reaction mixture was diluted with water and then filtered. The solid was washed with water and dried before being suspended in EtOAc, ultra sonicated for 20 seconds, filtered and dried to give the title compound (A142) as a light brown solid (0.347 g, 79%). LCMS-B: rt=6.78 min; m/z=440 [M+H]$^+$.

(c) 2-(2-(2-(2-((6-Acetylpyridin-3-yl)amino)-5-(trifluoromethyl)pyrimidin-4-yl)ethyl)phenyl)acetamide (A143)

A solution of 2-(2-((2-((6-acetylpyridin-3-yl)amino)-5-(trifluoromethyl)pyrimidin-4-yl)ethynyl)phenyl)acetamide (A142) (0.347 g, 0.790 mmol) in DMF (20 mL), EtOH (3 mL) and $Et_3N$ (1 mL) containing 10% palladium on carbon (0.110 g) was stirred under a hydrogen atmosphere for 20 hours. The reaction mixture was filtered through a pad of Celite and the solvent was concentrated in vacuo. The crude material was adsorbed onto silica gel and purified by silica gel column chromatography (CombiFlash Rf, 24 g $SiO_2$ Cartridge, 0-10% MeOH in DCM) to give the title compound (A143) as a white solid (0.200 g, 57%). LCMS-B: 6.80 min; m/z 444 [M+H]$^+$.

(d) 2-(2-(2-(2-((6-(1-Aminoethyl)pyridin-3-yl)amino)-5-(trifluoromethyl)pyrimidin-4-yl)ethyl)phenyl)acetamide (40)

Ammonium acetate (0.250 g, 3.23 mmol) was added to a solution of 2-(2-(2-(2-((6-acetylpyridin-3-yl)amino)-5-(trifluoromethyl)pyrimidin-4-yl)ethyl)phenyl)acetamide (A143) (0.072 g, 0.162 mmol) in MeOH (4 mL) and THF (2 mL) and the mixture was stirred for 20 minutes under a nitrogen atmosphere. Sodium cyanoborohydride (7 mg, 0.1 mmol) was added and the mixture was stirred for 5 hours. Additional sodium cyanoborohydride (7 mg, 0.1 mmol) was added and the mixture was stirred for a total of 22 hours at 35° C. The aqueous phase was basified with solid potassium hydroxide (pH 10) and extracted with EtOAc (3×30 mL). The combined organic phases were washed with brine, dried ($Na_2SO_4$), and adsorbed on to silica. The product was purified by silica column chromatography (CombiFlash Rf, 12 g $SiO_2$ Cartridge, 0-20% MeOH in DCM) to give the title compound (40) as a white solid (0.042 g, 58%). LCMS-B: 4.30 min; m/z 445 [M+H]$^+$.

Biological Assays

The activity of compounds of the invention can be profiled using biochemical and cellular assays.

Primary potency at VEGFR3 can be assessed using an Alpha Screen™ technology biochemical assay.

The ability of compounds of the invention to inhibit VEGFR3 within cells can be assessed with an ELISA type assay.

VEGFR3 Biochemical Assay

Compounds of the invention may be tested for in vitro activity in the following assay: A biotin labelled peptide is used as substrate (amino acid sequence: Biotin-Glu-Gly-Pro-Trp-Leu-Glu-Glu-Glu-Glu-Glu-Ala-Tyr-Gly-Trp-Met-Asp-Phe-$NH_2$). VEGFR3 cytoplasmic domain (amino acids 798-1298) was purchased as N-terminal GST-fusion protein ("the enzyme"). The 15 μL assay reactions are run in Greiner brand white 384-well low volume plates. All reactions contained 10 mM HEPES pH 7.4, 10 mM $MgCl_2$, 0.01% (v/v) Tween-20, 50 μM $Na_3VO_4$, 0.01% (w/v) albumin from chicken egg white, 1 mM Dithiothreitol, 111 nM peptide substrate, 500 μM ATP, and 3.8 ng/reaction enzyme, with the enzyme being omitted from negative control reactions. Compounds were added in a volume of 100 mL from dilution series prepared in DMSO, positive and negative control reactions receiving the same volume DMSO without compound. The plates were sealed with adhesive seals and incubated for 90 minutes at 30 degree Celsius. The reactions were stopped with the detection reagents added at the same time as follows: Product formation was quantified as amplified luminescence between PerkinElmer AlphaScreen™ beads, using Streptavidin-coated donor and anti-phosphotyrosine (P-Tyr-100) acceptor beads. To each reaction, 5 μL containing 10 mM HEPES pH 7.4, 25 mM NaCl, 100 mM EDTA, 0.01% (v/v) Tween-20, and 6.25 μg/mL of each bead type were added. Plates were incubated for 6 hours before being read on a PerkinElmer EnVision™ plate reader in HTS Alphascreen™ mode. $IC_{50}$ values were obtained by calculating percent inhibition (% I) for each reaction relative to controls on the same plate (% I=(I−CN)/(CP−CN) where CN/CP are the averages of the negative/positive reactions, respectively), then fitting the % I data vs. compound concentration [I] to % I=(A+((B−A)/(1+((C/[I])^D)))) where A is the lower asymptote, B is the upper asymptote, C is the $IC_{50}$ value, and D is the slope factor.

The above assay was also run in a modified form in some cases (indicated below with *). In these cases, VEGFR3 cytoplasmic domain (amino acids 818-1177, lacking 949-1002 of UniProt accession number P35916) was expressed and purified as N-terminal Hexa-His-fusion protein ("the enzyme"), rather than using the N-terminal GST-fusion protein. The assay conditions were the same as above but with 1 μM ATP and 8 ng/reaction of the enzyme. The comparable performance of both assay versions was monitored using benchmark compounds as described in the literature.

VEGFR3 Biochemical Assay Results

| Compound | $IC_{50}$ (nM) |
| --- | --- |
| 1 | 161 |
| 2 | 39 |
| 3 | 97 |

-continued

| Compound | IC$_{50}$ (nM) |
|---|---|
| 4 | 35 |
| 5 | 28 |
| 6 | 23 |
| 7 | 40 |
| 8 | 34 |
| 9 | 68 |
| 10 | 76 |
| 11 | 26 |
| 12 | 20 |
| 13 | 67 |
| 14 | 81 |
| 15 | 31 |
| 16 | 22 |
| 17 | 67 |
| 18 | 46 |
| 19 | 70 |
| 20 | 37 |
| 21 | 44 |
| 22 | 101 |
| 23 | 72 |
| 24 | 34 |
| 25 | 278 |
| 26 | 24 |
| 27 | 118 |
| 28 | 24 |
| 29 | 17 |
| 30 | 9 |
| 31 | 23 |
| 32 | 52 |
| 33 | 28 |
| 34 | 71 |
| 35 | 23 |
| 36 | 50 |
| 37 | 12 |
| 38 | 76 |
| 39 | 10 |
| 40 | 187 |
| 41 | 26 |

VEGFR3 Phospho ELISA Assay

Compounds of the invention may be tested for in vitro activity in the following assay:

Adult human dermal lymphatic microvascular endothelial cells (HMVEC-dLyAD) (Cat# CC-2810, Lonza) were seeded into clear-bottom, TC treated 12 well plates (Cat #665180, Greiner Bio-One) in EGM-2MV (Cat# CC-3202, Lonza) at 180,000 cells/well (volume 1 mL), and the plates incubated at 37° C. and 5% $CO_2$ for 6 hours. The media was replaced with EBM-2 (Cat # CC-3156, Lonza)+0.1% BSA (Cat# A8412, Sigma) and cells incubated for a further period (overnight at 37° C. and 5% $CO_2$).

96 well Maxisorp immuno plates (Cat #439454, Nunc) were coated with 100 μL of Total VEGFR3 capture antibody (Part #841888, Human Total VEGFR3/FLT4 ELISA Kit, Cat # DYC3491, R&D Systems), or Phospho VEGFR3 Capture antibody (Part #841885, Human Phospho VEGFR3/FLT4 ELISA Kit, Cat# DYC2724, R&D Systems). The plates were covered and incubated at room temperature overnight.

The coating antibody was flicked out and the plates washed three times with Wash Buffer (Phosphate buffered saline (137 mM NaCl, 2.7 nM KCl, 8.1 nM $Na_2HPO_4$, 1.5 mL $KH_2PO_4$, pH 7.2-7.4), 0.05% Tween 20). 300 μL of blocking buffer (5% v/v Tween 20, 5% w/v sucrose in PBS) was then added to wells and plate incubated for 2 hours at room temperature. Blocking solution is flicked out and plates washed three times and tapped dry.

Compound dilution series were prepared in EBM-2 (Cat # CC-3156, Lonza)+0.1% BSA (Cat#A8412, Sigma) with constant 0.1% DMSO concentration. 439 μL of sample or vehicle control was added to the cell monolayers. Cells are treated for 1 hour at 37° C. and 5% $CO_2$. 250 ng/mL Recombinant human VEGFC (Cat #2179-VC, R & D Systems) added to wells and plates incubated for an additional 10 minutes at 37° C. and 5% $CO_2$.

The media and compounds were removed and the cell monolayer washed once in Dulbecco's Phosphate Buffered Saline (Cat #21600-044, Invitrogen). 130 μL of Lysis buffer added to wells and cell lysate harvested and transferred to tubes and stored on ice. Complete lysis buffer was prepared by adding 10 μL Protease Inhibitor Cocktail (Cat # P8340, Sigma-Aldrich), 10 μL PMSF (Phenylmethanesulfonyl fluoride, Cat # P7626, Sigma-Aldrich, prepared as 500 mM DMSO stock) per 1 mL of Phosphosafe™ Extraction Reagent (Cat #71296, Merck).

The harvested samples were then diluted 1:2 in IC Diluent #18 (5% Tween 20/PBS) and 100 μL transferred to the Total and Phospho VEGFR3 coated, blocked and washed 96 well plates and incubated for 2 hours at room temperature. The plates were then washed three times in wash buffer as described above and tapped dry.

For detection of Total VEGFR3 100 μL of Detection antibody (Total VEGFR3 Detection Antibody Part#841888 in Total VEGFR3 kit) diluted in IC Diluent #1 (1% w/v BSA (Cat # A7906, Sigma-Aldrich)/PBS) was added to wells and the plate incubated for 2 hours at room temperature. The plate was then washed three times in wash buffer and tapped dry. 100 μL of streptavidin-HPR diluted in IC diluent #1 Streptavidin-HRP, Part #890803 in Total VEGFR3 kit) was added to wells and incubated at room temperature for 20 minutes followed by washing as described above 100 μL Substrate solution (3,3',5,5'-Tetramethylbenzidine (TMB) Liquid Substrate System for ELISA, Cat # T0440, Sigma-Aldrich) was added and the plate incubated for 20 minutes in the dark at room temperature followed by the addition of 50 μL stop solution (2 M $H_2SO_4$).

Total VEGFR3 levels were quantified using a Multiskan Ascent plate reader and Ascent software fitted with 450 nm filter.

For detection of Phospho VEGFR3, 100 μL of Detection antibody (Anti-Phospho-Tyrosine-HRP Detection Antibody, Part #841403 in Phospho VEGFR3 kit) was diluted in IC Diluent #1 (1% w/v BSA/PBS), added to the wells and the plate incubated for 2 hours at room temperature. The plate was then washed three times in wash buffer as described above and tapped dry. 100 μL Substrate solution (3,3',5,5'-Tetramethylbenzidine (TMB) Liquid Substrate System for ELISA, Cat # T0440, Sigma-Aldrich) was added and the plate incubated for 20 minutes in the dark at room temperature followed by the addition of 50 μL stop solution (2 M $H_2SO_4$).

Phospho VEGFR3 levels were quantified using a Multiscan ascent plate reader and ascent software fitted with 450 nm filter.

IC$_{50}$ values are determined by first calculating the level of phospho VEGFR3 relative to Total VEGFR3 according to the following formula:

$$SRP = \frac{SP}{ST}$$

Where SRP is the Sample Relative Phospho level, SP is Phospho VEGFR3 reading and ST is Total VEGFR3 reading.

Percent inhibition (% I) for each lysate relative to vehicle control (VEGFC stimulated) is then calculated according to the following formula:

$$\% \, I = \frac{SRPVehicle - SRPTest}{SRPVehicle} * 100$$

Where SRP is the Sample Relative Phospho level as calculated above.

% I is plotted against compound concentration and data fitted using a Sigmoidal dose response with $IC_{50}$ determined from curve.

VEGFR3 Phospho ELISA Assay Results

| Compound | IC50 (nM) |
| --- | --- |
| 2 | 121 |
| 3 | 156 |
| 4 | 2216 |
| 5 | 210 |
| 6 | 62 |
| 9 | 379 |
| 11 | 39 |
| 12 | 116 |
| 13 | 1034 |
| 16 | 214 |
| 18 | 18 |
| 24 | 169 |
| 26 | 83 |
| 28 | 190 |
| 31 | 107 |
| 33 | 1254 |
| 37 | 26 |

VEGFR2 Phospho ELISA Assay

Compounds of the invention may be tested for in vitro activity in the following assay:

Adult human umbilical vein endothelial cells (HUVEC) (Cat# CC-2519, Lonza) were seeded into clear-bottom, TC treated 12 well plates (Cat #665180, Greiner Bio-One) in EGM-2 (Cat# CC-3162, Lonza) at 180,000 cells/well (volume 1 mL), and the plates incubated at 37° C. and 5% $CO_2$ for 6 hours. The media was replaced with EBM-2 (Cat # CC-3156, Lonza)+0.1% BSA (Cat# A8412, Sigma) and cells incubated for a further period (overnight at 37° C. and 5% $CO_2$).

96 well Maxisorp immuno plates (Cat #439454, Nunc) were coated with 100 µL of Total VEGFR2 capture antibody (Part #841434, Human Total VEGFR2/FLT4 ELISA Kit, Cat #DYC1780, R&D Systems), or Phospho VEGFR2 Capture antibody (Part #841419, Human Phospho VEGFR2/FLT4 ELISA Kit, Cat# DYC1766, R&D Systems). The plates were covered and incubated at room temperature overnight.

The coating antibody was flicked out and the plates washed three times with Wash Buffer (Phosphate buffered saline (137 mM NaCl, 2.7 nM KCl, 8.1 nM $Na_2HPO_4$, 1.5 mL $KH_2PO_4$, pH 7.2-7.4), 0.05% Tween 20). 300 µL of Blocking buffer (1% v/v BSA (Cat# A8412, Sigma) in PBS) was then added to wells and plate incubated for 2 hours at room temperature. Blocking solution is flicked out and plates washed three times and tapped dry.

Compound dilution series were prepared in EBM-2 (Cat # CC-3156, Lonza)+0.1% BSA (Cat# A8412, Sigma) with constant 0.1% DMSO concentration. 427.5 µL of sample or vehicle control was added to the cell monolayers. Cells are treated for 1 hour at 37° C. and 5% $CO_2$. 50 ng/mL Recombinant human VEGF (Cat #293-VC, R & D Systems) added to wells and plates incubated for an additional 10 minutes at 37° C. and 5% $CO_2$.

The media and compounds were removed and the cell monolayer washed once in Dulbecco's Phosphate Buffered Saline (Cat #21600-044, Invitrogen). 130 µL of Lysis buffer added to wells and cell lysate harvested and transferred to tubes and stored on ice. Complete lysis buffer was prepared by adding 10 µL Protease Inhibitor Cocktail (Cat # P8340, Sigma-Aldrich), 10 µL PMSF (Phenylmethanesulfonyl fluoride, Cat # P7626, Sigma-Aldrich, prepared as 500 mM DMSO stock) per 1 mL of Phosphosafe™ Extraction Reagent (Cat #71296, Merck).

The harvested samples were then diluted 1:2 in IC Diluent #12 (1% NP-40, 20 nM Tris (pH 8.0), 137 mM NaCl, 10% glycerol, 2 mM EDTA, 1 mM activated sodium orthovanadate) and 100 µL transferred to the Total and Phospho VEGFR2 coated, blocked and washed 96 well plates and incubated for 2 hours at room temperature. The plates were then washed three times in wash buffer as described above and tapped dry.

For detection of Total VEGFR2100 µL of Detection antibody (Total VEGFR2 Detection Antibody Part#841435 in Total VEGFR2 kit) diluted in IC Diluent #14 (20 mM Tris, 137 mM CaCl, 0.05% Tween20, 0.1% BSA) was added to wells and the plate incubated for 2 hours at room temperature. The plate was then washed three times in wash buffer and tapped dry. 100 µL of streptavidin-HPR diluted in IC diluent #14 Streptavidin-HRP, Part #890803 in Total VEGFR2 kit) was added to wells and incubated at room temperature for 20 minutes followed by washing as described above. 100 µL Substrate solution (3,3',5,5'-Tetramethylbenzidine (TMB) Liquid Substrate System for ELISA, Cat # T0440, Sigma-Aldrich) was added and the plate incubated for 20 minutes in the dark at room temperature followed by the addition of 50 µL stop solution (2 M $H_2SO_4$).

Total VEGFR2 levels were quantified using a Multiskan Ascent plate reader and Ascent software fitted with 450 nm filter.

For detection of Phospho VEGFR2, 100 µL of Detection antibody (Anti-Phospho-Tyrosine-HRP Detection Antibody, Part #841403 in Phospho VEGFR2 kit) was diluted in IC Diluent 14 (20 mM Tris, 137 mM $Ca_2Cl$, 0.05% Tween20, 0.1% BSA), was added to the wells and the plate incubated for 2 hours at room temperature. The plate was then washed three times in wash buffer as described above and tapped dry. 100 µL Substrate solution (3,3',5,5'-Tetramethylbenzidine (TMB) Liquid Substrate System for ELISA, Cat # T0440, Sigma-Aldrich) was added and the plate incubated for 20 minutes in the dark at room temperature followed by the addition of 50 µL stop solution (2 M $H_2SO_4$).

Phospho VEGFR2 levels were quantified using a Multiscan ascent plate reader and ascent software fitted with 450 nm filter.

$IC_{50}$ values are determined by first calculating the level of phospho VEGFR2 relative to Total VEGFR2 according to the following formula:

$$SRP = \frac{SP}{ST}$$

where SRP is the Sample Relative Phospho level, SP is Phospho VEGFR2 reading and ST is Total VEGFR2 reading.

Percent inhibition (% I) for each lysate relative to vehicle control (VEGF-A stimulated) is then calculated according to the following formula:

$$\% I = \frac{SRPVehicle - SRPTest}{SRPVehicle} * 100$$

where SRP is the Sample Relative Phospho level as calculated above.

% I is plotted against compound concentration and data fitted using a Sigmoidal dose response with $IC_{50}$ determined from plotted curve.

VEGFR2 Phospho ELISA Assay Results

| Compound | $IC_{50}$ (nM) |
|---|---|
| 2 | 4397 |
| 4 | >10000 |
| 18 | 2548 |
| 24 | >10000 |
| 26 | 4071 |
| 28 | 6840 |
| 31 | 5100 |
| 33 | >10000 |
| 37 | 200 |

P397Y-FAK Inhibition MSD Platform Cellular Biomarker Assay

Compounds of the invention may be tested for in vitro activity in the following assay:

96-well plates (cat#MA6000, Meso Scale Discovery) are coated with 30 µL/well of mouse monoclonal FAK antibody [63D5] (cat#ab72140, Abcam) pre-diluted in PBS to a concentration of 1 mg/mL. The plates are sealed with adhesive film and incubated for 16 hours at 4° C. The antibody is then flicked out of the plates and 150 µL of 3% [w/v] Blocker A (cat#R93AA-1, Meso Scale Discovery) is added. The plates are resealed with adhesive film and incubated at room temperature on a shaker set at medium speed for 2 hours. The plates are then washed three times with a solution containing 50 mM Tris-HCl pH 7.5, 0.15 M NaCl and 0.02% Tween-20, before cell lysate addition described below.

Cells are split 1:2 into T150 cell culture flasks 2 days prior to compound treatment. On the day prior to compound treatment, 200 µL media containing 20,000 cells is seeded into all wells of white, clear-bottom, TC treated, µclear, 96-well microtitre plates (cat#655098, Greiner Bio-One), and the plates are incubated at 37° C. and 5% $CO_2$ for 36 hours. 1 µL/well of compound is then added from dilution series prepared in DMSO. Negative control wells receive the same volume of DMSO without compounds, and positive control wells receive 2 µM of a control compound in the same volume of DMSO. Cells are treated for 1 hour at 37° C. and 5% $CO_2$. The media/compounds are then flicked off and 55 µL/well of ice-cold complete lysis buffer is added. Complete lysis buffer is prepared by adding 1 tablet PhosSTOP complete phosphatase inhibitor (cat#04906837001, Roche) and 1 tablet Complete, Mini, EDTA-free, protease inhibitor (cat#04693159001, Roche) per 10 mL of incomplete lysis buffer (150 mM NaCl, 20 mM Tris-HCl pH 7.5, 1 mM EDTA, 1 mM EGTA, 1% Triton-X 100). Plates are incubated on ice for 30 minutes, with 30 seconds high speed plate shaking every 5 minutes. 40 µL/well of cell lysate is transferred to the coated, blocked and washed 96-well microtitre plates described above. The 96-well plates are sealed with adhesive film and incubated for 16 hours at 4° C. The plates are then washed three times with a solution containing 50 mM Tris-HCl pH 7.5, 0.15 M NaCl and 0.02% Tween-20 and tapped dry. 25 µL/well of detection solution (1% [w/v] Blocker A (cat#R93AA-1, Meso Scale Discovery) in 50 mM Tris-HCl pH 7.5, 0.15 M NaCl and 0.02% Tween-20, with 1:600 rabbit polyclonal FAK phospho Y397 antibody (cat#ab39967, Abcam), 1:1000 anti-rabbit sulfo-tag antibody (cat#R32AB-1 Meso Scale Discovery) and 1:40 reconstituted Blocker D-M (cat#D609-0100, Rockland Immunochemicals for Research)) is added, and the plates resealed with adhesive film and incubated for 1 hour at room temperature on a plate shaker set to medium speed. Plates are then washed three times with a solution containing 50 mM Tris-HCl pH 7.5, 0.15 M NaCl and 0.02% Tween-20 and tapped dry. 150 µL/well of Read Buffer T+Surfactant (cat#R92TC-1, Meso Scale Discovery) is then added, and pFAK-397 levels quantified using a Meso Scale Discovery SECTOR Imager 6000 instrument.

$IC_{50}$ values are determined by first calculating percent inhibition (% I) for each lysate relative to controls on the same plate (% I=(S−CP)/(CN−CP)) where S is the sample result, CN is the average result of DMSO only treated negative controls, and CP is the average result of 2 µM treated positive controls. % I is plotted against compound concentration [I] and the data fitted using the following equation, %I=(A+((B−A)/(1+((C/[I])^D)))), where A is the lower asymptote, B is the upper asymptote, C is the IC50 value, and D is the slope factor.

P397Y-FAK Inhibition MSD Platform Cellular Biomarker Assay Results for MDA-231-LNA Cells

| Compound | $IC_{50}$ (nM) |
|---|---|
| 3 | 62 |
| 5 | >2000 |
| 6 | 940 |
| 11 | 16 |
| 12 | 30 |
| 16 | >2000 |
| 18 | 25 |
| 19 | 7 |
| 20 | <50% |
| 21 | 119 |
| 22 | 944 |
| 24 | >2000 |
| 26 | >2000 |
| 28 | >2000 |
| 31 | >2000 |
| 33 | >2000 |

The invention claimed is:

1. A compound of the formula (I) or a stereoisomer, or a salt or a solvate thereof:

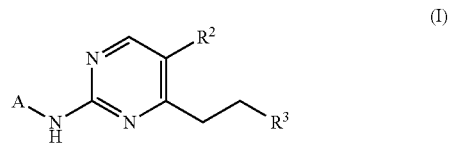

(I)

wherein:

A is an optionally substituted 5 or 6 membered heteroaryl group linked to the NH group through an aromatic ring carbon atom, in which the heteroaryl ring system contains 1 to 4 heteroatoms selected from N, O and S, and;

A may bear a substituent $R^{1A}$ which is not alpha to the NH group and may optionally further bear one, two or three substituents $R^{1C}$ which are not alpha to the NH group, where $R^{1A}$ is selected from:

(i) CH(R$^{C1}$)NHZ$^1$, where R$^{C1}$ is selected from H, C$_{1-2}$ alkyl and Z$^1$ is selected from H, C$_{1-3}$ alkyl optionally substituted by OH, C(=O)OC$_{1-3}$ alkyl and C(=O)Me;

(ii) XNHZ$^2$, where X is selected from CMe$_2$, cyclopropylidene, cyclobutylidene, cyclopentylidene and oxetanylidine and Z$^2$ is selected from H, C$_{1-3}$ alkyl optionally substituted by OH, C(=O)OC$_{1-3}$ alkyl and C(=O)Me;

(iii) a group selected from R$^{1A1}$ to R$^{1A11}$:

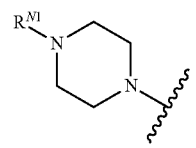
(R$^{1A1}$)

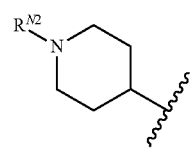
(R$^{1A2}$)

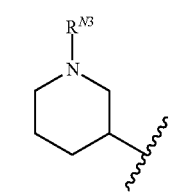
(R$^{1A3}$)

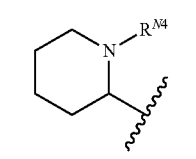
(R$^{1A4}$)

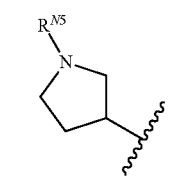
(R$^{1A5}$)

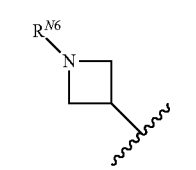
(R$^{1A6}$)

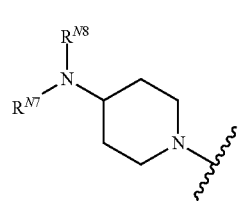
(R$^{1A7}$)

-continued

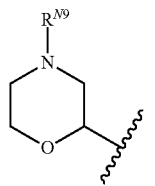
(R$^{1A8}$)

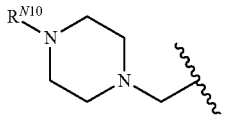
(R$^{1A9}$)

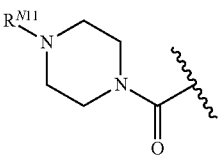
(R$^{1A10}$)

(R$^{1A11}$)

wherein:
R$^{N1}$ is selected from H, C$_{1-4}$ alkyl, C$_{3-4}$ cycloalkyl and C(=O)Me;
R$^{N2}$ is selected from H, C$_{1-4}$ alkyl, C$_{3-4}$ cycloalkyl and C(=O)Me;
R$^{N3}$ is selected from H, C$_{1-4}$ alkyl, C$_{3-4}$ cycloalkyl and C(=O)Me;
R$^{N4}$ is selected from H and CH$_3$;
R$^{N5}$ is selected from H, C$_{1-4}$ alkyl, C$_{3-4}$ cycloalkyl and C(=O)Me;
R$^{N6}$ is selected from H, C$_{1-4}$ alkyl, C$_{3-4}$ cycloalkyl and C(=O)Me;
R$^{N7}$ and R$^{N8}$ are independently selected from H and CH$_3$;
R$^{N9}$ is selected from H, C$_{1-4}$ alkyl, C$_{3-4}$ cycloalkyl and C(=O)Me;
R$^{N10}$ is selected from H, C$_{1-4}$ alkyl, C$_{3-4}$ cycloalkyl and C(=O)Me;
R$^{N11}$ is selected from H, C$_{1-4}$ alkyl, C$_{3-4}$ cycloalkyl and C(=O)Me; and
R$^{N12}$ is selected from H, C$_{1-4}$ alkyl, C$_{3-4}$ cycloalkyl and C(=O)Me;
and where each R$^{1C}$ is independently selected from:
(i) C$_{1-3}$ alkyl;
(ii) CF$_3$;
(iii) F;
(iv) Cl;
(v) O—(C$_{1-3}$ alkyl);
(vi) CN; and
(vii) =O
R$^2$ is selected from H, halo, C$_{1-4}$ alkyl, CF$_3$, CF$_2$H, CN and methoxy;
R$^3$ is selected from substituted phenyl and a substituted 6 membered heteroaryl group, where the heteroaryl ring system contains 1 or 2 N heteroatoms, where R$^3$ bears a substituent R$^4$ either alpha or beta to the —C$_2$H$_4$— group, and may additionally bear further substituents selected from F, methyl and CF$_3$; and
R$^4$ is —CH$_2$—C(O)N(R$^{N13}$)Z$^3$, where R$^{N13}$ is selected from H and CH$_3$; and Z$^3$ is selected from H, CH$_3$ and OCH$_3$.

2. A compound, or a stereoisomer, or a salt or a solvate thereof, according to claim 1, wherein A is an optionally substituted 6 membered heteroaryl group.

3. A compound, or a stereoisomer, or a salt or a solvate thereof, according to claim 2, wherein A is optionally substituted pyridyl.

4. A compound, or a stereoisomer, or a salt or a solvate thereof, according to claim 3, wherein A is selected from:

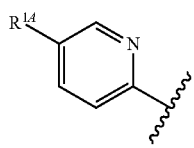
(A⁵ᴬ)

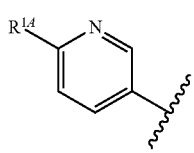
(A⁶ᴬ)

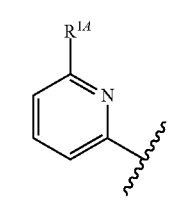
(A⁷ᴬ)

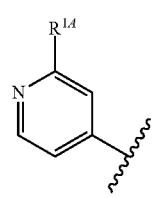
(A⁸ᴬ)

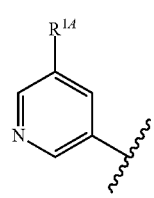
(A⁹ᴬ)

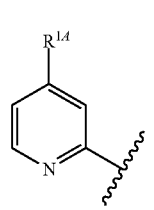
(A¹⁰ᴬ)

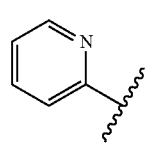
(A¹¹ᴬ)

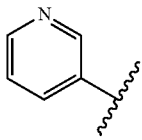
(A¹²ᴬ)

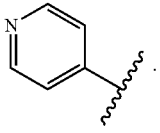
(A¹³ᴬ)

5. A compound, or a stereoisomer, or a salt or a solvate thereof, according to claim 4, wherein A is

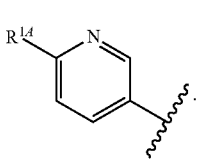
(A⁶ᴬ)

6. A compound, or a stereoisomer, or a salt or a solvate thereof, according to claim 1, wherein A is an optionally substituted 5 membered heteroaryl group.

7. A compound, or a stereoisomer, or a salt or a solvate thereof, according to claim 6, wherein A is optionally substituted pyrazolyl.

8. A compound, or a stereoisomer, or a salt or a solvate thereof, according to claim 7, wherein A is selected from:

(A¹⁴ᴬ)

(A¹⁵ᴬ)

(A¹⁶ᴬ)

(A¹⁷ᴬ)

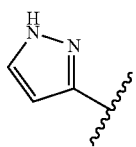
(A^{18A})

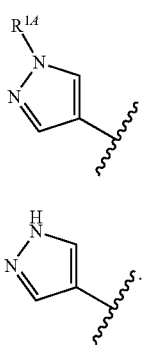
(A^{19A})

(A^{20A})

9. A compound, or a stereoisomer, or a salt or a solvate thereof, according to claim 8, wherein A is

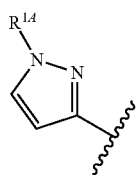 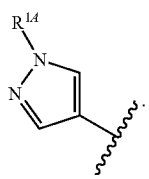
(A^{19A})

10. A compound, or a stereoisomer, or a salt or a solvate thereof, according to claim 1, where no $R^{1C}$ substituents are present on A.

11. A compound, or a stereoisomer, or a salt or a solvate thereof, according to claim 1, where $R^{1C}$ is methyl.

12. A compound, or a stereoisomer, or a salt or a solvate thereof, according to claim 1, where a single $R^{1C}$ substituent is present.

13. A compound, or a stereoisomer, or a salt or a solvate thereof, according to claim 1, wherein $R^{1A}$ is selected from:

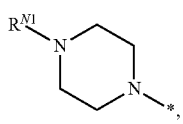
(R^{1A1})

wherein $R^{N1}$ is C(=O)Me,

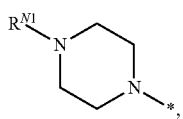
(R^{1A1})

wherein $R^{N1}$ is H, methyl or ethyl,

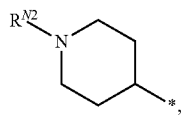
(R^{1A2})

wherein $R^{N2}$ is selected from H, methyl and ethyl,

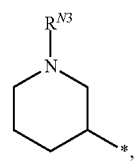
(R^{1A3})

wherein $R^{N3}$ is selected from H and methyl,

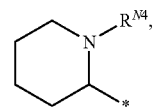
(R^{1A4})

wherein $R^{N4}$ is selected from H and methyl,

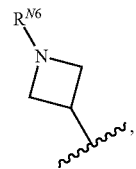
(R^{1A5})

wherein $R^{N5}$ is selected from H and methyl, (R^{1A6})

wherein $R^{N6}$ is selected from H and methyl,

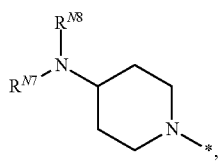
(R^{1A7})

wherein $R^{N7}$ and $R^{N8}$ are both H or both methyl,

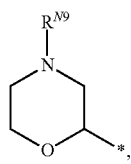

wherein $R^{N9}$ is H,

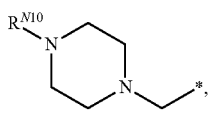

wherein $R^{N10}$ is selected from H and methyl,

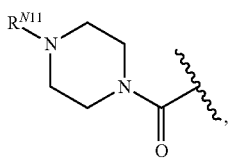

wherein $R^{N11}$ is selected from H and methyl, and

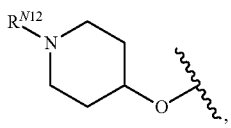

where $R^{N12}$ is selected from H and methyl.

14. A compound, or a stereoisomer, or a salt or a solvate thereof, according claim 1, wherein $R^{1A}$ is selected from:

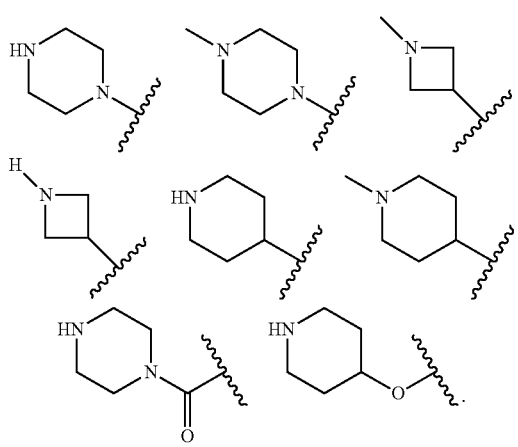

15. A compound, or a stereoisomer, or a salt or a solvate thereof, according to claim 1, wherein $R^2$ is H.

16. A compound, or a stereoisomer, or a salt or a solvate thereof, according to claim 15, wherein $R^2$ is methyl.

17. A compound, or a stereoisomer, or a salt or a solvate thereof, according to claim 15, wherein $R^2$ is $CF_3$.

18. A compound, or a stereoisomer, or a salt or a solvate thereof, according to claim 1, wherein $R^3$ has the structure:

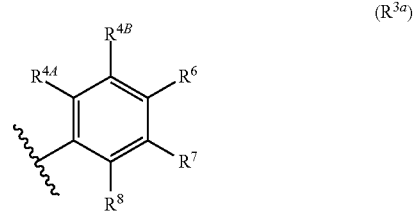

where $R^6$, $R^7$ and $R^8$ are independently selected from H, F, methyl and $CF_3$; and
one of $R^{4A}$ and $R^{4B}$ is $R^4$, and the other of $R^{4A}$ and $R^{4B}$ is selected from H, F, methyl and $CF_3$.

19. A compound, or a stereoisomer, or a salt or a solvate thereof, according to claim 1, wherein $R^3$ is a substituted 6 membered heteroaryl group, where the heteroaryl ring system contains 1 or 2 N heteroatoms.

20. A compound, or a stereoisomer, or a salt or a solvate thereof, according to claim 19, wherein $R^3$ is selected from one of the following structures:

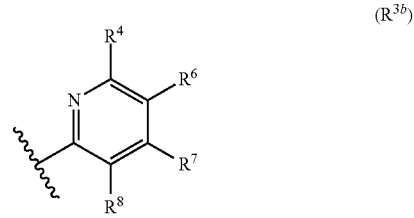

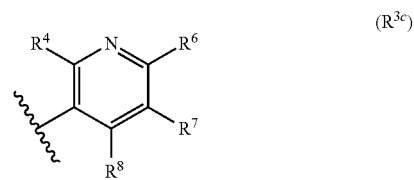

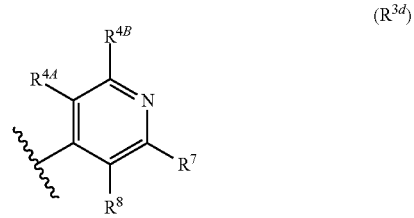

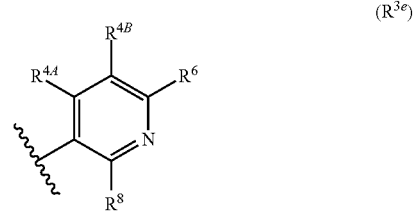

-continued

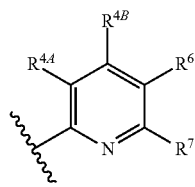
(R3f)

where R6, R7 and R8 (if present) are independently selected from H, F, methyl and CF3;
one of R4A and R4B (if present) is R4, and the other is selected from H, F, methyl and CF3.

21. A compound, or a stereoisomer, or a salt or a solvate thereof, of formula (I) according to claim 1 wherein:
A is an optionally substituted 5 or 6 membered heteroaryl group linked to the NH group through an aromatic ring carbon atom, in which the heteroaryl ring system contains 1 or 2 N atoms, and;
A may bear a substituent $R^{1A}$ which is not alpha to the NH group and may optionally further bear a substituent $R^{1C}$ which is not alpha to the NH group, where $R^{1A}$ is selected from:
(i) $CH(R^{C1})NHZ^1$, where $R^{C1}$ is selected from $C_{1-2}$ alkyl and $Z^1$ is selected from H and $C_{1-3}$ alkyl optionally substituted by OH;
(ii) $XNHZ^2$, where X is cyclobutylidene, and $Z^2$ is $C(=O)OC_{1-3}$ alkyl;
(iii) a group selected from:

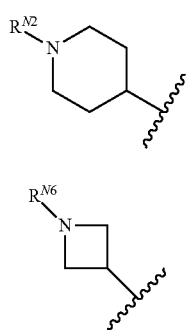
(R1A2)
(R1A6)

wherein:
$R^{N2}$ is selected from H and $C_{1-4}$ alkyl;
$R^{N6}$ is H;
and where $R^{1C}$ is $C_{1-3}$ alkyl;
$R^2$ is selected from $C_{1-4}$ alkyl and CF3;
$R^3$ is substituted phenyl, where $R^3$ bears a substituent $R^4$ alpha to the —$C_2H_4$— group, and may additionally bear a further substituent F; and
$R^4$ is —$CH_2$—$C(O)N(R^{N13})Z^3$, where $R^{N13}$ is H; and $Z^3$ is H.

22. A compound, or a stereoisomer, or a salt or a solvate thereof, of formula (I) according to claim 1 wherein:
A is an optionally substituted 5 or 6 membered heteroaryl group linked to the NH group through an aromatic ring carbon atom, in which the heteroaryl ring system contains 1 or 2 N atoms, and;
A may bear a substituent $R^{1A}$ which is not alpha to the NH group and may optionally further bear a substituent $R^{1C}$ which is not alpha to the NH group, where $R^{1A}$ is $R^{1A2}$:

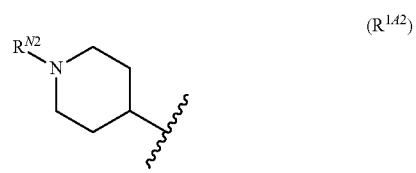
(R1A2)

wherein:
$R^{N2}$ is selected from H and $C_{1-4}$ alkyl;
and where $R^{1C}$ is $C_{1-3}$ alkyl;
$R^2$ is selected from $C_{1-4}$ alkyl;
$R^3$ is substituted phenyl, where $R^3$ bears a substituent $R^4$ alpha to the —$C_2H_4$— group; and
$R^4$ is —$CH_2$—$C(O)N(R^{N13})Z^3$, where $R^{N13}$ is H; and $Z^3$ is H.

23. A compound, or a stereoisomer, or a salt or a solvate thereof, of formula (I) according to claim 1 wherein:
A is selected from:

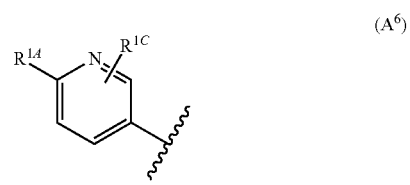
(A6)

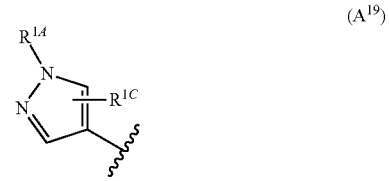
(A19)

(A21)

wherein $R^{1A}$ is selected from:
(i) $CH(R^{C1})NHZ^1$, where $R^{C1}$ is selected from H and methyl and $Z^1$ is selected from H and $CH_2CH_2OH$;
(ii) $XNHZ^2$, where X is selected from cyclobutylidene and oxetanylidine and $Z^2$ is selected from H and $C(=O)OMe$;
(iii) a group selected from $R^{1A1}$, $R^{1A2}$, $R^{1A6}$ and $R^{1A11}$:

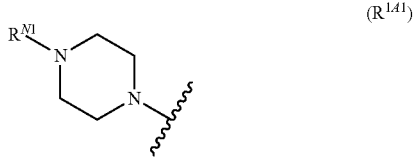
(R1A1)

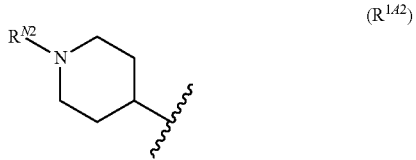
(R1A2)

($R^{I46}$)

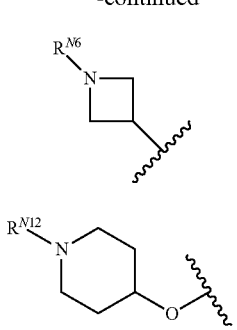

($R^{I411}$)

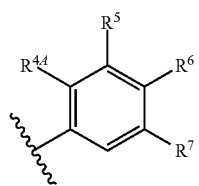

wherein:
$R^{N1}$ is selected from H and Me;
$R^{N2}$ is selected from H and Me;
$R^{N6}$ is selected from H and Me; and
$R^{N12}$ is selected from H and Me;
and where there may be a single $R^{1C}$ group which is methyl; $R^2$ is selected from H, methyl and $CF_3$;
$R^3$ is:

($R^{3a}$)

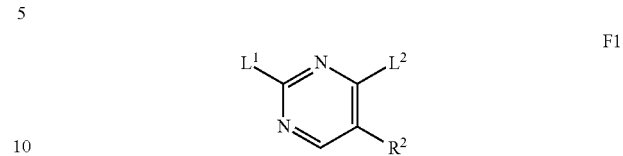

where $R^5$, $R^6$ and $R^7$ are independently selected from H, F, methyl and $CF_3$, and only one of them is not H; and
$R^4$ is —$CH_2$—C(O)$NH_2$.

24. A compound, or a stereoisomer, or a salt or a solvate thereof, selected from the group consisting of the following compounds:
 2-(2-(2-(5-methyl-2-((6-(piperidin-4-yl)pyridin-3-yl)amino)pyrimidin-4-yl)ethyl)phenyl)acetamide (4),
 2-(2-(2-(5-methyl-2-((6-(1-methylpiperidin-4-yl)pyridin-3-yl)amino)pyrimidin-4-yl)ethyl)phenyl)acetamide (5),
 2-(2-(2-(2-((6-(piperidin-4-yl)pyridin-3-yl)amino)-5-(trifluoromethyl)pyrimidin-4-yl)ethyl)phenyl)acetamide (13),
 2-(2-(2-(2-((6-(1-methylpiperidin-4-yl)pyridin-3-yl)amino)-5-(trifluoromethyl)pyrimidin-4-yl)ethyl)phenyl)acetamide (14),
 2-(2-(2-(5-methyl-2-(pyridin-3-ylamino)pyrimidin-4-yl)ethyl)phenyl)acetamide (24),
 2-(2-(2-(5-methyl-2-((1-methyl-1H-pyrazol-4-yl)amino)pyrimidin-4-yl)ethyl)phenyl)acetamide (28),
 2-(2-(2-(2-((1-(azetidin-3-yl)-1H-pyrazol-4-yl)amino)-5-methylpyrimidin-4-yl)ethyl)phenyl)acetamide (30),
 2-(2-(2-(5-Methyl-2-((1-(piperidin-4-yl)-1H-pyrazol-4-yl)amino)pyrimidin-4-yl)ethyl)phenyl)acetamide (33),
 2-(2-(2-(2-((1-(piperidin-4-yl)-1H-pyrazol-4-yl)amino)-5-(trifluoromethyl)pyrimidin-4-yl)ethyl)phenyl)acetamide (35), 2-(2-(2-(2-((1-(1-methylpiperidin-4-yl)-1H-pyrazol-4-yl)amino)-5-(trifluoromethyl)pyrimidin-4-yl)ethyl)phenyl)acetamide (36), and
 2-(2-(2-(2-((6-(1-aminoethyl)pyridin-3-yl)amino)-5-chloropyrimidin-4-yl)ethyl)phenyl)acetamide (40),
 or a stereoisomer, a salt or a solvate thereof.

25. A process for the preparation of a compound, or a stereoisomer, or a salt or a solvate thereof, according to claim 1, comprising reacting a compound of formula F1

F1 with a compound of formula A-$NH_2$ to displace the group $L^1$, and with a compound of formula HC≡$R^3$ to displace the group $L^2$, or
with a compound of formula HC≡$R^3$ to displace the group $L^2$, and with a compound of formula A-$NH_2$ to displace the group $L^1$,
$L^1$ and $L^2$ are leaving groups.

26. A pharmaceutical agent comprising a compound, or stereoisomer, or a salt or a solvate thereof, according to claim 1.

27. A composition comprising a compound, or a stereoisomer, or a salt or a solvate thereof, according to claim 1, and a pharmaceutically acceptable carrier or diluent.

28. A method of inhibiting VEGFR3 in vitro or in vivo, comprising contacting a cell with an effective amount of a compound, or a stereoisomer, or a salt or a solvate thereof, according to claim 1.

29. A method for treating cancer selected from melanoma, breast cancer and cancer of the head or neck, comprising administering an effective amount of a compound, or a stereoisomer, or a salt or a solvate thereof, according to claim 1 to a subject in need thereof.

30. The composition of claim 27, further comprising an anti-tumour agent selected from the group consisting of an antiproliferative drug, an antineoplastic drug, a cytostatic agent, an anti-invasion agent, an inhibitor of growth factor function, an antiangiogenic agent, an antilymphangiogenic agent, a vascular damaging agent, and combinations thereof.

31. A compound, or a stereoisomer, or a salt or a solvate thereof, according to claim 18, wherein the group of $R^{4A}$ and $R^{4B}$ that is not $R^4$, and $R^6$, $R^7$ and $R^8$ are all H.

32. A compound according to claim 18, wherein one of the group of $R^{4A}$ and $R^{4B}$ that is not $R^4$, $R^6$, $R^7$ and $R^8$ is not H.

33. A compound according to claim 32, wherein the group that is not H is either $R^6$ or $R^7$.

34. A compound according to claim 18, wherein the group $R^{4A}$ is $R^4$, and $R^{4B}$, $R^6$, $R^7$ and $R^8$ are all H.

35. A compound according to claim 20, wherein the group of $R^{4A}$ and $R^{4B}$ (if present) that is not $R^4$, and $R^6$, $R^7$ and $R^8$ (if present) are all H.

36. A compound according to claim 20, wherein one of the group of $R^{4A}$ and $R^{4B}$ (if present) that is not $R^4$, and $R^6$, $R^7$ and $R^8$ (if present) is not H.

37. A compound according to claim 20, wherein $R^3$ is of structure $R^{3d}$ or $R^{3e}$.

38. A compound according to claim 1, wherein $R^4$ is alpha to the —$C_2H_4$— group.

39. A compound according to claims 1, wherein $R^4$ is beta to the —$C_2H_4$— group.

40. A compound according to claim 1, wherein $R^{N13}$ is H or Me.

41. A compound according to claim 1, wherein $Z^3$ is H, Me or OMe.

* * * * *